US008365976B2

(12) United States Patent
Hess et al.

(10) Patent No.: US 8,365,976 B2
(45) Date of Patent: Feb. 5, 2013

(54) SURGICAL STAPLES HAVING DISSOLVABLE, BIOABSORBABLE OR BIOFRAGMENTABLE PORTIONS AND STAPLING INSTRUMENTS FOR DEPLOYING THE SAME

(75) Inventors: Christopher J. Hess, Cincinnati, OH (US); Michael A. Murray, Bellevue, KY (US); Jerome R. Morgan, Cincinnati, OH (US); James W. Voegele, Cincinnati, OH (US); Robert Gill, Mason, OH (US); Michael Clem, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1047 days.

(21) Appl. No.: 11/541,374

(22) Filed: Sep. 29, 2006

(65) Prior Publication Data

US 2008/0078808 A1    Apr. 3, 2008

(51) Int. Cl.
 *A61B 17/064* (2006.01)
(52) U.S. Cl. .............. 227/181.1; 606/151; 606/219
(58) Field of Classification Search ............ 227/181.1, 227/175.1; 606/219, 151
 See application file for complete search history.

(56) References Cited

U.S. PATENT DOCUMENTS

| 66,052 | A | 6/1867 | Smith |
| 2,037,727 | A | 4/1936 | Chapelle |
| 2,214,870 | A | 9/1940 | West |
| 2,441,096 | A | 5/1948 | Happe |
| 2,526,902 | A | 10/1950 | Rublee |
| 2,804,848 | A | 9/1957 | O'Farrell et al. |
| 2,808,482 | A | 10/1957 | Zanichkowsky et al. |
| 2,853,074 | A | 9/1958 | Olson |
| 3,032,769 | A | 5/1962 | Palmer |
| 3,075,062 | A | 1/1963 | Iaccarino |
| 3,078,465 | A | 2/1963 | Bobrov |
| 3,266,494 | A | 8/1966 | Brownrigg et al. |
| 3,269,630 | A | 8/1966 | Fleischer |
| 3,357,296 | A | 12/1967 | Lefever |

(Continued)

FOREIGN PATENT DOCUMENTS

| CA | 2458946 A1 | 3/2003 |
| CA | 2512960 A1 | 1/2006 |

(Continued)

OTHER PUBLICATIONS

U.S. Appl. No. 11/541,164, filed Sep. 29, 2006.

(Continued)

*Primary Examiner* — Hemant M Desai
*Assistant Examiner* — Gloria R Weeks

(57) ABSTRACT

A surgical staple including a crown comprised of a dissolvable, bioabsorbable, or biofragmentable material, a first deformable member, and a second member. In at least one embodiment, the crown connects the first member and the second member, however, after the crown has been dissolved, the first member is unconnected to the second member and, as a result, the first and second members can move relative to each other. Accordingly, the staple can be rigid during the early stages of healing and can be flexible during the latter stages of healing, for example. In various embodiments, the first and second members of the staple are also comprised of a dissolvable, bioabsorbable, or biofragmentable material. In these embodiments, the first and second members can be constructed so that the crown and first and second members dissolve at different rates and/or dissolve away at different times.

12 Claims, 116 Drawing Sheets

U.S. PATENT DOCUMENTS

| | | |
|---|---|---|
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Siegel et al. |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A * | 12/1984 | Krumme ............... 606/219 |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,156,614 A | 10/1992 | Green et al. |
| 5,158,567 A | 10/1992 | Green |
| 5,163,598 A | 11/1992 | Peters et al. |
| 5,171,247 A | 12/1992 | Hughett et al. |

| Patent | Date | Inventor(s) |
|---|---|---|
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A * | 11/1993 | Conners .................. 606/219 |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A * | 2/1994 | Hermes .................. 606/219 |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A * | 2/1995 | Tsuruta et al. .................. 606/41 |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,452,837 A | 9/1995 | Williamson, IV et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,470,006 A | 11/1995 | Rodak |
| 5,470,007 A | 11/1995 | Plyley et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |

| Patent No. | Date | Name |
|---|---|---|
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A * | 9/1997 | Bishop et al. .................. 606/143 |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,715,987 A | 2/1998 | Kelley et al. |
| 5,715,988 A | 2/1998 | Palmer |
| 5,716,366 A | 2/1998 | Yates |

| | | | | | |
|---|---|---|---|---|---|
| 5,718,359 A | 2/1998 | Palmer et al. | 5,855,583 A | 1/1999 | Wang et al. |
| 5,718,360 A | 2/1998 | Green et al. | 5,860,975 A | 1/1999 | Goble et al. |
| 5,718,548 A | 2/1998 | Costellessa | 5,865,361 A | 2/1999 | Milliman et al. |
| 5,720,744 A | 2/1998 | Eggleston et al. | 5,868,760 A | 2/1999 | McGuckin, Jr. |
| D393,067 S | 3/1998 | Geary et al. | 5,871,135 A | 2/1999 | Williamson, IV et al. |
| 5,725,536 A | 3/1998 | Oberlin et al. | 5,873,885 A | 2/1999 | Weidenbenner |
| 5,725,554 A | 3/1998 | Simon et al. | 5,876,401 A | 3/1999 | Schulze et al. |
| 5,728,121 A | 3/1998 | Bimbo et al. | 5,878,193 A | 3/1999 | Wang et al. |
| 5,730,758 A | 3/1998 | Allgeyer | 5,878,937 A | 3/1999 | Green et al. |
| 5,732,871 A | 3/1998 | Clark et al. | 5,878,938 A | 3/1999 | Bittner et al. |
| 5,732,872 A | 3/1998 | Bolduc et al. | 5,891,160 A | 4/1999 | Williamson, IV et al. |
| 5,735,445 A | 4/1998 | Vidal et al. | 5,893,506 A | 4/1999 | Powell |
| 5,735,848 A | 4/1998 | Yates et al. | 5,894,979 A | 4/1999 | Powell |
| 5,735,874 A | 4/1998 | Measamer et al. | 5,897,562 A | 4/1999 | Bolanos et al. |
| 5,738,474 A | 4/1998 | Blewett | 5,899,914 A | 5/1999 | Zirps et al. |
| 5,738,648 A | 4/1998 | Lands et al. | 5,901,895 A | 5/1999 | Heaton et al. |
| 5,743,456 A | 4/1998 | Jones et al. | 5,902,312 A | 5/1999 | Frater et al. |
| 5,747,953 A | 5/1998 | Philipp | 5,904,693 A | 5/1999 | Dicesare et al. |
| 5,749,889 A | 5/1998 | Bacich et al. | 5,906,625 A | 5/1999 | Bito et al. |
| 5,749,893 A | 5/1998 | Vidal et al. | 5,908,402 A | 6/1999 | Blythe |
| 5,752,644 A | 5/1998 | Bolanos et al. | 5,908,427 A | 6/1999 | McKean et al. |
| 5,752,965 A | 5/1998 | Francis et al. | 5,911,353 A | 6/1999 | Bolanos et al. |
| 5,755,717 A | 5/1998 | Yates et al. | 5,915,616 A | 6/1999 | Viola et al. |
| 5,758,814 A | 6/1998 | Gallagher et al. | 5,918,791 A | 7/1999 | Sorrentino et al. |
| 5,762,255 A | 6/1998 | Chrisman et al. | 5,919,198 A | 7/1999 | Graves, Jr. et al. |
| 5,762,256 A | 6/1998 | Mastri et al. | 5,928,256 A | 7/1999 | Riza |
| 5,766,188 A | 6/1998 | Igaki | 5,931,847 A | 8/1999 | Bittner et al. |
| 5,766,205 A | 6/1998 | Zvenyatsky et al. | 5,931,853 A | 8/1999 | McEwen et al. |
| 5,769,892 A | 6/1998 | Kingwell | 5,937,951 A | 8/1999 | Izuchukwu et al. |
| 5,772,578 A | 6/1998 | Heimberger et al. | 5,938,667 A | 8/1999 | Peyser et al. |
| 5,772,659 A | 6/1998 | Becker et al. | 5,941,442 A | 8/1999 | Geiste et al. |
| 5,776,130 A | 7/1998 | Buysse et al. | 5,944,172 A | 8/1999 | Hannula |
| 5,779,130 A | 7/1998 | Alesi et al. | 5,944,715 A | 8/1999 | Goble et al. |
| 5,779,131 A | 7/1998 | Knodel et al. | 5,948,030 A | 9/1999 | Miller et al. |
| 5,779,132 A | 7/1998 | Knodel et al. | 5,951,552 A | 9/1999 | Long et al. |
| 5,782,396 A | 7/1998 | Mastri et al. | 5,951,574 A | 9/1999 | Stefanchik et al. |
| 5,782,397 A | 7/1998 | Koukline | 5,954,259 A | 9/1999 | Viola et al. |
| 5,782,749 A | 7/1998 | Riza | 5,964,774 A | 10/1999 | McKean et al. |
| 5,782,859 A | 7/1998 | Nicholas et al. | 5,971,916 A | 10/1999 | Koren |
| 5,784,934 A | 7/1998 | Izumisawa | 5,988,479 A | 11/1999 | Palmer |
| 5,785,232 A | 7/1998 | Vidal et al. | 6,003,517 A | 12/1999 | Sheffield et al. |
| 5,787,897 A | 8/1998 | Kieturakis | 6,004,319 A | 12/1999 | Goble et al. |
| 5,792,135 A | 8/1998 | Madhani et al. | 6,010,054 A | 1/2000 | Johnson et al. |
| 5,792,165 A | 8/1998 | Klieman et al. | 6,012,494 A | 1/2000 | Balazs |
| 5,794,834 A | 8/1998 | Hamblin et al. | 6,013,076 A | 1/2000 | Goble et al. |
| 5,796,188 A | 8/1998 | Bays | 6,015,406 A | 1/2000 | Goble et al. |
| 5,797,536 A | 8/1998 | Smith et al. | 6,017,322 A | 1/2000 | Snoke et al. |
| 5,797,537 A | 8/1998 | Oberlin et al. | 6,017,356 A | 1/2000 | Frederick et al. |
| 5,797,538 A | 8/1998 | Heaton et al. | 6,022,352 A | 2/2000 | Vandewalle |
| 5,797,906 A | 8/1998 | Rhum et al. | 6,024,741 A | 2/2000 | Williamson, IV et al. |
| 5,797,959 A | 8/1998 | Castro et al. | 6,024,748 A | 2/2000 | Manzo et al. |
| 5,799,857 A | 9/1998 | Robertson et al. | 6,027,501 A | 2/2000 | Goble et al. |
| 5,807,378 A | 9/1998 | Jensen et al. | 6,032,849 A | 3/2000 | Mastri et al. |
| 5,807,393 A | 9/1998 | Williamson, IV et al. | 6,033,378 A | 3/2000 | Lundquist et al. |
| 5,809,441 A | 9/1998 | McKee | 6,033,399 A | 3/2000 | Gines |
| 5,810,811 A | 9/1998 | Yates et al. | 6,033,427 A | 3/2000 | Lee |
| 5,810,855 A | 9/1998 | Rayburn et al. | 6,039,733 A | 3/2000 | Buysse et al. |
| 5,813,813 A | 9/1998 | Daum et al. | 6,039,734 A | 3/2000 | Goble |
| 5,814,057 A | 9/1998 | Oi et al. | 6,045,560 A | 4/2000 | McKean et al. |
| 5,817,084 A | 10/1998 | Jensen | 6,050,472 A | 4/2000 | Shibata |
| 5,817,091 A | 10/1998 | Nardella et al. | 6,053,390 A | 4/2000 | Green et al. |
| 5,817,093 A | 10/1998 | Williamson, IV et al. | 6,056,746 A | 5/2000 | Goble et al. |
| 5,817,109 A | 10/1998 | McGarry et al. | 6,063,097 A | 5/2000 | Oi et al. |
| 5,817,119 A | 10/1998 | Klieman et al. | 6,063,098 A | 5/2000 | Houser et al. |
| 5,820,009 A | 10/1998 | Melling et al. | 6,068,627 A | 5/2000 | Orszulak et al. |
| 5,823,066 A | 10/1998 | Huitema et al. | 6,071,233 A | 6/2000 | Ishikawa et al. |
| 5,826,776 A | 10/1998 | Schulze et al. | 6,074,386 A | 6/2000 | Goble et al. |
| 5,827,271 A | 10/1998 | Buysse et al. | 6,077,286 A | 6/2000 | Cuschieri et al. |
| 5,829,662 A | 11/1998 | Allen et al. | 6,079,606 A | 6/2000 | Milliman et al. |
| 5,833,690 A | 11/1998 | Yates et al. | 6,082,577 A | 7/2000 | Coates et al. |
| 5,833,695 A | 11/1998 | Yoon | 6,083,234 A | 7/2000 | Nicholas et al. |
| 5,833,696 A | 11/1998 | Whitfield et al. | 6,083,242 A | 7/2000 | Cook |
| 5,836,503 A | 11/1998 | Ehrenfels et al. | 6,086,600 A | 7/2000 | Kortenbach |
| 5,836,960 A | 11/1998 | Kolesa et al. | 6,090,106 A | 7/2000 | Goble et al. |
| 5,839,639 A | 11/1998 | Sauer et al. | 6,093,186 A | 7/2000 | Goble |
| 5,843,132 A | 12/1998 | Ilvento | 6,099,537 A | 8/2000 | Sugai et al. |
| 5,846,254 A | 12/1998 | Schulze et al. | 6,099,551 A | 8/2000 | Gabbay |
| 5,849,011 A | 12/1998 | Jones et al. | 6,102,271 A | 8/2000 | Longo et al. |
| 5,855,311 A | 1/1999 | Hamblin et al. | 6,109,500 A | 8/2000 | Alli et al. |

| Patent | Kind | Date | Inventors |
|---|---|---|---|
| 6,117,158 | A | 9/2000 | Measamer et al. |
| 6,119,913 | A | 9/2000 | Adams et al. |
| 6,120,433 | A | 9/2000 | Mizuno et al. |
| 6,123,241 | A | 9/2000 | Walter et al. |
| H1904 | H | 10/2000 | Yates et al. |
| 6,126,058 | A | 10/2000 | Adams et al. |
| 6,126,670 | A | 10/2000 | Walker et al. |
| 6,131,789 | A | 10/2000 | Schulze et al. |
| 6,132,368 | A | 10/2000 | Cooper |
| 6,139,546 | A | 10/2000 | Koenig et al. |
| 6,155,473 | A | 12/2000 | Tompkins et al. |
| 6,156,056 | A | 12/2000 | Kearns et al. |
| 6,159,146 | A | 12/2000 | El Gazayerli |
| 6,159,200 | A | 12/2000 | Verdura et al. |
| 6,162,208 | A | 12/2000 | Hipps |
| 6,165,175 | A | 12/2000 | Wampler et al. |
| 6,165,184 | A | 12/2000 | Verdura et al. |
| 6,168,605 | B1 | 1/2001 | Measamer et al. |
| 6,171,316 | B1 | 1/2001 | Kovac et al. |
| 6,171,330 | B1 | 1/2001 | Benchetrit |
| 6,174,308 | B1 | 1/2001 | Goble et al. |
| 6,179,776 | B1 | 1/2001 | Adams et al. |
| 6,181,105 | B1 | 1/2001 | Cutolo et al. |
| 6,193,129 | B1 | 2/2001 | Bittner et al. |
| 6,197,042 | B1 | 3/2001 | Ginn et al. |
| 6,202,914 | B1 | 3/2001 | Geiste et al. |
| 6,214,028 | B1 | 4/2001 | Yoon et al. |
| 6,220,368 | B1 | 4/2001 | Ark et al. |
| 6,223,835 | B1 | 5/2001 | Habedank et al. |
| 6,228,081 | B1 | 5/2001 | Goble |
| 6,228,084 | B1 | 5/2001 | Kirwan, Jr. |
| 6,231,565 | B1 | 5/2001 | Tovey et al. |
| 6,234,178 | B1 | 5/2001 | Goble et al. |
| 6,241,139 | B1 | 6/2001 | Milliman et al. |
| 6,241,723 | B1 | 6/2001 | Heim et al. |
| 6,249,076 | B1 | 6/2001 | Madden et al. |
| 6,250,532 | B1 | 6/2001 | Green et al. |
| 6,258,107 | B1 | 7/2001 | Balázs et al. |
| 6,261,286 | B1 | 7/2001 | Goble et al. |
| 6,264,086 | B1 | 7/2001 | McGuckin, Jr. |
| 6,264,087 | B1 | 7/2001 | Whitman |
| 6,270,508 | B1 | 8/2001 | Klieman et al. |
| 6,273,897 | B1 | 8/2001 | Dalessandro et al. |
| 6,277,114 | B1 | 8/2001 | Bullivant et al. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,306,134 | B1 | 10/2001 | Goble et al. |
| 6,309,403 | B1 | 10/2001 | Minor et al. |
| 6,315,184 | B1 | 11/2001 | Whitman |
| 6,320,123 | B1 | 11/2001 | Reimers |
| 6,324,339 | B1 | 11/2001 | Hudson et al. |
| 6,325,799 | B1 | 12/2001 | Goble |
| 6,325,810 | B1 | 12/2001 | Hamilton et al. |
| 6,330,965 | B1 | 12/2001 | Milliman et al. |
| 6,331,181 | B1 | 12/2001 | Tierney et al. |
| 6,331,761 | B1 | 12/2001 | Kumar et al. |
| 6,334,860 | B1 | 1/2002 | Dorn |
| 6,336,926 | B1 | 1/2002 | Goble |
| 6,346,077 | B1 | 2/2002 | Taylor et al. |
| 6,352,503 | B1 | 3/2002 | Matsui et al. |
| 6,358,224 | B1 | 3/2002 | Tims et al. |
| 6,364,877 | B1 | 4/2002 | Goble et al. |
| 6,364,888 | B1 | 4/2002 | Niemeyer et al. |
| 6,373,152 | B1 | 4/2002 | Wang et al. |
| 6,387,113 | B1 | 5/2002 | Hawkins et al. |
| 6,387,114 | B2 | 5/2002 | Adams |
| 6,398,781 | B1 | 6/2002 | Goble et al. |
| 6,398,797 | B2 | 6/2002 | Bombard et al. |
| 6,406,440 | B1 | 6/2002 | Stefanchik |
| 6,409,724 | B1 | 6/2002 | Penny et al. |
| H2037 | H | 7/2002 | Yates et al. |
| 6,416,486 | B1 | 7/2002 | Wampler |
| 6,416,509 | B1 | 7/2002 | Goble et al. |
| RE37,814 | E * | 8/2002 | Allgeyer ............... 606/219 |
| 6,436,097 | B1 | 8/2002 | Nardella |
| 6,436,107 | B1 | 8/2002 | Wang et al. |
| 6,436,122 | B1 | 8/2002 | Frank et al. |
| 6,439,446 | B1 | 8/2002 | Perry et al. |
| 6,440,146 | B2 | 8/2002 | Nicholas et al. |
| 6,443,973 | B1 | 9/2002 | Whitman |
| 6,468,275 | B1 | 10/2002 | Wampler et al. |
| 6,471,106 | B1 | 10/2002 | Reining |
| 6,482,200 | B2 | 11/2002 | Shippert |
| 6,485,490 | B2 | 11/2002 | Wampler et al. |
| 6,488,196 | B1 | 12/2002 | Fenton, Jr. |
| 6,488,197 | B1 | 12/2002 | Whitman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,492,785 | B1 | 12/2002 | Kasten et al. |
| 6,494,896 | B1 | 12/2002 | D'Alessio et al. |
| 6,503,257 | B2 | 1/2003 | Grant et al. |
| 6,503,259 | B2 | 1/2003 | Huxel et al. |
| 6,505,768 | B2 | 1/2003 | Whitman |
| 6,510,854 | B2 | 1/2003 | Goble |
| 6,511,468 | B1 | 1/2003 | Cragg et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,522,101 | B2 | 2/2003 | Malackowski |
| 6,543,456 | B1 | 4/2003 | Freeman |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,861 | B2 | 4/2003 | Knox et al. |
| 6,558,379 | B1 | 5/2003 | Batchelor et al. |
| 6,565,560 | B1 | 5/2003 | Goble et al. |
| 6,569,085 | B2 | 5/2003 | Kortenbach et al. |
| 6,569,171 | B2 | 5/2003 | DeGuillebon et al. |
| 6,578,751 | B2 | 6/2003 | Hartwick |
| 6,582,427 | B1 | 6/2003 | Goble et al. |
| 6,588,643 | B2 | 7/2003 | Bolduc et al. |
| 6,589,164 | B1 | 7/2003 | Flaherty |
| 6,592,597 | B2 | 7/2003 | Grant et al. |
| 6,596,432 | B2 | 7/2003 | Kawakami et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,605,078 | B2 | 8/2003 | Adams |
| 6,605,669 | B2 | 8/2003 | Awokola et al. |
| 6,616,686 | B2 | 9/2003 | Coleman et al. |
| 6,619,529 | B2 | 9/2003 | Green et al. |
| 6,620,166 | B1 | 9/2003 | Wenstrom, Jr. et al. |
| 6,629,630 | B2 | 10/2003 | Adams |
| 6,629,974 | B2 | 10/2003 | Penny et al. |
| 6,629,988 | B2 | 10/2003 | Weadock |
| 6,636,412 | B2 | 10/2003 | Smith |
| 6,638,108 | B2 | 10/2003 | Tachi |
| 6,638,285 | B2 | 10/2003 | Gabbay |
| 6,644,532 | B2 | 11/2003 | Green et al. |
| 6,648,816 | B2 | 11/2003 | Irion et al. |
| D484,243 | S | 12/2003 | Ryan et al. |
| D484,595 | S | 12/2003 | Ryan et al. |
| D484,596 | S | 12/2003 | Ryan et al. |
| 6,656,193 | B2 | 12/2003 | Grant et al. |
| 6,666,875 | B1 | 12/2003 | Sakurai et al. |
| 6,669,073 | B2 | 12/2003 | Milliman et al. |
| D484,977 | S | 1/2004 | Ryan et al. |
| 6,676,660 | B2 | 1/2004 | Wampler et al. |
| 6,679,410 | B2 | 1/2004 | Würsch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,685,727 | B2 | 2/2004 | Fisher et al. |
| 6,695,199 | B2 | 2/2004 | Whitman |
| 6,698,643 | B2 | 3/2004 | Whitman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |

| Patent | Date | Inventor |
|---|---|---|
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |

| | | | | | | |
|---|---|---|---|---|---|---|
| 7,182,239 B1 | 2/2007 | Myers | | 7,479,608 B2 | 1/2009 | Smith |
| 7,188,758 B2 | 3/2007 | Viola et al. | | 7,481,349 B2 | 1/2009 | Holsten et al. |
| 7,195,627 B2 | 3/2007 | Amoah et al. | | 7,481,824 B2 | 1/2009 | Boudreaux et al. |
| 7,204,835 B2 | 4/2007 | Latterell et al. | | 7,485,133 B2 | 2/2009 | Cannon et al. |
| 7,207,233 B2 | 4/2007 | Wadge | | 7,490,749 B2 | 2/2009 | Schall et al. |
| 7,207,471 B2 | 4/2007 | Heinrich et al. | | 7,494,039 B2 | 2/2009 | Racenet et al. |
| 7,207,472 B2 | 4/2007 | Wukusick et al. | | 7,494,499 B2 | 2/2009 | Nagase et al. |
| 7,208,005 B2 | 4/2007 | Frecker et al. | | 7,501,198 B2 | 3/2009 | Barlev et al. |
| 7,210,609 B2 | 5/2007 | Leiboff et al. | | 7,506,790 B2 | 3/2009 | Shelton, IV |
| 7,211,081 B2 | 5/2007 | Goble | | 7,510,107 B2 | 3/2009 | Timm et al. |
| 7,211,084 B2 | 5/2007 | Goble et al. | | 7,524,320 B2 | 4/2009 | Tierney et al. |
| 7,214,224 B2 | 5/2007 | Goble | | 7,530,985 B2 | 5/2009 | Takemoto et al. |
| 7,217,285 B2 | 5/2007 | Vargas et al. | | 7,546,940 B2 | 6/2009 | Milliman et al. |
| 7,220,260 B2 | 5/2007 | Fleming et al. | | 7,547,312 B2 | 6/2009 | Bauman et al. |
| 7,225,963 B2 | 6/2007 | Scirica | | 7,549,563 B2 | 6/2009 | Mather et al. |
| 7,225,964 B2 | 6/2007 | Mastri et al. | | 7,549,564 B2 | 6/2009 | Boudreaux |
| 7,234,624 B2 | 6/2007 | Gresham et al. | | 7,552,854 B2 | 6/2009 | Wixey et al. |
| 7,235,089 B1 | 6/2007 | McGuckin, Jr. | | 7,556,185 B2 | 7/2009 | Viola |
| 7,235,302 B2 | 6/2007 | Jing et al. | | 7,556,186 B2 | 7/2009 | Milliman |
| 7,237,708 B1 | 7/2007 | Guy et al. | | 7,559,452 B2 | 7/2009 | Wales et al. |
| 7,241,288 B2 | 7/2007 | Braun | | 7,563,862 B2 | 7/2009 | Sieg et al. |
| 7,246,734 B2 | 7/2007 | Shelton, IV | | 7,566,300 B2 | 7/2009 | Devierre et al. |
| 7,247,161 B2 | 7/2007 | Johnston et al. | | 7,568,604 B2 | 8/2009 | Ehrenfels et al. |
| 7,252,660 B2 | 8/2007 | Kunz | | 7,568,619 B2 | 8/2009 | Todd et al. |
| 7,255,696 B2 | 8/2007 | Goble et al. | | 7,575,144 B2 | 8/2009 | Ortiz et al. |
| 7,258,262 B2 | 8/2007 | Mastri et al. | | 7,588,175 B2 | 9/2009 | Timm et al. |
| 7,260,431 B2 | 8/2007 | Libbus et al. | | 7,588,176 B2 | 9/2009 | Timm et al. |
| 7,265,374 B2 | 9/2007 | Lee et al. | | 7,597,229 B2 | 10/2009 | Boudreaux et al. |
| 7,267,679 B2 | 9/2007 | McGuckin, Jr. et al. | | 7,600,663 B2 | 10/2009 | Green |
| 7,273,483 B2 | 9/2007 | Wiener et al. | | 7,604,150 B2 | 10/2009 | Boudreaux |
| 7,278,562 B2 | 10/2007 | Mastri et al. | | 7,604,151 B2 | 10/2009 | Hess et al. |
| 7,278,563 B1 | 10/2007 | Green | | 7,611,038 B2 | 11/2009 | Racenet et al. |
| 7,278,994 B2 | 10/2007 | Goble | | 7,615,003 B2 | 11/2009 | Stefanchik et al. |
| 7,282,048 B2 | 10/2007 | Goble et al. | | 7,624,902 B2 | 12/2009 | Marczyk et al. |
| 7,295,907 B2 | 11/2007 | Lu et al. | | 7,631,793 B2 | 12/2009 | Rethy et al. |
| 7,296,724 B2 | 11/2007 | Green et al. | | 7,637,409 B2 | 12/2009 | Marczyk |
| 7,297,149 B2 | 11/2007 | Vitali et al. | | 7,641,092 B2 | 1/2010 | Kruszynski et al. |
| 7,300,450 B2 | 11/2007 | Vleugels et al. | | 7,641,093 B2 | 1/2010 | Doll et al. |
| 7,303,106 B2 | 12/2007 | Milliman et al. | | 7,651,498 B2 | 1/2010 | Shifrin et al. |
| 7,303,107 B2 | 12/2007 | Milliman et al. | | 7,656,131 B2 | 2/2010 | Embrey et al. |
| 7,303,108 B2 | 12/2007 | Shelton, IV | | 7,658,311 B2 | 2/2010 | Boudreaux |
| 7,303,556 B2 | 12/2007 | Metzger | | 7,658,312 B2 | 2/2010 | Vidal et al. |
| 7,308,998 B2 | 12/2007 | Mastri et al. | | 7,665,646 B2 | 2/2010 | Prommersberger |
| 7,322,975 B2 | 1/2008 | Goble et al. | | 7,669,747 B2 | 3/2010 | Weisenburgh, II et al. |
| 7,324,572 B2 | 1/2008 | Chang | | 7,673,782 B2 | 3/2010 | Hess et al. |
| 7,328,829 B2 | 2/2008 | Arad et al. | | 7,674,255 B2 | 3/2010 | Braun |
| 7,330,004 B2 | 2/2008 | DeJonge et al. | | 7,682,307 B2 | 3/2010 | Danitz et al. |
| 7,334,717 B2 | 2/2008 | Rethy et al. | | 7,686,826 B2 | 3/2010 | Lee et al. |
| 7,336,184 B2 | 2/2008 | Smith et al. | | 7,691,098 B2 | 4/2010 | Wallace et al. |
| 7,338,513 B2 | 3/2008 | Lee et al. | | 7,699,204 B2 | 4/2010 | Viola |
| 7,348,763 B1 | 3/2008 | Reinhart et al. | | 7,714,239 B2 | 5/2010 | Smith |
| 7,351,258 B2 | 4/2008 | Ricotta et al. | | 7,717,312 B2 | 5/2010 | Beetel |
| 7,357,287 B2 | 4/2008 | Shelton, IV et al. | | 7,721,930 B2 | 5/2010 | McKenna et al. |
| 7,364,060 B2 | 4/2008 | Milliman | | 7,721,931 B2 | 5/2010 | Shelton, IV et al. |
| 7,377,928 B2 | 5/2008 | Zubik et al. | | 7,721,936 B2 | 5/2010 | Shalton, IV et al. |
| 7,388,217 B2 | 6/2008 | Buschbeck et al. | | 7,722,610 B2 | 5/2010 | Viola et al. |
| 7,397,364 B2 | 7/2008 | Govari | | 7,726,537 B2 | 6/2010 | Olson et al. |
| 7,398,907 B2 | 7/2008 | Racenet et al. | | 7,726,538 B2 | 6/2010 | Holsten et al. |
| 7,398,908 B2 | 7/2008 | Holsten et al. | | 7,731,072 B2 | 6/2010 | Timm et al. |
| 7,404,508 B2 | 7/2008 | Smith et al. | | 7,735,703 B2 | 6/2010 | Morgan et al. |
| 7,404,509 B2 | 7/2008 | Ortiz et al. | | 7,738,971 B2 | 6/2010 | Swayze et al. |
| 7,418,078 B2 | 8/2008 | Blanz et al. | | 7,743,960 B2 | 6/2010 | Whitman et al. |
| 7,419,080 B2 | 9/2008 | Smith et al. | | 7,744,627 B2 | 6/2010 | Orban, III et al. |
| 7,422,136 B1 | 9/2008 | Marczyk | | 7,753,245 B2 | 7/2010 | Boudreaux et al. |
| 7,424,965 B2 | 9/2008 | Racenet et al. | | 7,766,209 B2 | 8/2010 | Baxter, III et al. |
| 7,431,188 B1 | 10/2008 | Marczyk | | 7,766,894 B2 | 8/2010 | Weitzner et al. |
| 7,431,694 B2 | 10/2008 | Stefanchik et al. | | 7,771,396 B2 | 8/2010 | Stefanchik et al. |
| 7,434,715 B2 | 10/2008 | Shelton, IV et al. | | 7,772,720 B2 | 8/2010 | McGee et al. |
| 7,434,717 B2 | 10/2008 | Shelton, IV et al. | | 7,776,060 B2 | 8/2010 | Mooradian et al. |
| 7,438,209 B1 | 10/2008 | Hess et al. | | 7,780,054 B2 | 8/2010 | Wales |
| 7,439,354 B2 | 10/2008 | Lenges et al. | | 7,780,055 B2 | 8/2010 | Scirica et al. |
| 7,441,685 B1 | 10/2008 | Boudreaux | | 7,780,663 B2 | 8/2010 | Yates et al. |
| 7,442,201 B2 | 10/2008 | Pugsley et al. | | 7,780,685 B2 | 8/2010 | Hunt et al. |
| 7,455,208 B2 | 11/2008 | Wales et al. | | 7,784,662 B2 | 8/2010 | Wales et al. |
| 7,461,767 B2 | 12/2008 | Viola et al. | | 7,793,812 B2 | 9/2010 | Moore et al. |
| 7,464,847 B2 | 12/2008 | Viola et al. | | 7,798,386 B2 | 9/2010 | Schall et al. |
| 7,467,849 B2 | 12/2008 | Silverbrook et al. | | 7,803,151 B2 | 9/2010 | Whitman |
| 7,472,814 B2 | 1/2009 | Mastri et al. | | 7,806,891 B2 | 10/2010 | Nowlin et al. |
| 7,473,253 B2 | 1/2009 | Dycus et al. | | 7,810,692 B2 | 10/2010 | Hall et al. |

| | | | | | | |
|---|---|---|---|---|---|---|
| 7,810,693 B2 | 10/2010 | Broehl et al. | 2003/0105478 A1 | 6/2003 | Whitman et al. | |
| 7,815,565 B2 | 10/2010 | Stefanchik et al. | 2003/0130677 A1 | 7/2003 | Whitman et al. | |
| 7,819,296 B2 | 10/2010 | Hueil et al. | 2003/0139741 A1 | 7/2003 | Goble et al. | |
| 7,819,297 B2 | 10/2010 | Doll et al. | 2003/0153908 A1 | 8/2003 | Goble et al. | |
| 7,819,298 B2 | 10/2010 | Hall et al. | 2003/0195387 A1 | 10/2003 | Kortenbach et al. | |
| 7,819,299 B2 | 10/2010 | Shelton, IV et al. | 2003/0205029 A1 | 11/2003 | Chapolini et al. | |
| 7,824,401 B2 | 11/2010 | Manzo et al. | 2003/0216732 A1 | 11/2003 | Truckai et al. | |
| 7,828,794 B2 | 11/2010 | Sartor | 2003/0216778 A1 | 11/2003 | Weadock | |
| 7,828,808 B2 | 11/2010 | Hinman et al. | 2003/0220660 A1* | 11/2003 | Kortenbach et al. | 606/151 |
| 7,832,408 B2 | 11/2010 | Shelton, IV et al. | 2004/0002726 A1 | 1/2004 | Nunez et al. | |
| 7,832,611 B2 | 11/2010 | Boyden et al. | 2004/0006335 A1 | 1/2004 | Garrison | |
| 7,832,612 B2 | 11/2010 | Baxter, III et al. | 2004/0006340 A1 | 1/2004 | Latterell et al. | |
| 7,836,400 B2 | 11/2010 | May et al. | 2004/0006372 A1 | 1/2004 | Racenet et al. | |
| 7,837,080 B2 | 11/2010 | Schwemberger | 2004/0028502 A1* | 2/2004 | Cummins | 411/457 |
| 7,837,081 B2 | 11/2010 | Holsten et al. | 2004/0030333 A1 | 2/2004 | Goble | |
| 7,845,533 B2 | 12/2010 | Marczyk et al. | 2004/0034357 A1* | 2/2004 | Beane et al. | 606/73 |
| 7,845,534 B2 | 12/2010 | Viola et al. | 2004/0034369 A1 | 2/2004 | Sauer et al. | |
| 7,846,149 B2 | 12/2010 | Jankowski | 2004/0044364 A1 | 3/2004 | DeVries et al. | |
| 7,857,185 B2 | 12/2010 | Swayze et al. | 2004/0068161 A1 | 4/2004 | Couvillon, Jr. | |
| 7,857,186 B2 | 12/2010 | Baxter, III et al. | 2004/0068307 A1 | 4/2004 | Goble | |
| 7,861,906 B2 | 1/2011 | Doll et al. | 2004/0078037 A1 | 4/2004 | Batchelor et al. | |
| 7,866,527 B2 | 1/2011 | Hall et al. | 2004/0093024 A1 | 5/2004 | Lousararian et al. | |
| 7,870,989 B2 | 1/2011 | Viola et al. | 2004/0094597 A1 | 5/2004 | Whitman et al. | |
| 7,887,530 B2 | 2/2011 | Zemlok et al. | 2004/0097987 A1 | 5/2004 | Pugsley et al. | |
| 7,900,805 B2 | 3/2011 | Shelton, IV et al. | 2004/0101822 A1 | 5/2004 | Wiesner et al. | |
| 7,905,380 B2 | 3/2011 | Shelton, IV et al. | 2004/0108357 A1 | 6/2004 | Milliman et al. | |
| 7,905,381 B2 | 3/2011 | Baxter, III et al. | 2004/0111081 A1 | 6/2004 | Whitman et al. | |
| 7,909,191 B2 | 3/2011 | Baker et al. | 2004/0115022 A1 | 6/2004 | Albertson et al. | |
| 7,909,221 B2 | 3/2011 | Viola et al. | 2004/0116952 A1 | 6/2004 | Sakurai et al. | |
| 7,913,891 B2 | 3/2011 | Doll et al. | 2004/0122471 A1 | 6/2004 | Toby et al. | |
| 7,914,543 B2 | 3/2011 | Roth et al. | 2004/0147909 A1 | 7/2004 | Johnston et al. | |
| 7,918,377 B2 | 4/2011 | Measamer et al. | 2004/0164123 A1 | 8/2004 | Racenet et al. | |
| 7,922,061 B2 | 4/2011 | Shelton, IV et al. | 2004/0167572 A1 | 8/2004 | Roth et al. | |
| 7,922,063 B2 | 4/2011 | Zemlok et al. | 2004/0173659 A1 | 9/2004 | Green et al. | |
| 7,934,630 B2 | 5/2011 | Shelton, IV et al. | 2004/0181219 A1 | 9/2004 | Goble et al. | |
| 7,938,307 B2 | 5/2011 | Bettuchi | 2004/0186470 A1 | 9/2004 | Goble et al. | |
| 7,942,303 B2 | 5/2011 | Shah | 2004/0222268 A1 | 11/2004 | Bilotti et al. | |
| 7,942,890 B2 | 5/2011 | D'Agostino et al. | 2004/0230214 A1 | 11/2004 | Donofrio et al. | |
| 7,950,560 B2 | 5/2011 | Zemlok et al. | 2004/0232199 A1 | 11/2004 | Shelton, IV et al. | |
| 7,954,682 B2 | 6/2011 | Giordano et al. | 2004/0232201 A1 | 11/2004 | Wenchell et al. | |
| 7,954,684 B2 | 6/2011 | Boudreaux | 2004/0243151 A1 | 12/2004 | Demmy et al. | |
| 7,954,686 B2 | 6/2011 | Baxter, III et al. | 2004/0243163 A1 | 12/2004 | Casiano et al. | |
| 7,959,050 B2 | 6/2011 | Smith et al. | 2004/0243176 A1 | 12/2004 | Hahnen et al. | |
| 7,959,051 B2 | 6/2011 | Smith et al. | 2004/0254566 A1 | 12/2004 | Plicchi et al. | |
| 7,963,963 B2 | 6/2011 | Francischelli et al. | 2004/0254608 A1 | 12/2004 | Huitema et al. | |
| 7,967,180 B2 | 6/2011 | Scirica | 2004/0267310 A1 | 12/2004 | Racenet et al. | |
| 7,972,298 B2 | 7/2011 | Wallace et al. | 2005/0006434 A1 | 1/2005 | Wales et al. | |
| 7,980,443 B2 | 7/2011 | Scheib et al. | 2005/0021026 A1 | 1/2005 | Baily | |
| 8,002,795 B2 | 8/2011 | Beetel | 2005/0023324 A1 | 2/2005 | Doll et al. | |
| 8,011,551 B2 | 9/2011 | Marczyk et al. | 2005/0032511 A1 | 2/2005 | Malone et al. | |
| 8,020,743 B2 | 9/2011 | Shelton, IV | 2005/0033357 A1 | 2/2005 | Braun | |
| 8,034,077 B2 | 10/2011 | Smith et al. | 2005/0054946 A1 | 3/2005 | Krzyzanowski | |
| 8,038,046 B2 | 10/2011 | Smith et al. | 2005/0059997 A1 | 3/2005 | Bauman et al. | |
| 8,056,787 B2 | 11/2011 | Boudreaux et al. | 2005/0070929 A1 | 3/2005 | Dalessandro et al. | |
| 8,062,330 B2 | 11/2011 | Prommersberger et al. | 2005/0070958 A1 | 3/2005 | Swayze et al. | |
| 8,066,167 B2 | 11/2011 | Measamer et al. | 2005/0072827 A1 | 4/2005 | Mollenauer | |
| D650,074 S | 12/2011 | Hunt et al. | 2005/0080454 A1 | 4/2005 | Drews et al. | |
| 8,083,120 B2 | 12/2011 | Shelton, IV et al. | 2005/0085693 A1 | 4/2005 | Belson et al. | |
| 8,097,017 B2 | 1/2012 | Viola | 2005/0103819 A1 | 5/2005 | Racenet et al. | |
| 8,113,410 B2 | 2/2012 | Hall et al. | 2005/0107814 A1 | 5/2005 | Johnston et al. | |
| 8,123,103 B2 | 2/2012 | Milliman | 2005/0107824 A1 | 5/2005 | Hillstead et al. | |
| 8,136,712 B2 | 3/2012 | Zingman | 2005/0113820 A1 | 5/2005 | Goble et al. | |
| 8,141,762 B2 | 3/2012 | Bedi et al. | 2005/0119525 A1 | 6/2005 | Takemoto | |
| 8,157,145 B2 | 4/2012 | Shelton, IV et al. | 2005/0119669 A1 | 6/2005 | Demmy | |
| 8,157,153 B2 | 4/2012 | Shelton, IV et al. | 2005/0124855 A1 | 6/2005 | Jaffe et al. | |
| 8,161,977 B2 | 4/2012 | Shelton, IV et al. | 2005/0125009 A1 | 6/2005 | Perry et al. | |
| 8,167,185 B2 | 5/2012 | Shelton, IV et al. | 2005/0131173 A1 | 6/2005 | McDaniel et al. | |
| 8,167,895 B2 | 5/2012 | D'Agostino et al. | 2005/0131211 A1 | 6/2005 | Bayley et al. | |
| 8,172,124 B2 | 5/2012 | Shelton, IV et al. | 2005/0131390 A1 | 6/2005 | Heinrich et al. | |
| 8,211,125 B2 | 7/2012 | Spivey | 2005/0131436 A1 | 6/2005 | Johnston et al. | |
| 8,220,468 B2 | 7/2012 | Cooper et al. | 2005/0131437 A1 | 6/2005 | Johnston et al. | |
| 8,241,271 B2 | 8/2012 | Millman et al. | 2005/0131457 A1 | 6/2005 | Douglas et al. | |
| 8,245,898 B2 | 8/2012 | Smith et al. | 2005/0137454 A1 | 6/2005 | Saadat et al. | |
| 2002/0022836 A1 | 2/2002 | Goble et al. | 2005/0137455 A1 | 6/2005 | Ewers et al. | |
| 2002/0029036 A1 | 3/2002 | Goble et al. | 2005/0143759 A1 | 6/2005 | Kelly | |
| 2002/0117534 A1 | 8/2002 | Green et al. | 2005/0145671 A1 | 7/2005 | Viola | |
| 2002/0134811 A1 | 9/2002 | Napier et al. | 2005/0145675 A1 | 7/2005 | Hartwick et al. | |
| 2002/0165541 A1 | 11/2002 | Whitman | 2005/0154258 A1 | 7/2005 | Tartaglia et al. | |
| 2003/0093103 A1 | 5/2003 | Malackowski et al. | 2005/0165415 A1 | 7/2005 | Wales | |

| Pub. No. | Date | Inventor |
|---|---|---|
| 2005/0165419 A1 | 7/2005 | Sauer et al. |
| 2005/0165435 A1 | 7/2005 | Johnston et al. |
| 2005/0169974 A1* | 8/2005 | Tenerz et al. ................ 424/445 |
| 2005/0171522 A1 | 8/2005 | Christopherson |
| 2005/0173490 A1 | 8/2005 | Shelton, IV |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0230453 A1 | 10/2005 | Viola |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263562 A1 | 12/2005 | Shelton, IV et al. |
| 2005/0263563 A1 | 12/2005 | Racenet et al. |
| 2005/0267455 A1 | 12/2005 | Eggers et al. |
| 2005/0274768 A1* | 12/2005 | Cummins et al. ........ 227/175.1 |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0047308 A1 | 3/2006 | Ortiz et al. |
| 2006/0049229 A1 | 3/2006 | Milliman et al. |
| 2006/0052825 A1* | 3/2006 | Ransick et al. ................ 606/219 |
| 2006/0060630 A1 | 3/2006 | Shelton, IV et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0151567 A1 | 7/2006 | Roy |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0190028 A1 | 8/2006 | Wales et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0070574 A1 | 3/2007 | Nerheim et al. |
| 2007/0073340 A1 | 3/2007 | Shelton, IV et al. |
| 2007/0073341 A1 | 3/2007 | Smith |
| 2007/0075114 A1 | 4/2007 | Shelton, IV et al. |
| 2007/0078484 A1 | 4/2007 | Talarico et al. |
| 2007/0083193 A1 | 4/2007 | Werneth et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0246505 A1 | 10/2007 | Pace-Floridia et al. |
| 2007/0260278 A1 | 11/2007 | Wheeler et al. |
| 2007/0262116 A1 | 11/2007 | Hueil et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0295780 A1 | 12/2007 | Shelton et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |

| Pub. No. | Date | Inventor |
|---|---|---|
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0012704 A1 | 1/2010 | Tarinelli Racenet et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0186219 A1 | 7/2010 | Smith |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0312261 A1 | 12/2010 | Suzuki et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |

| | | |
|---|---|---|
| 2011/0121051 A1 | 5/2011 | Shelton, IV et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0022523 A1 | 1/2012 | Smith et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |

FOREIGN PATENT DOCUMENTS

| | | |
|---|---|---|
| CA | 2514274 A1 | 1/2006 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |

| | | | | | | | |
|---|---|---|---|---|---|---|---|
| EP | 0770355 | A1 | 5/1997 | EP | 1479345 | A1 | 11/2004 |
| EP | 0503662 | B1 | 6/1997 | EP | 1479347 | A1 | 11/2004 |
| EP | 0447121 | B1 | 7/1997 | EP | 1479348 | A1 | 11/2004 |
| EP | 0625077 | B1 | 7/1997 | EP | 0754437 | B2 | 12/2004 |
| EP | 0633749 | B1 | 8/1997 | EP | 1025807 | B1 | 12/2004 |
| EP | 0710090 | B1 | 8/1997 | EP | 1001710 | B1 | 1/2005 |
| EP | 0578425 | B1 | 9/1997 | EP | 1520521 | A1 | 4/2005 |
| EP | 0625335 | B1 | 11/1997 | EP | 1520523 | A1 | 4/2005 |
| EP | 0552423 | B1 | 1/1998 | EP | 1520525 | A1 | 4/2005 |
| EP | 0592244 | B1 | 1/1998 | EP | 1522264 | A1 | 4/2005 |
| EP | 0648476 | B1 | 1/1998 | EP | 1523942 | A2 | 4/2005 |
| EP | 0649290 | B1 | 3/1998 | EP | 1550408 | A1 | 7/2005 |
| EP | 0598618 | B1 | 9/1998 | EP | 1557129 | A1 | 7/2005 |
| EP | 0676173 | B1 | 9/1998 | EP | 1064883 | B1 | 8/2005 |
| EP | 0678007 | B1 | 9/1998 | EP | 1067876 | B1 | 8/2005 |
| EP | 0603472 | B1 | 11/1998 | EP | 0870473 | B1 | 9/2005 |
| EP | 0605351 | B1 | 11/1998 | EP | 1157666 | B1 | 9/2005 |
| EP | 0878169 | A1 | 11/1998 | EP | 0880338 | B1 | 10/2005 |
| EP | 0879742 | A1 | 11/1998 | EP | 1158917 | B1 | 11/2005 |
| EP | 0695144 | B1 | 12/1998 | EP | 1344498 | B1 | 11/2005 |
| EP | 0722296 | B1 | 12/1998 | EP | 1330989 | B1 | 12/2005 |
| EP | 0760230 | B1 | 2/1999 | EP | 0771176 | B2 | 1/2006 |
| EP | 0623316 | B1 | 3/1999 | EP | 1621138 | A2 | 2/2006 |
| EP | 0650701 | B1 | 3/1999 | EP | 1621139 | A2 | 2/2006 |
| EP | 0537572 | B1 | 6/1999 | EP | 1621141 | A2 | 2/2006 |
| EP | 0923907 | A1 | 6/1999 | EP | 1621145 | A2 | 2/2006 |
| EP | 0843906 | B1 | 3/2000 | EP | 1621151 | A2 | 2/2006 |
| EP | 0552050 | B1 | 5/2000 | EP | 1034746 | B1 | 3/2006 |
| EP | 0833592 | B1 | 5/2000 | EP | 1632191 | A2 | 3/2006 |
| EP | 0830094 | B1 | 9/2000 | EP | 1065981 | B1 | 5/2006 |
| EP | 1034747 | A1 | 9/2000 | EP | 1082944 | B1 | 5/2006 |
| EP | 1034748 | A1 | 9/2000 | EP | 1652481 | A2 | 5/2006 |
| EP | 0694290 | B1 | 11/2000 | EP | 1382303 | B1 | 6/2006 |
| EP | 1050278 | A1 | 11/2000 | EP | 1253866 | B1 | 7/2006 |
| EP | 1053719 | A1 | 11/2000 | EP | 1032318 | B1 | 8/2006 |
| EP | 1053720 | A1 | 11/2000 | EP | 1045672 | B1 | 8/2006 |
| EP | 1055399 | A1 | 11/2000 | EP | 1617768 | B1 | 8/2006 |
| EP | 1055400 | A1 | 11/2000 | EP | 1693015 | A2 | 8/2006 |
| EP | 1080694 | A1 | 3/2001 | EP | 1400214 | B1 | 9/2006 |
| EP | 1090592 | A1 | 4/2001 | EP | 1702567 | A2 | 9/2006 |
| EP | 1095627 | A1 | 5/2001 | EP | 1129665 | B1 | 11/2006 |
| EP | 1256318 | B1 | 5/2001 | EP | 1400206 | B1 | 11/2006 |
| EP | 0806914 | B1 | 9/2001 | EP | 1721568 | A1 | 11/2006 |
| EP | 0768840 | B1 | 12/2001 | EP | 1256317 | B1 | 12/2006 |
| EP | 0908152 | B1 | 1/2002 | EP | 1285633 | B1 | 12/2006 |
| EP | 0872213 | B1 | 5/2002 | EP | 1728473 | A1 | 12/2006 |
| EP | 0862386 | B1 | 6/2002 | EP | 1728475 | A2 | 12/2006 |
| EP | 0949886 | B1 | 9/2002 | EP | 1479346 | B1 | 1/2007 |
| EP | 1238634 | A2 | 9/2002 | EP | 1484024 | B1 | 1/2007 |
| EP | 0858295 | B1 | 12/2002 | EP | 1754445 | A2 | 2/2007 |
| EP | 0656188 | 61 | 1/2003 | EP | 1759812 | A1 | 3/2007 |
| EP | 1284120 | A1 | 2/2003 | EP | 1767163 | A1 | 3/2007 |
| EP | 1287788 | A1 | 3/2003 | EP | 1769756 | A1 | 4/2007 |
| EP | 0717966 | B1 | 4/2003 | EP | 1769758 | A1 | 4/2007 |
| EP | 0869742 | B1 | 5/2003 | EP | 1581128 | B1 | 5/2007 |
| EP | 0829235 | B1 | 6/2003 | EP | 1785097 | A2 | 5/2007 |
| EP | 0887046 | B1 | 7/2003 | EP | 1790293 | A2 | 5/2007 |
| EP | 0852480 | B1 | 8/2003 | EP | 1800610 | A1 | 6/2007 |
| EP | 0891154 | B1 | 9/2003 | EP | 1300117 | B1 | 8/2007 |
| EP | 0813843 | B1 | 10/2003 | EP | 1813199 | A1 | 8/2007 |
| EP | 0873089 | B1 | 10/2003 | EP | 1813201 | A1 | 8/2007 |
| EP | 0856326 | B1 | 11/2003 | EP | 1813203 | A1 | 8/2007 |
| EP | 1374788 | A1 | 1/2004 | EP | 1813207 | A1 | 8/2007 |
| EP | 0741996 | B1 | 2/2004 | EP | 1813209 | A1 | 8/2007 |
| EP | 0814712 | B1 | 2/2004 | EP | 1487359 | B1 | 10/2007 |
| EP | 1402837 | A1 | 3/2004 | EP | 1599146 | B1 | 10/2007 |
| EP | 0705570 | B1 | 4/2004 | EP | 1839596 | A1 | 10/2007 |
| EP | 0959784 | B1 | 4/2004 | EP | 1402821 | B1 | 12/2007 |
| EP | 1407719 | A2 | 4/2004 | EP | 1872727 | A1 | 1/2008 |
| EP | 1086713 | B1 | 5/2004 | EP | 1897502 | A1 | 3/2008 |
| EP | 0996378 | B1 | 6/2004 | EP | 1330201 | B1 | 6/2008 |
| EP | 1426012 | A1 | 6/2004 | EP | 1702568 | B1 | 7/2008 |
| EP | 0833593 | B2 | 7/2004 | EP | 1943957 | A2 | 7/2008 |
| EP | 1442694 | A1 | 8/2004 | EP | 1943976 | A2 | 7/2008 |
| EP | 0888749 | B1 | 9/2004 | EP | 1593337 | B1 | 8/2008 |
| EP | 0959786 | B1 | 9/2004 | EP | 1970014 | A1 | 9/2008 |
| EP | 1459695 | A1 | 9/2004 | EP | 1980213 | A2 | 10/2008 |
| EP | 1473819 | A1 | 11/2004 | EP | 1759645 | B1 | 11/2008 |
| EP | 1477119 | A1 | 11/2004 | EP | 1990014 | A2 | 11/2008 |

| | | | | | | |
|---|---|---|---|---|---|---|
| EP | 1693008 B1 | 12/2008 | | WO | WO 92/20295 A1 | 11/1992 |
| EP | 1759640 B1 | 12/2008 | | WO | WO 92/21300 A1 | 12/1992 |
| EP | 2000102 A2 | 12/2008 | | WO | WO 93/08755 A1 | 5/1993 |
| EP | 1736104 B1 | 3/2009 | | WO | WO 93/13718 A1 | 7/1993 |
| EP | 1749486 B1 | 3/2009 | | WO | WO 93/14690 A1 | 8/1993 |
| EP | 2039316 A2 | 3/2009 | | WO | WO 93/15648 A1 | 8/1993 |
| EP | 1721576 B1 | 4/2009 | | WO | WO 93/15850 A1 | 8/1993 |
| EP | 1733686 B1 | 4/2009 | | WO | WO 93/19681 A1 | 10/1993 |
| EP | 2044890 A1 | 4/2009 | | WO | WO 94/00060 A1 | 1/1994 |
| EP | 1550413 B1 | 6/2009 | | WO | WO 94/11057 A1 | 5/1994 |
| EP | 1745748 B1 | 8/2009 | | WO | WO 94/12108 A1 | 6/1994 |
| EP | 2090256 A2 | 8/2009 | | WO | WO 94/18893 A1 | 9/1994 |
| EP | 1813208 B1 | 11/2009 | | WO | WO 94/22378 A1 | 10/1994 |
| EP | 1607050 B1 | 12/2009 | | WO | WO 94/23659 A1 | 10/1994 |
| EP | 1566150 B1 | 4/2010 | | WO | WO 95/02369 A1 | 1/1995 |
| EP | 1813206 B1 | 4/2010 | | WO | WO 95/03743 A1 | 2/1995 |
| EP | 1769754 B1 | 6/2010 | | WO | WO 95/06817 A1 | 3/1995 |
| EP | 1535565 B1 | 10/2010 | | WO | WO 95/09576 A1 | 4/1995 |
| EP | 1702570 B1 | 10/2010 | | WO | WO 95/09577 A1 | 4/1995 |
| EP | 1785098 B1 | 10/2010 | | WO | WO 95/14436 A1 | 6/1995 |
| EP | 1627605 B1 | 12/2010 | | WO | WO 95/17855 A1 | 7/1995 |
| EP | 1813205 B1 | 6/2011 | | WO | WO 95/18383 A1 | 7/1995 |
| EP | 1785102 B1 | 1/2012 | | WO | WO 95/18572 A1 | 7/1995 |
| FR | 999646 A | 2/1952 | | WO | WO 95/19739 A1 | 7/1995 |
| FR | 1112936 A | 3/1956 | | WO | WO 95/20360 A1 | 8/1995 |
| FR | 2765794 A | 1/1999 | | WO | WO 95/23557 A1 | 9/1995 |
| GB | 939929 A | 10/1963 | | WO | WO 95/24865 A1 | 9/1995 |
| GB | 1210522 A | 10/1970 | | WO | WO 95/25471 A3 | 9/1995 |
| GB | 1217159 A | 12/1970 | | WO | WO 95/26562 A1 | 10/1995 |
| GB | 1339394 A | 12/1973 | | WO | WO 95/29639 A1 | 11/1995 |
| GB | 2109241 A | 6/1983 | | WO | WO 96/04858 A1 | 2/1996 |
| GB | 2272159 A | 5/1994 | | WO | WO 96/19151 A1 | 6/1996 |
| GB | 2284242 A | 5/1995 | | WO | WO 96/19152 A1 | 6/1996 |
| GB | 2336214 A | 10/1999 | | WO | WO 96/20652 A1 | 7/1996 |
| GB | 2425903 A | 11/2006 | | WO | WO 96/21119 A1 | 7/1996 |
| JP | S 58500053 A | 1/1983 | | WO | WO 96/22055 A1 | 7/1996 |
| JP | 61-98249 A | 5/1986 | | WO | WO 96/23448 A1 | 8/1996 |
| JP | 63-203149 | 8/1988 | | WO | WO 96/24301 A1 | 8/1996 |
| JP | 3-12126 A | 1/1991 | | WO | WO 96/27337 A1 | 9/1996 |
| JP | 5-212039 A | 8/1993 | | WO | WO 96/31155 A1 | 10/1996 |
| JP | 6007357 A | 1/1994 | | WO | WO 96/35464 A1 | 11/1996 |
| JP | 7051273 A | 2/1995 | | WO | WO 96/39085 A1 | 12/1996 |
| JP | 8033641 A | 2/1996 | | WO | WO 96/39086 A1 | 12/1996 |
| JP | 8229050 A | 9/1996 | | WO | WO 96/39087 A1 | 12/1996 |
| JP | 2000033071 A | 2/2000 | | WO | WO 96/39088 A1 | 12/1996 |
| JP | 2000171730 A | 6/2000 | | WO | WO 96/39089 A1 | 12/1996 |
| JP | 2000287987 A | 10/2000 | | WO | WO 97/00646 A1 | 1/1997 |
| JP | 2000325303 A | 11/2000 | | WO | WO 97/00647 A1 | 1/1997 |
| JP | 2001-514541 A | 9/2001 | | WO | WO 97/06582 A1 | 2/1997 |
| JP | 2001286477 A | 10/2001 | | WO | WO 97/10763 A1 | 3/1997 |
| JP | 2002143078 A | 5/2002 | | WO | WO 97/10764 A1 | 3/1997 |
| JP | 2002369820 A | 12/2002 | | WO | WO 97/11648 A2 | 4/1997 |
| JP | 2004-344663 | 12/2004 | | WO | WO 97/11649 A1 | 4/1997 |
| JP | 2005-028149 A | 2/2005 | | WO | WO 97/15237 A1 | 5/1997 |
| JP | 2005505322 T | 2/2005 | | WO | WO 97/24073 A1 | 7/1997 |
| JP | 2005103293 A | 4/2005 | | WO | WO 97/24993 A1 | 7/1997 |
| JP | 2005131163 A | 5/2005 | | WO | WO 97/30644 A1 | 8/1997 |
| JP | 2005131164 A | 5/2005 | | WO | WO 97/34533 A1 | 9/1997 |
| JP | 2005131173 A | 5/2005 | | WO | WO 97/37598 A1 | 10/1997 |
| JP | 2005131211 A | 5/2005 | | WO | WO 97/39688 A2 | 10/1997 |
| JP | 2005131212 A | 5/2005 | | WO | WO 98/17180 A1 | 4/1998 |
| JP | 2005137423 A | 6/2005 | | WO | WO 98/27880 A1 | 7/1998 |
| JP | 2005152416 A | 6/2005 | | WO | WO 98/30153 A1 | 7/1998 |
| JP | 2005-523105 A | 8/2005 | | WO | WO 98/47436 A1 | 10/1998 |
| JP | 2005524474 A | 8/2005 | | WO | WO 99/03407 A1 | 1/1999 |
| JP | 2006-281405 A | 10/2006 | | WO | WO 99/03408 A1 | 1/1999 |
| RU | 2008830 C1 | 3/1994 | | WO | WO 99/03409 A1 | 1/1999 |
| RU | 2187249 C2 | 8/2002 | | WO | WO 99/12483 A1 | 3/1999 |
| RU | 2225170 C2 | 3/2004 | | WO | WO 99/12487 A1 | 3/1999 |
| SU | 189517 A | 1/1967 | | WO | WO 99/12488 A1 | 3/1999 |
| SU | 328636 A | 9/1972 | | WO | WO 99/15086 A1 | 4/1999 |
| SU | 886900 A1 | 12/1981 | | WO | WO 99/15091 A1 | 4/1999 |
| SU | 1009439 A | 4/1983 | | WO | WO 99/23933 A2 | 5/1999 |
| SU | 1333319 A2 | 8/1987 | | WO | WO 99/23959 A1 | 5/1999 |
| SU | 1377053 | 2/1988 | | WO | WO 99/25261 A1 | 5/1999 |
| SU | 1561964 A1 | 5/1990 | | WO | WO 99/29244 A1 | 6/1999 |
| SU | 1722476 A1 | 3/1992 | | WO | WO 99/34744 A1 | 7/1999 |
| WO | WO 82/02824 A1 | 9/1982 | | WO | WO 99/45849 A1 | 9/1999 |
| WO | WO 91/15157 A1 | 10/1991 | | WO | WO 99/48430 A1 | 9/1999 |

| | | | |
|---|---|---|---|
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/043571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A1 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |
| WO | WO 2008/109125 A1 | 9/2008 |
| WO | WO 2010/063795 A1 | 6/2010 |

OTHER PUBLICATIONS

U.S. Appl. No. 11/529,879, filed Sep. 29, 2006.
U.S. Appl. No. 11/541,050, filed Sep. 29, 2006.
U.S. Appl. No. 11/541,151, filed Sep. 29, 2006.
U.S. Appl. No. 11/529,904, filed Sep. 29, 2006.
U.S. Appl. No. 11/529,935, filed Sep. 29, 2006.
U.S. Appl. No. 11/541,123, filed Sep. 29, 2006.
U.S. Appl. No. 11/541,182, filed Sep. 29, 2006.
U.S. Appl. No. 11/541,098, filed Sep. 29, 2006.
U.S. Appl. No. 11/475,412, filed Jun. 27, 2006.
U.S. Appl. No. 11/497,898, filed Aug. 2, 2006.
Office Action issued on Jun. 28, 2007 in U.S. Appl. No. 11/541,050.
Office Action issued on Jun. 29, 2007 in U.S. Appl. No. 11/529,935.
Office Action issued on Jun. 28, 2007 in U.S. Appl. No. 11/541,098.
Office Action issued on Sep. 27, 2006 in U.S. Appl. No. 11/231,456.
Office Action issued on Sep. 19, 2007 in U.S. Appl. No. 11/541,151.
Office Action issued on Sep. 20, 2007 in U.S. Appl. No. 11/529,879.
International Search Report for PCT/US2007/017586, Jan. 25, 2008 (6 pages).
Disclosed Anonymously, "Motor-Driven Surgical Stapler Improvements," Research Disclosure Database No. 526041, Published: Feb. 2008.

U.S. Appl. No. 11/824,299, filed Jun. 29, 2007.

U.S. Appl. No. 11/824,136, filed Jun. 29, 2007.

U.S. Appl. No. 11/824,363, filed Jun. 29, 2007.

European Examination Report, Application 08770620.6, dated Jun. 4, 2010 (4 pages).

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Written Opinion for PCT/US2007/017586, Jan. 25, 2008 (6 pages).

U.S. Appl. No. 13/488,903, filed Jun. 5, 2012.

U.S. Appl. No. 13/310,107, filed Dec. 2, 2011.

U.S. Appl. No. 13/369,629, filed Feb. 9, 2012.

\* cited by examiner

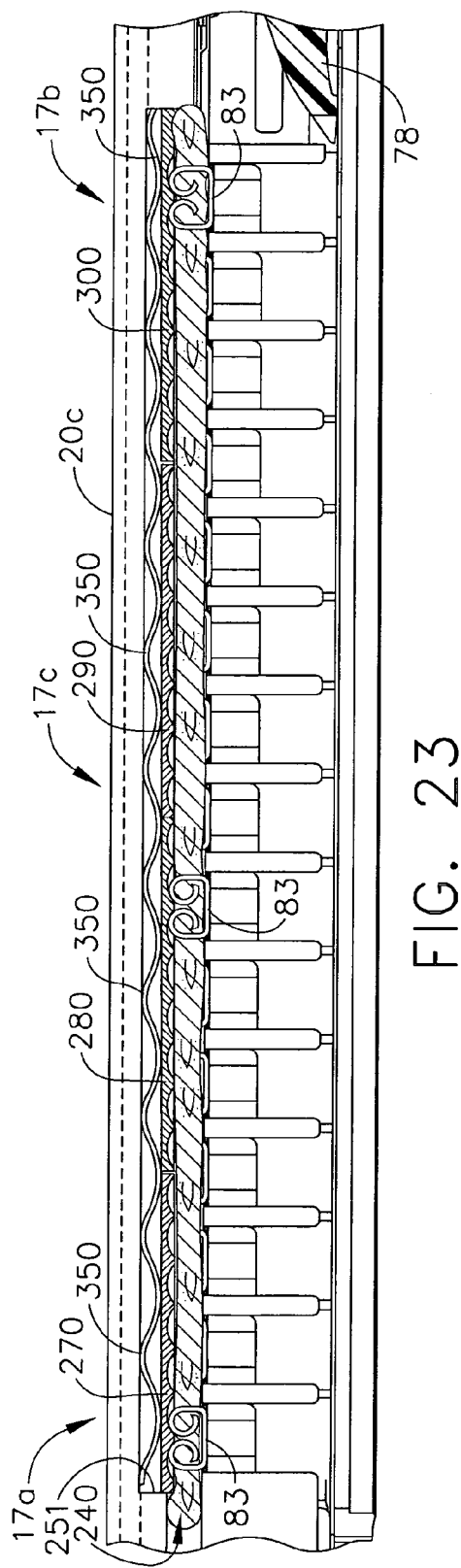
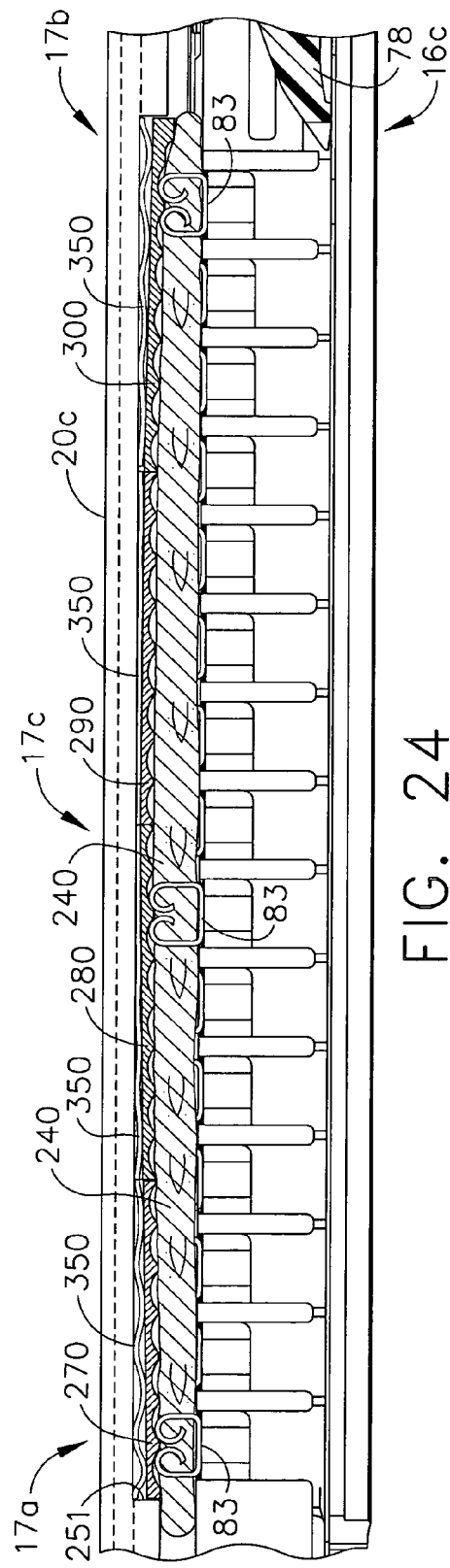
FIG. 23
FIG. 24

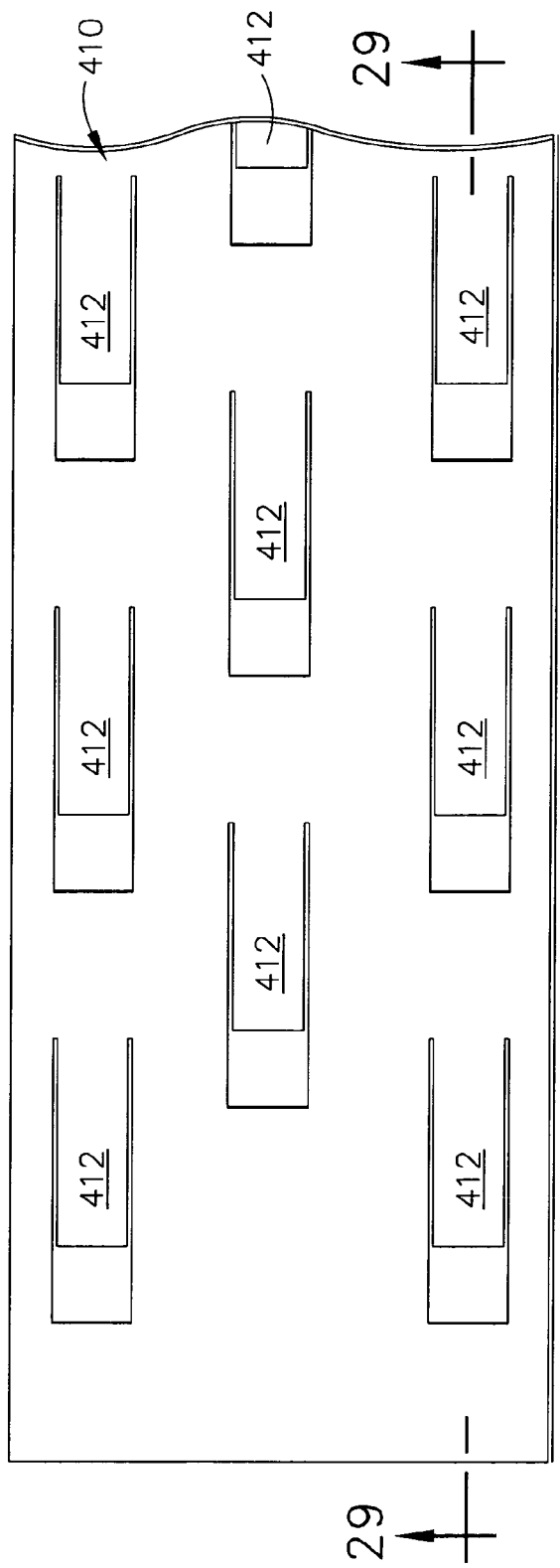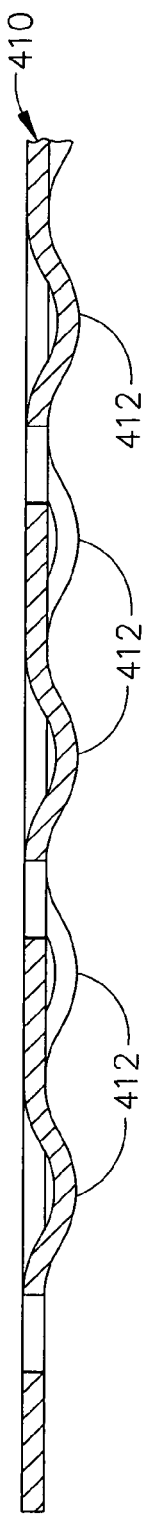
FIG. 28
FIG. 29

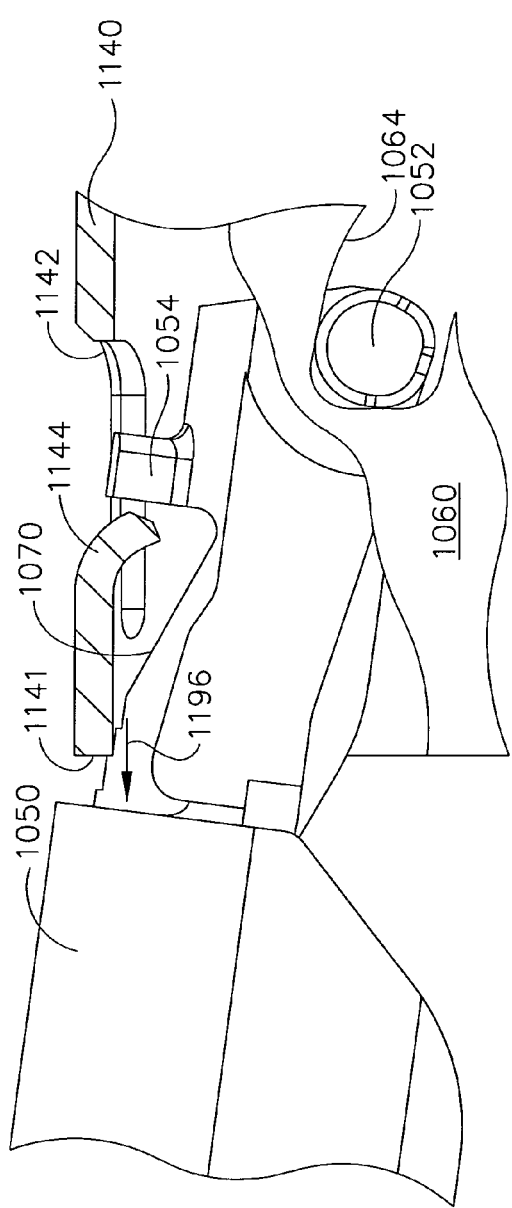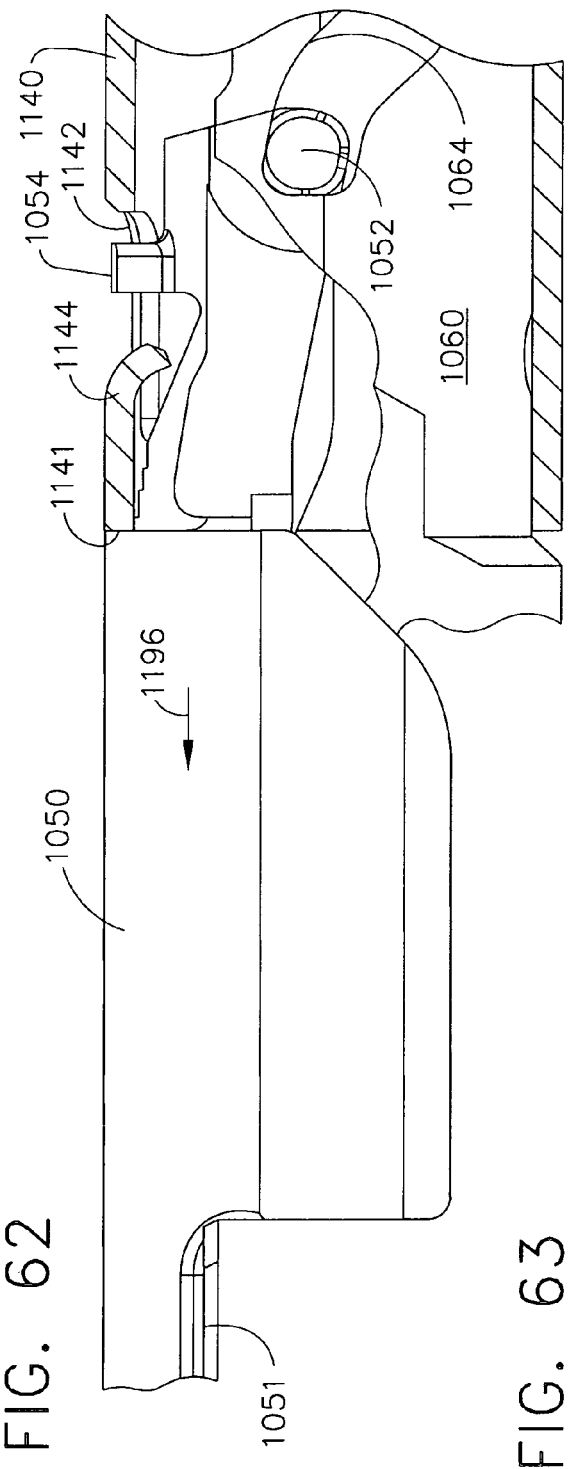
FIG. 62
FIG. 63

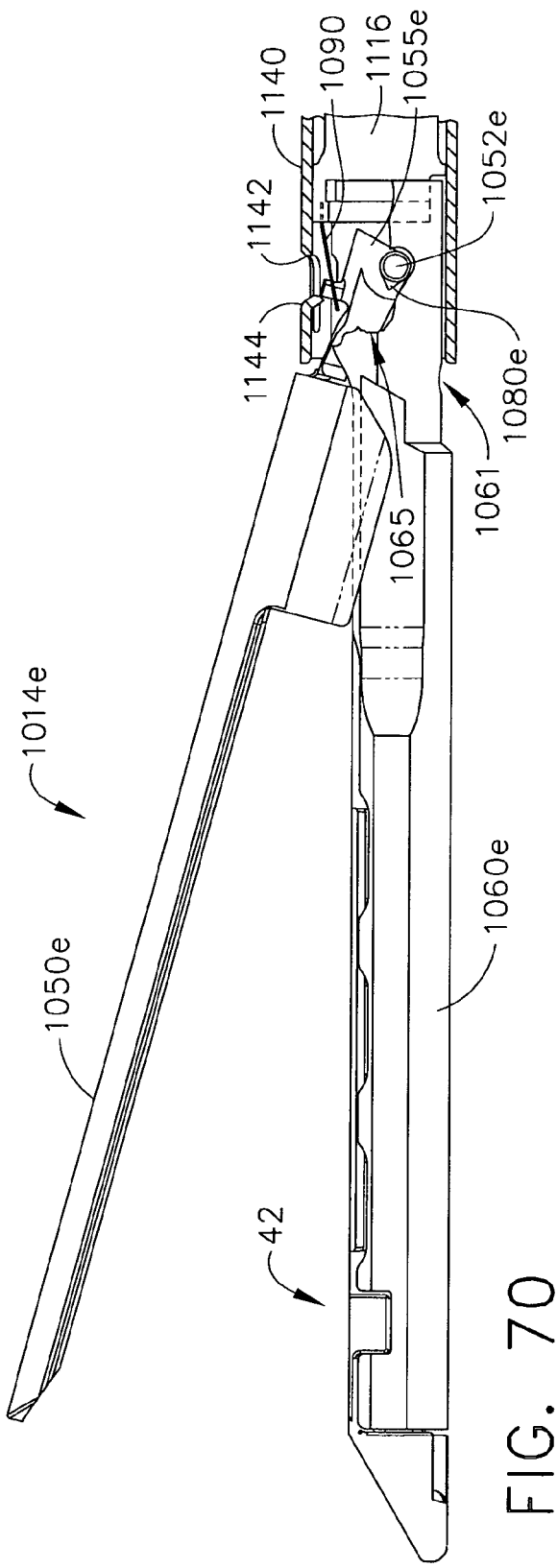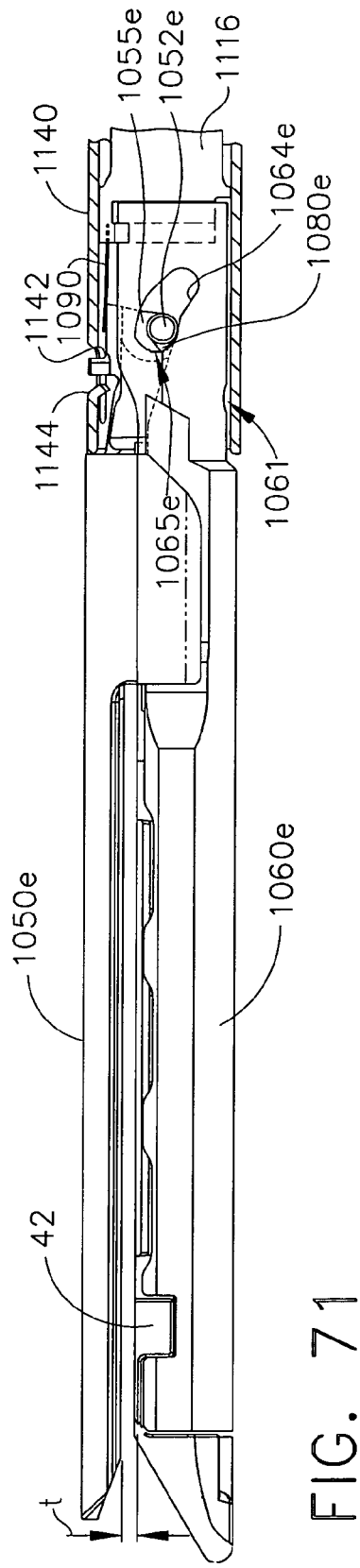
FIG. 70
FIG. 71

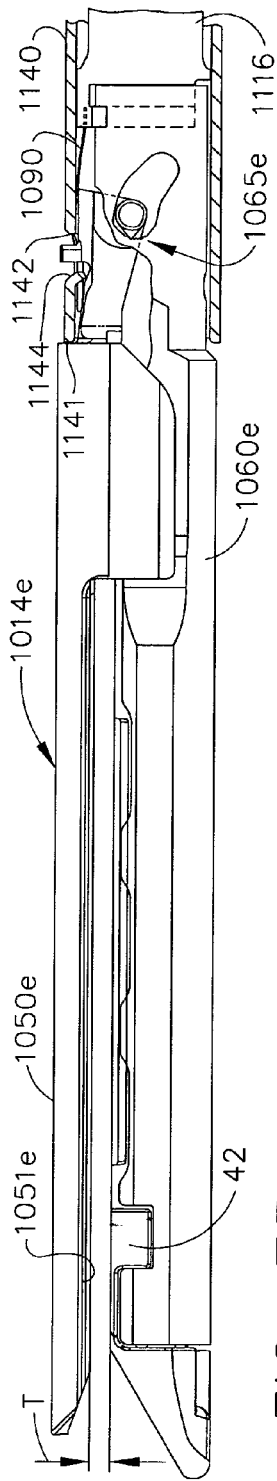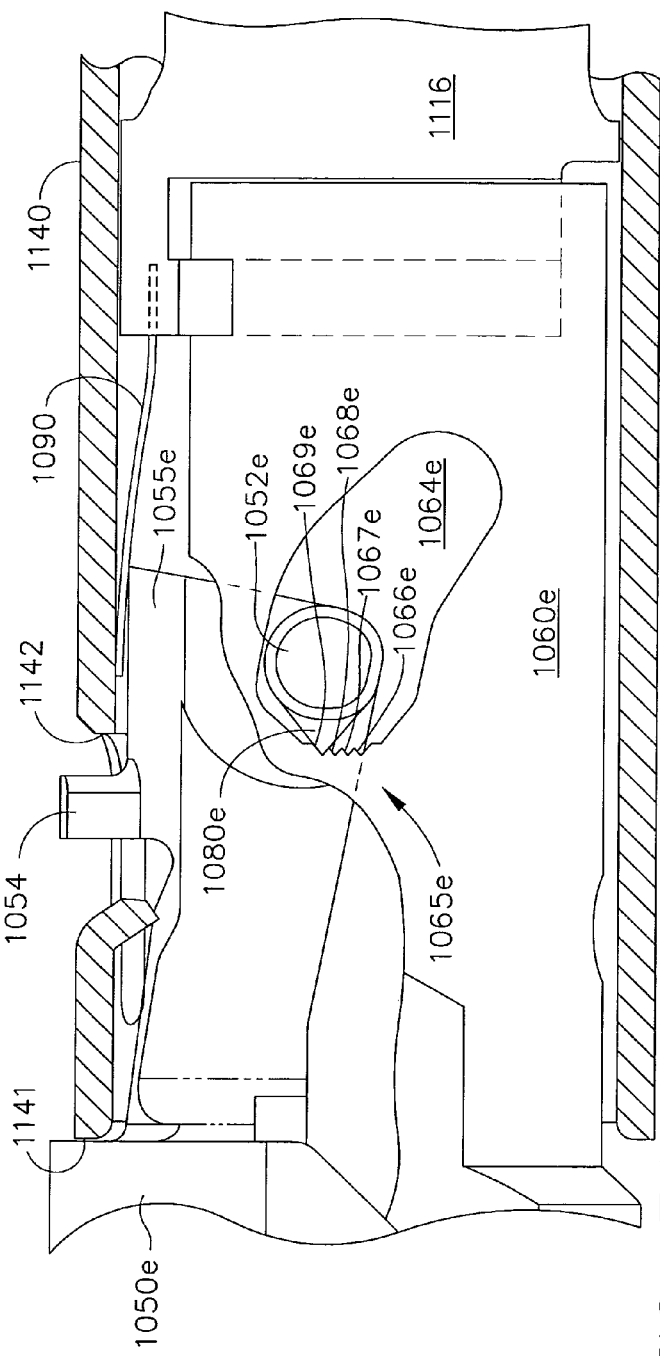

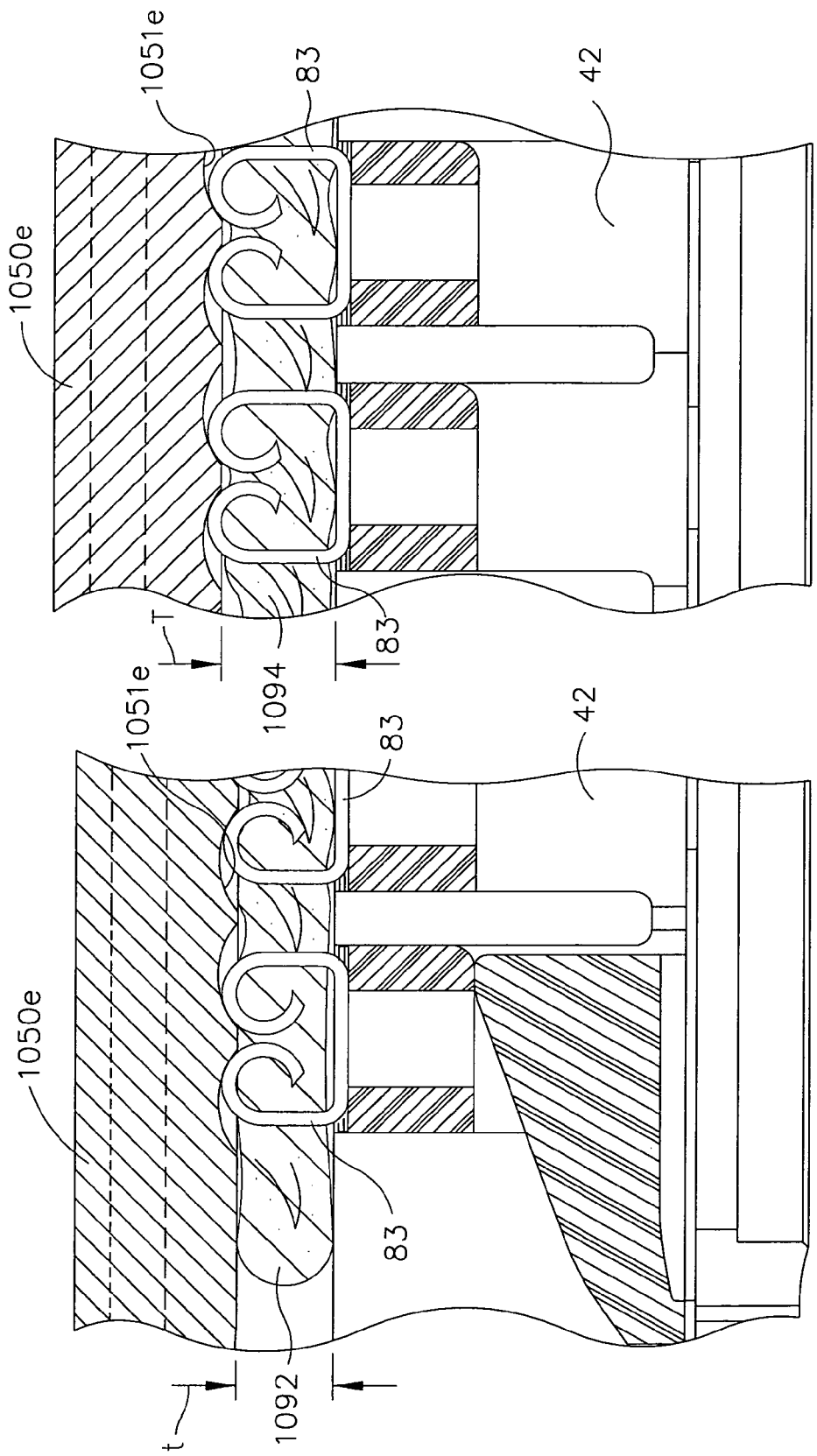

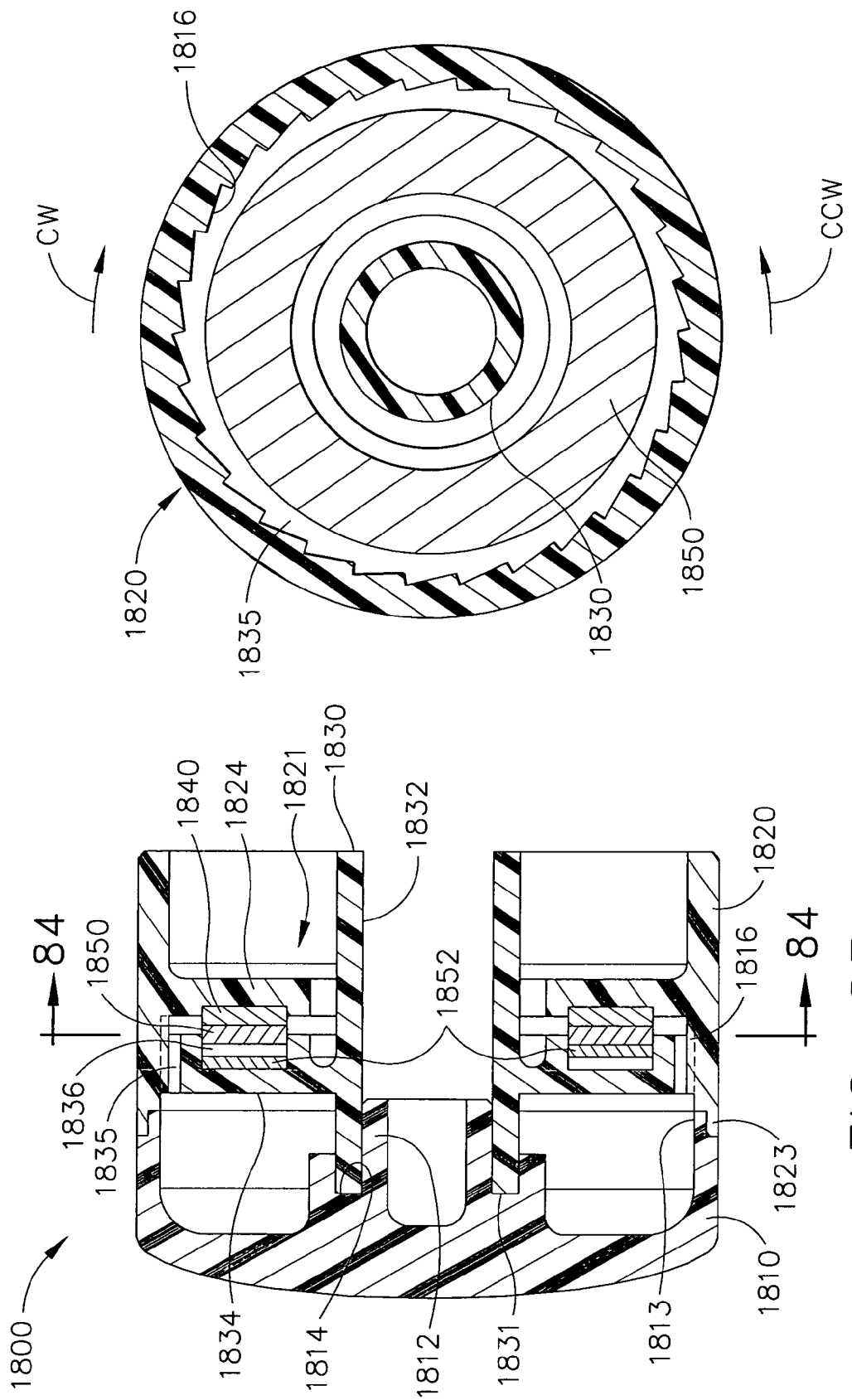

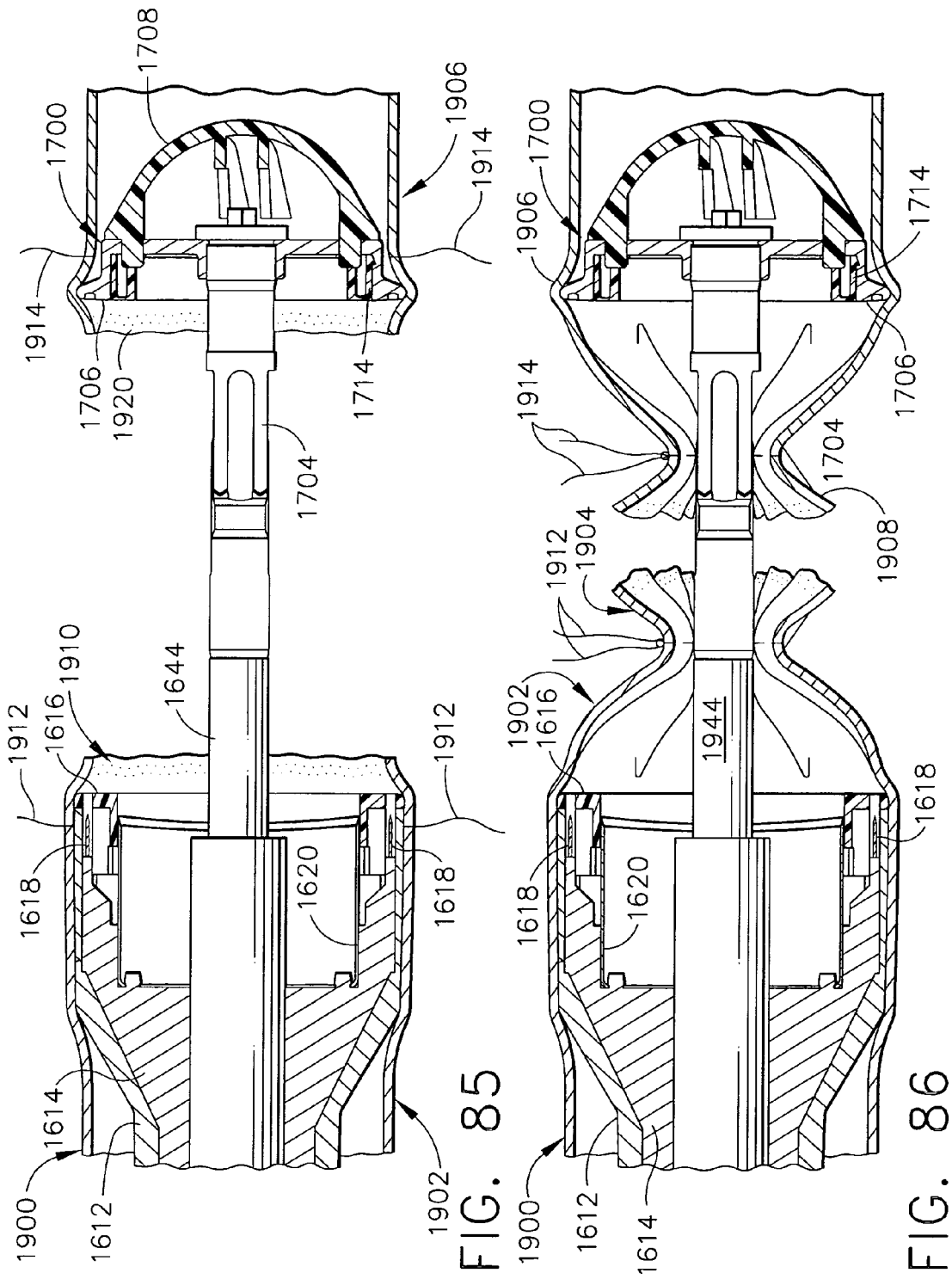

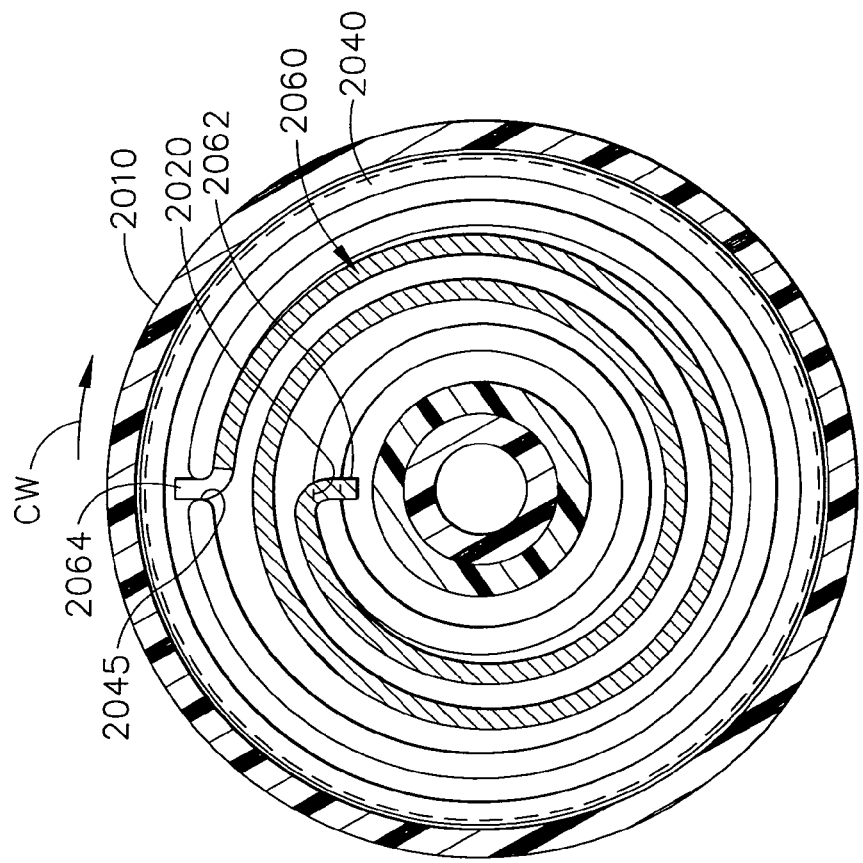
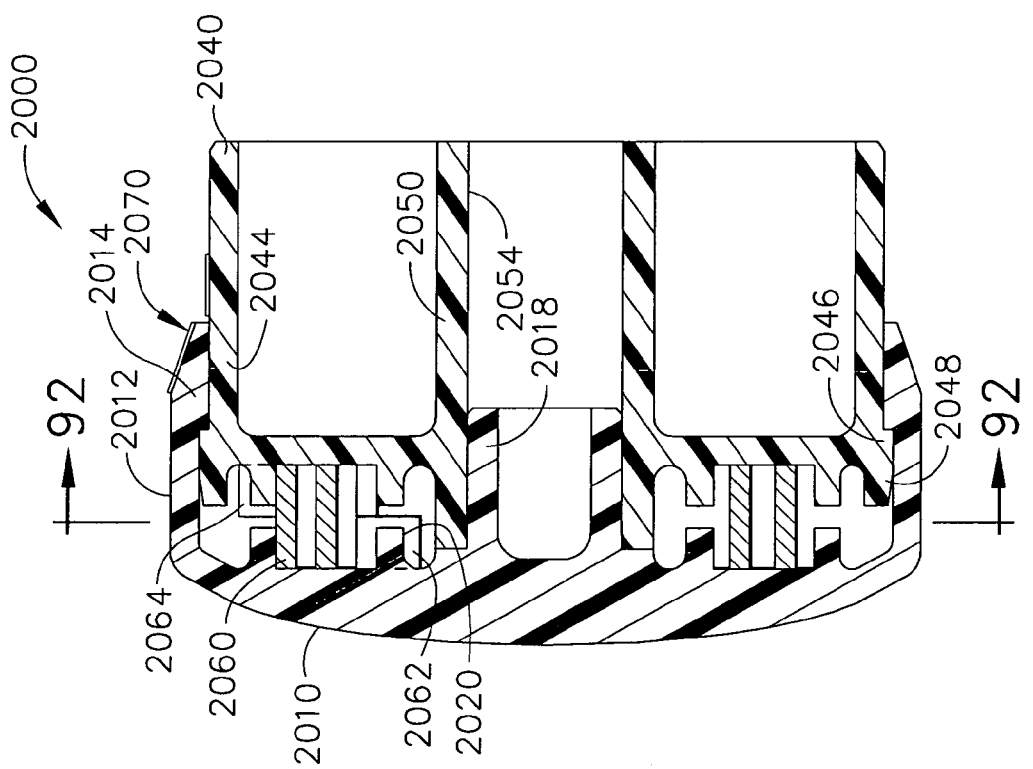

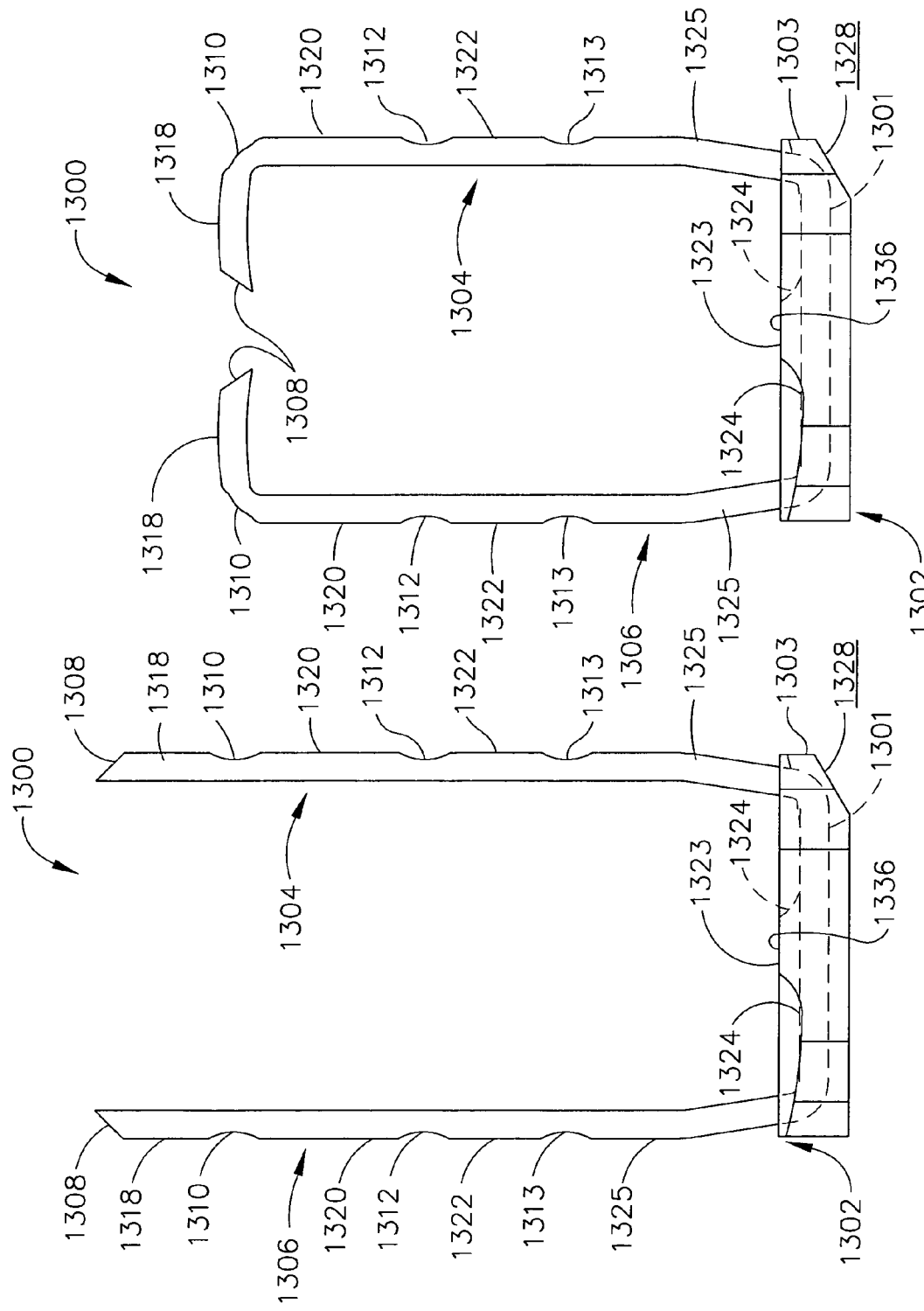

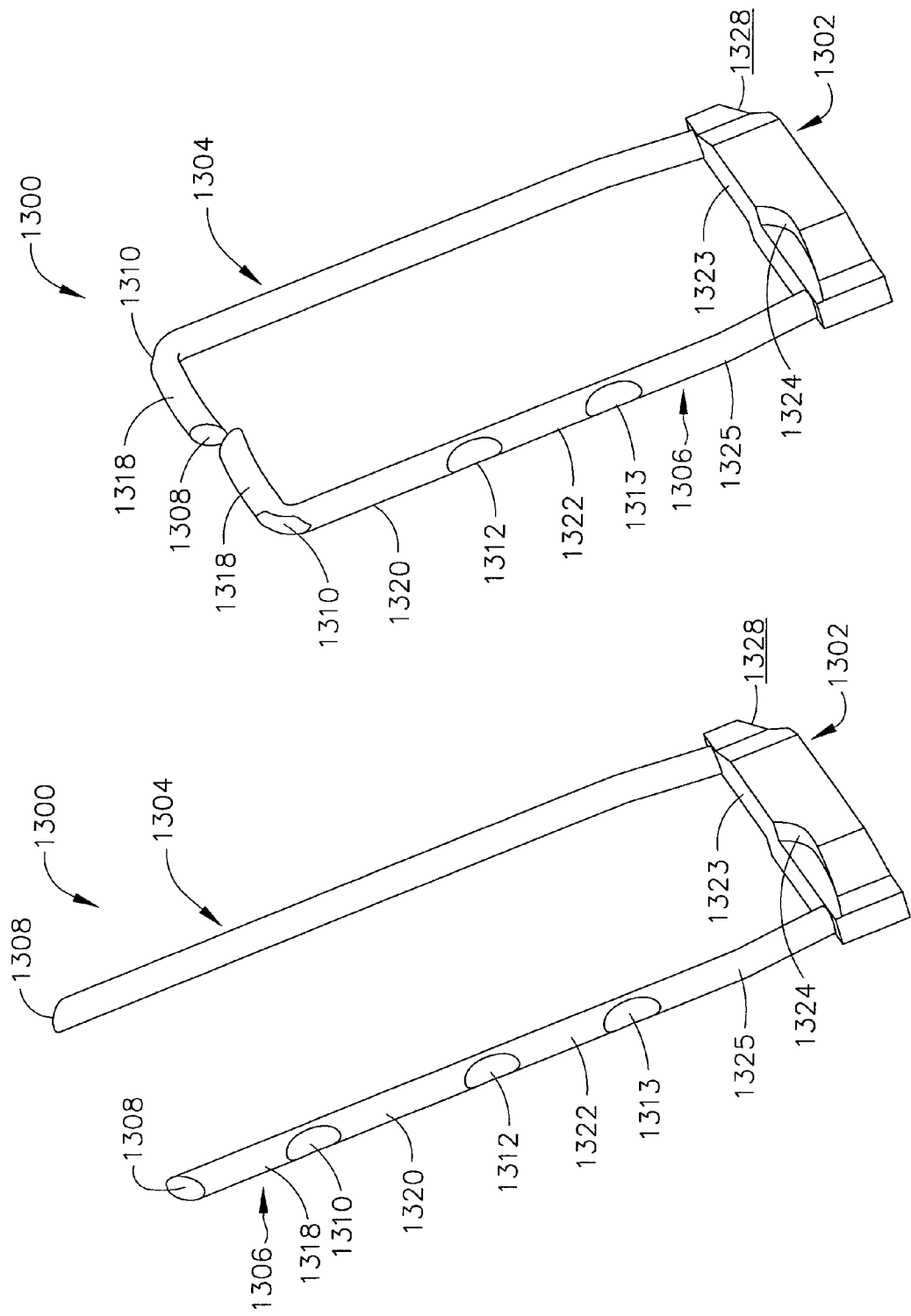

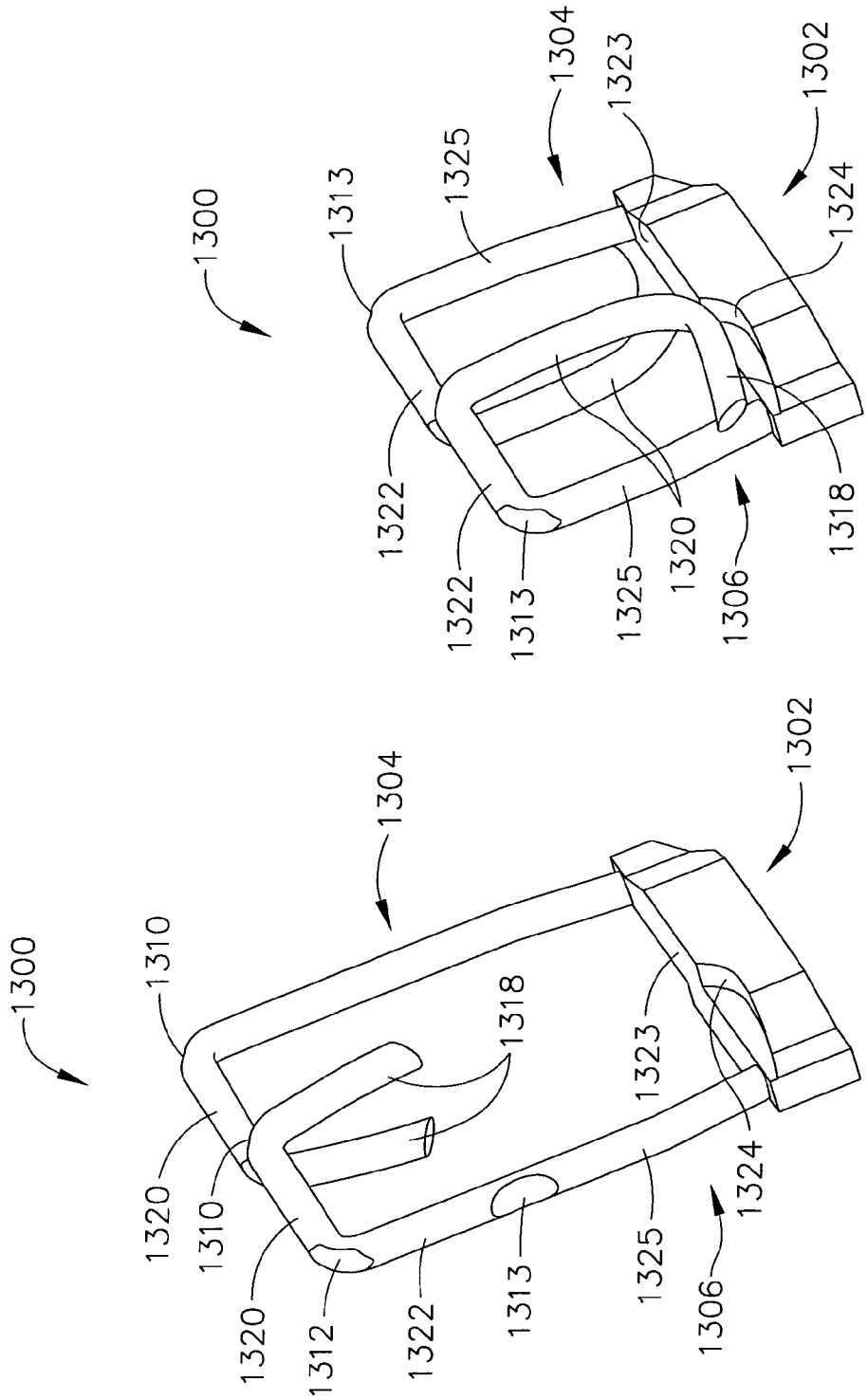

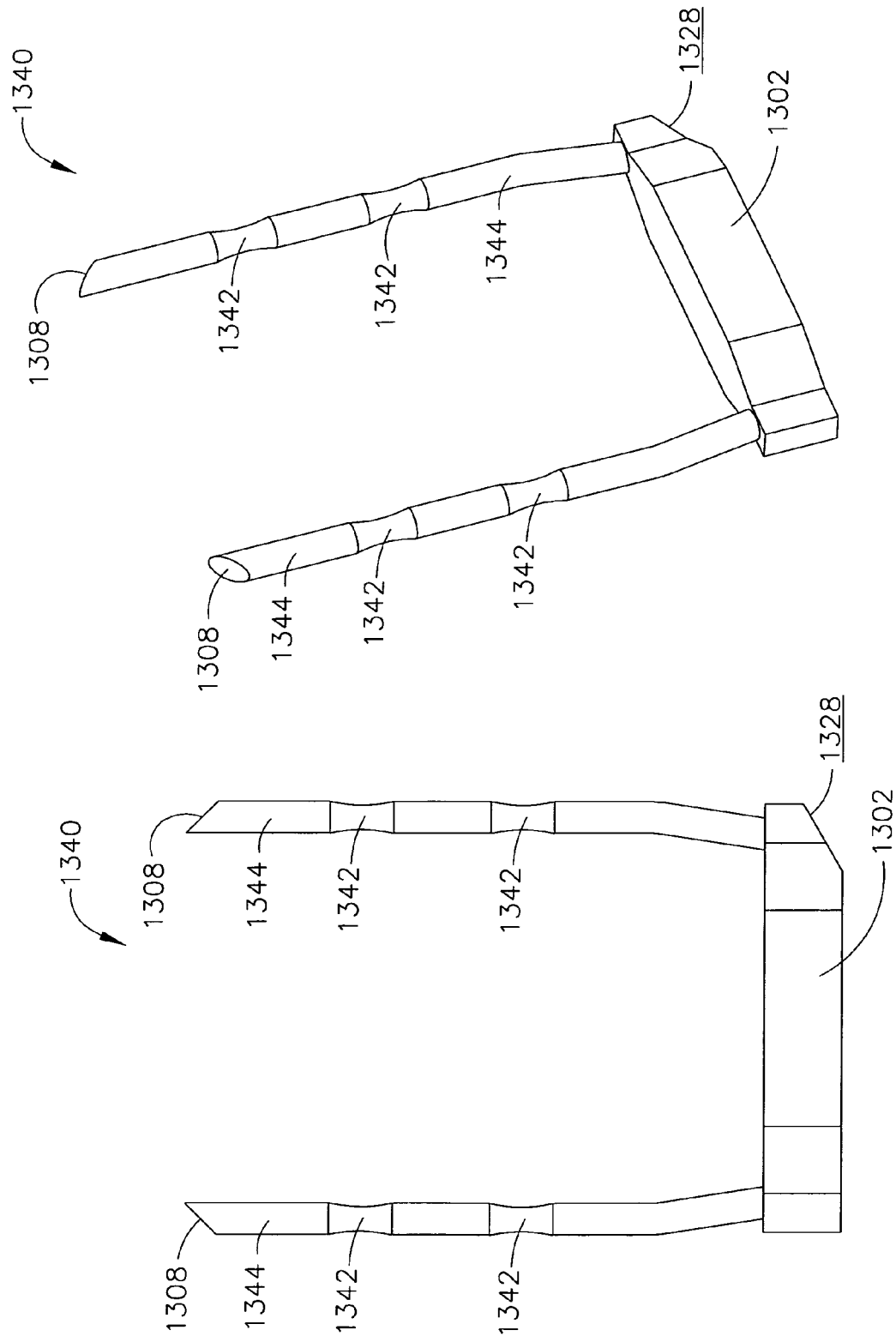

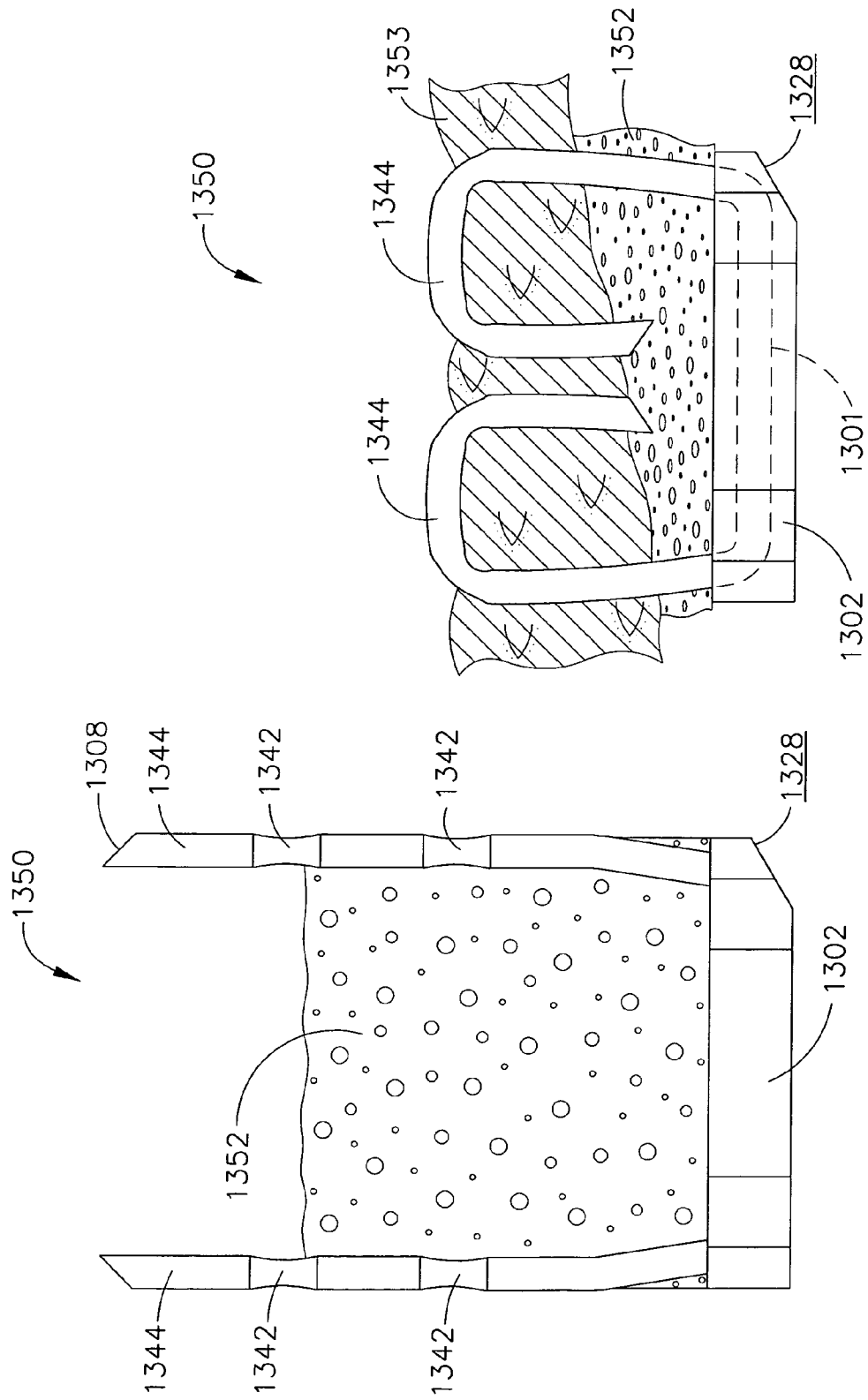

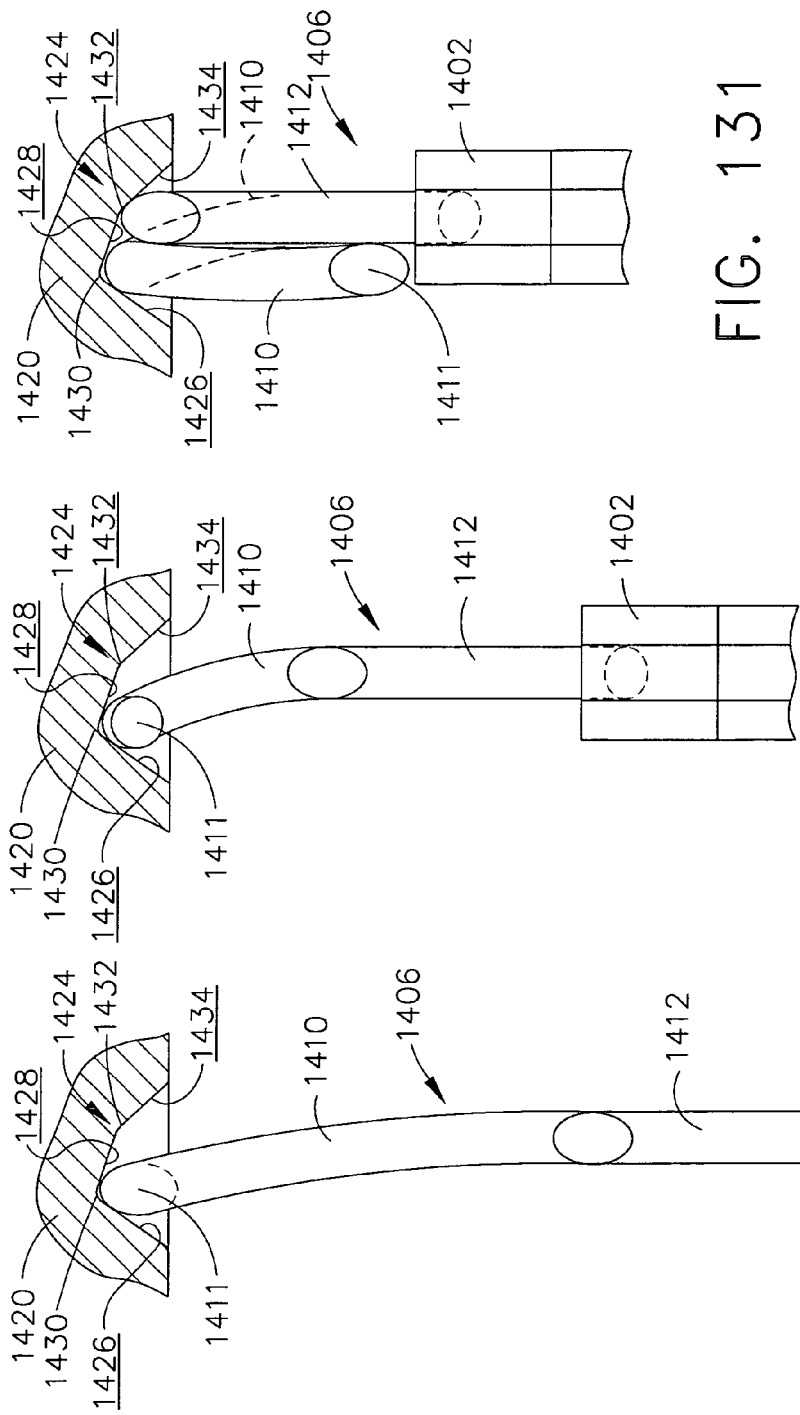

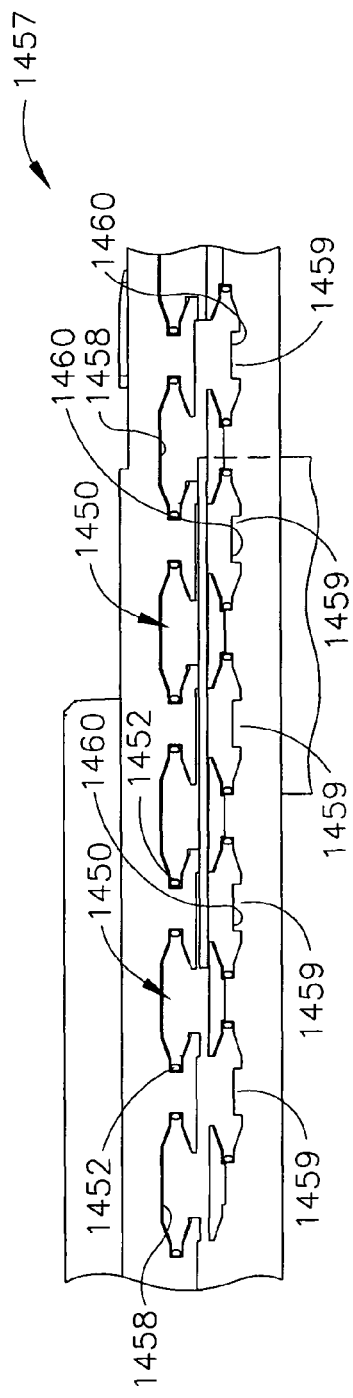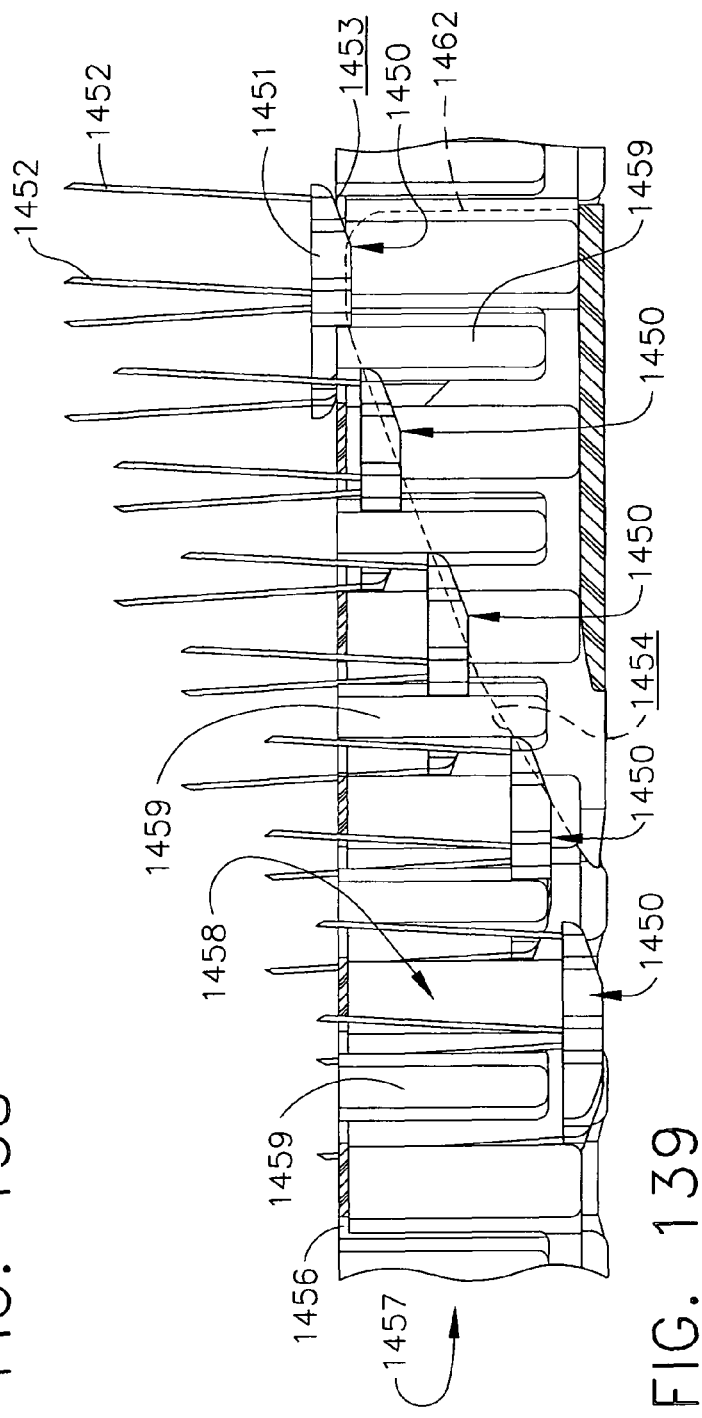
FIG. 138
FIG. 139

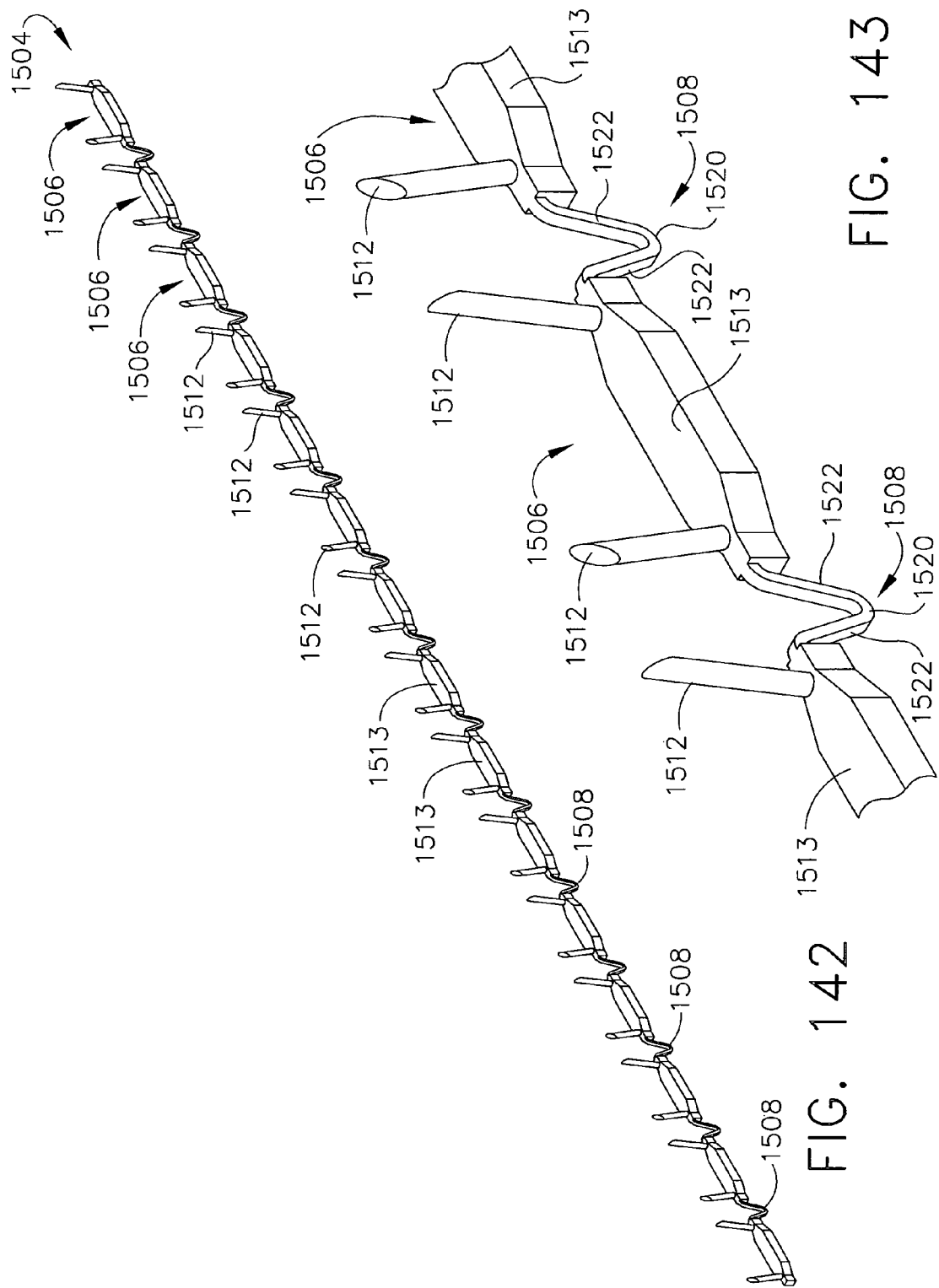

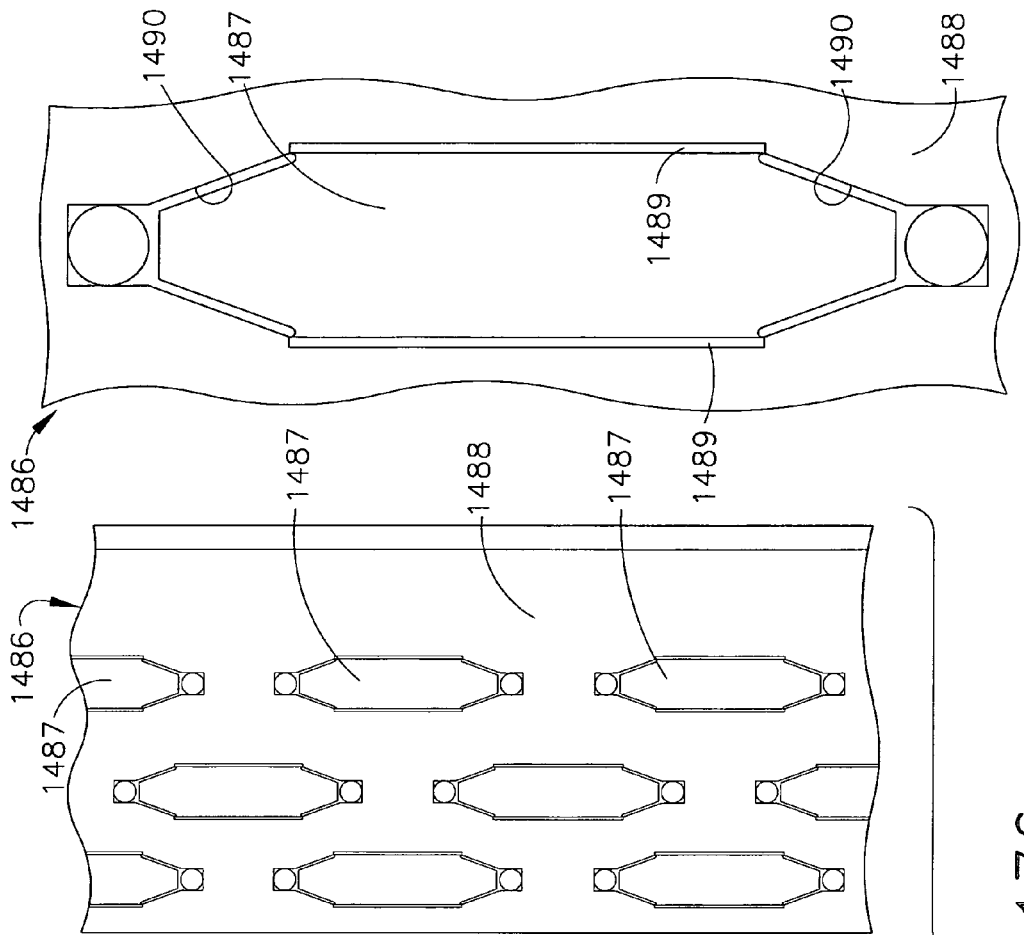
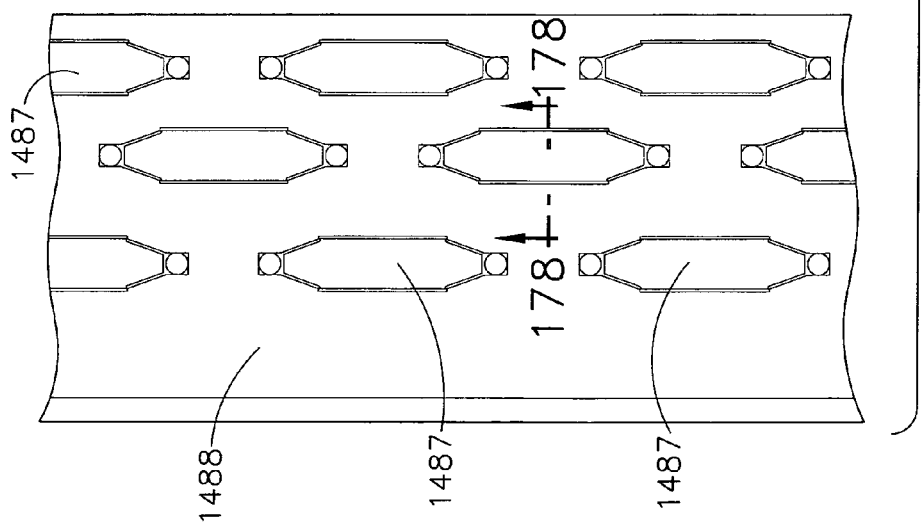
FIG. 176
FIG. 177

SURGICAL STAPLES HAVING DISSOLVABLE, BIOABSORBABLE OR BIOFRAGMENTABLE PORTIONS AND STAPLING INSTRUMENTS FOR DEPLOYING THE SAME

CROSS REFERENCE TO RELATED APPLICATIONS

The subject application is related to eleven and commonly-owned applications filed on even date herewith, the disclosure of each is hereby incorporated by reference in their entirety, these eleven applications being respectively entitled:

(1) U.S. patent application Ser. No. 11/540,735, now U.S. Pat. No. 7,467,740, entitled Surgical Stapling Instruments Having Flexible Channel and Anvil Features For Adjustable Staple Heights to Frederick E. Shelton, IV, Jerome R. Morgan, Michael A. Murray, Richard W. Timm, James T. Spivey, James W. Voegele, Leslie M. Fugikawa, and Eugene L. Timperman;

(2) U.S. patent application Ser. No. 11/540,734, now U.S. Pat. No. 7,472,815, entitled Surgical Stapling Instruments With Collapsible Features For Controlling Staple Height to Frederick E. Shelton, IV, Jeffrey S. Swayze, Leslie M. Fugikawa, and Eugene L. Timperman;

(3) U.S. patent application Ser. No. 11/541,050, now U.S. Publication No. 2008/0078804, entitled Surgical Cutting and Stapling Instrument With Self Adjusting Anvil to Frederick E. Shelton, IV and Joshua Uth;

(4) U.S. patent application Ser. No. 11/541,151, now U.S. Pat. No. 7,665,647, entitled Surgical Cutting and Stapling Device With Closure Apparatus For Limiting Maximum Tissue Compression Force to Frederick E. Shelton, IV and Jeffrey S. Swayze;

(5) U.S. patent application Ser. No. 11/541,164, now U.S. Pat. No. 7,506,791, entitled Surgical Stapling Instrument With Mechanical Mechanism For Limiting Maximum Tissue Compression to Todd Phillip Omaits, Bennie Thompson, Frederick E. Shelton, IV and Eugene L. Timperman;

(6) U.S. patent application Ser. No. 11/529,904, now U.S. Publication No. 2008/0078800, entitled Surgical Stapling Instruments and Staples to Christopher J. Hess, William B. Weisenburgh, II, Jerome R. Morgan, James W. Voegele, Frederick E. Shelton, IV and Joshua Uth;

(7) U.S. patent application Ser. No. 11/529,879, now U.S. Publication No. 2008/0078806, entitled Surgical Stapling Instrument With Mechanical Indicator To Show Levels of Tissue Compression to Todd. P. Omaits, Bennie Thompson, Frederick E. Shelton, IV, and Eugene L. Timperman;

(8) U.S. patent application Ser. No. 11/541,098, now U.S. Publication No. 2008/0078807, entitled Connected Surgical Staples and Stapling Instruments For Deploying The Same to Christopher J. Hess, William B. Weisenburgh, II, Jerome R. Morgan, Frederick E. Shelton, IV, Leslie M. Fugikawa, and Eugene L. Timperman (9) U.S. patent application Ser. No. 11/529,935, now U.S. Publication No. 2008/0078803, entitled Surgical Staples Having Attached Drivers and Stapling Instruments For Deploying the Same to Christopher J. Hess, Jerome R. Morgan, Michael Clem, Frederick E. Shelton, IV, and William B. Weisenburgh, II;

(10) U.S. patent application Ser. No. 11/541,182, now U.S. Publication No. 2008/0078802, entitled Surgical Staples and Stapling Instruments to Christopher J. Hess, William B. Weisenburgh, II, Jerome R. Morgan, Frederick E. Shelton, IV, and Darrel Powell; and

(11) U.S. patent application Ser. No. 11/541,123, now U.S. Pat. No. 7,794,475, entitled Surgical Staples Having Compressible or Crushable Members For Securing Tissue Therein and Stapling Instruments For Deploying The Same to Christopher J. Hess, Jerome R. Morgan, William B. Weisenburgh, II, James W. Voegele, Carl Shurtleff, Mark Ortiz, Michael Stokes, Frederick E. Shelton, IV, and Jeffrey S. Swayze.

FIELD OF THE INVENTION

The present invention generally relates to endoscopic and open surgical instrumentation and, more particularly, to surgical staples and staplers including, but not limited to, open surgical stapling devices, laparoscopic surgical stapling devices, endoscopic and intralumenal surgical stapling devices.

BACKGROUND

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Recently, an improved "E-beam" firing bar was described for a surgical stapling and severing instrument that advantageously included a top pin that slides within an internal slot formed in the upper jaw (anvil) and has a middle pin and bottom foot that slides on opposite sides of a lower jaw of an end effector, or more particularly a staple applying assembly. Distal to the middle pin, a contacting surface actuates a staple cartridge held within an elongate staple channel that forms the lower jaw. Between the contacting surface and the top pin, a cutting surface, or knife, severs tissue clamped between the anvil and the staple cartridge of the lower jaw. Since both jaws are thus engaged by the E-beam, the E-beam maintains a desired spacing between the jaws to ensure proper staple formation. Thus, if a lesser amount of tissue is clamped, the E-beam holds up the anvil to ensure sufficient spacing for the staples to properly form against an undersurface of the anvil. In addition, if a greater amount of tissue is clamped, the E-beam draws down the anvil to ensure that the spacing does not exceed the length of the staple such that the ends of each staple are not sufficiently bent to achieve a desired degree of retention. Such an E-beam firing bar is described in U.S. patent application Ser. No. 10/443,617, entitled "Surgical Stapling Instrument Incorporating an E-Beam Firing Mechanism", filed on May 20, 2003, now U.S. Pat. No. 6,978,921, issued Dec. 27, 2005, the disclosure of which is hereby incorporated by reference in its entirety.

While an E-beam firing bar has many advantages for a surgical stapling and severing instrument, often it is desirable to sever and staple tissue of various thicknesses. A thin layer of tissue may result in staples that only form loosely, perhaps requiring the need for bolstering material. A thick layer of tissue may result in formed staples that exert a strong compressive force on the captured tissue, perhaps resulting in necrosis, bleeding or poor staple formation/retention. Rather than limiting the range of tissue thicknesses that are appropriate for a given surgical stapling and severing instrument, it would be desirable to accommodate a wider range of tissue thickness with the same surgical stapling and severing instrument.

Consequently, a significant need exists for an improved surgical stapling and severing instrument that incorporates a staple applying assembly (end effector) that adjusts to the amount of tissue that is clamped.

In addition, the staple drivers that are commonly employed in existing staple applying assemblies are traditionally made as stiff as possible to assure proper "B" form staple height. Because of this stiff construction, these drivers do not provide any flexibility for adjusting the formed height of the staple to a particular thickness of tissue clamped within the assembly.

Thus, another significant need exists for staple drivers that are able to facilitate the adjustment of the formed height of the staples in response to variations in tissue thickness.

In various types of endocutter arrangements, the anvil is opened and closed by axially actuating a closure tube assembly that serves to interface with closure features on the proximal end of the anvil. The anvil is commonly formed with trunnions that are received in somewhat elongated slots in the proximal end of the channel. The trunnions serve to pivotally support the staple cartridge and permit the anvil to move into axial alignment while pivoting to a closed position. Unfortunately, however, this arrangement lacks means for limiting or adjusting the amount of clamping forces applied to the anvil during the clamping process. Thus, the same amount of clamping forces generated by the closure tube assembly are applied to the anvil regardless of the thickness of the tissue to be clamped therein. Such arrangement can result in thinner tissues being over clamped which could lead to excessive bleeding and possibly damage or even destroy the tissue.

Thus, there is another need for a closure system that includes means for limiting or adjusting the amount of closure forces applied to the anvil based on the thickness of the tissue to be clamped between the anvil and the staple cartridge.

In certain types of surgical procedures the use of surgical staples has become the preferred method of joining tissue, and, specially configured surgical staplers have been developed for these applications. For example, intra-luminal or circular staplers have been developed for use in a surgical procedure known as an anastomosis. Circular staplers useful to perform an anastomosis are disclosed, for example, in U.S. Pat. No. 5,104,025 and U.S. Pat. No. 5,309,927 which are each herein incorporated by reference.

An anastomosis is a surgical procedure wherein sections of intestine are joined together after a connecting section has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

In general, a conventional circular stapler typically consists of an elongated shaft having a proximal actuating mechanism and a distal stapling mechanism mounted to the shaft. The distal stapling mechanism typically consists of a fixed stapling cartridge containing a plurality of staples configured in a concentric circular array. A round cutting knife is concentrically mounted in the cartridge interior to the staples. The knife is moveable in an axial, distal direction. Extending axially from the center of the cartridge is a trocar shaft. The trocar shaft is moveable, axially, with respect to the cartridge and elongated shaft. An anvil member is mounted to the trocar shaft. The anvil member has a conventional staple anvil mounted to it for forming the ends of the staples. The distance between the distal face of the staple cartridge and the staple anvil is controlled by an adjustment mechanism mounted to the proximal end of the stapler shaft. Tissue contained between the staple cartridge and the staple anvil is simultaneously stapled and cut when the actuating mechanism is engaged by the surgeon.

When performing an anastomosis using a circular stapler, typically, the intestine is stapled using a conventional surgical stapler with double rows of staples being emplaced on either side of a target section (i.e., specimen) of intestine. The target section is typically simultaneously cut as the section is stapled. Next, after removing the specimen, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. Typically the distal end of the stapler is inserted transanally. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby engaging the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, a concentric circular blade is driven through the intestinal tissue ends, cutting the ends adjacent to the inner row of staples. The surgeon then withdraws the stapler from the intestine and the anastomosis is complete.

During the stapling process, however, the surgeon must be careful not to over compress the material that is being stapled to avoid killing or detrimentally damaging that tissue. While some prior staplers are fitted with an indicator mechanism for providing the surgeon with some indication of the spacing between the anvil and the staple cartridge, it is desirable for the stapler to include a mechanism that provides a means for avoiding over compression of the tissue.

SUMMARY

The present invention includes, in various embodiments, a surgical staple having a first shape and a deformed second shape for connecting tissue together. In at least one embodiment, the surgical staple includes a crown comprised of a dissolvable, bioabsorbable, or biofragmentable material, a first deformable member, and a second member. In these embodiments, the crown connects the first member and the second member, however, after the crown has been dissolved, the first member is unconnected to the second member and, as a result, the first and second members can move relative to each other. Accordingly, the staple can be rigid during the early stages of healing and can be flexible during the latter stages of healing, for example. In various embodiments, the first and second members of the staple are also comprised of a dissolvable, bioabsorbable, or biofragmentable material. In these embodiments, the first and second members can be constructed so that the crown and first and second members dissolve at different rates and/or dissolve away at different times. Further, the dissolvable, bioabsorbable or biofragmentable material can also include a therapeutic drug mixed therein which is eluted from the material as it dissolves in situ.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 23 is another partial longitudinal cross-sectional view of the staple applying assembly of FIGS. 20-22 clamping another piece of tissue therein.

FIG. 24 is another partial longitudinal cross-sectional of the staple applying assembly of FIGS. 20-23 clamping another piece of tissue therein.

FIG. 28 is a top view of a portion of a biasing plate embodiment of the present invention.

FIG. 29 is a cross-sectional view of a portion of the biasing plate of FIG. 28 taken along line 29-29 in FIG. 28.

FIG. 62 is a partially enlarged view of a distal end of a closure tube assembly interacting with a partially closed anvil with some of the components shown in cross-section for clarity.

FIG. 63 is another partially enlarged view of the closure tube and anvil of FIG. 62 with the anvil illustrated in a fully closed position and some elements shown in cross-section for clarity.

FIG. 70 is a cross-sectional view of another endocutter embodiment of the present invention with the anvil thereof in an open position and some components shown in solid form for clarity.

FIG. 71 is another cross-sectional view of the endocutter embodiment of FIG. 70 with the anvil in a fully closed position and some components shown in solid form for clarity.

FIG. 73 is another cross-sectional view of the endocutter embodiment of FIG. 70 with the anvil in a maximum clamping position with some components shown in solid form for clarity.

FIG. 74 is an enlarged cross-sectional view of a portion of the anvil and the closure tube assembly of the embodiments depicted in FIG. 73 with the anvil in its maximum clamping position.

FIG. 75 is an enlarged cross-sectional view of a portion of the endocutter depicted in FIGS. 70-74 clamping a thin piece of tissue.

FIG. 76 is another enlarged cross-sectional view of a portion of the endocutter depicted in FIGS. 70-75 clamping a thicker piece of tissue.

FIG. 83 is a cross-sectional view of a knob assembly embodiment of the present invention.

FIG. 84 is a cross-sectional view of the knob assembly of FIG. 83 taken along line 84-84 in FIG. 83.

FIG. 85 is a partial cross-sectional view of a stapler embodiment of the present invention inserted into separated portions of intestine.

FIG. 86 is another cross-sectional view of the staple and intestine arrangement of FIG. 85 with the proximal and distal ends of the intestine being sutured around the anvil shaft.

FIG. 91 is cross-sectional view of a closure actuator that may be employed with the stapler of FIGS. 89 and 90.

FIG. 92 is a cross-sectional view of the closure actuator of FIG. 91 taken along line 92-92 in FIG. 91.

FIG. 96 is a side view of a surgical staple in an undeployed shape in accordance with an embodiment of the present invention;

FIG. 97 is a side view of the staple of FIG. 96 in a first deformed shape;

FIG. 101 is a perspective view of the staple of FIG. 96;

FIG. 102 is a perspective view of the staple of FIG. 97;

FIG. 103 is a perspective view of the staple of FIG. 98;

FIG. 104 is a perspective view of the staple of FIG. 99;

FIG. 106 is a side view of a surgical staple in accordance with an alternative embodiment of the present invention;

FIG. 107 is a perspective view of the staple of FIG. 106;

FIG. 113 is a side view of a surgical staple in accordance with an embodiment of the present invention including a crushable member;

FIG. 114 is a side view of the staple of FIG. 113 in a deformed shape;

FIG. 118 is a top view of the staple of FIG. 117;

FIG. 119 is a side view of a surgical staple in accordance with an embodiment of the present invention including a spring;

FIG. 120 is a side view of the staple of FIG. 119 in a deformed shape;

FIG. 121 is a top view of the staple of FIG. 120;

FIG. 122 is a perspective view of first and second deformable members of a staple in accordance with an embodiment of the present invention;

FIG. 123 is a perspective view of a dissolvable, or bioabsorbable, material overmolded onto the deformable members of FIG. 122;

FIG. 124 is a perspective view of the staple of FIG. 123 in a deformed shape;

FIG. 125 is a perspective view of the staple of FIG. 124 where a portion of the dissolvable material has been dissolved and the first and second deformable members have moved relative to one another;

FIG. 126 is a perspective view of the staple of FIG. 125 after the dissolvable material has completely dissolved;

FIG. 127 is a partial cross-sectional view of a surgical stapler having an anvil, and a staple cartridge for removably storing staples in accordance with an embodiment of the present invention;

FIG. 128 is a partial cross-sectional view of the stapler of FIG. 127 illustrating several staples in various deformed shapes;

FIG. 129 is a partial cross-sectional view of the stapler of FIG. 127 taken along line 129-129 in FIG. 127;

Figure 129:
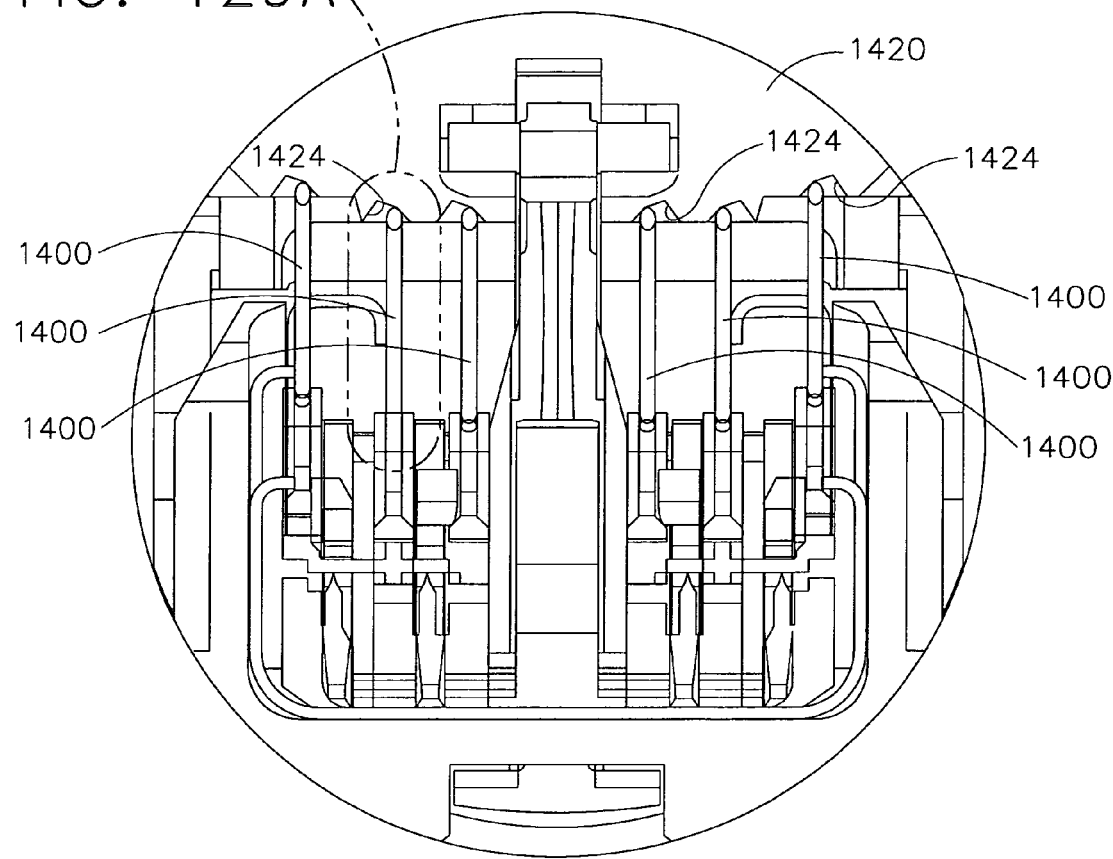
Figure 132:
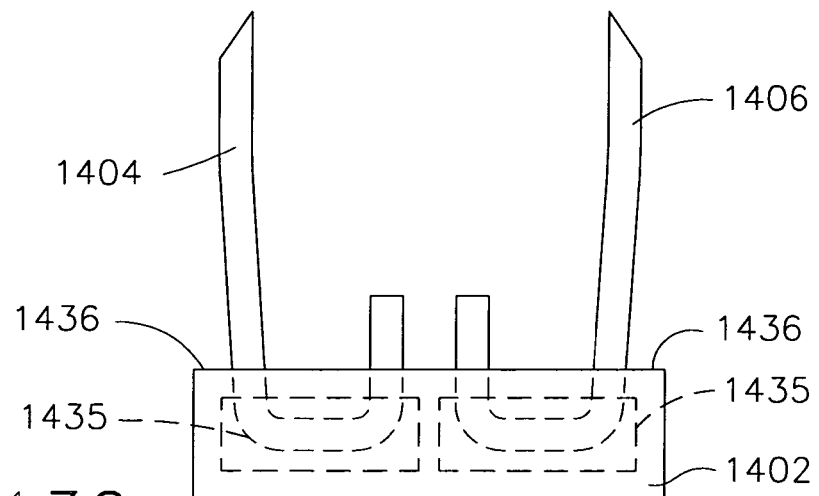
Figure 133:
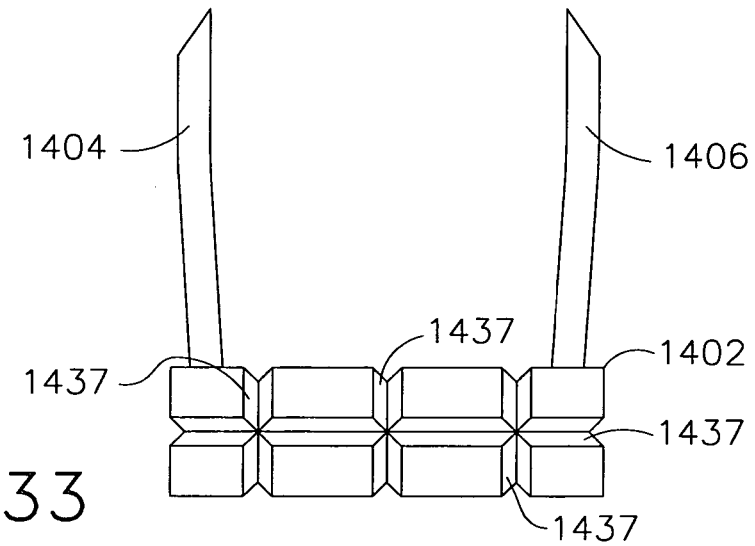
Figure 134:
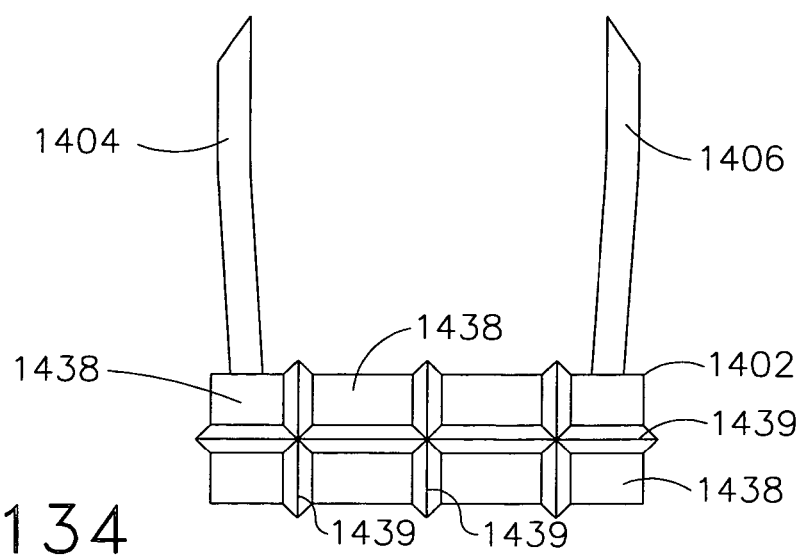
Figure 135:
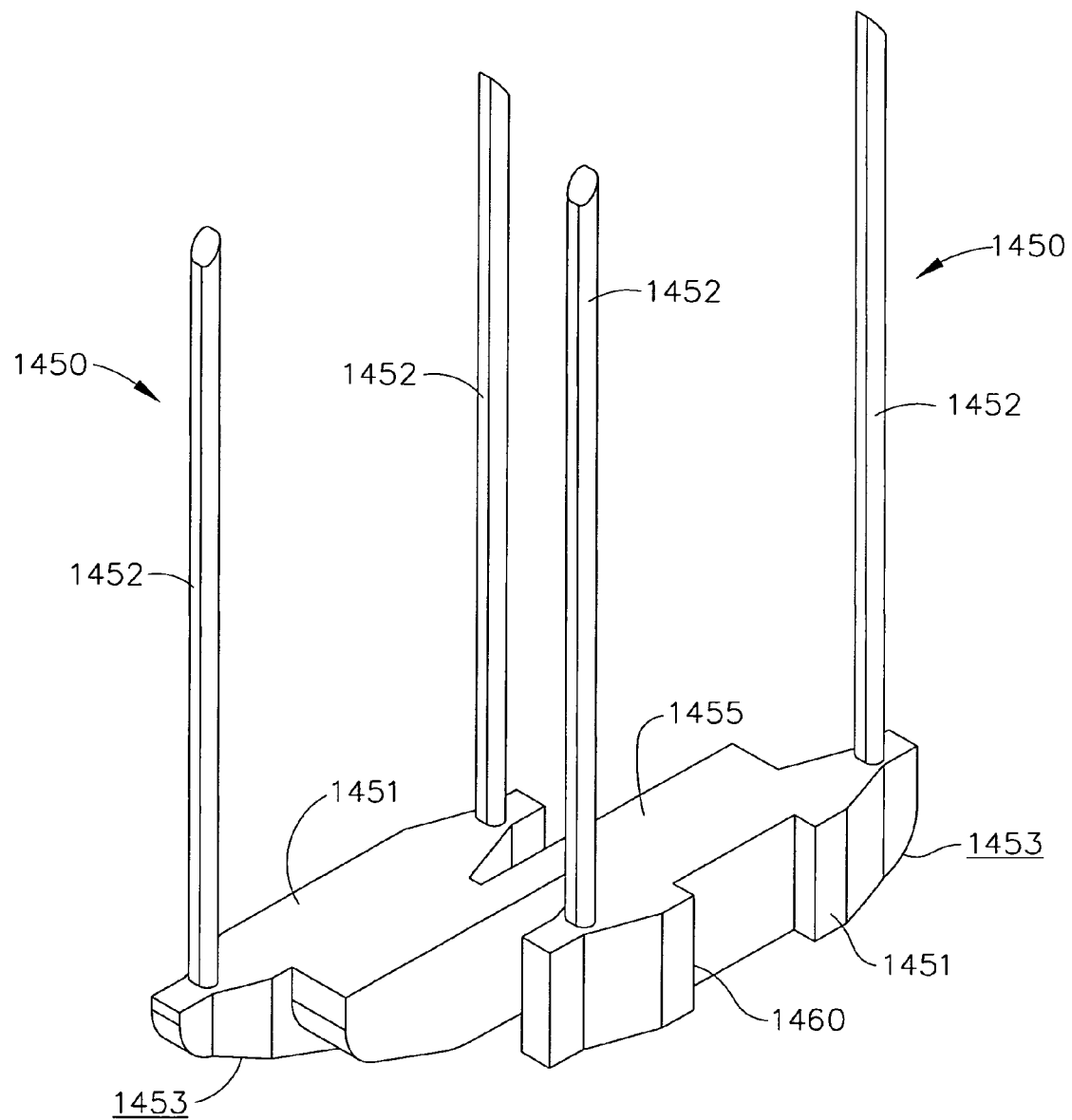
Figure 136:
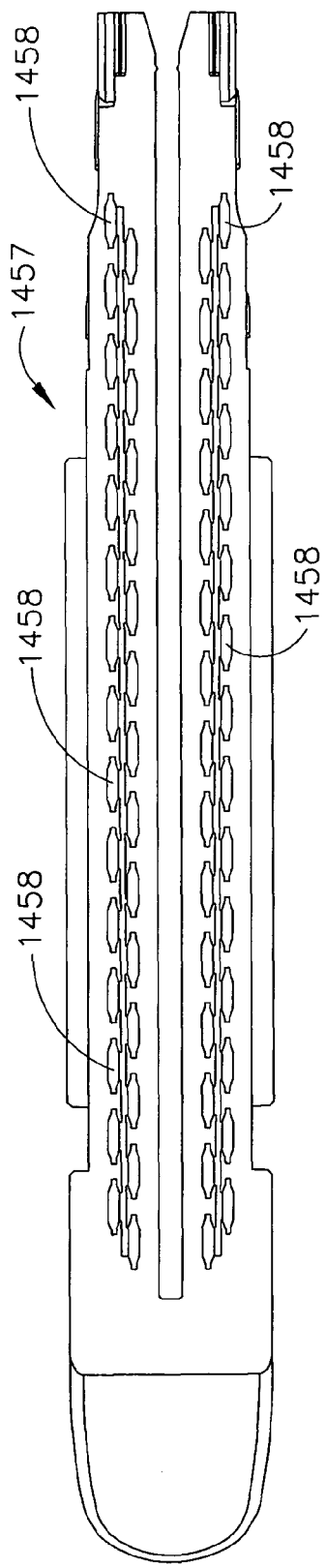
Figure 137:
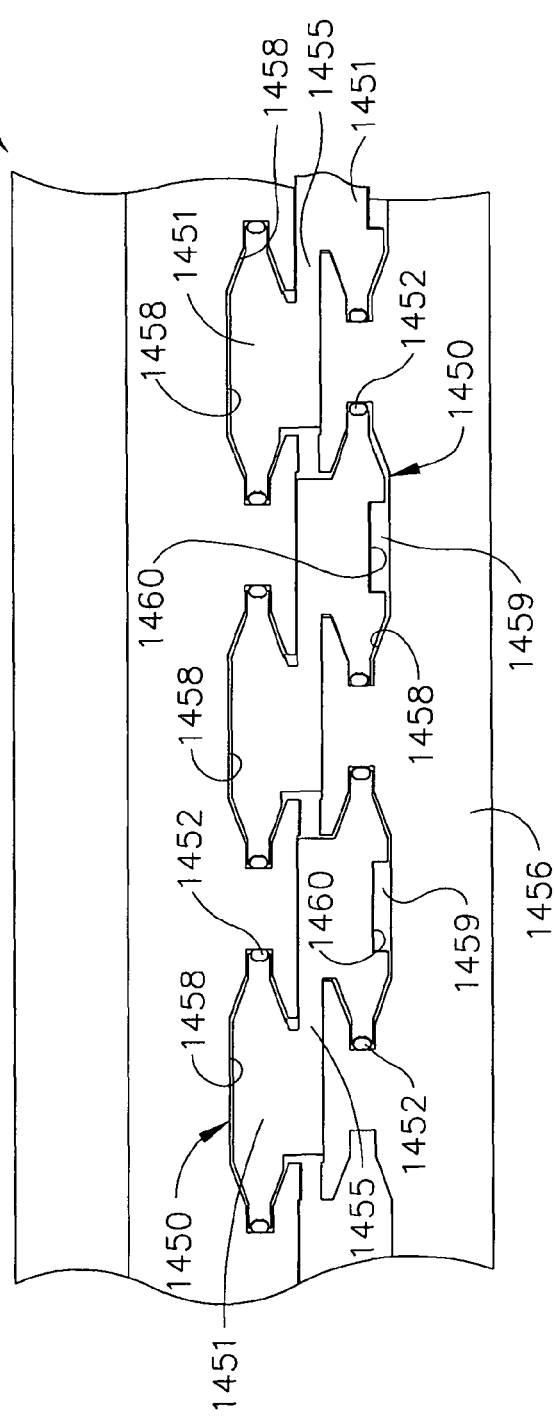

FIG. 129A is a detail view of a staple in FIG. 129;

FIG. 130 is a detail view of the staple of FIG. 129A in a first deformed shape;

FIG. 131 is a detail view of the staple of FIG. 129A in a second deformed shape;

FIG. 132 is a side view of a staple in accordance with an alternative embodiment of the present invention having two materials overmolded onto the deformable members;

FIG. 133 is a detail view of a staple in accordance with an alternative embodiment of the present invention;

FIG. 134 is a detail view of a staple in accordance with an alternative embodiment of the present invention;

FIG. 135 is a perspective view of staples in accordance with an embodiment of the present invention;

FIG. 136 is a top view of a staple cartridge configured to accommodate the staples of FIG. 135;

FIG. 137 is a detail view of the staple cartridge of FIG. 136;

FIG. 138 is a second detail view of the staple cartridge of FIG. 136; and

FIG. 139 is a cross-sectional view of the staple cartridge of FIG. 136 having the staples of FIG. 135 therein.

Figure 140:
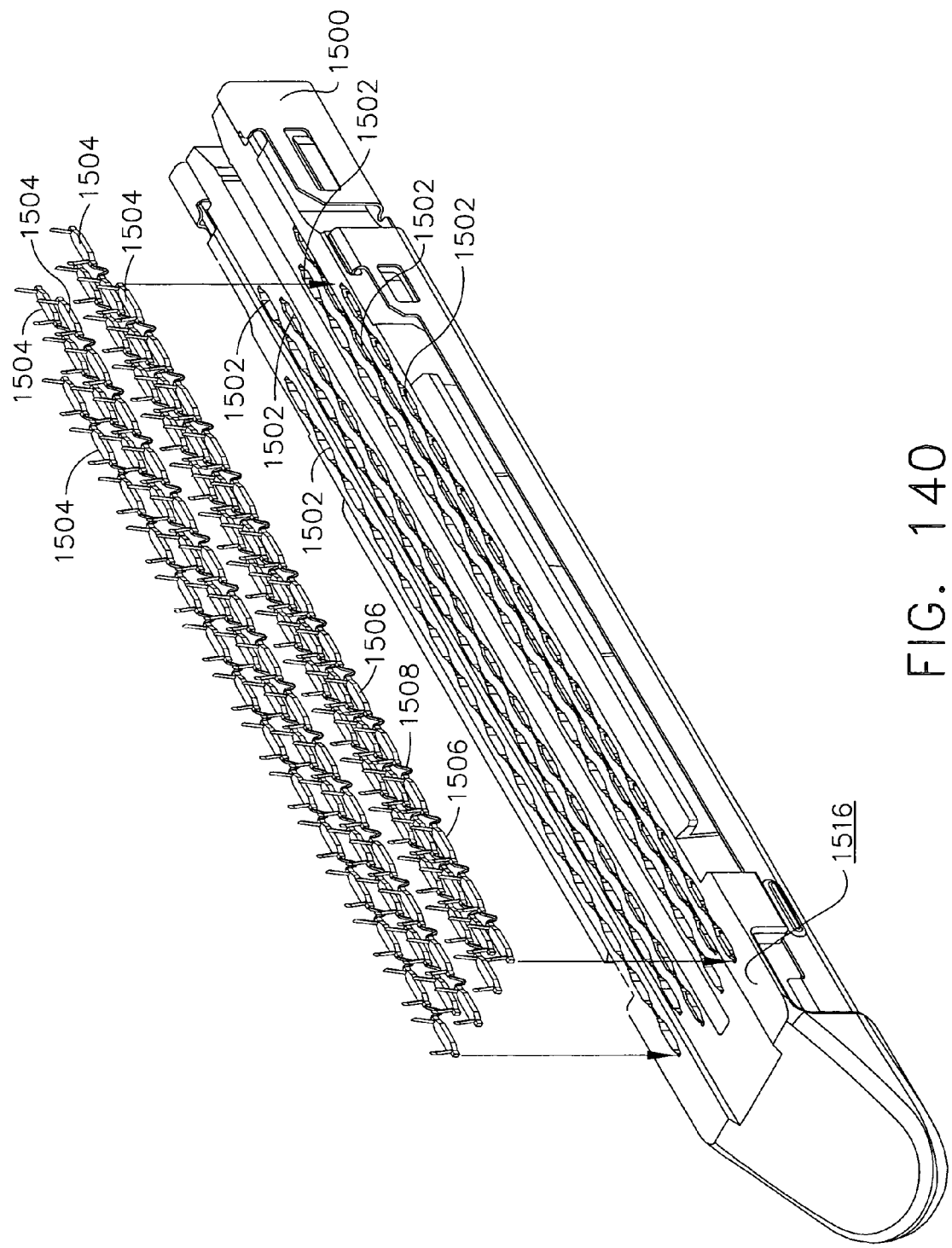
Figure 141:
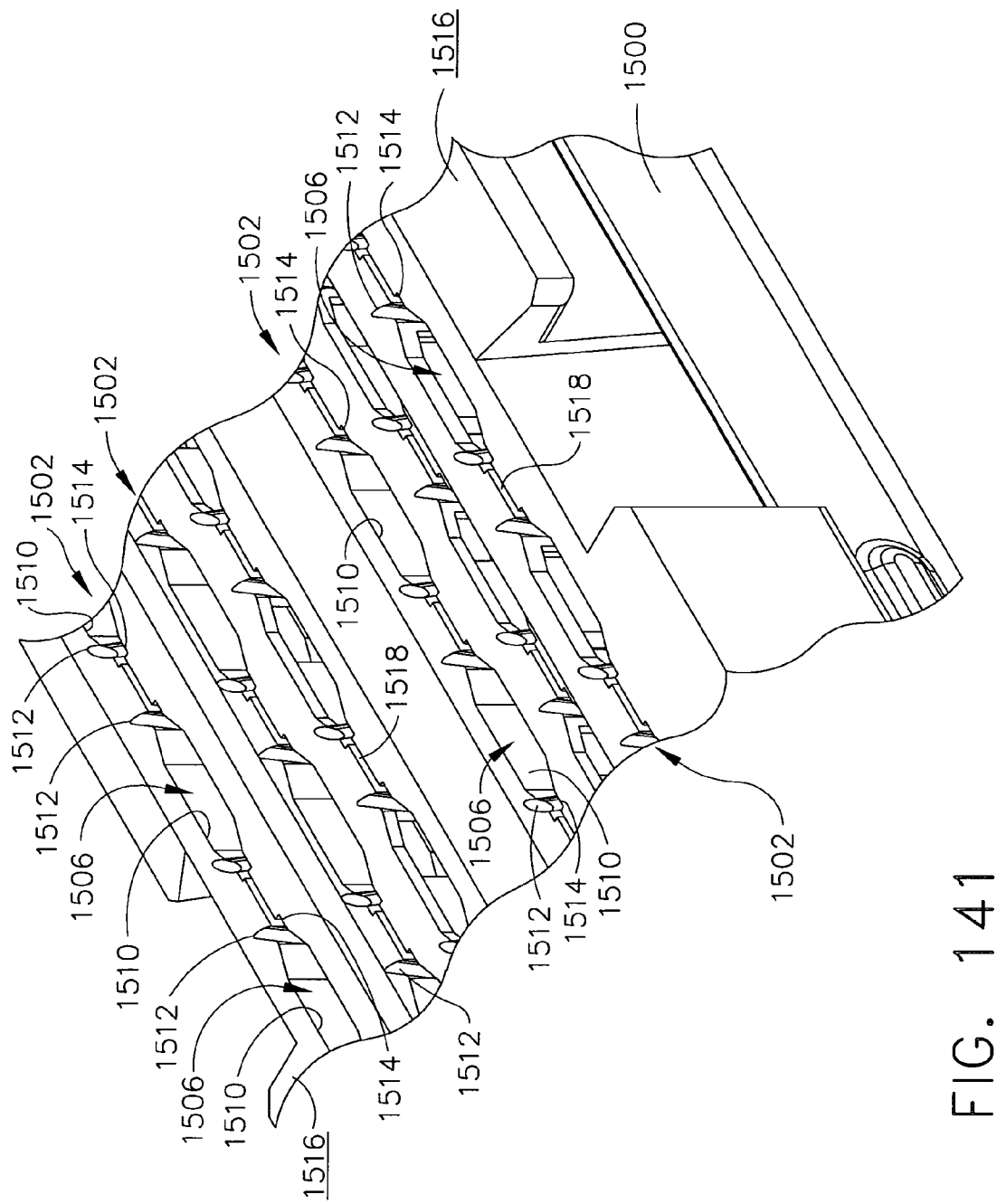
Figure 144:
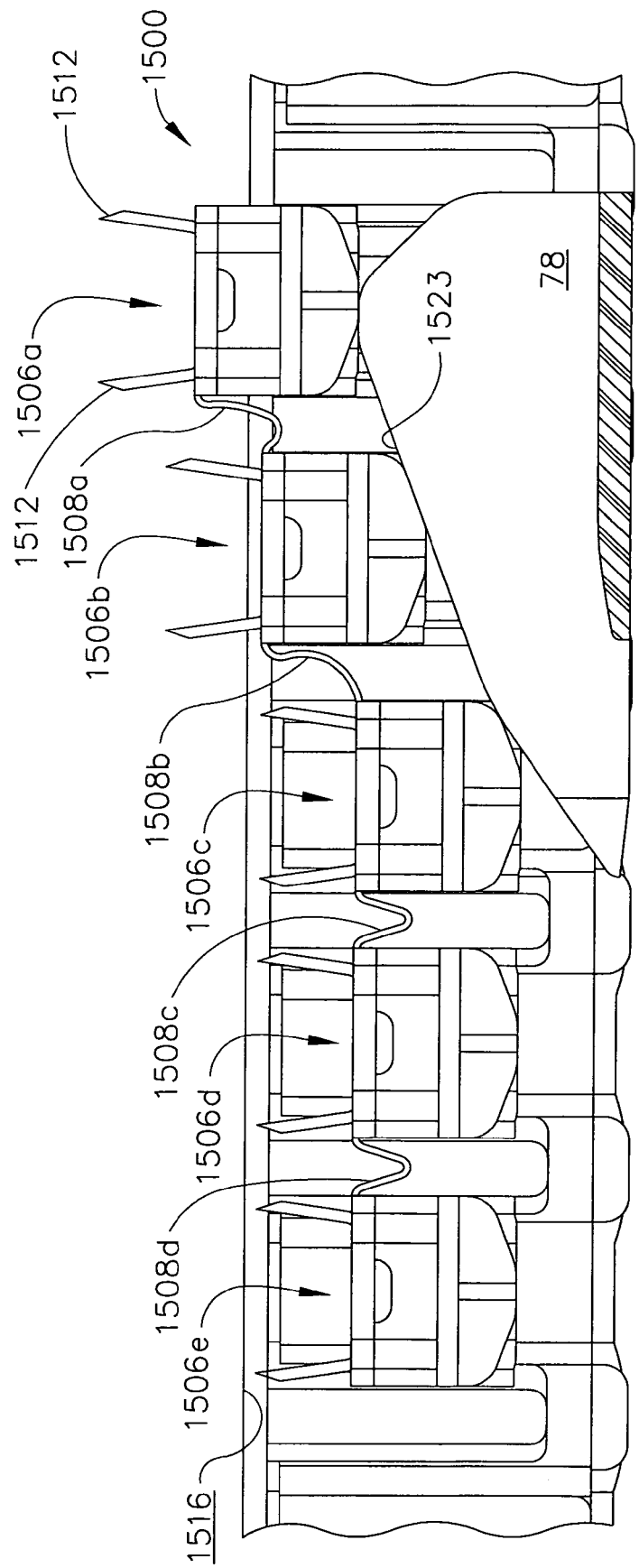
Figures 145, 146:
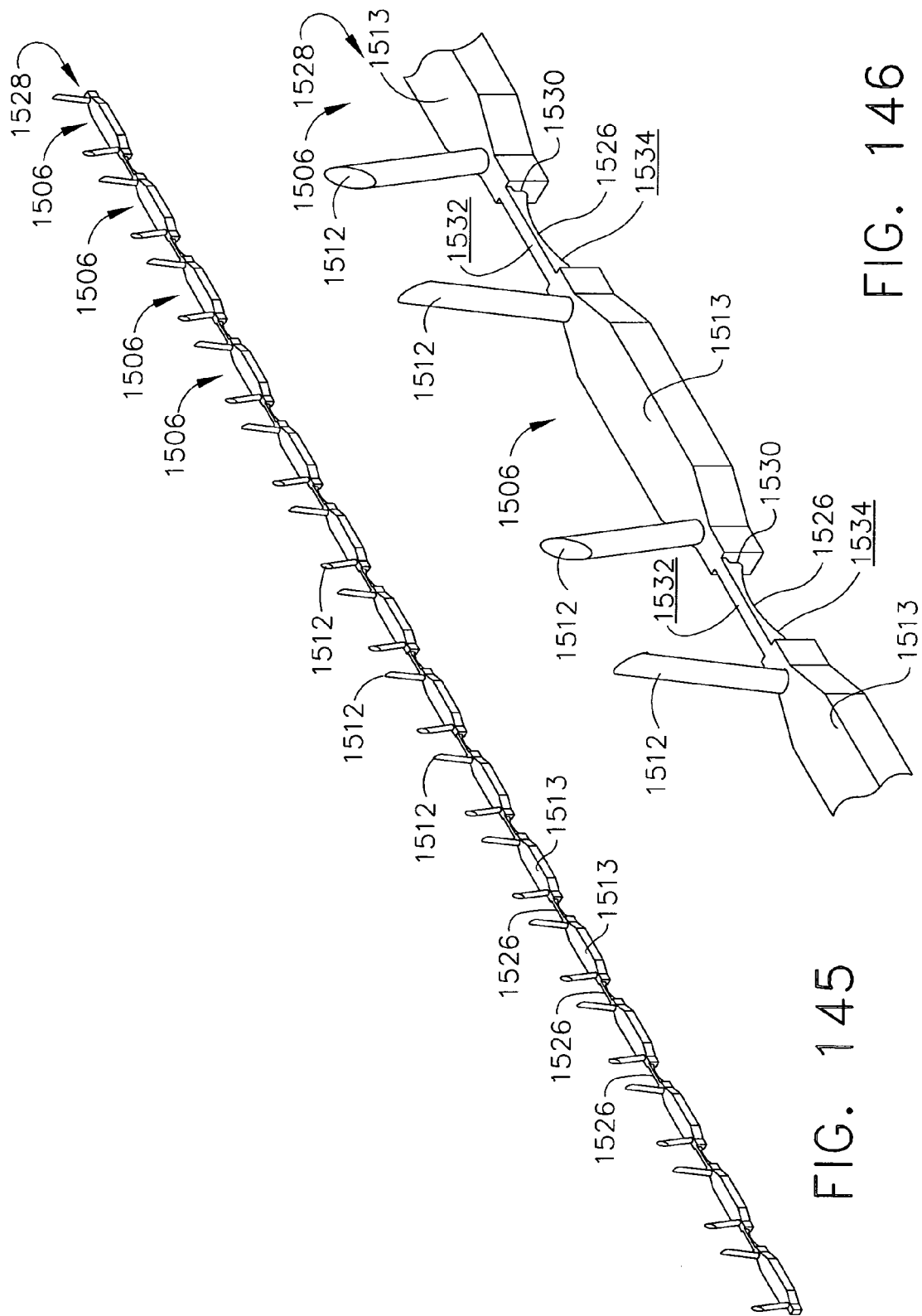
Figure 147:
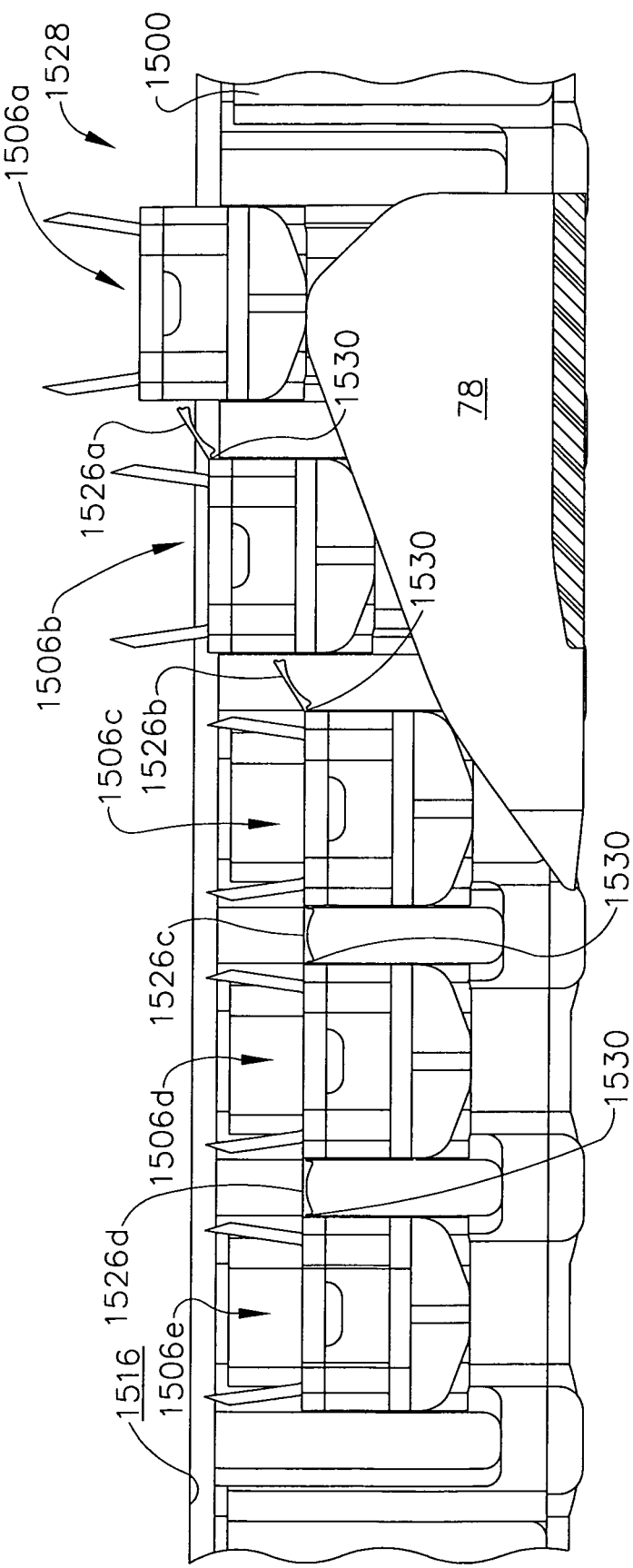
Figures 148, 149:
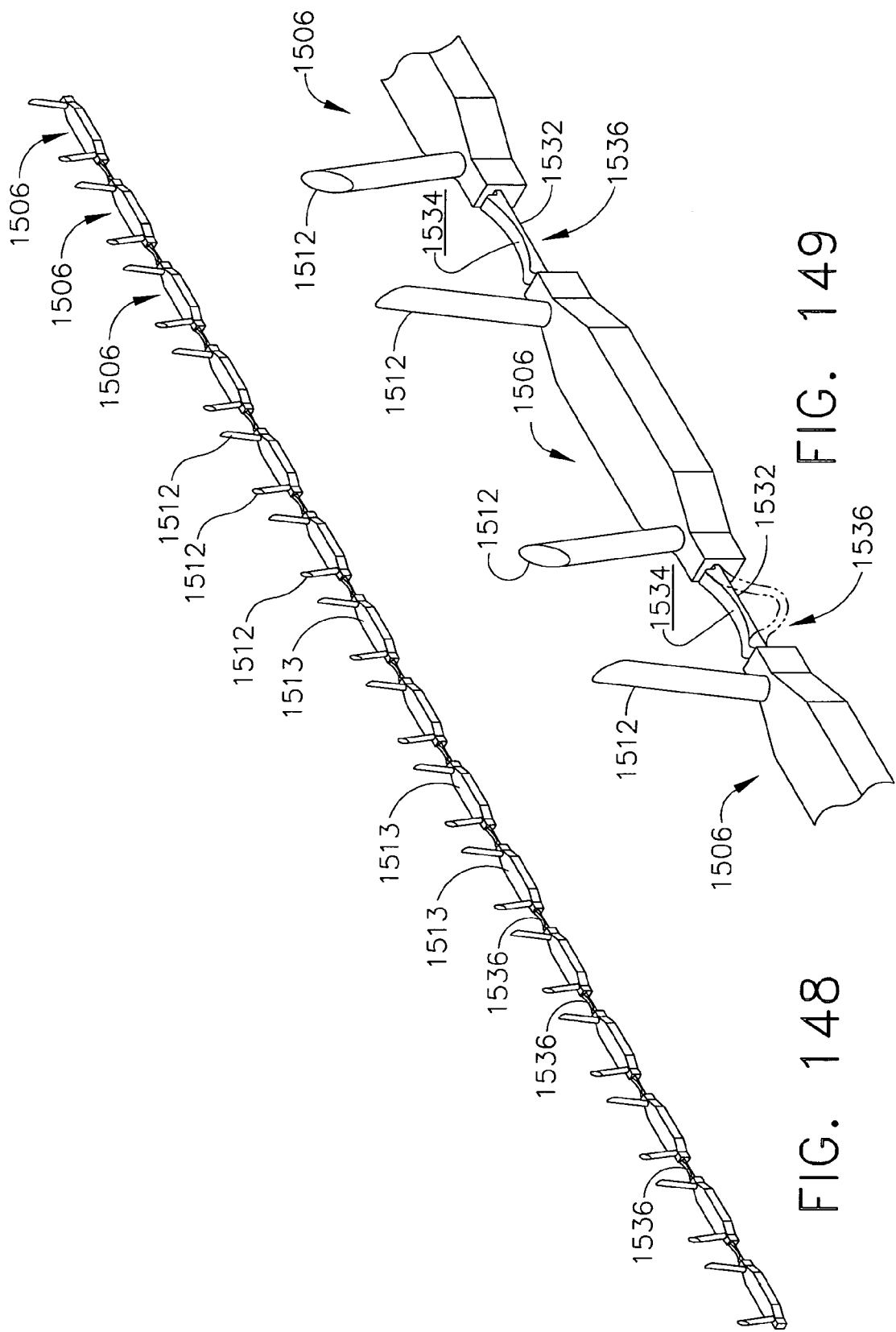
Figure 150:
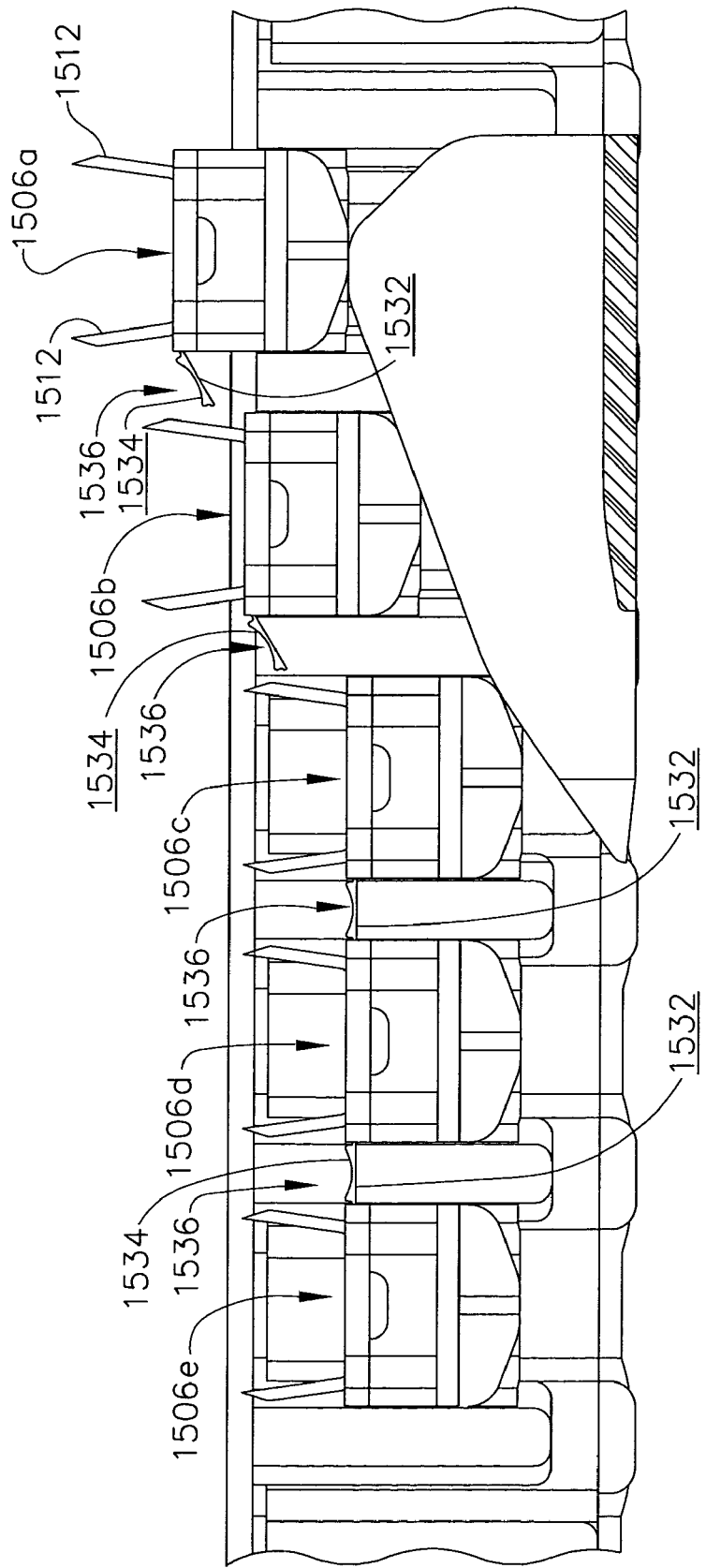
Figure 151:
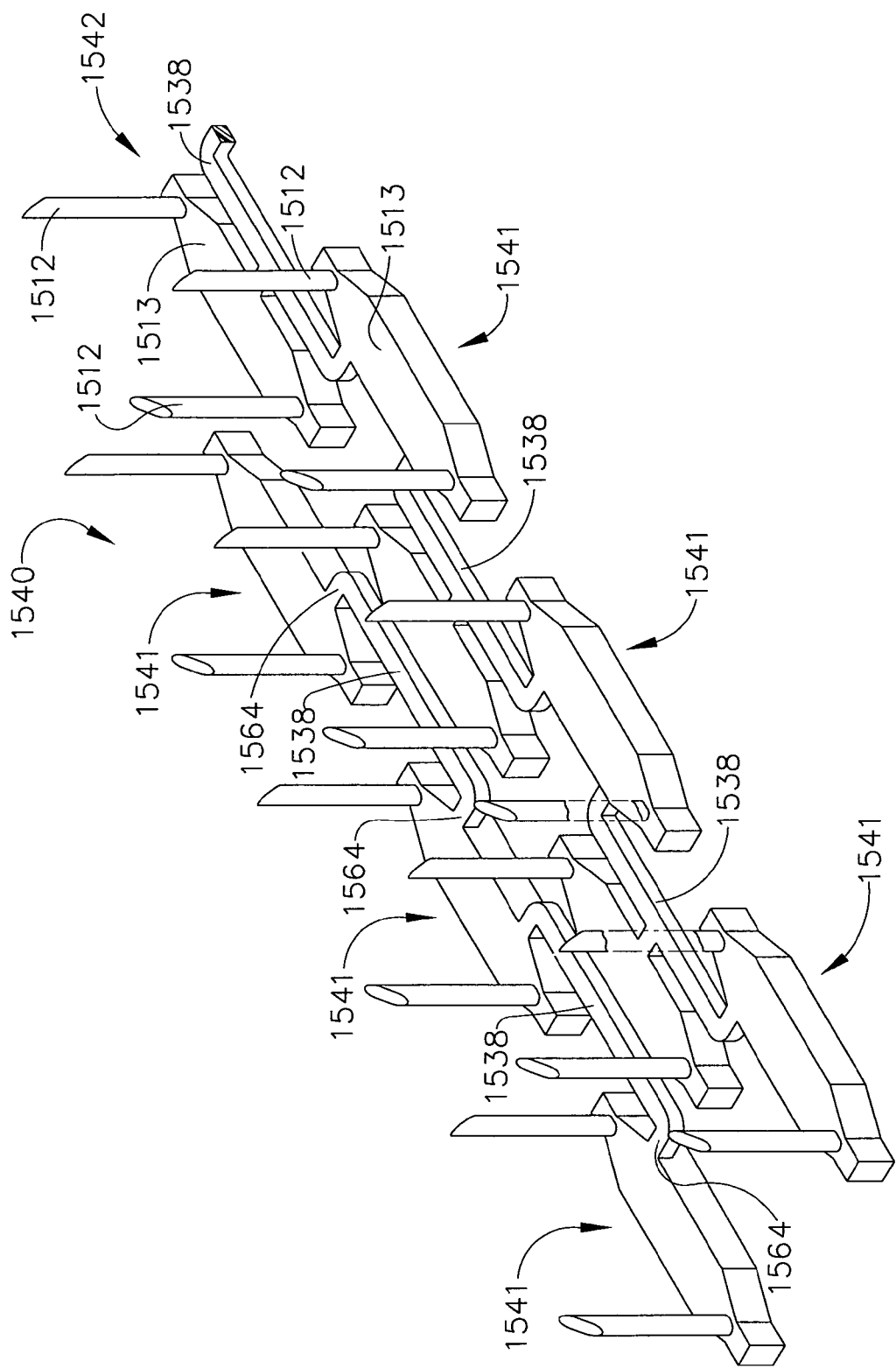
Figure 152:
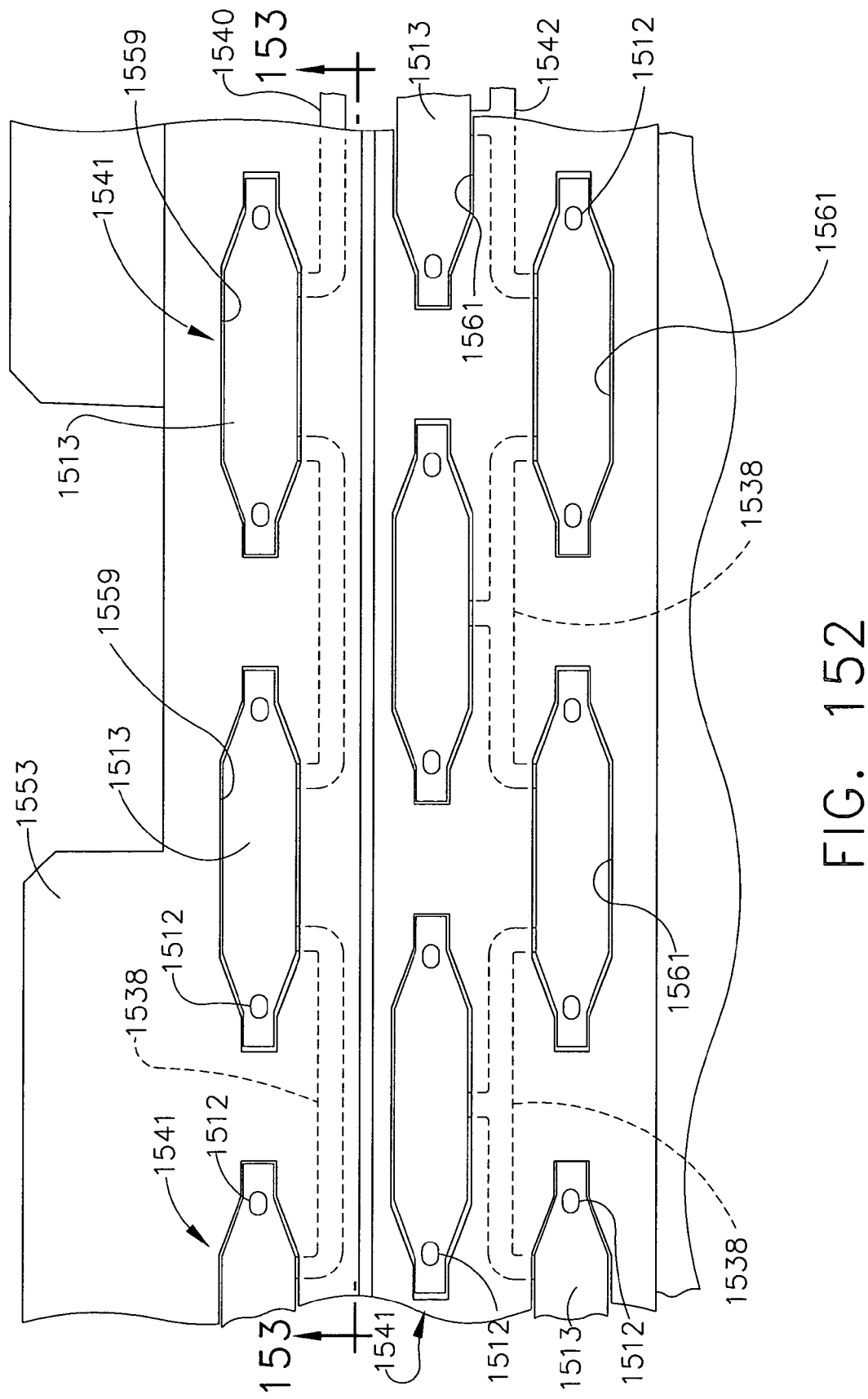
Figure 153:
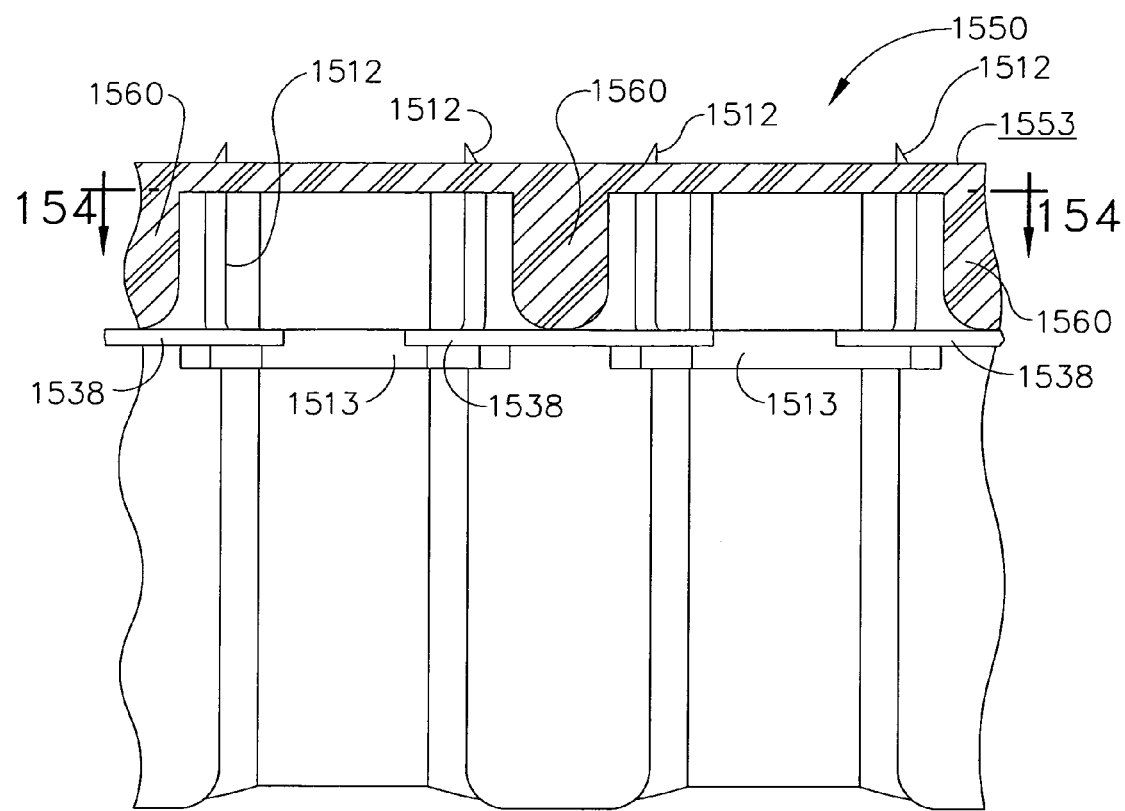
Figure 154:
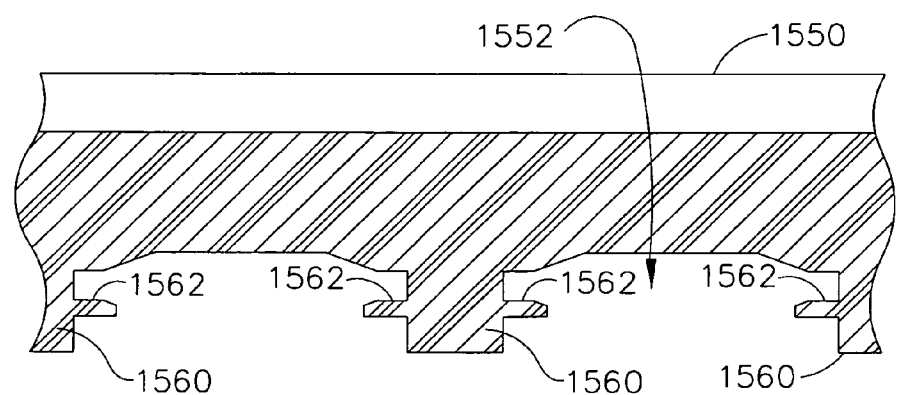
Figure 156:
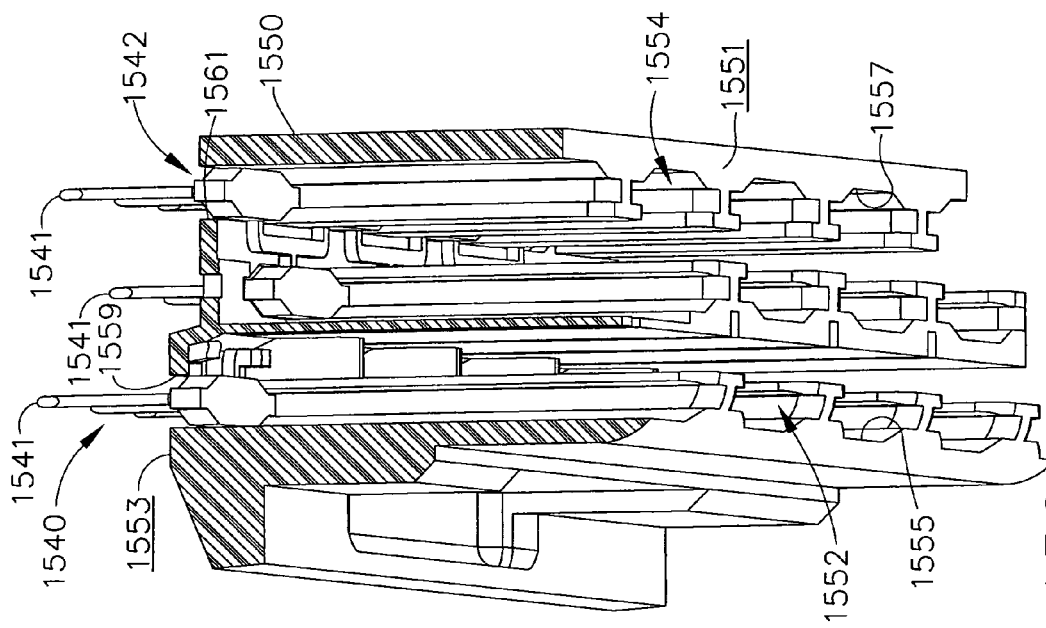
Figure 155:
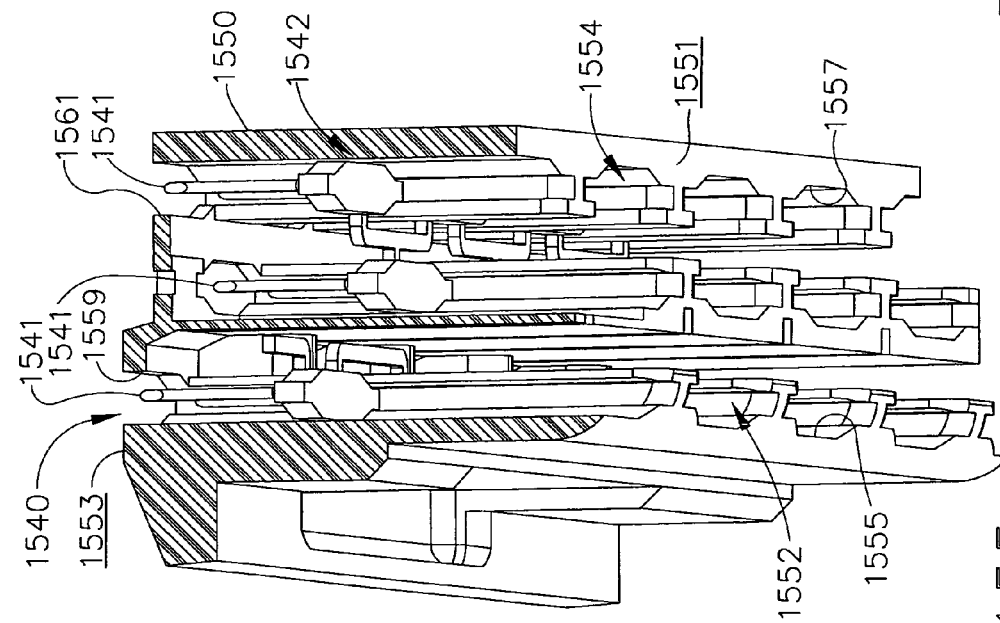
Figure 157:
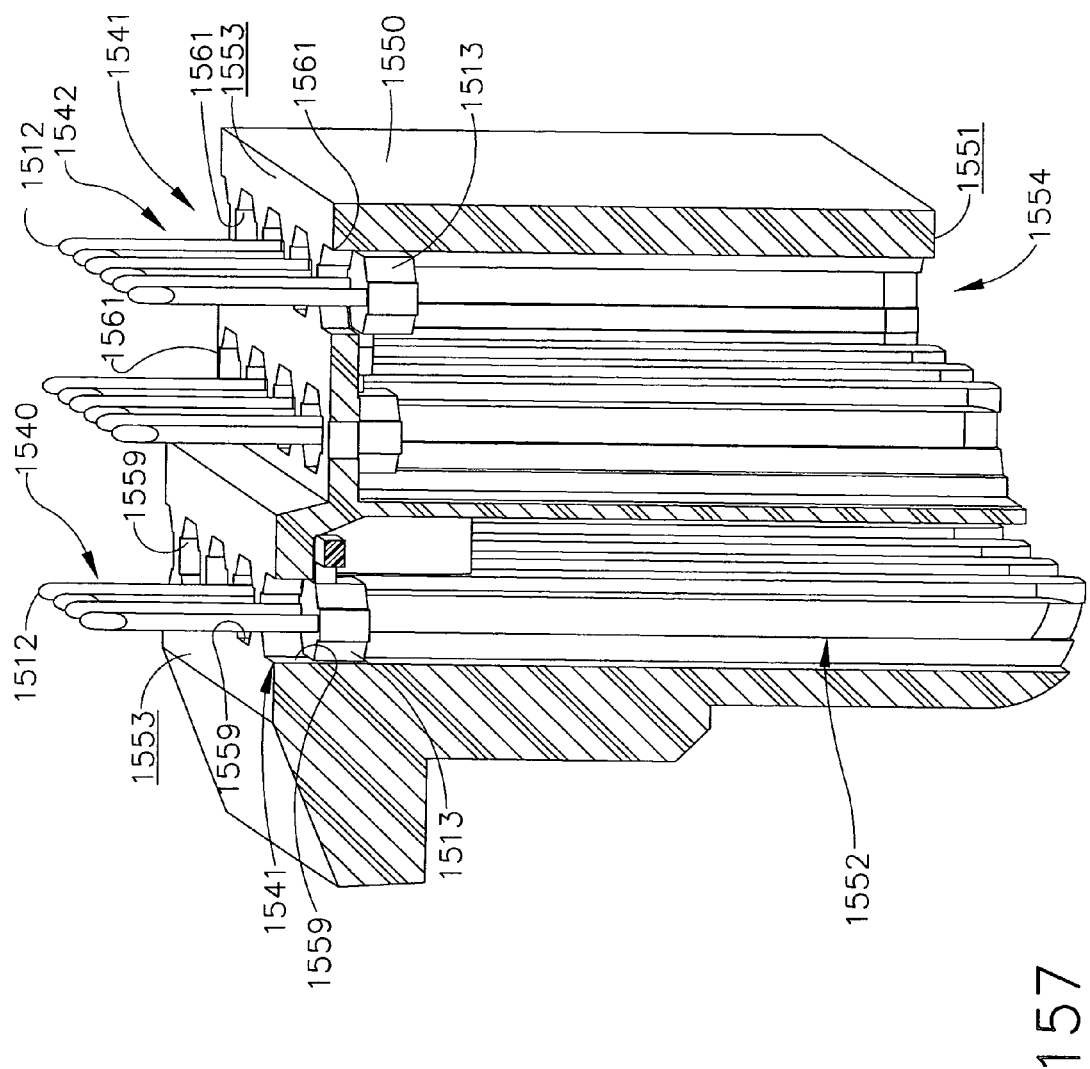
Figure 158:
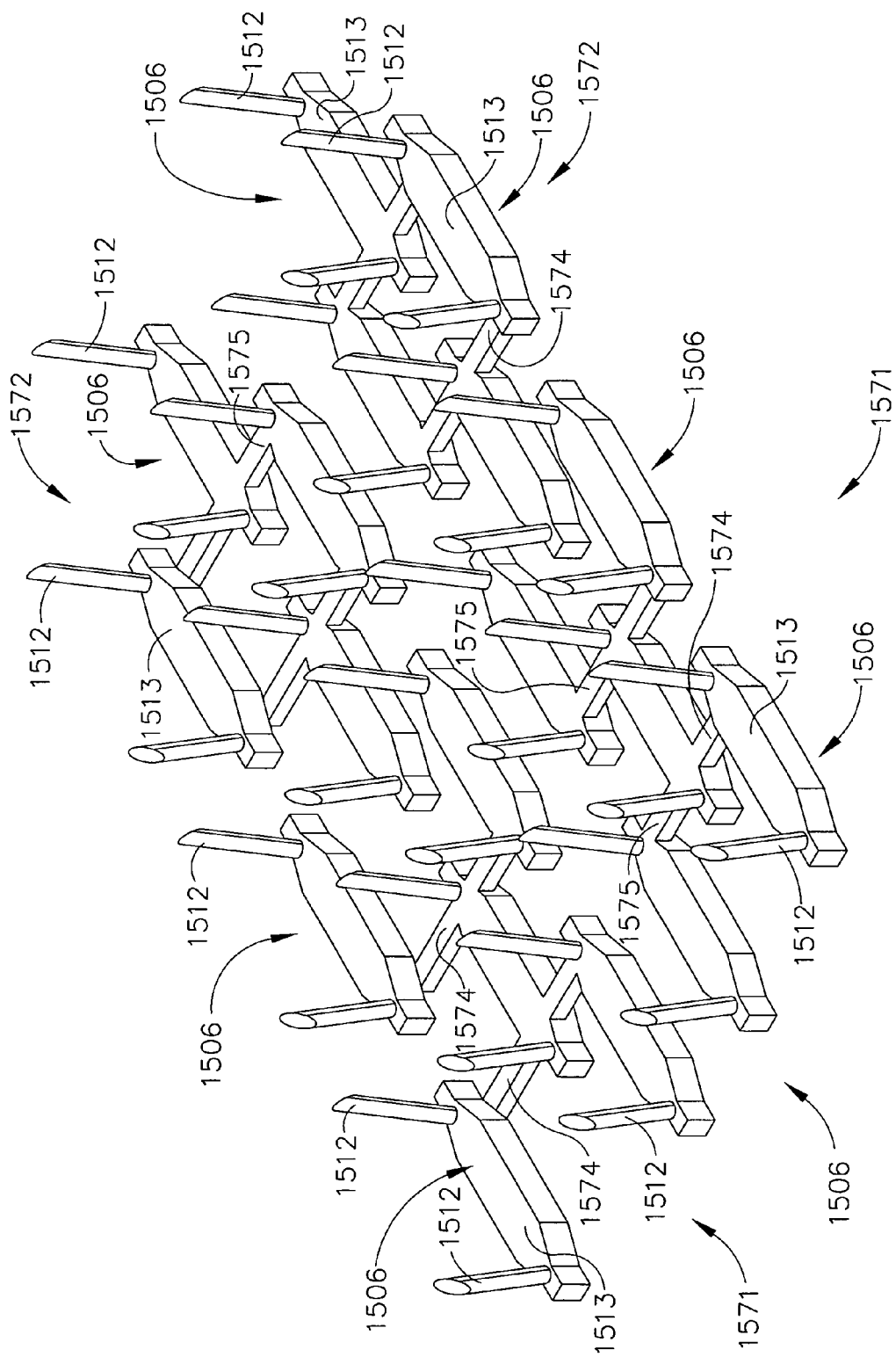
Figure 159:
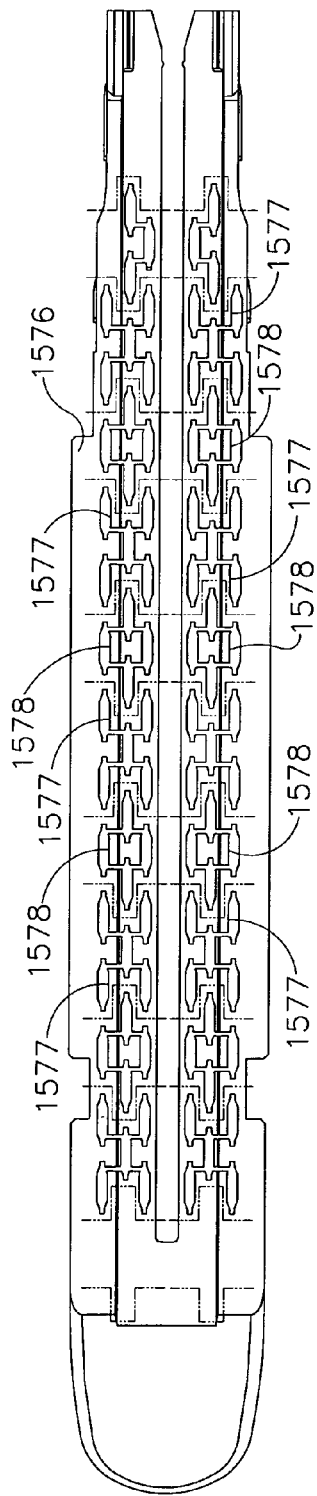
Figure 159A:
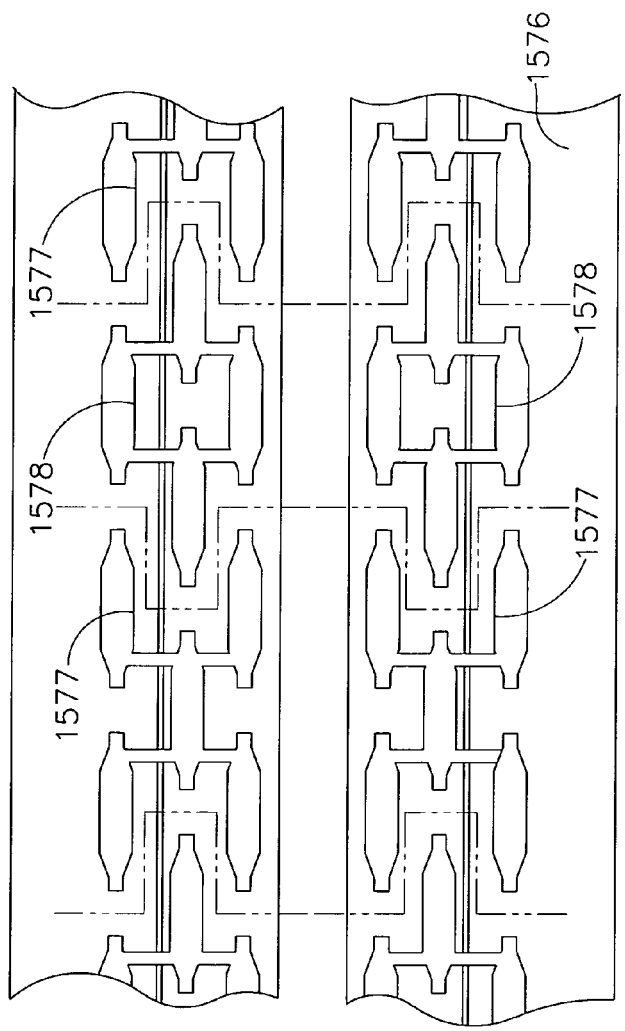
Figure 160:
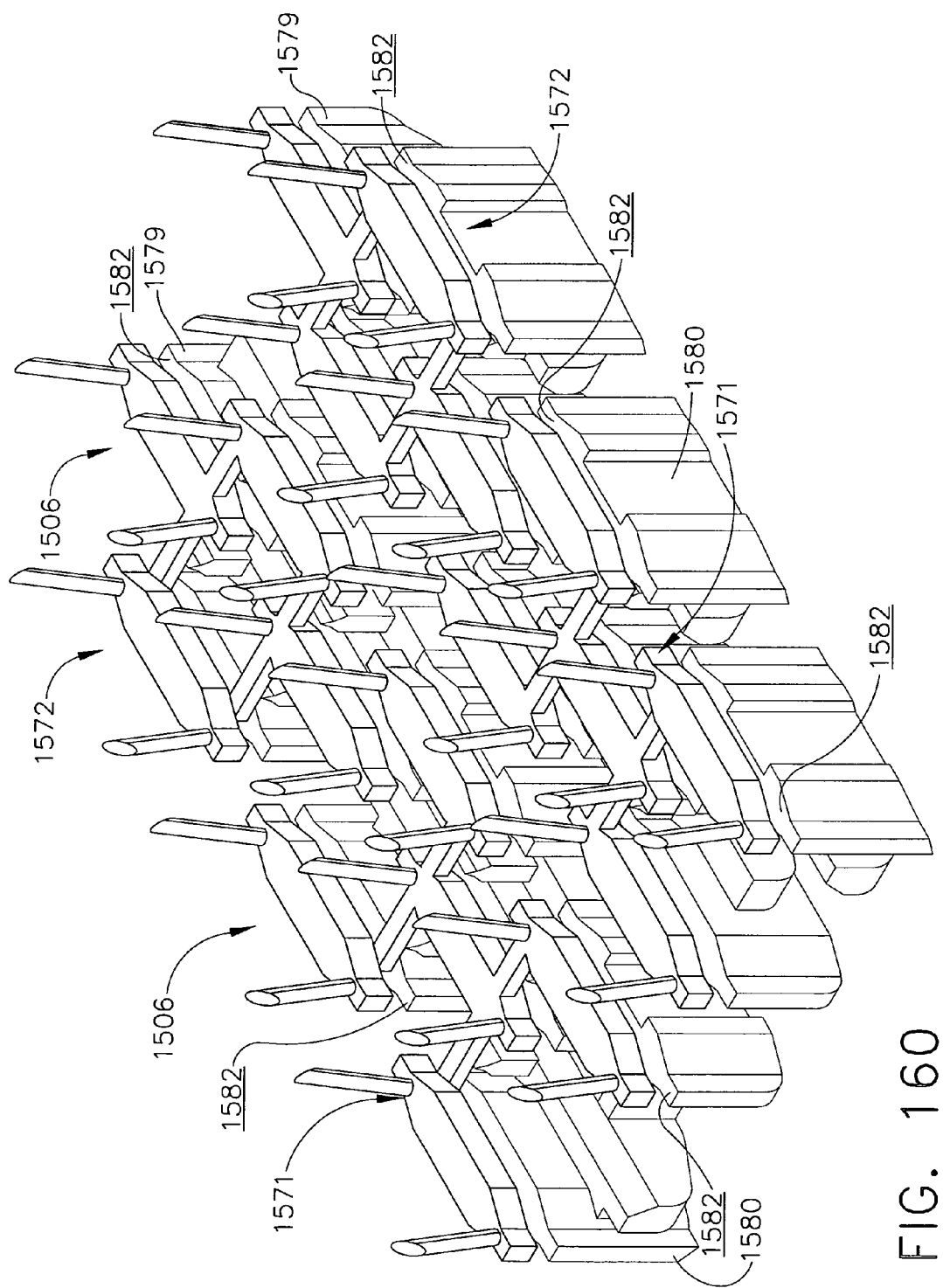
Figure 161:
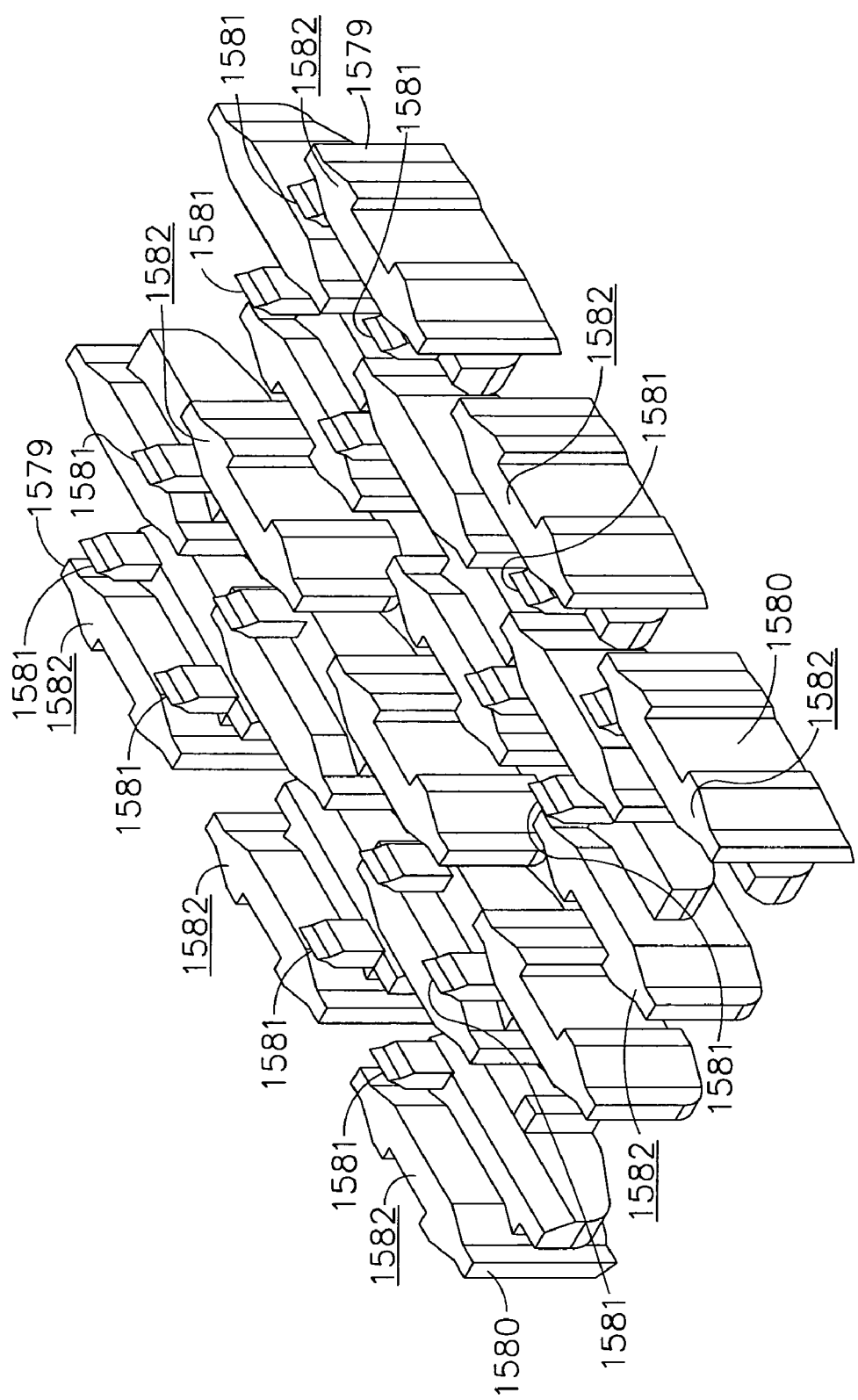
Figure 162:
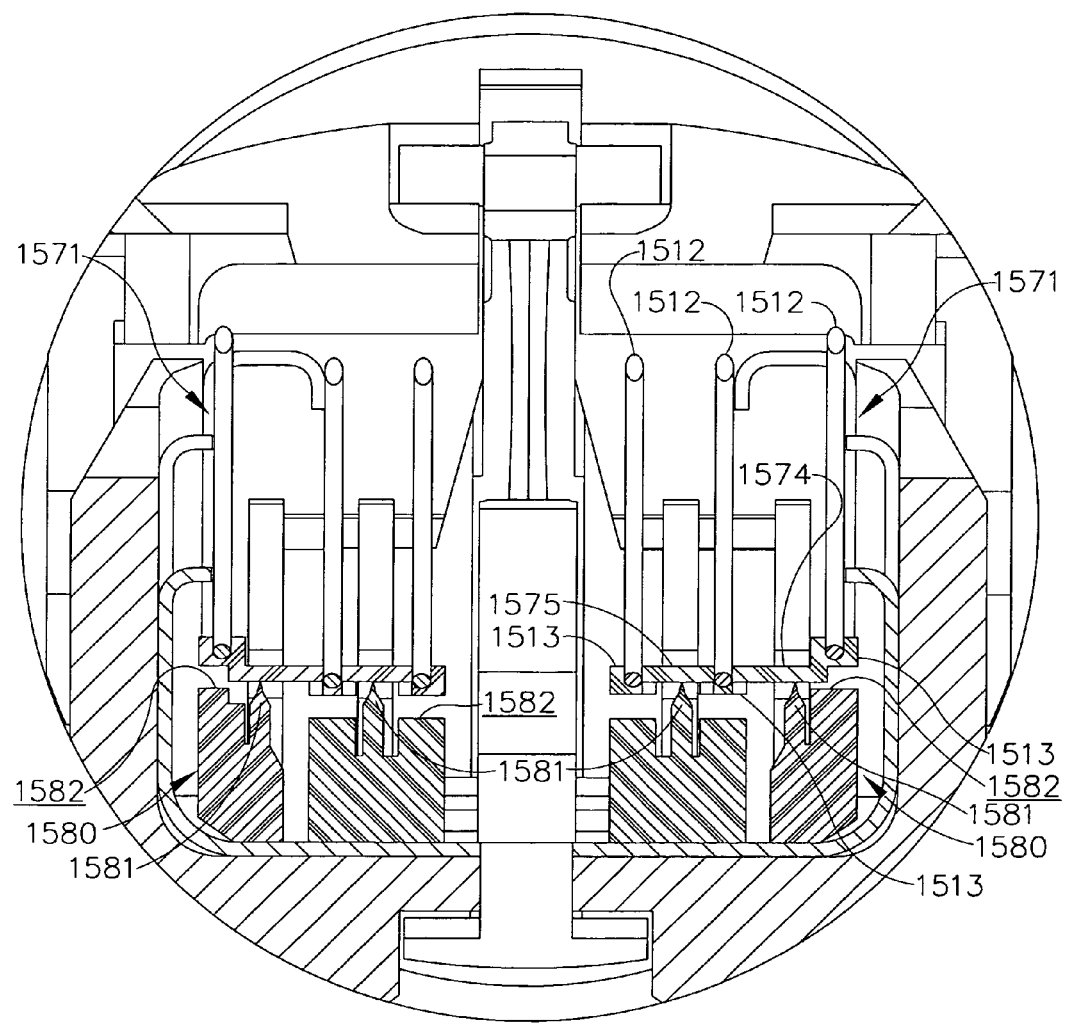
Figure 163:
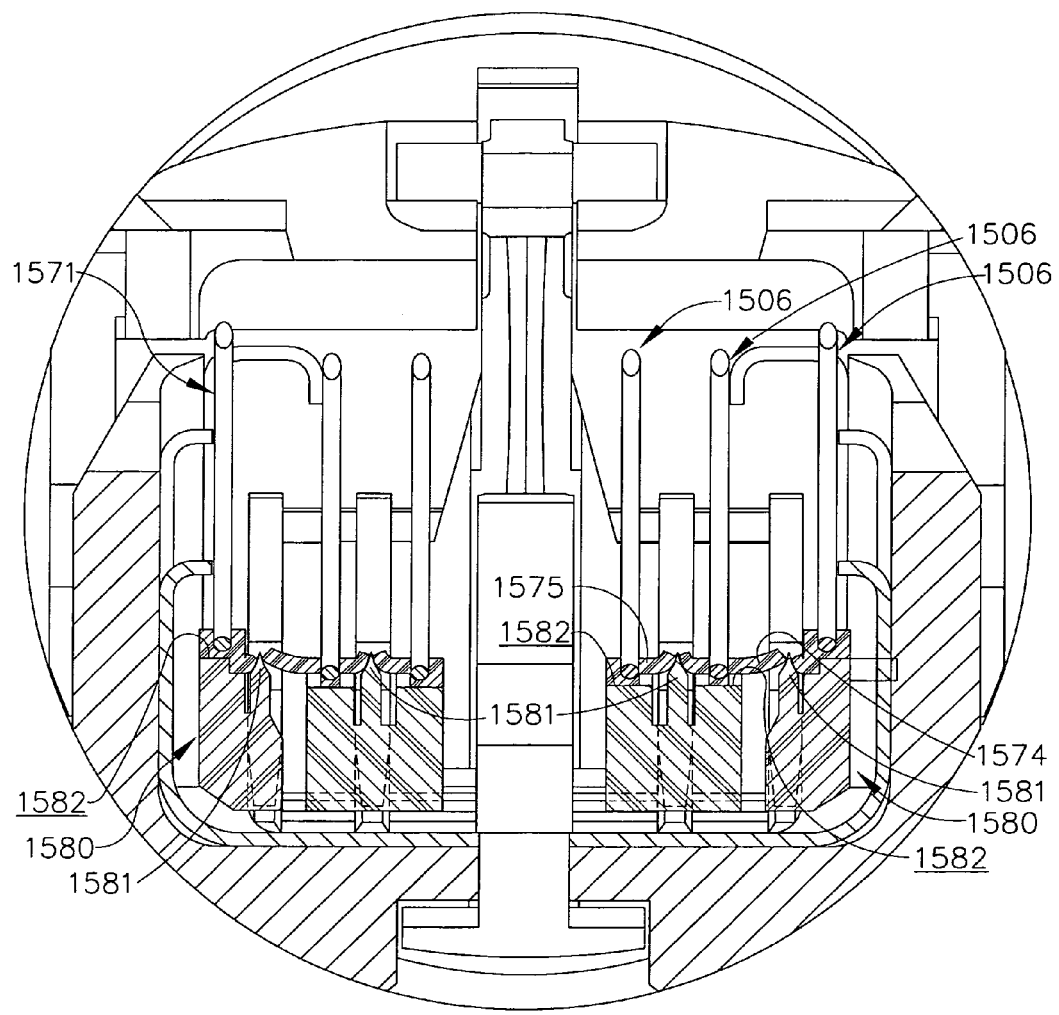
Figure 164:
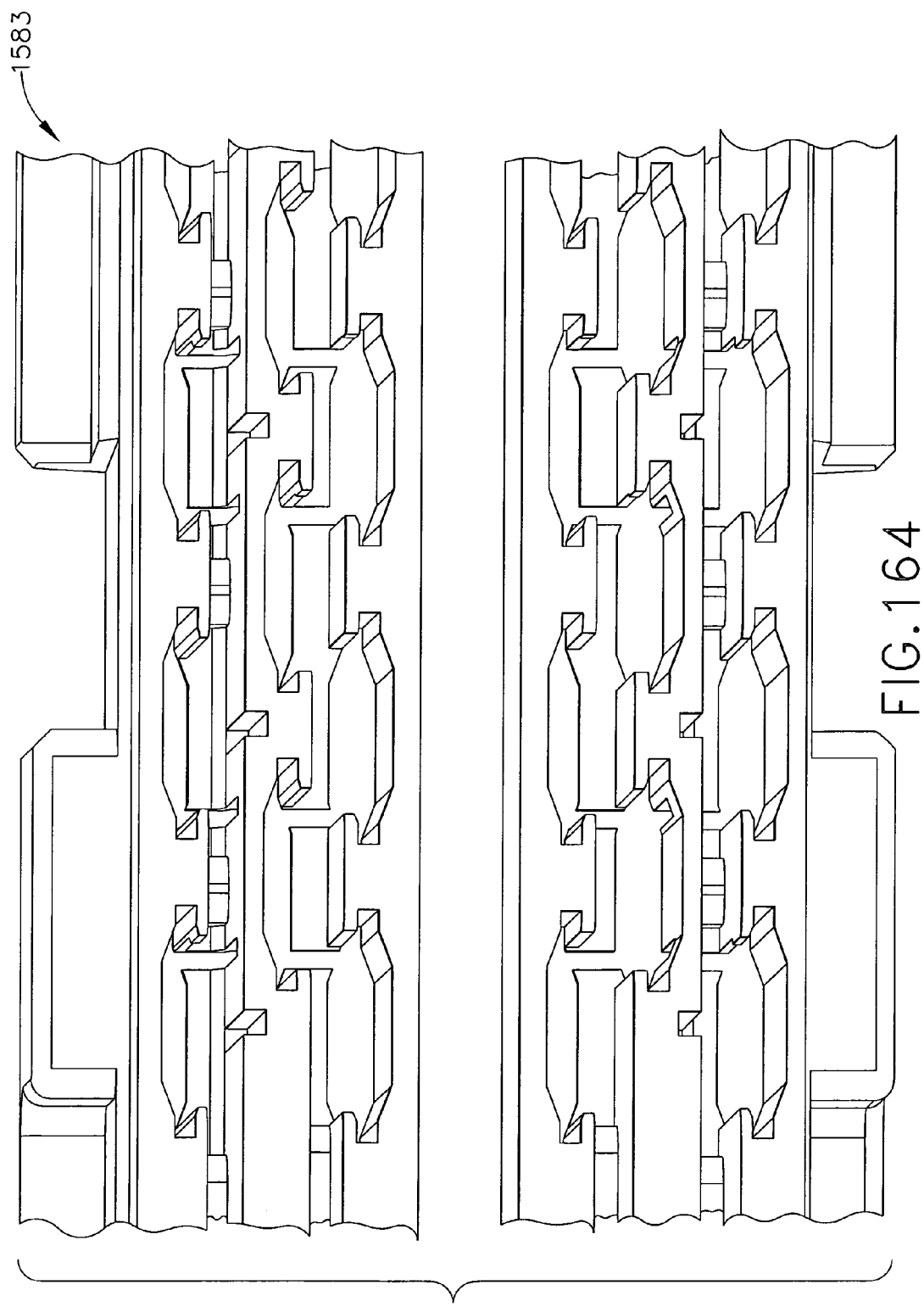
Figure 164A:
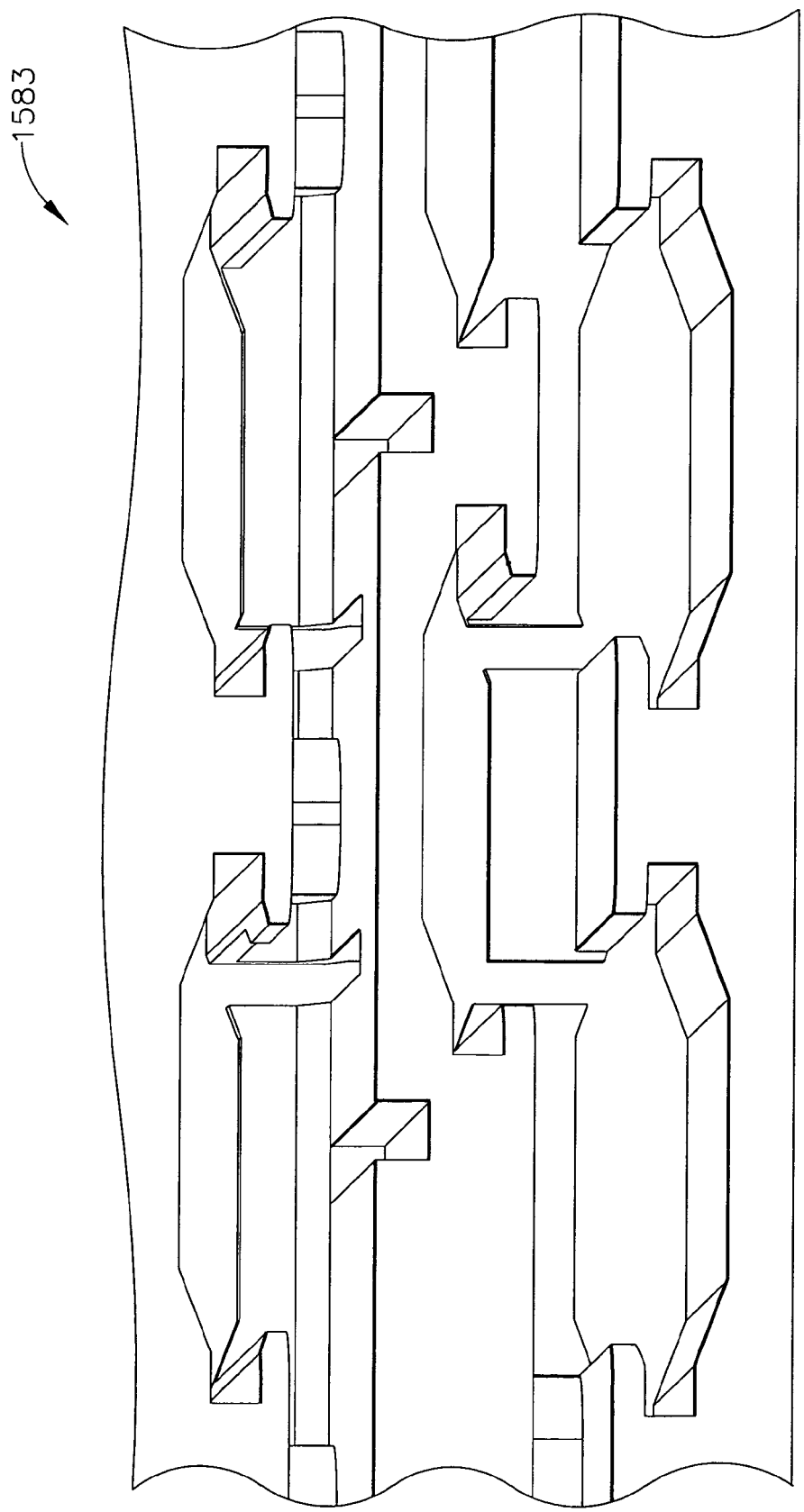
Figure 165:
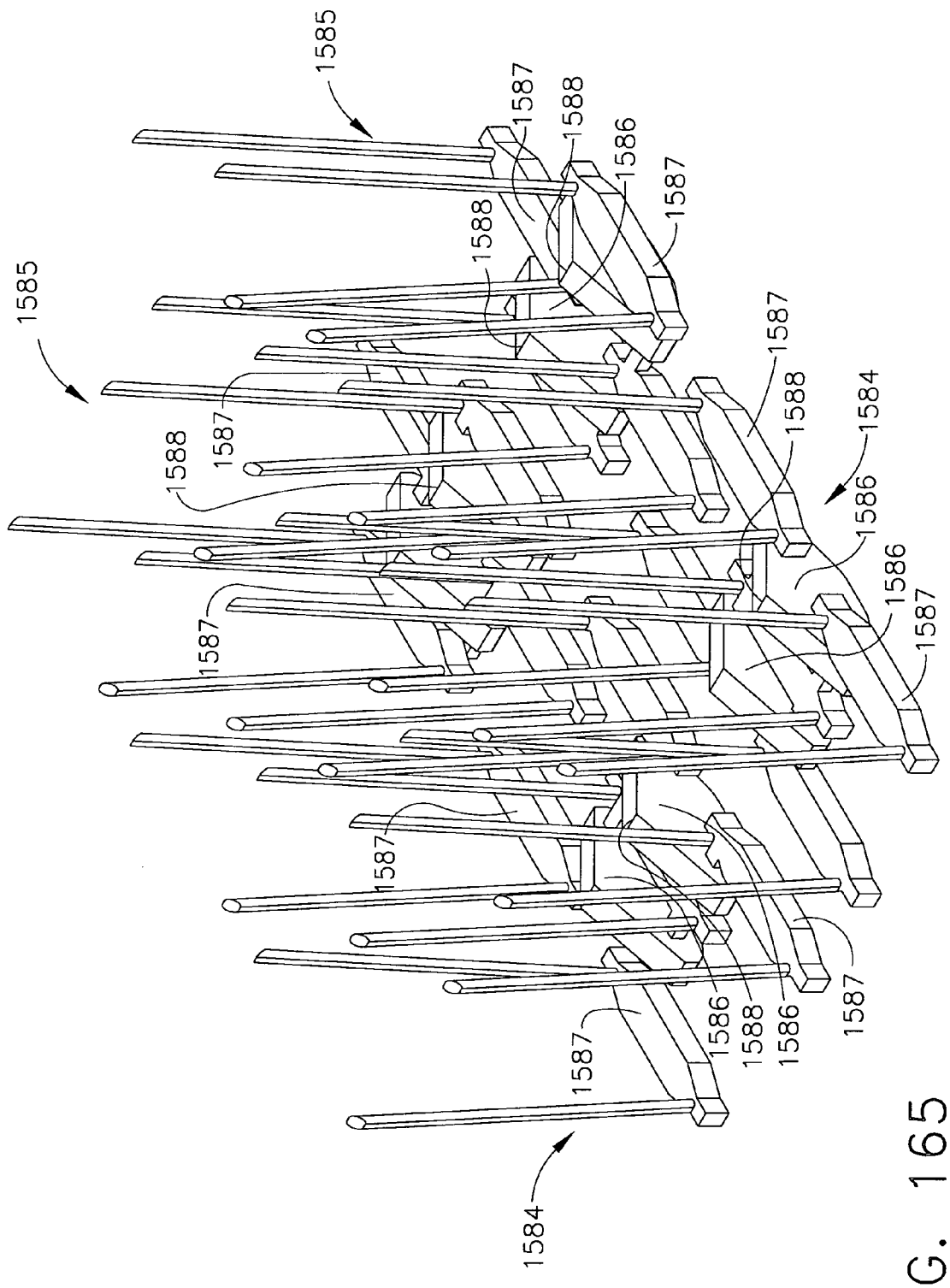
Figure 166:
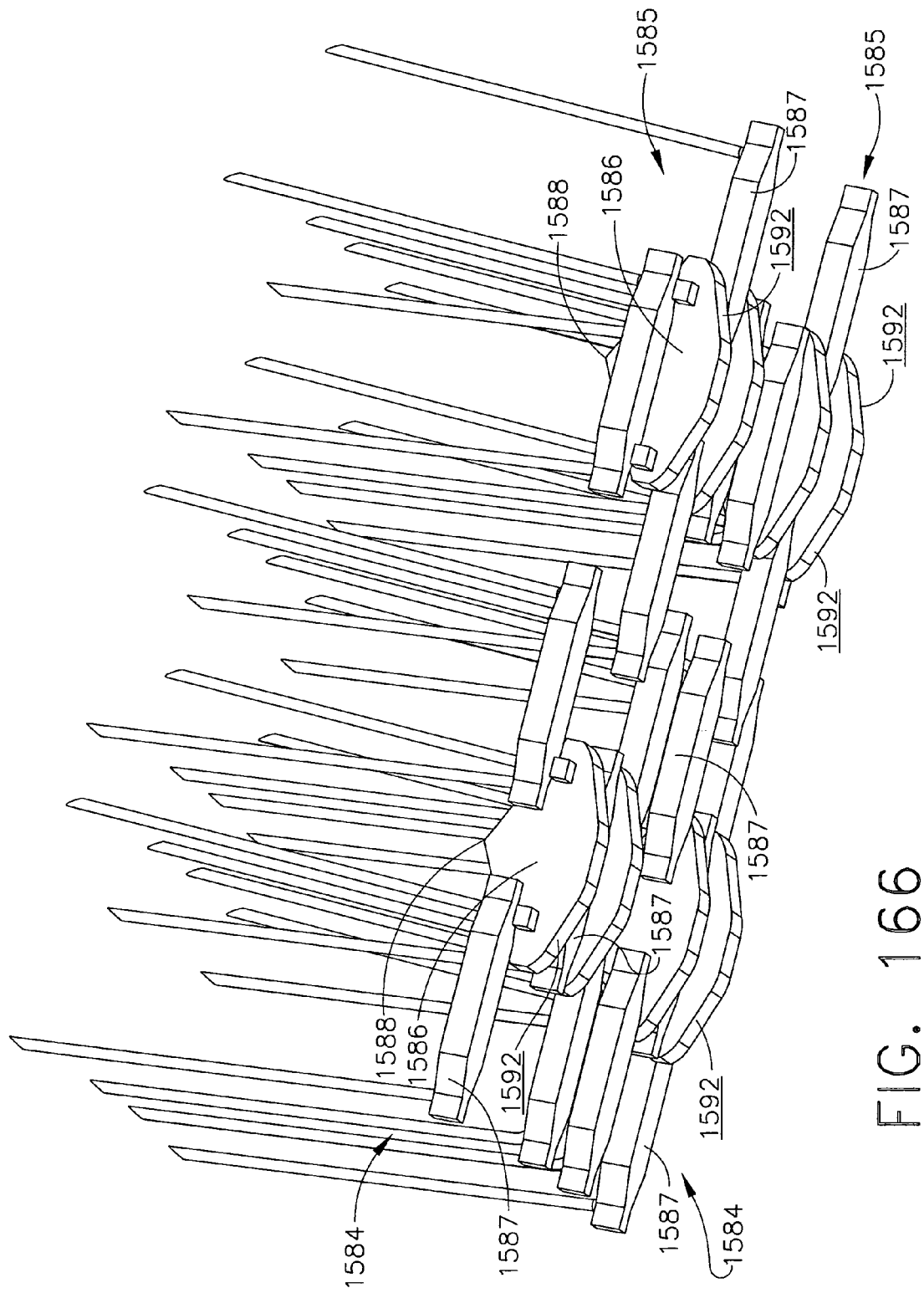
Figure 167:
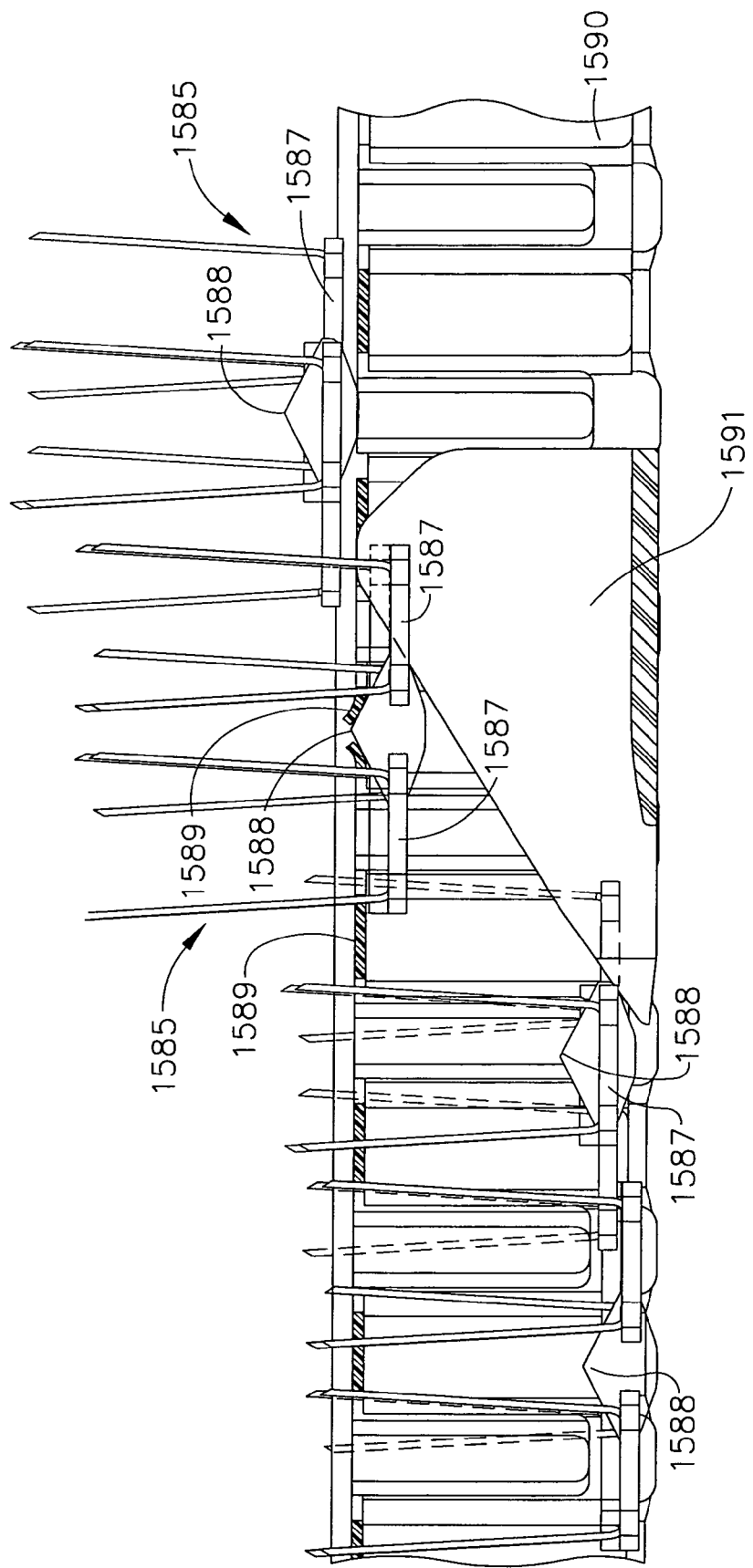
Figure 168:
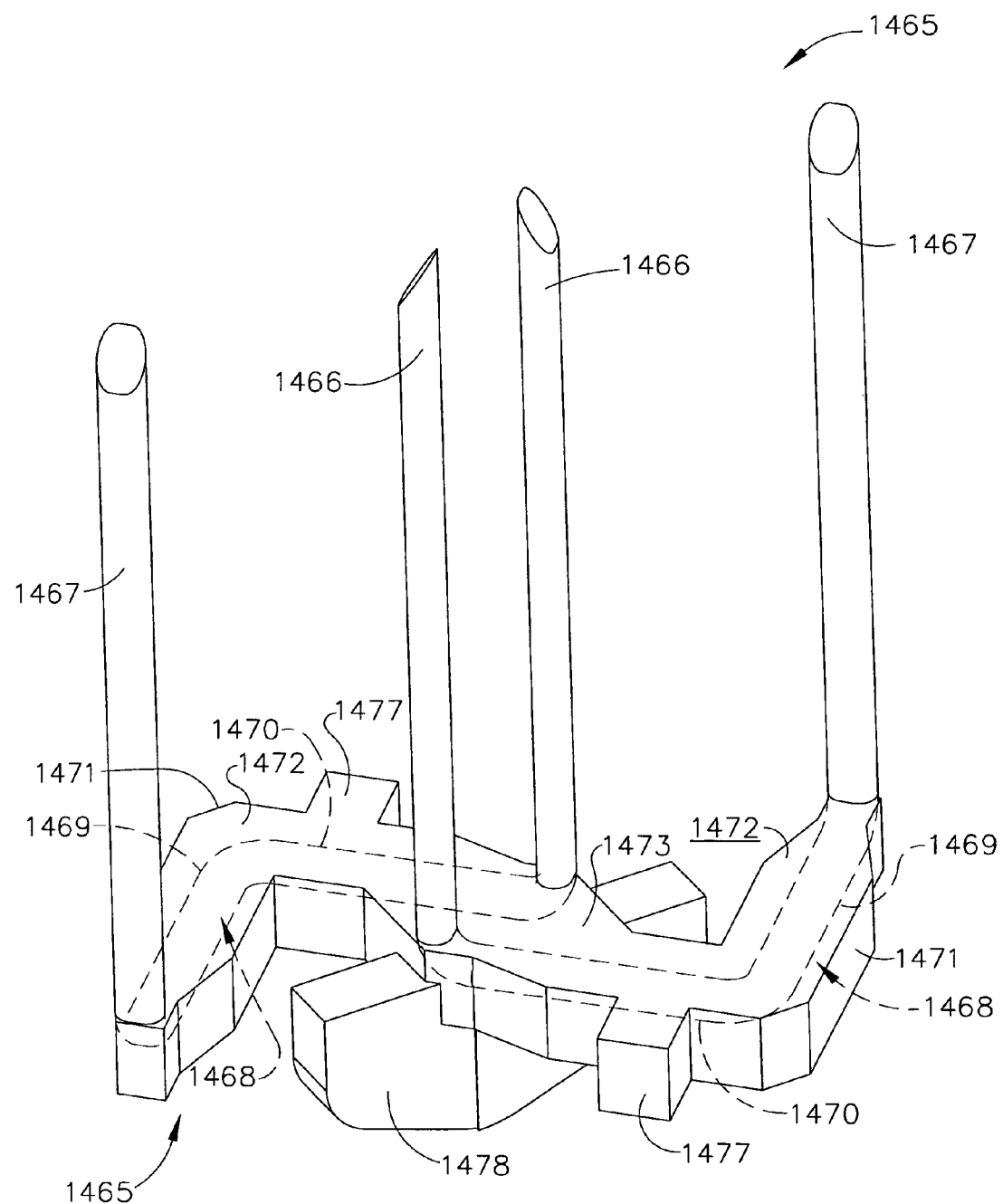
Figure 169:
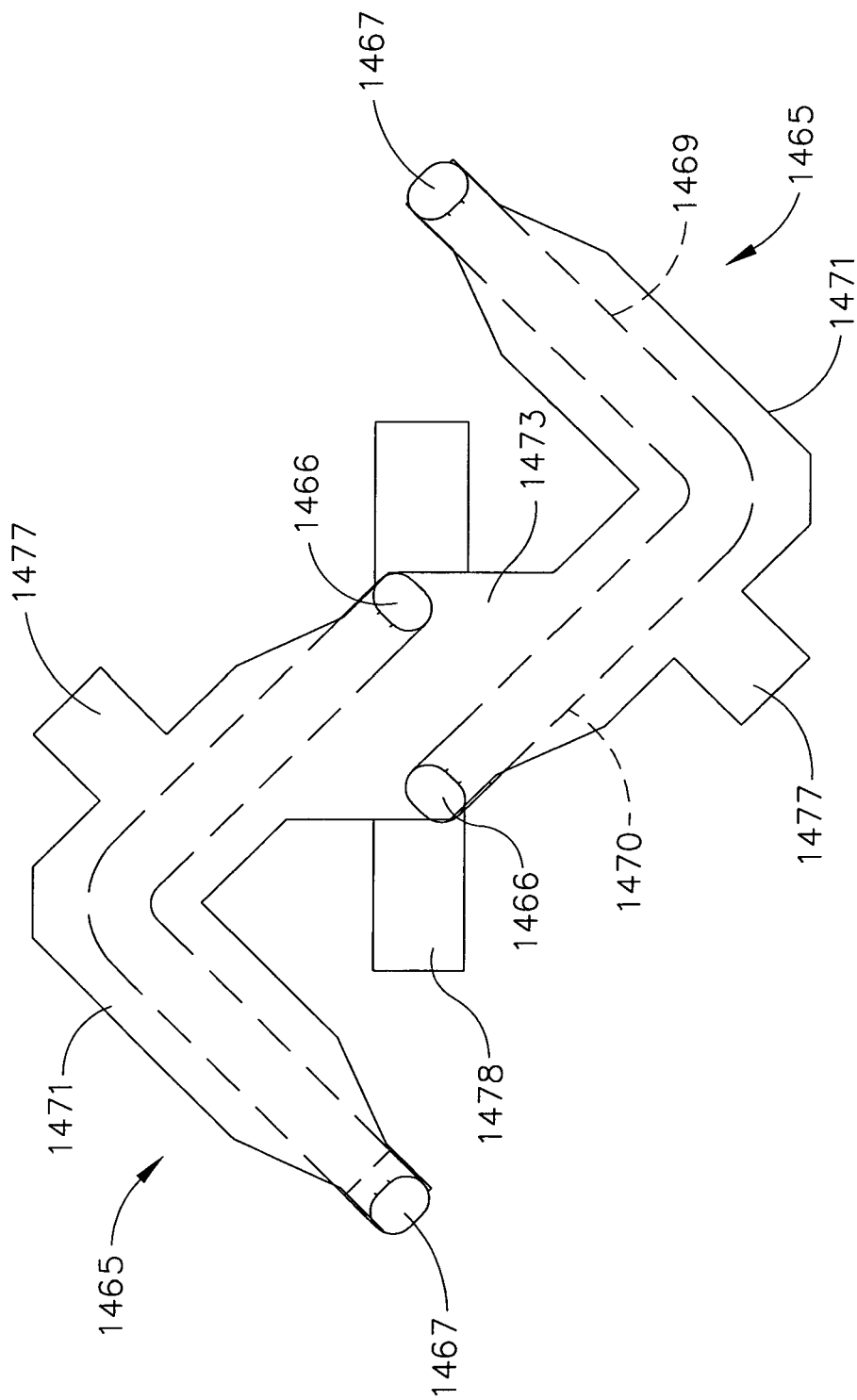
Figure 170:
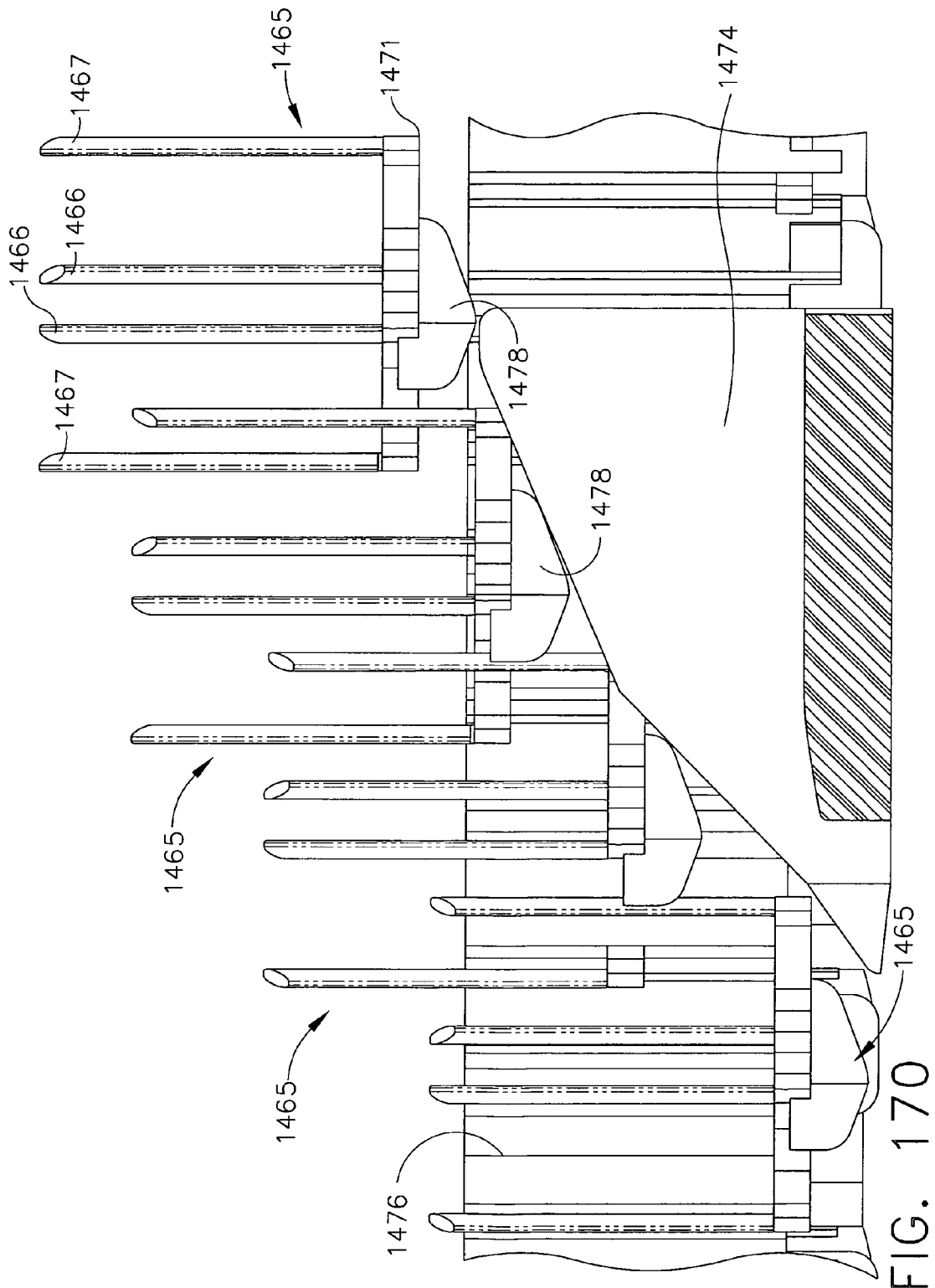
Figure 171:
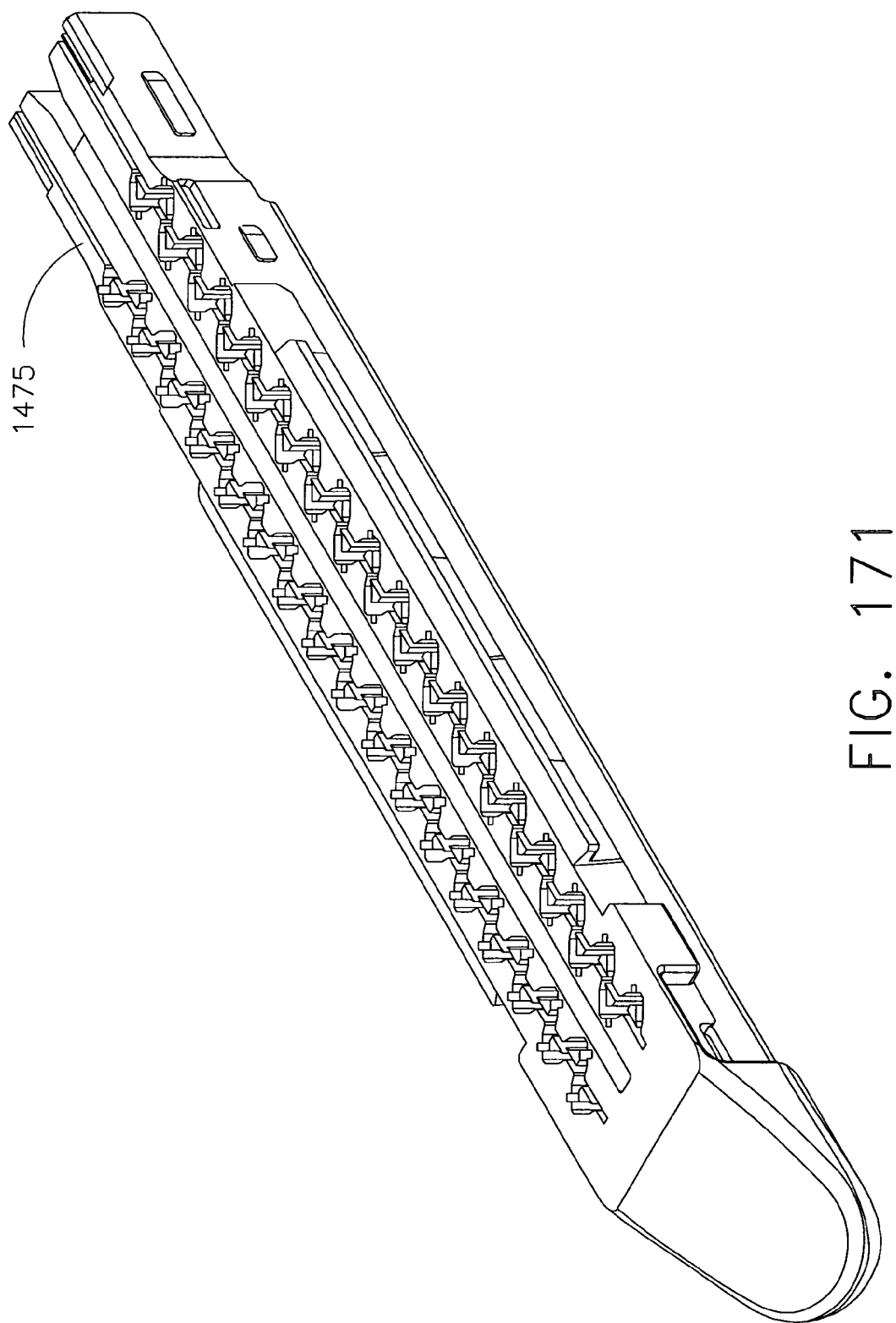
Figure 172:
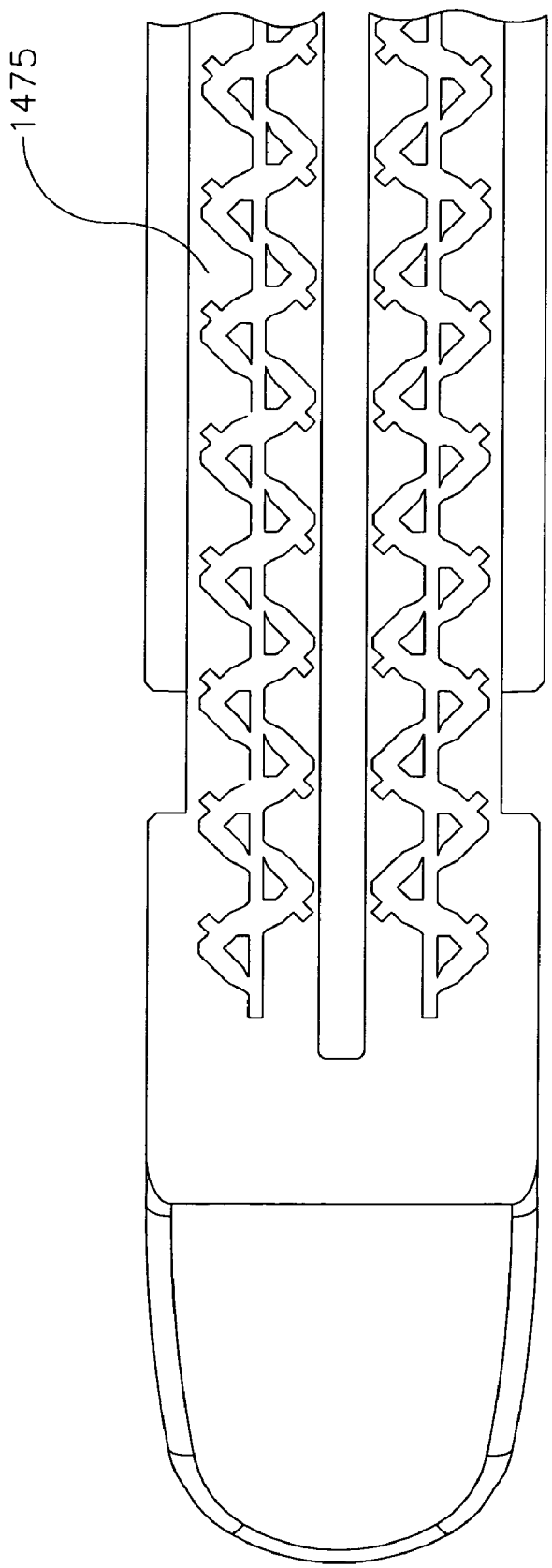
Figure 173:
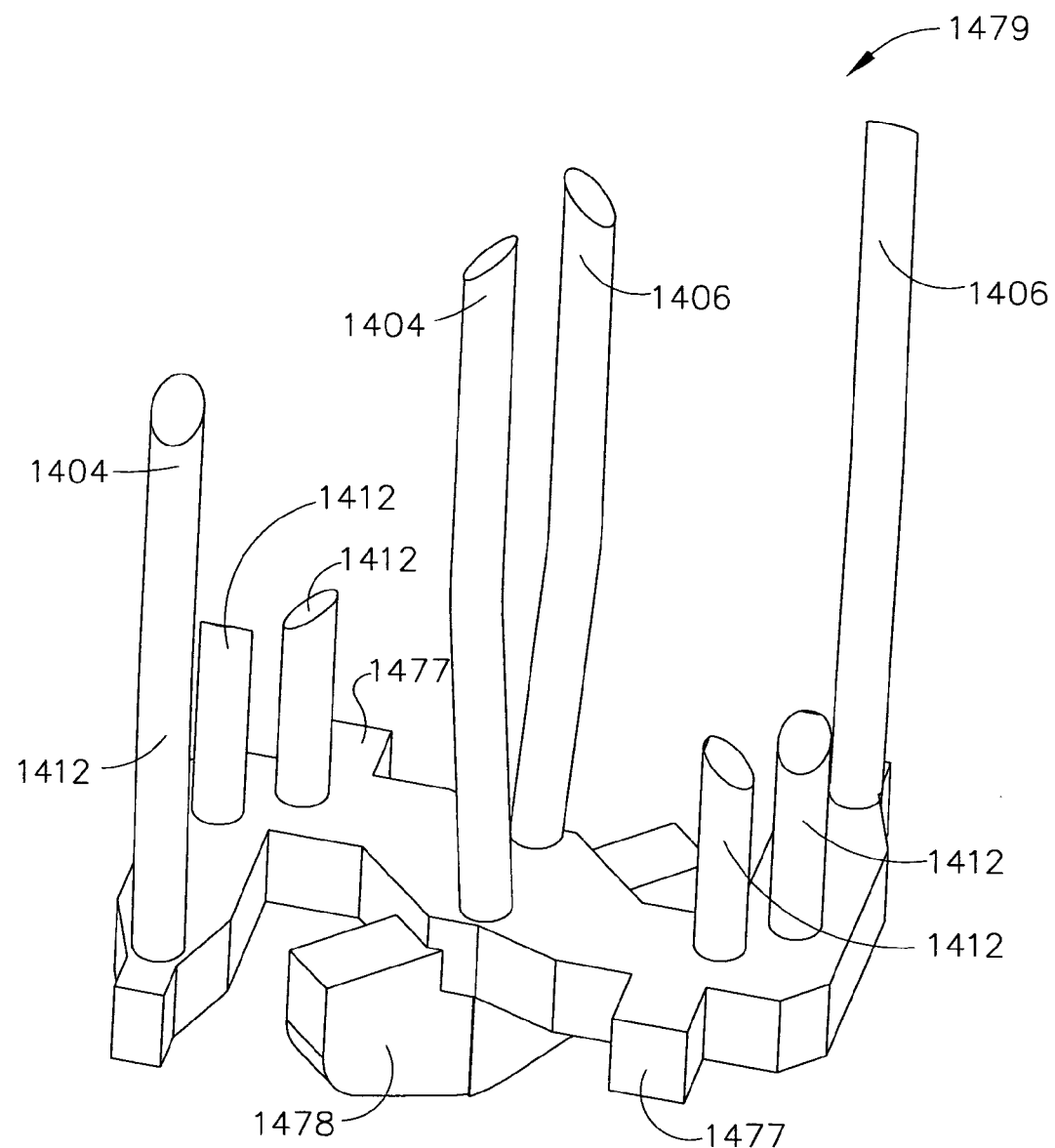
Figure 175:
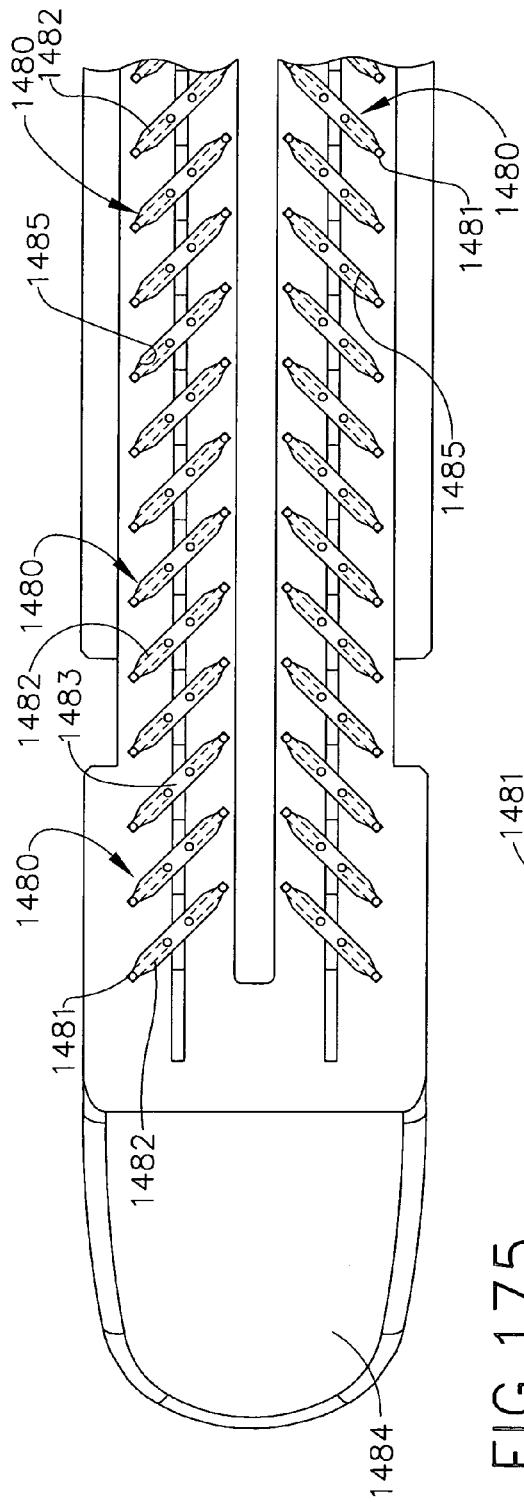
Figure 174:
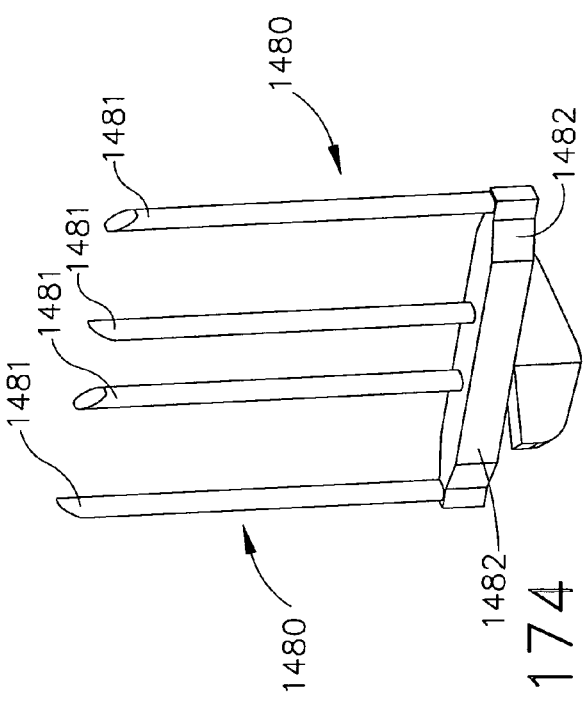

FIG. 140 is a perspective view of staples and a staple cartridge of a stapler in accordance with an embodiment of the present invention;

FIG. 141 is a detail view of the staple cartridge of FIG. 140;

FIG. 142 is a perspective view of a strip of the staples of FIG. 140;

FIG. 143 is a detail view of the staples of FIG. 142;

FIG. 144 is a side cross-sectional view of the staples and staple cartridge of FIG. 140;

FIG. 145 is a perspective view of a strip of staples in accordance with an alternative embodiment of the present invention;

FIG. 146 is a detail view of the staples of FIG. 145;

FIG. 147 is a side cross-sectional view of a stapler deploying the staples of FIG. 145;

FIG. 148 is a perspective view of a strip of staples in accordance with an alternative embodiment of the present invention;

FIG. 149 is a detail view of the staples of FIG. 148;

FIG. 150 is a side cross-sectional view of a stapler deploying the staples of FIG. 149;

FIG. 151 is a perspective view of a strip of staples in accordance with an alternative embodiment of the present invention;

FIG. 152 is a view of the staple strip of FIG. 151 stored within a staple cartridge;

FIG. 153 is a cross-sectional view of the staple cartridge of FIG. 152 taken along line 153-153 in FIG. 152;

FIG. 154 is a cross-sectional view of the staple cartridge of FIG. 152 taken along line 154-154 in FIG. 153;

FIG. 155 is a cross-sectional perspective view of the staple cartridge of FIG. 152 with staples positioned in a first position;

FIG. 156 is a cross-sectional perspective view of the staple cartridge of FIG. 152 with the staples positioned in a second position;

FIG. 157 is an additional cross-sectional perspective view of the staple cartridge of FIG. 152;

FIG. 158 is a perspective view of staples in accordance with an embodiment of the present invention connected in a "puck" configuration;

FIG. 159 is a bottom view of a staple cartridge in accordance with an alternative embodiment of the present invention configured to receive the staples of FIG. 158;

FIG. 159A is a detail view of the staple cartridge of FIG. 159;

FIG. 160 is a perspective of the staples of FIG. 158 positioned over drivers of the staple cartridge of FIG. 159;

FIG. 161 is a perspective view of the drivers of FIG. 160;

FIG. 162 is a cross-sectional view of the staple cartridge of FIG. 159;

FIG. 163 is a second cross-sectional view of the staple cartridge of FIG. 159;

FIG. 164 is a bottom view of a staple cartridge in accordance with an alternative embodiment of the present invention;

FIG. 164A is a detail view of the staple cartridge of FIG. 164;

FIG. 165 is a perspective view of staples in accordance with an alternative embodiment of the present invention;

FIG. 166 is a second perspective view of the staples of FIG. 165;

FIG. 167 is a cross-sectional view of the staples of FIG. 165 being deployed by a stapler in accordance with an embodiment of the present invention;

FIG. 168 is a perspective view of a staple assembly in accordance with an embodiment of the present invention;

FIG. 169 is a top view of the staple assembly of FIG. 168;

FIG. 170 is a perspective view of a staple cartridge configured to receive the staple assembly of FIG. 169;

FIG. 171 is a top view of the staple cartridge of FIG. 170;

FIG. 172 is a cross-sectional view of the staples of FIG. 168 and the staple cartridge of FIG. 170;

FIG. 173 is a perspective view of a staple assembly in accordance with an alternative embodiment of the present invention;

FIG. 174 is a perspective view of a staple assembly in accordance with an alternative embodiment of the present invention for forming non-parallel staple patterns;

FIG. 175 is a top view of the staple of FIG. 174 positioned within a staple cartridge in accordance with an embodiment of the present invention;

FIG. 176 is a top view of staples and a staple cartridge in accordance with an embodiment of the present invention;

FIG. 177 is a detail view of the staple cartridge of FIG. 176; and

Figure 178:
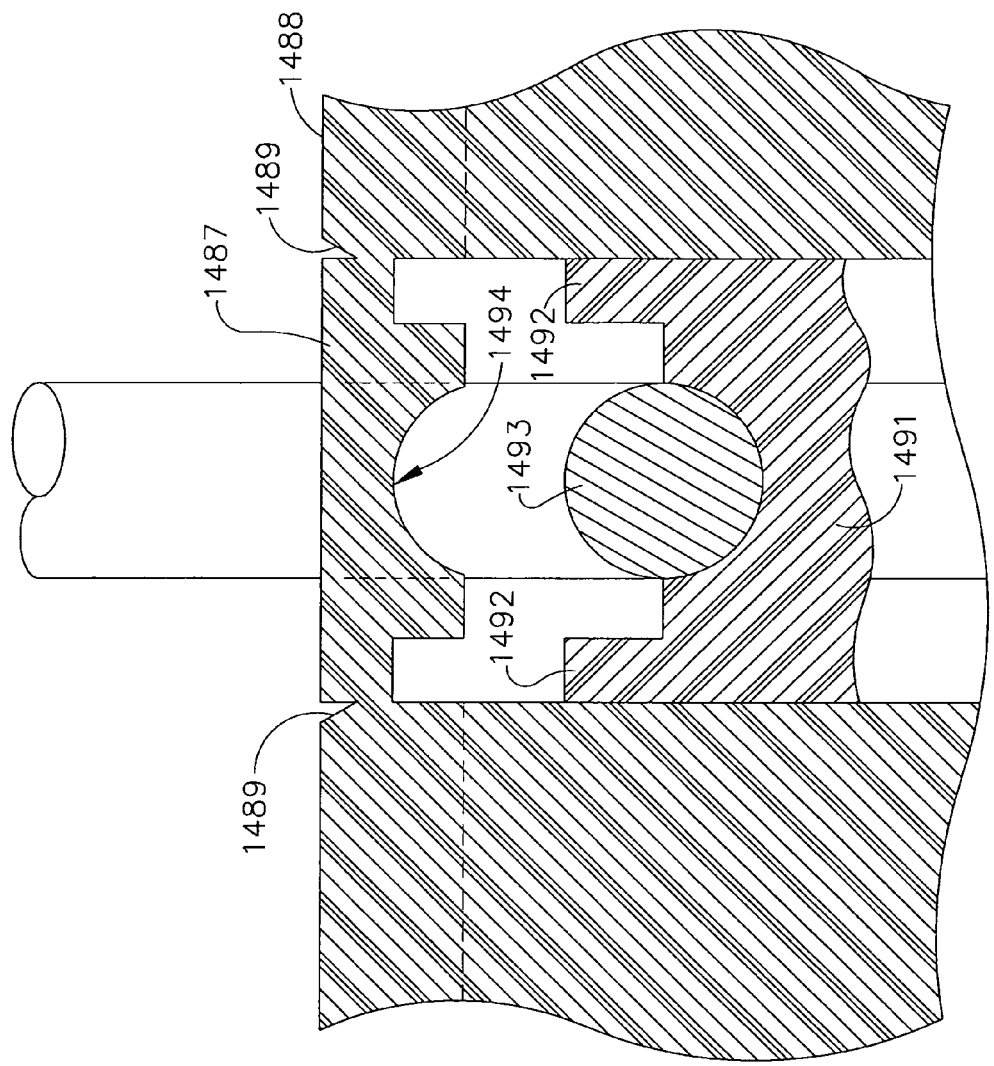

FIG. 178 is a cross-sectional view illustrating the shearable deck of the staple cartridge of FIG. 176.

DETAILED DESCRIPTION

Figure 1:
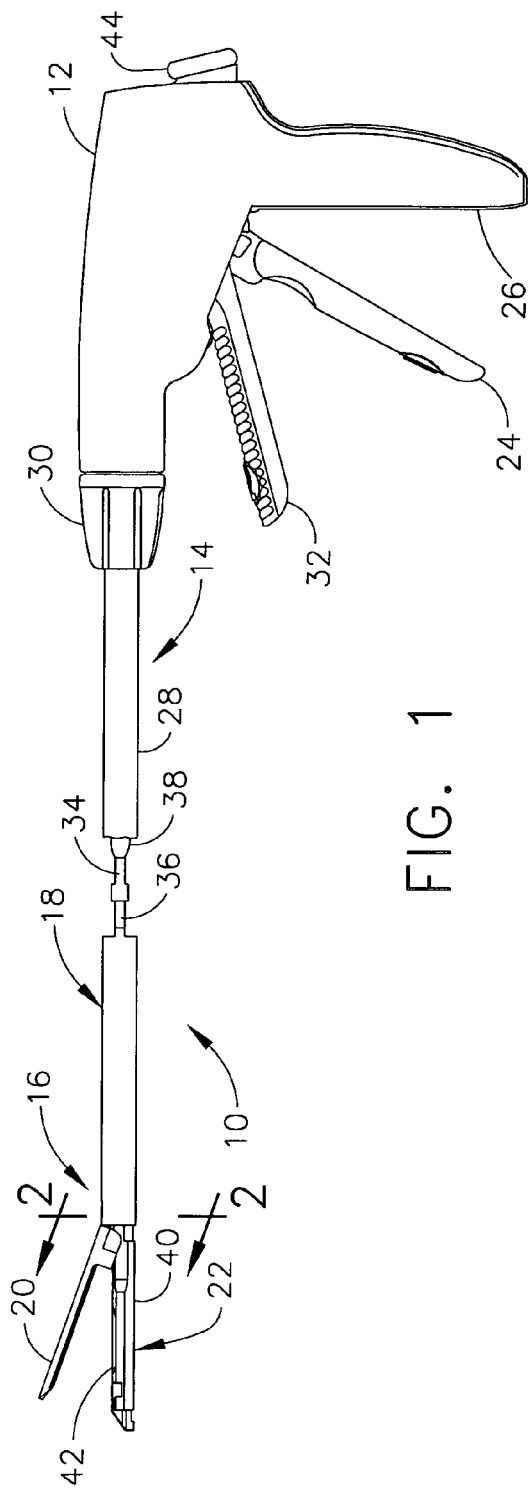
FIG. 1 is a left side view in elevation of a surgical stapling and severing instrument with an open end effector (staple applying assembly) with a shaft partially cut away to expose a firing member of a proximal firing rod and distal firing bar guided by a frame ground and encompassed by a closure sleeve.

Turning to the Drawings, wherein like numerals denote like components throughout the several views, in FIG. 1, a surgical stapling and severing instrument 10 includes a handle portion 12 that is manipulated to position an implement portion 14 including a fastening end effector, depicted as a staple applying assembly 16, distally attached to an elongate shaft 18. The implement portion 14 is sized for insertion through a cannula of a trocar (not shown) for an endoscopic or laparoscopic surgical procedure with an upper jaw (anvil) 20 and a lower jaw 22 of the staple applying assembly 16 closed by depression of a closure trigger 24 toward a pistol grip 26 of the handle portion 12, which advances an outer closure sleeve 28 of the elongate shaft 18 to pivot shut the anvil 20.

Once inserted into an insufflated body cavity or lumen, the surgeon may rotate the implement portion 14 about its longitudinal axis by twisting a shaft rotation knob 30 that engages across a distal end of the handle 12 and a proximal end of the elongate shaft 18. Thus positioned, the closure trigger 24 may be released, opening the anvil 20 so that tissue may be grasped and positioned. Once satisfied with the tissue held in the staple applying assembly 16, the surgeon depresses the closure trigger 24 until locked against the pistol grip 26, clamping tissue inside of the staple applying assembly 16.

Then a firing trigger 32 is depressed, drawn toward the closure trigger 24 and pistol grip 26, thereby applying a firing force or motion thereto to distally advance a firing member from an unfired position. The firing member is depicted as including a proximal firing rod 34 attached to a distal firing bar 36, that is supported within a frame ground 38 that connects the handle portion 12 to the staple applying assembly 16. During the staple firing motion, the firing bar 36 engages an elongate staple channel 40 and actuates a staple cartridge 42 contained therein, both forming the lower jaw 22. The firing bar 36 also engages the closed anvil 20. After releasing the firing trigger 32 to apply a retraction force or motion to the firing bar 36, depression of a closure release button 44 unclamps the closure trigger 24 so that the closure sleeve 28 may be retracted to pivot and open the anvil 20 to release the severed and stapled tissue from the staple applying assembly 16.

It should be appreciated that spatial terms such as vertical, horizontal, right, left etc., are given herein with reference to the figures assuming that the longitudinal axis of the surgical instrument 10 is co-axial to the central axis of the elongate shaft 18, with the triggers 24, 32 extending downwardly at an acute angle from the bottom of the handle assembly 12. In actual practice, however, the surgical instrument 10 may be oriented at various angles and, as such, these spatial terms are used relative to the surgical instrument 10 itself. Further, "proximal" is used to denote a perspective of a clinician who is behind the handle assembly 12 who places the implement portion 14 distal, or away from him or herself. However, surgical instruments are used in many orientations and positions, and these terms are not intended to be limiting and absolute.

Figure 2:
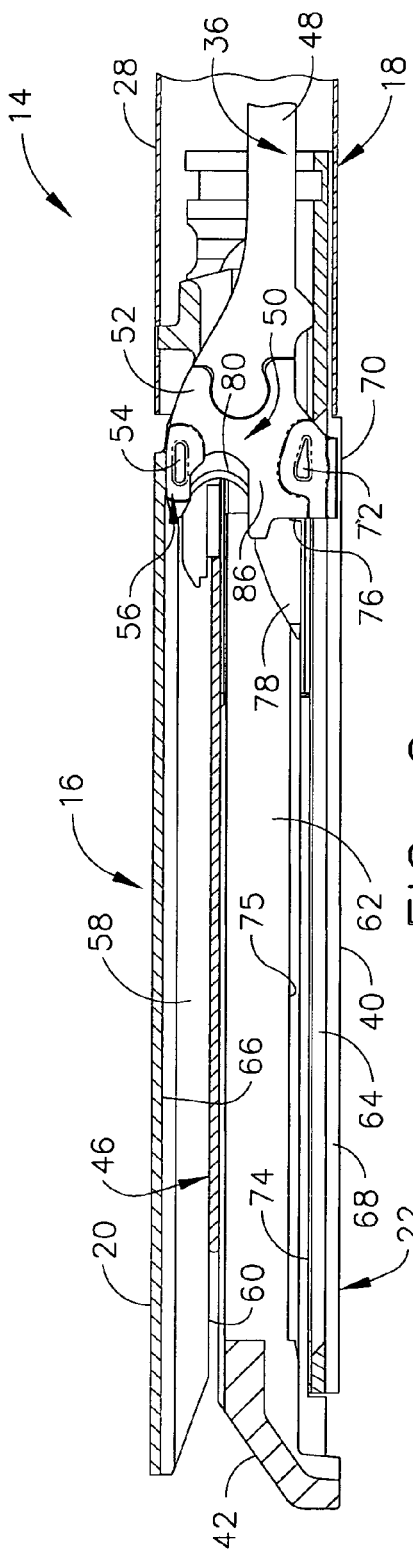
FIG. 2 is a left side view of a closed end effector (staple applying assembly) with a retracted force adjusted height firing bar consistent with the present invention of the surgical stapling and severing instrument of FIG. 1 taken in longitudinal vertical cross section along lines 2-2.
Figure 3:
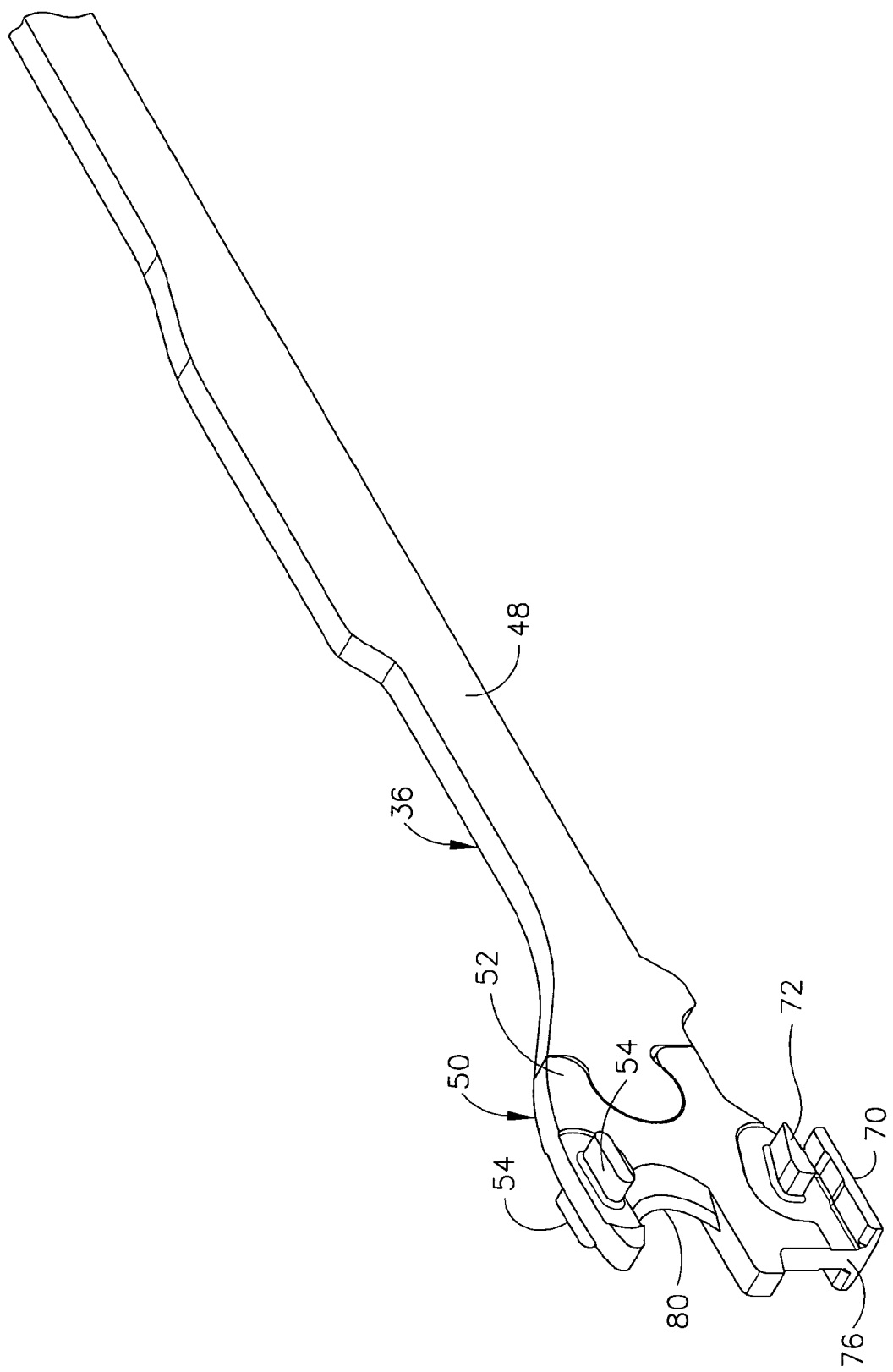
FIG. 3 is a left isometric view of the force adjusted (compliant) height firing bar of FIG. 2.

In FIG. 2, the staple applying assembly 16 is closed upon compressed tissue 46. In FIGS. 2-3, the firing bar 36 has a proximal portion 48 that is attached to a distal E-beam 50 that translates within the staple applying assembly 16. As depicted with the firing bar 36 retracted, a vertical portion 52 of the E-beam 50 resides essentially aft of the staple cartridge 42, as after a new staple cartridge 42 has been inserted into the elongate staple channel 40. An upper pin 54 that extends laterally from an upper portion of the vertical portion 52 of the E-beam 50 initially resides within an anvil pocket 56 recessed near a proximal pivoting end of the anvil 20. As the E-beam 50 is distally advanced during the staple firing motion, the vertical portion 52 passes through a narrow longitudinal anvil slot 58 (FIGS. 1, 11) formed in a staple forming undersurface 60 of the anvil 20, a proximally open vertical slot 62 formed in cartridge 42 and an underlying longitudinal channel slot 64 formed in the elongate staple channel 40.

Figure 11:
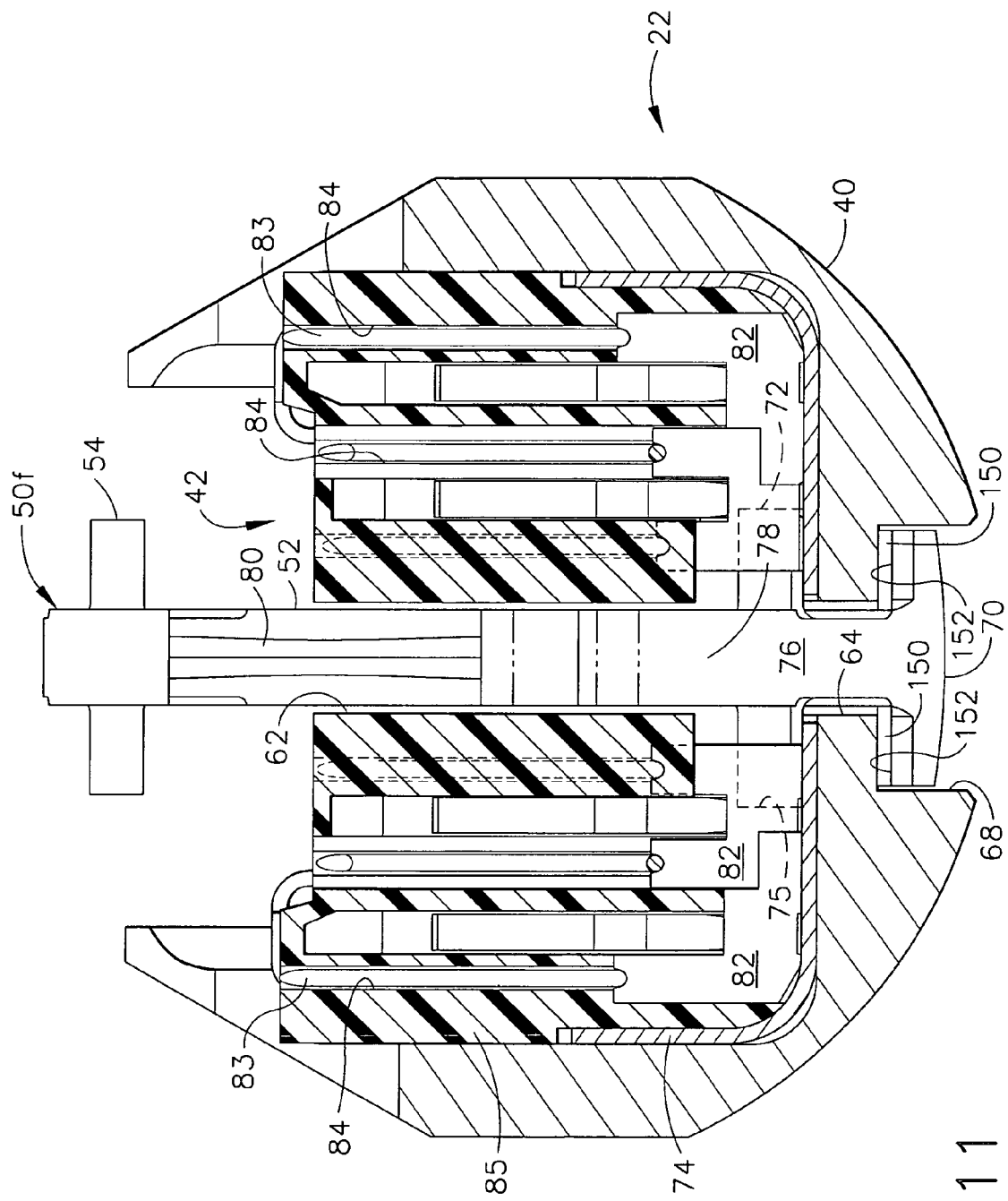
FIG. 11 is a front view in elevation taken in vertical and transverse cross section through the padded lower foot of the end effector (staple applying assembly) of the surgical stapling and severing instrument of FIG. 1.

In FIGS. 2, 11, the narrow longitudinal anvil slot 58 (FIG. 2) communicates upwardly to a laterally widened longitudinal anvil channel 66 sized to slidingly receive the upper pin 54. The longitudinal channel slot 64 communicates downwardly to a laterally widened longitudinal channel track 68 that receives a lower foot 70, which is sized to slide therein and is attached at a bottom of the vertical portion 52 of the E-beam 50. A laterally widened middle pin 72 extending from the vertical portion 52 of the E-beam 50 is positioned to slide along a top surface of a bottom tray 74 of the staple cartridge 42, which in turn rests upon the elongate staple channel 40. A longitudinal firing recess 75 formed in the staple cartridge 42 above the bottom tray 74 is sized to allow the middle pin 72 to translate through the staple cartridge 42.

A distal driving surface 76 of the vertical portion 52 of the E-beam 50 is positioned to translate through the proximally open vertical slot 62 of the staple cartridge 42 and distally drive a wedge sled 78 proximally positioned in the staple cartridge 42. The vertical portion 52 of the E-beam 50 includes a cutting surface 80 along a distal edge above the distal driving surface 76 and below the upper pin 54 that severs the clamped tissue 46 simultaneously with this stapling.

With particular reference to FIG. 11, it should be appreciated that the wedge sled 78 drives upwardly staple drivers 82 that in turn drive upwardly staples 83 out of staple apertures 84 formed in a staple body 85 of the staple cartridge 42 to form against the undersurface 60 of the anvil 20 which is in confronting relationship relative to an upper surface 43 of staple cartridge 42 (FIG. 2).

In FIGS. 2, 11, advantageously, the illustrative spacing, denoted by arrow 86 (FIG. 2), between the upper pin 54 is compliantly biased toward a compressed state wherein 0.015 inches of compressed tissue 46 is contained in the staple applying assembly 16. However, a larger amount of compressed tissue 46 up to about 0.025 inches is allowed by an inherent flexure of the E-beam 50. Excessive flexure, of perhaps up to 0.030 inches, is avoided should the length of staples be insufficient to form with the additional height. It should be appreciated that these dimensions are illustrative for a staple height of 0.036 inches. The same would be true for each category of staple, however.

Figure 4:
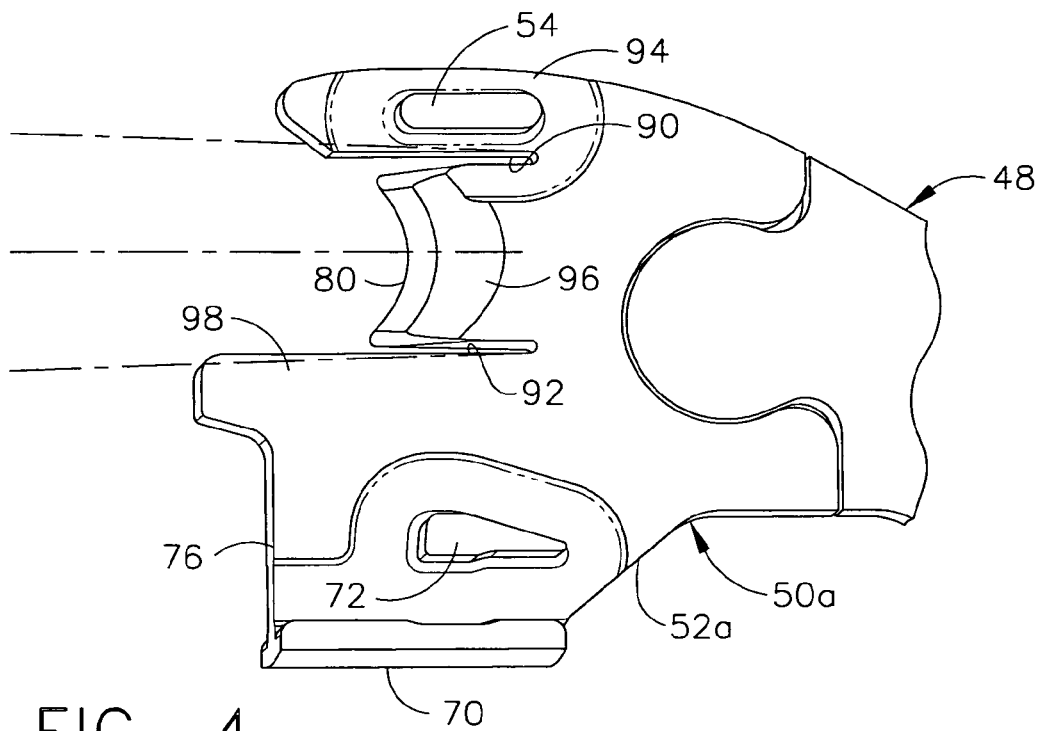
FIG. 4 is a left side view of a distal portion ("E-beam") of a first version of the force adjusted height firing bar of FIG. 2 having horizontal slits formed respectively between the top pin and cutting surface and between the middle pin and the cutting surface to enhance vertical flexure.

In FIG. 4. a first version of a compliant E-beam 50a includes top and bottom horizontal slits 90, 92 from a distal edge of the vertical portion 52a, perhaps formed by electro drilling machine (EDM). The vertical portion 52a thus contains a vertically compliant top distally projecting arm 94 containing the upper pin 54, a knife flange 96 containing the cutting surface 80, and a lower vertical portion 98 containing the distal driving surface 76, middle pin 72 and lower foot 70. The horizontal slits 90, 92 allow a compliant vertical spacing by allowing the top distally arm 94 to pivot upwardly to adjust to increased force from compressed tissue 46 (not shown).

Figure 5:
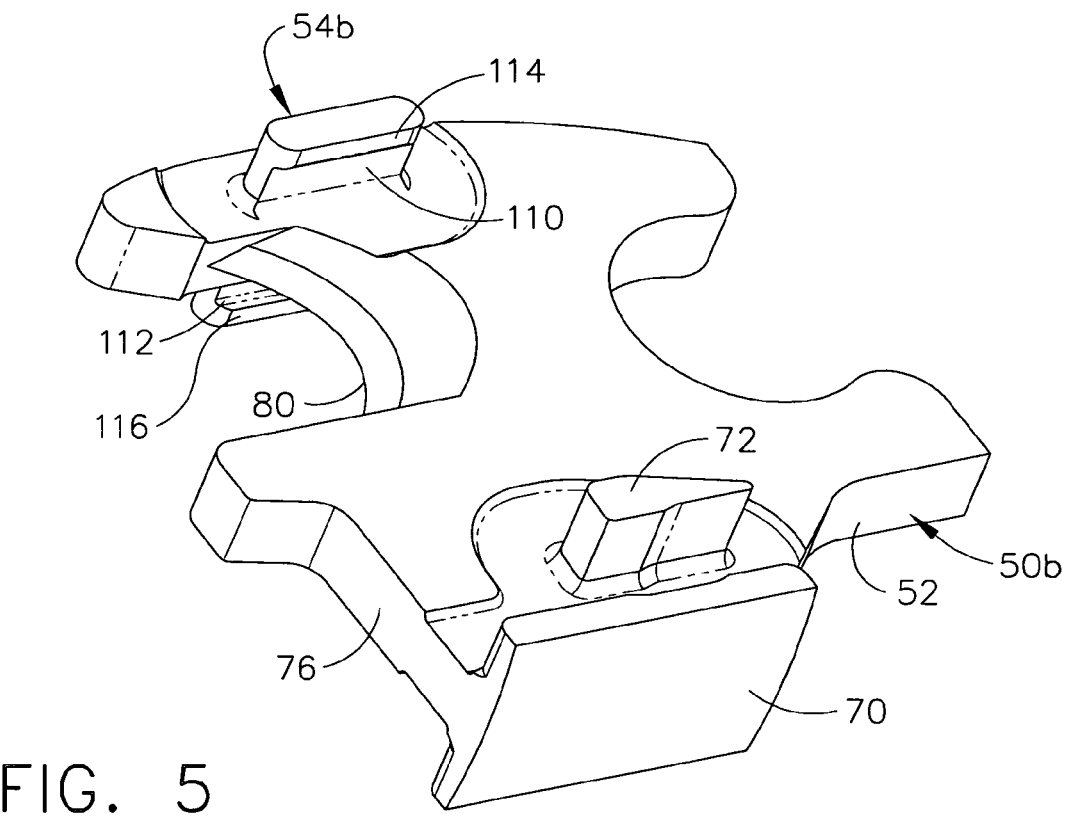
FIG. 5 is a lower left isometric view of a distal portion ("E-beam") of a second version of the force adjusted firing bar of FIG. 2 having a relieved lower area of an upper pin to enhance vertical flexure.
Figure 6:
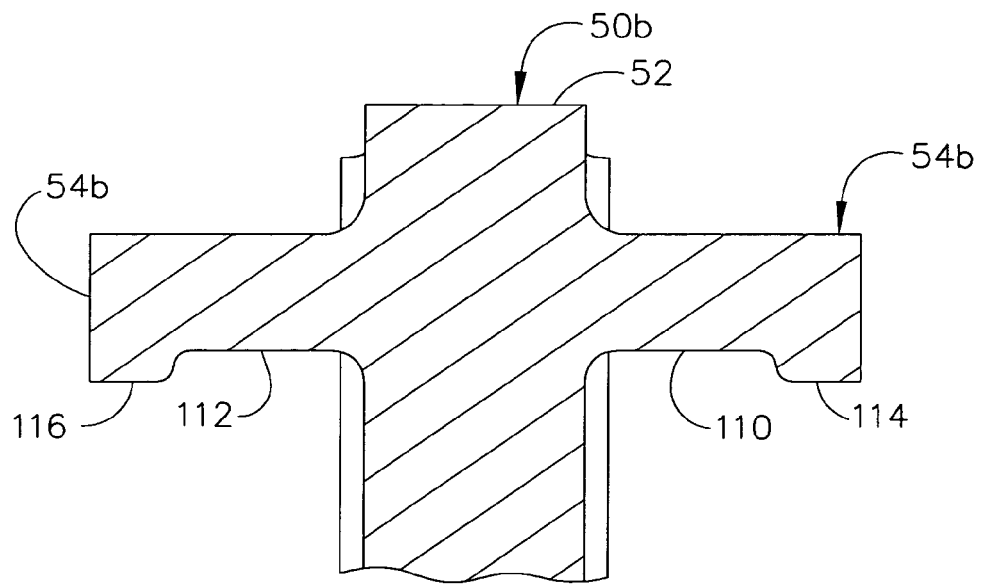
FIG. 6 is a front view in elevation of an upper portion of the E-beam of FIG. 5 taken in vertical and transverse cross section through the upper pin along lines 6-6.

In FIGS. 5-6, a second version of a compliant E-beam 50b includes left and right lower relieved areas 110, 112 formed into an upper pin 54b to each side of the vertical portion 52, leaving left and right lower bearing points 114, 116 respectively. The outboard position of the bearing points 114, 116 provides a long moment arm to exert the force to flex. It should be appreciated given the benefit of the present disclosure that the dimensions of the relieved areas 110, 112 and the choice of materials for the compliant E-beam 50b may be selected for a desired degree of flexure, given the staple size and other considerations.

Figure 7:
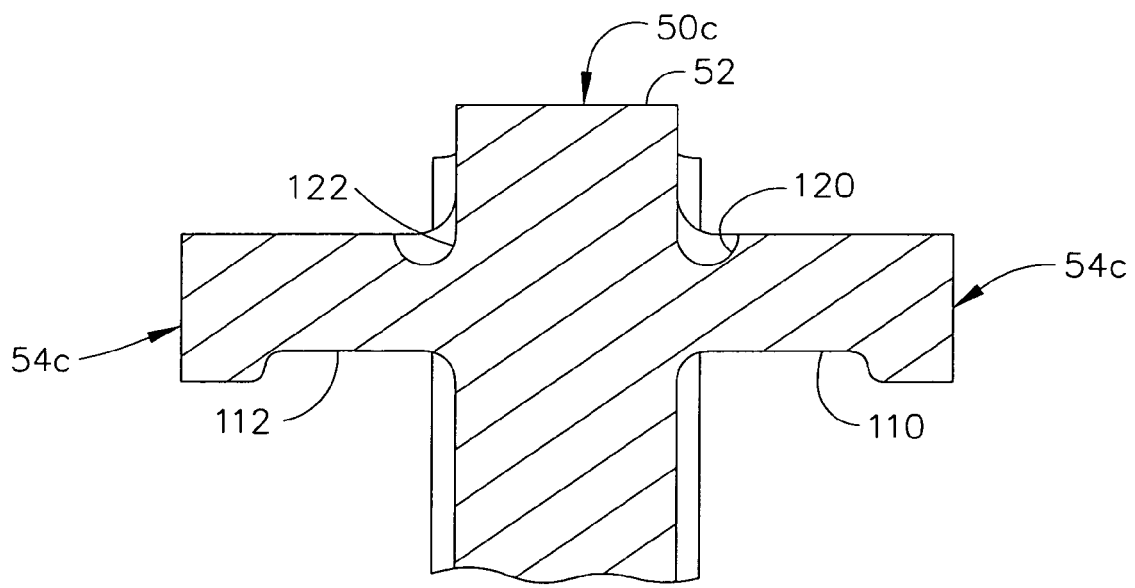
FIG. 7 is a front view of an upper portion of a third version of the E-beam of FIG. 5 taken in vertical and transverse cross section along lines 6-6 but further including relieved upper root attachments of the top pin for enhanced vertical flexure.

In FIG. 7, a third version of a compliant E-beam 50c is as described above in FIGS. 5-6 with further flexure provided by left and right upper narrow relieved areas 120, 122 formed into opposite top root surfaces of an upper pin 54c proximate to the vertical portion 52.

Figure 8:
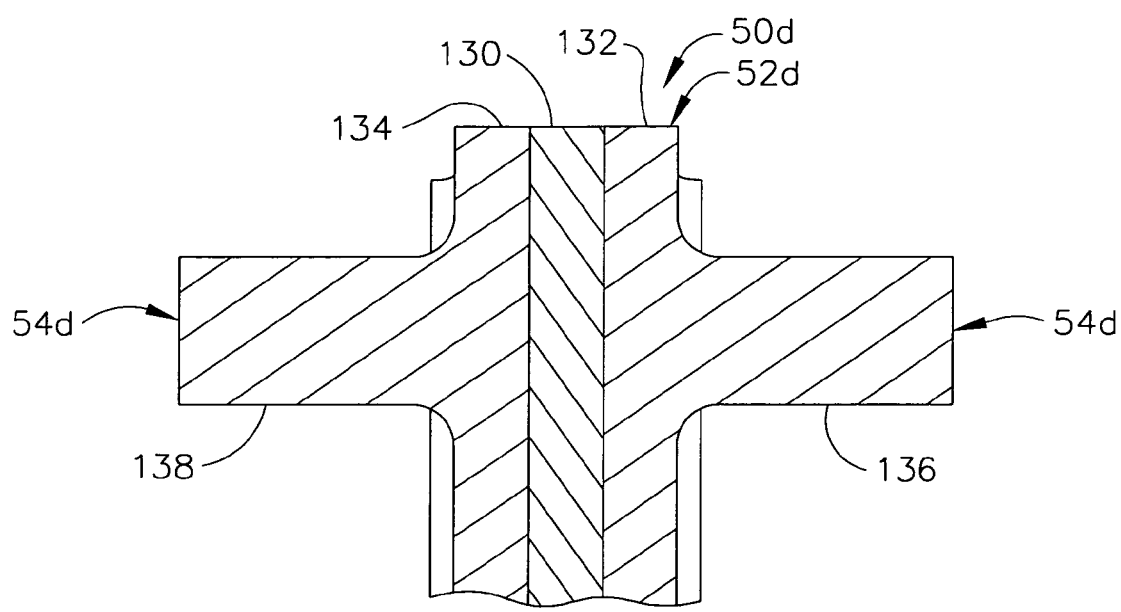
FIG. 8 is a front view of an upper portion of a fourth version of the E-beam of FIG. 5 taken in vertical and transverse cross section along lines 6-6 but including a resilient inner vertical laminate layer instead of a relieved undersurface of the top pin for enhanced vertical flexure.

In FIG. 8, a fourth version of a compliant E-beam 50d is as described for FIGS. 2-3 with an added feature of a composite/laminate vertical portion 52d that includes a central resilient vertical layer 130 sandwiched between left and right vertical layers 132, 134 that support respectively left and right portions 136, 138 of an upper pin 54d. As the left and right portions 136, 138 are flexed either up or down, the resulting bowing of the left and right vertical layers 132, 134 are accommodated by a corresponding compression or expansion of the central resilient vertical layer 130.

Figure 9:
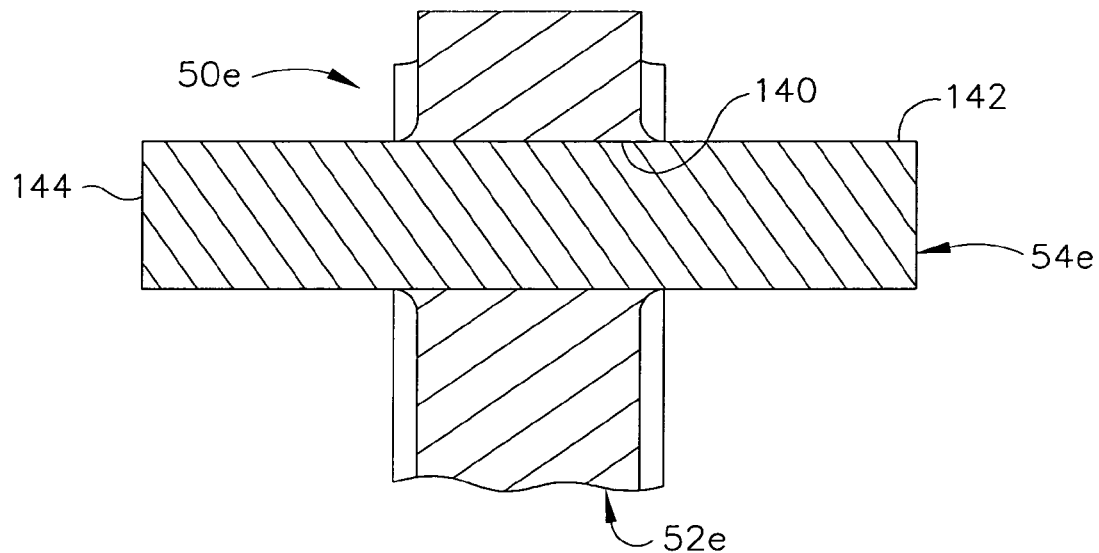
FIG. 9 is a front view of an upper portion of a fifth version of the E-beam of FIG. 5 taken in vertical and transverse cross section along lines 6-6 but including an upper pin formed of a resilient material instead of a relieved undersurface of the upper pin for enhanced vertical flexure.

In FIG. 9, a fifth version of a compliant E-beam 50e is as described for FIGS. 2-3 with an added feature of a discrete upper pin 54e formed of a more flexible material that is inserted through a horizontal aperture 140 through a vertical portion 52e. Thus, left and right outer ends 142, 144 of the discrete upper pin 54e flex in accordance with loading forces.

Figure 10:
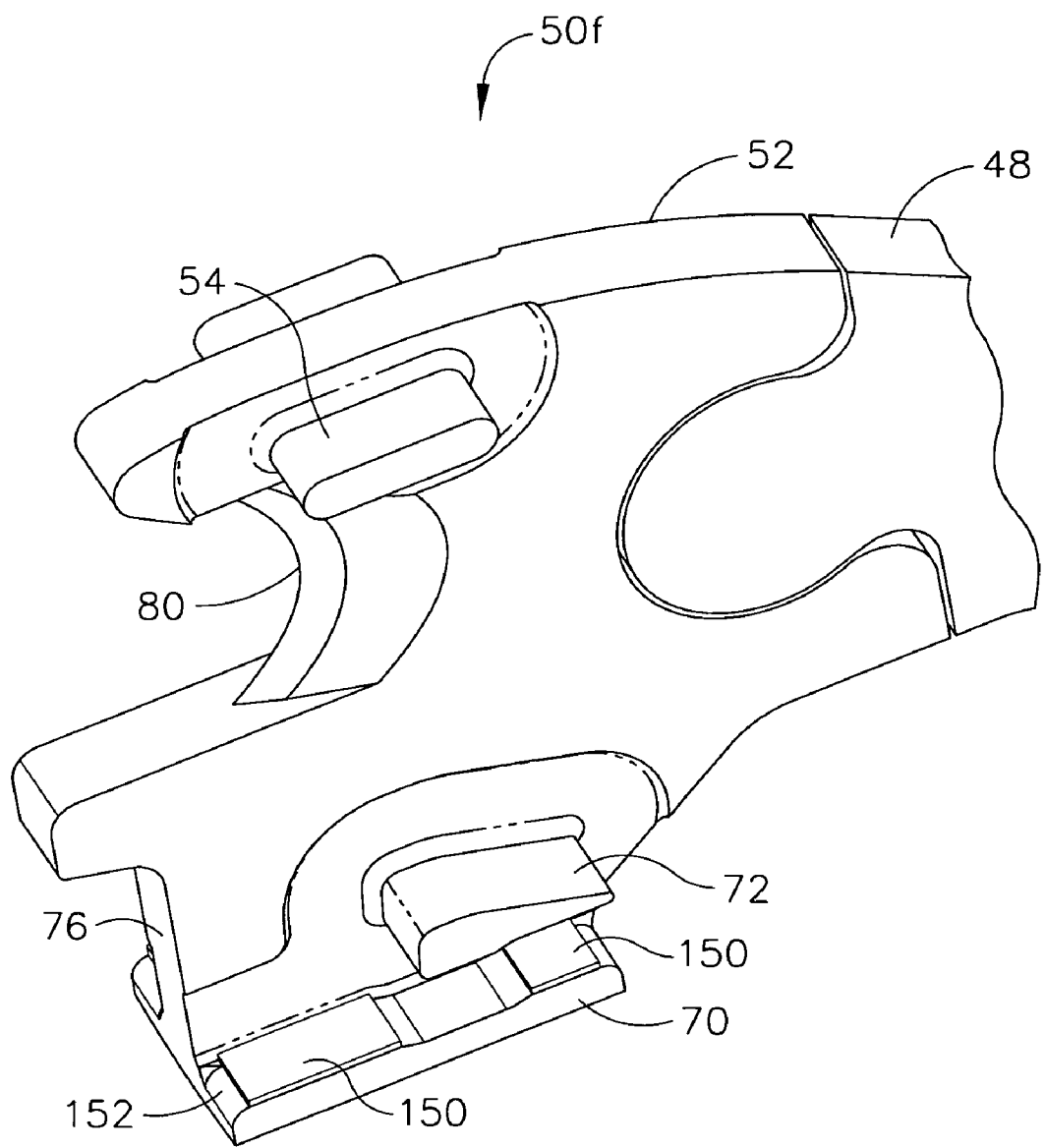
FIG. 10 is an upper left isometric view of a distal portion ("E-beam") of a sixth version of the force adjusted firing bar of FIG. 2 having resilient material upon a bottom foot to enhance vertical flexure.

Alternatively or in addition to incorporating flexure into an upper pin 54, in FIGS. 10-11, a sixth version of a compliant E-beam 50f as described for FIGS. 2-3 further includes resilient pads 150 that are attached to upper surfaces 152 of the bottom foot 70. The resilient pads 150 adjust the spacing of the upper pin 54 in accordance to the compression force experienced at the bottom foot 70.

Figure 12:
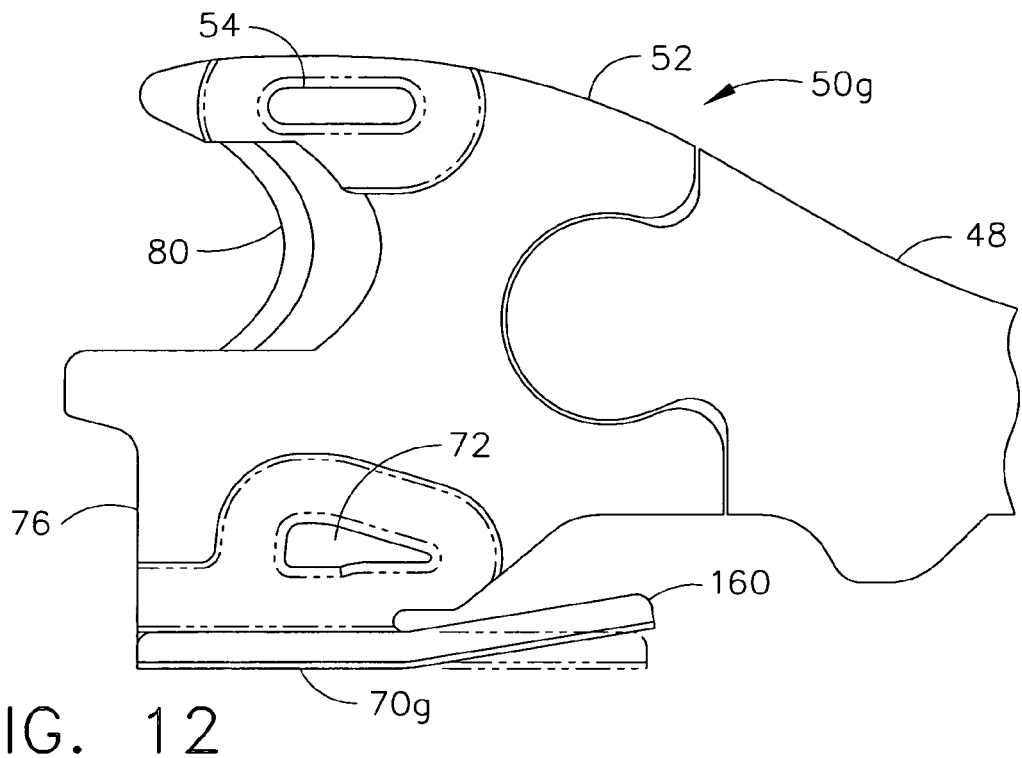
FIG. 12 is a left view in elevation of a distal portion ("E-beam") of a seventh version of the force adjusted firing bar of FIG. 2 having a proximally and upwardly extended spring arm attached to a lower foot to enhance vertical flexure.

In FIG. 12, a seventh version of a compliant E-beam 50g is as described above for FIGS. 2-3 with the added feature of a bottom foot (shoe) 70g having an upwardly aft extended spring finger 160 that resiliently urges the E-beam 50g downwardly to adjust vertical spacing in accordance with loading force.

Figure 13:
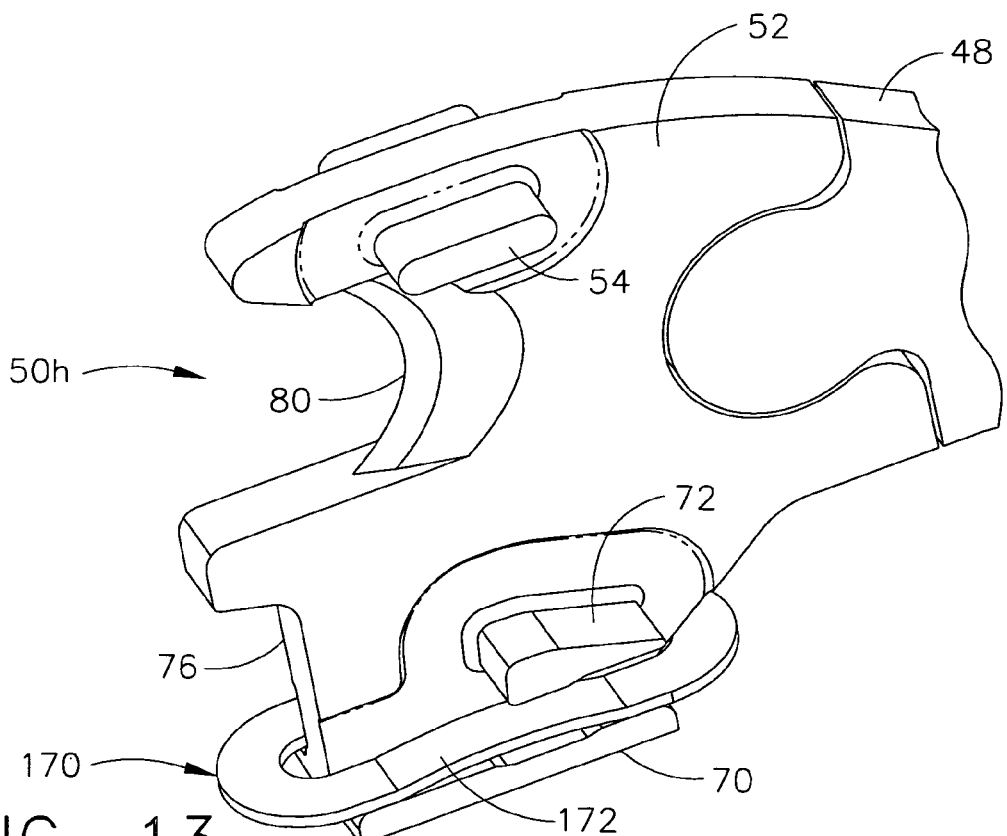
FIG. 13 is a left top isometric view of a distal portion ("E-beam") of an eighth version of the force adjusted firing bar of FIG. 2 having a spring washer encompassing a lower foot to enhance vertical flexure.

In FIG. 13, an eighth version of a compliant E-beam 50h is as described above in FIGS. 2-3 with the added feature of an oval spring washer 170 resting upon the bottom foot 70 encircling the vertical portion 52 and having an upwardly bowed central portion 172 that resiliently urges the E-beam 50h downwardly to adjust vertical spacing in accordance with loading force.

For another example, a compliant E-beam consistent with aspects of the present invention may include engagement to an anvil similar to the engagement in the illustrative versions of two structures that slide against opposite sides of the elongate staple channel. Similarly, a compliant E-beam may engage a lower jaw by having a laterally widened portion that slides internally within a channel formed in a lower jaw structure.

As yet an additional example, in the illustrative version, the staple cartridge 42 is replaceable so that the other portions of the staple applying assembly 16 may be reused. It should be appreciated given the benefit of the present disclosure that applications consistent with the present invention may include a larger disposable portion, such as a distal portion of an elongate shaft and the upper and lower jaws with a staple cartridge permanently engaged as part of the lower jaw.

As yet another example, the illustrative E-beam advantageously affirmatively spaces the upper and lower jaws from each other. Thus, the E-beam has inwardly engaging surfaces that pull the jaws together during firing in instances where a larger amount of compressed tissue tends to spread the jaws. Thereby the E-beam prevents malformation of staples due to exceeding their effective length. In addition, the E-beam has outwardly engaging surfaces that push the jaws apart during firing instances where a small amount of tissue or other structure attributes of the instrument tend to pinch the jaws together that may result in staple malformation. Either or both functions may be enhanced by applications consistent with aspects of the invention wherein inherent flexure in the E-beam adjusts to force to allow a degree of closing of the jaws or of opening of the jaws.

Figure 14:
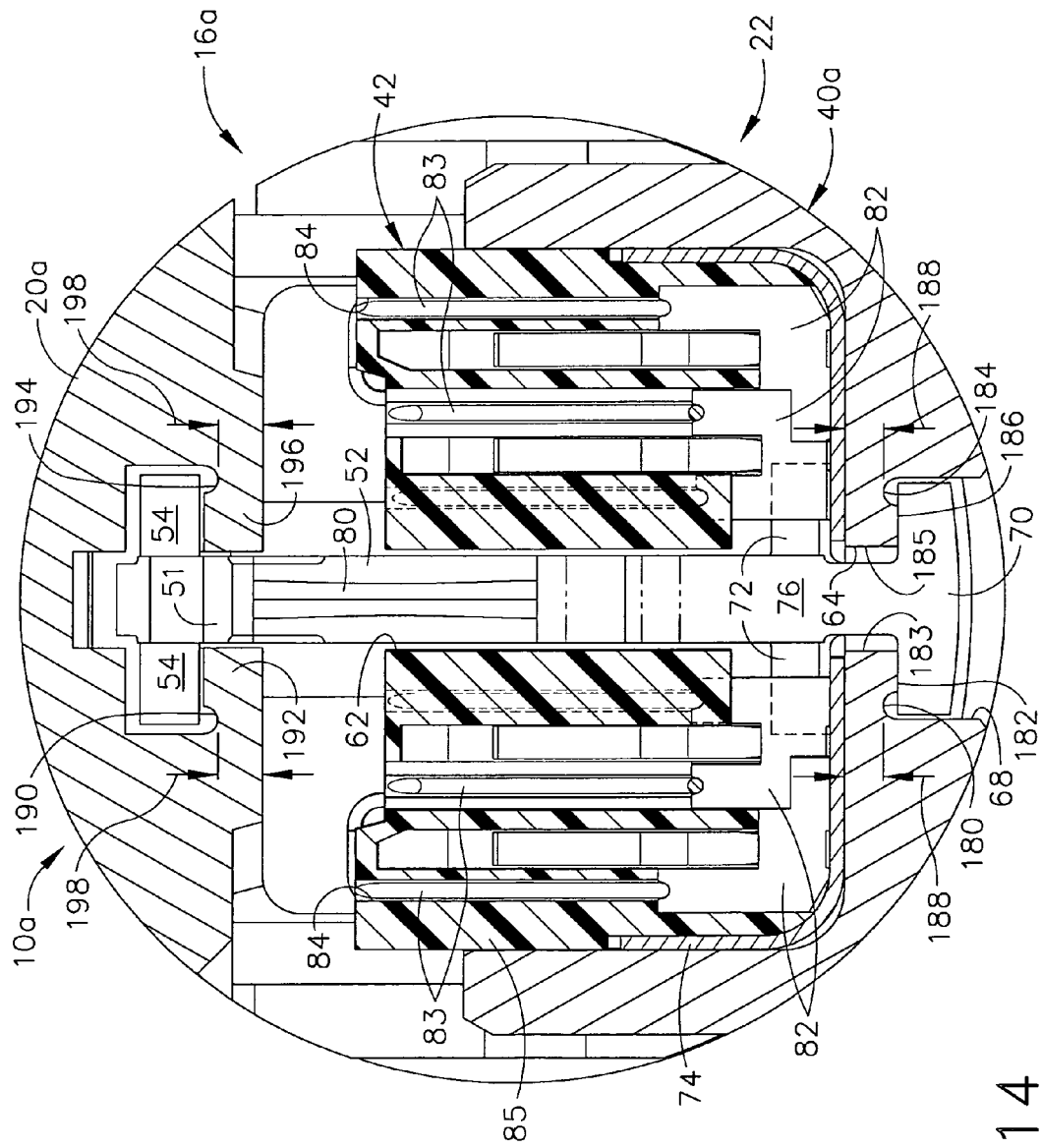
FIG. 14 is a cross-sectional end view of another staple applying assembly or end effector of the present invention in a clamped or closed position.
Figure 15:
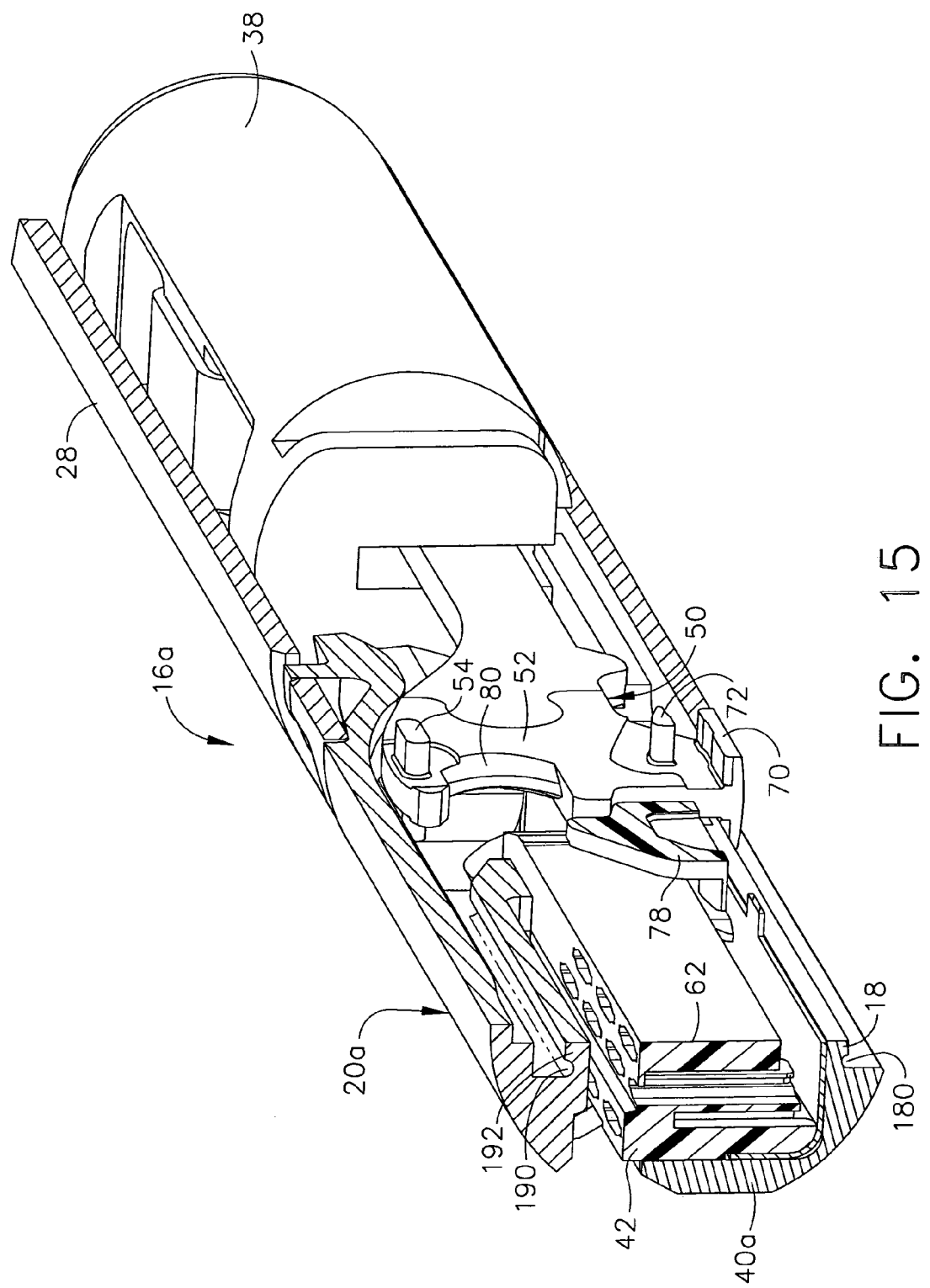
FIG. 15 is a partial perspective view of the staple applying assembly of FIG. 14 with some of the elements thereof shown in cross-section.

FIG. 14 is an end cross-sectional view of a surgical instrument 10a that has a staple applying assembly 16a of another embodiment of the present invention wherein like reference numerals are used to designate like elements and which employs an elongate channel 40a for supporting a staple cartridge 42 therein. In various embodiments, the channel 40a has resilient or flexible features configured to enable the staple applying assembly 40a to effectively accommodate different thicknesses of tissue. FIG. 15 is a partial perspective view of the staple applying assembly 16a with some components shown in cross-section for clarity. As can be seen in FIG. 14, in this embodiment, a first longitudinally extending relief area 180 and a second longitudinally extending relief area 184 are provided in the longitudinal channel 40a. The first longitudinally extending relief area 180 defines a first resilient or flexible channel ledge portion 182 and the second longitudinally extending relief area 184 defines a second resilient or flexible channel ledge portion 186. The elongate channel slot 64 through which the upper end 51 of the vertical portion 52 of the firing member in the form of E-beam 50 extends is formed between the free ends 183, 185 of the flexible ledges 182, 186, respectively. As can be further seen in FIG. 14, such arrangement permits the lower foot 70 of the E-beam 50 to bear upon the flexible ledge portions 182, 186 to accommodate differences in the thickness of the tissue clamped between the anvil 20 and the lower jaw 22 as the E-beam 50 transverses therethrough. It will be understood that the thickness 188 of the ledge portions 182, 186 may be selected to provided the desired amount of flexure to those portions of the elongate channel 40a. Also, the choice of materials for the elongate channel 40a may be selected for a desired degree of flexure, in view of the staple size and other considerations.

The elongate channel 40a as described above may be used in connection with a staple applying assembly that employs a conventional anvil 20. That is, the longitudinally extending anvil slot 58 may essentially have a "T" shape that is sized to accommodate the upper pins 54 and an upper end 51 of the vertical portion 52 of the E-beam 50. The embodiment depicted in FIGS. 14 and 15 employs an anvil 20a that has resilient or flexible features for further accommodating differences in tissue thicknesses clamped between the anvil 20a and the lower jaw 22. In particular, as can be seen in FIG. 14, a third longitudinally extending relief area 190 and a fourth longitudinally extending relief area 194 may be provided in the anvil 20a as shown. The third longitudinally extending relief area 190 defines a first anvil ledge portion 192 and the fourth longitudinally extending relief area 194 defines a second anvil ledge portion 196 upon which the upper pins 54 of the E-beam 50 may bear. Such arrangement provides a degree of flexure to the anvil 20a to accommodate differences in tissue thickness clamped between the anvil 20a and the lower jaw 22. It will be understood that the thickness 198 of the ledge portions 192, 196 may be selected to provided the desired amount of flexure to those portions of the anvil 20a. Also, the choice of materials for the anvil 20a may be selected for a desired degree of flexure, in view of the staple size and other considerations. Anvil 20a may be used in connection with the above-described channel arrangement as shown in FIGS. 14 and 15 or it may be employed with conventional channel arrangements without departing from the spirit and scope of the present invention.

The person of ordinary skill in the art will also appreciate that the anvil 20a and/or the channel 40a may be successfully employed with a conventional E-beam arrangement or any of the E-beam arrangements depicted herein. The E-beams disclosed herein may be reciprocatingly driven by control arrangements housed within the handle assembly. Examples of such control arrangements are disclosed in U.S. Pat. No. 6,978,921, issued Dec. 27, 2005, which has been herein incorporated by reference. Other known firing member configurations and control arrangements for applying firing and retraction forces or motions thereto could conceivably be employed without departing from the spirit and scope of the present invention.

Figure 16:
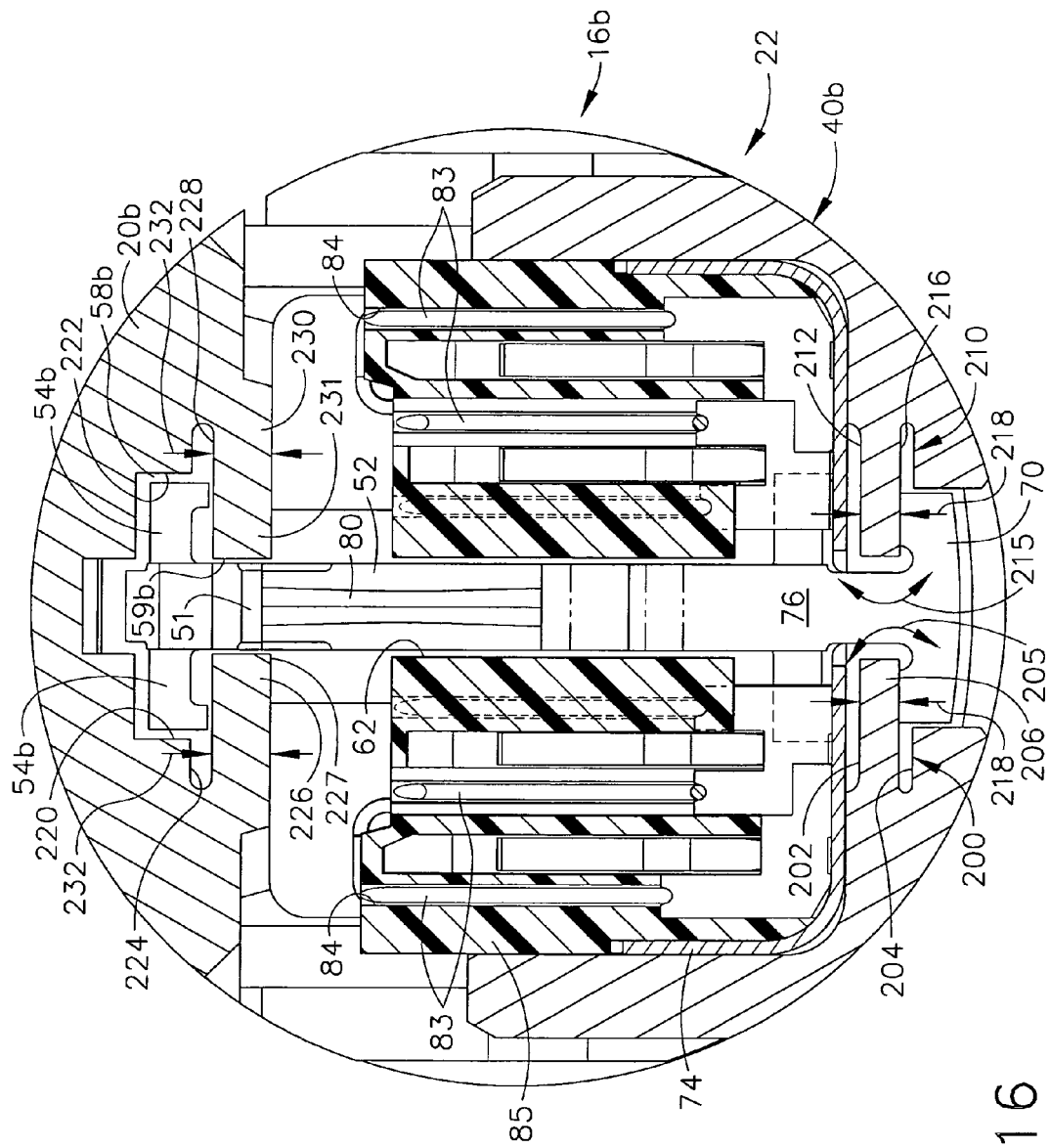
FIG. 16 is a cross-sectional end view of another staple applying assembly or end effector of the present invention in a clamped or closed position.
Figure 17:
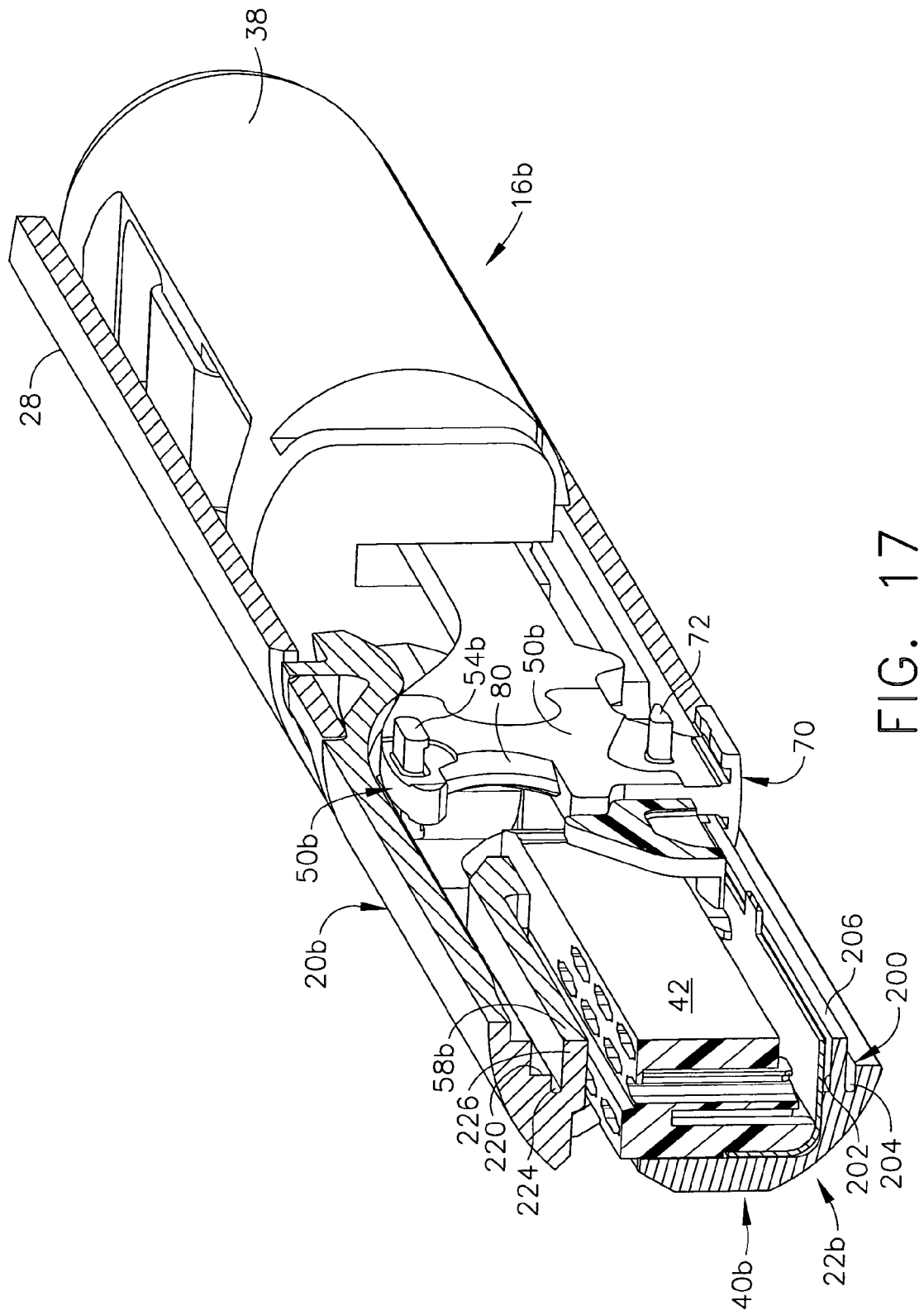
FIG. 17 is a partial perspective view of the staple applying assembly of FIG. 16 with some of the elements thereof shown in cross-section.

FIGS. 16 and 17 illustrate a staple applying assembly 16b that employs another version of a channel 40b and an anvil 20b that each have resilient or flexible portions to accommodate differences in tissue thicknesses clamped between the anvil 20b and the lower jaw 22b. As can be seen in those Figures, a first pair 200 of upper and lower longitudinally extending relieved or undercut areas 202, 204 are provided in the channel 40b to define a first cantilever-type support ledge 206 and a second pair 210 of relieved or undercut areas 212, 214 are provided in the channel 40b to define a second cantilever-type support ledge 216. The first pair relieved areas 202, 204 provide a degree of flexure to the first support ledge 206 to enable it to flex as illustrated by arrow 205. Likewise, the second pair 210 of relieved areas 212, 214 provide a degree of flexure to the second support ledge 216 to enable it to flex as illustrated by arrow 215. As with the above described embodiments, the thickness 208 of the support ledges 206 and 216 may be selected to provided the desired amount of flexure to those portions of the elongate channel 40b to accommodate different thicknesses of tissue. Also, the choice of materials for the elongate channel 40b may be selected for a desired degree of flexure, in view of the staple size and other considerations.

FIGS. 16 and 17 further illustrate an anvil 20b that has a T-shaped slot 58b that defines a first lateral wall portion 220 and a second lateral wall portion 222. In various embodiments, a first longitudinally extending undercut area 224 is provided in the first lateral wall portion 220 to define a resilient or flexible first ledge 226. Similarly, in various embodiments, a second longitudinally extending undercut area 228 is provided in the second lateral wall portion 222 to define a resilient or flexible second ledge 230. As can be seen in FIG. 16, the ends 227, 231 of the first and second ledges 226, 230, respectively serve to define a portion 59b of anvil slot 58b through which an upper end portion 51 of E-beam 50b extends. Such arrangement permits the upper pins 54b of the E-beam 50b may bear upon the first resilient ledge 226 and the second resilient ledge 230 to provide a degree of flexure to the anvil 20b to accommodate differences in tissue thickness clamped between the anvil 20b and the lower jaw 22b. It will be understood that the thickness 232 of the ledges 226, 230 may be selected to provided the anvil 20b with a desired amount of flexure to accommodate different tissue thicknesses. Also, the choice of materials for the anvil 20b may be selected for a desired degree of flexure, in view of the staple size and other considerations. Anvil 20b may be used in connection with the above-described channel 40b shown in FIGS. 16 and 17 or it may be employed with a conventional channel arrangement. The skilled artisan will also appreciate that the anvil 20a and/or the channel 40b may be successfully employed with a conventional E-beam arrangement or any of the E-beams described herein.

Figure 18:
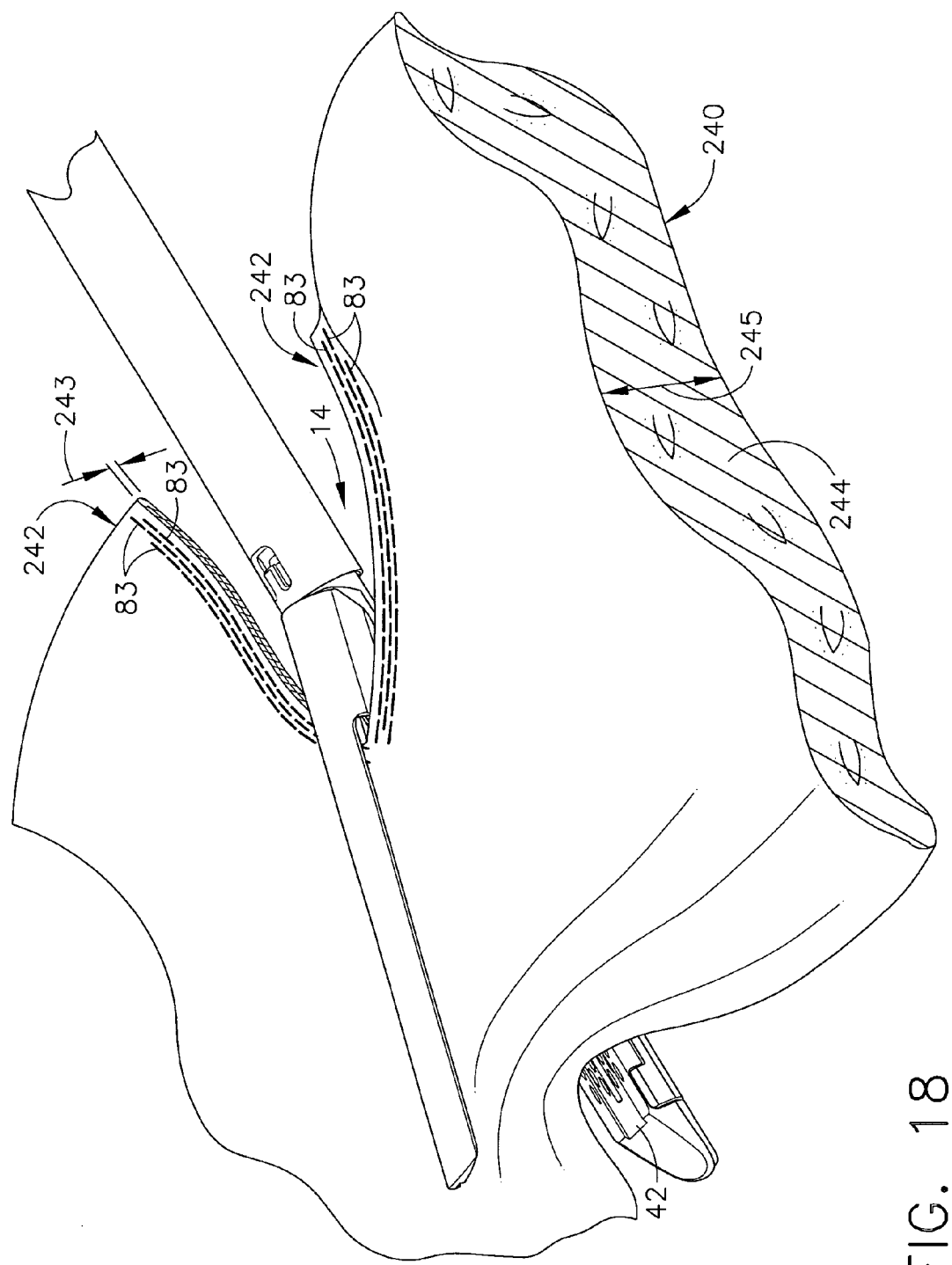
FIG. 18 is a partial perspective view of a staple applying assembly of the present invention clamping a piece of tissue that has been partially cut and stapled.

FIG. 18 illustrates the cutting and stapling of tissue 240 with any one of the various surgical cutting and stapling instrument embodiments of the present invention. A portion 242 of the tissue 240 illustrated in FIG. 18 has already been cut and stapled. After the clinician has cut and stapled the first portion 242, the instrument would be withdrawn to enable new staple cartridge 42 to be installed. FIG. 18 illustrates the position of the implement portion 14 prior to commencing the second cutting and stapling process. As can be seen in that Figure, the portion 242 of the tissue 240 that has been stapled has a thickness 243 that is less than the thickness 245 of other portions 244 of the tissue 240.

Figure 19:
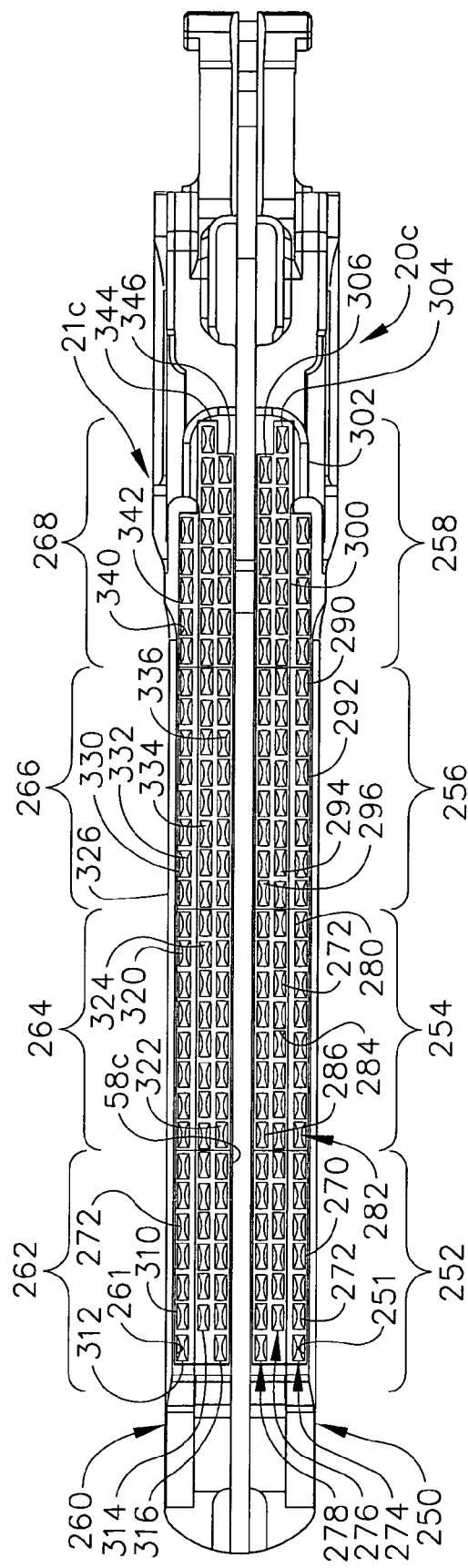
FIG. 19 is a bottom view of an anvil embodiment of the present invention.
Figure 20:
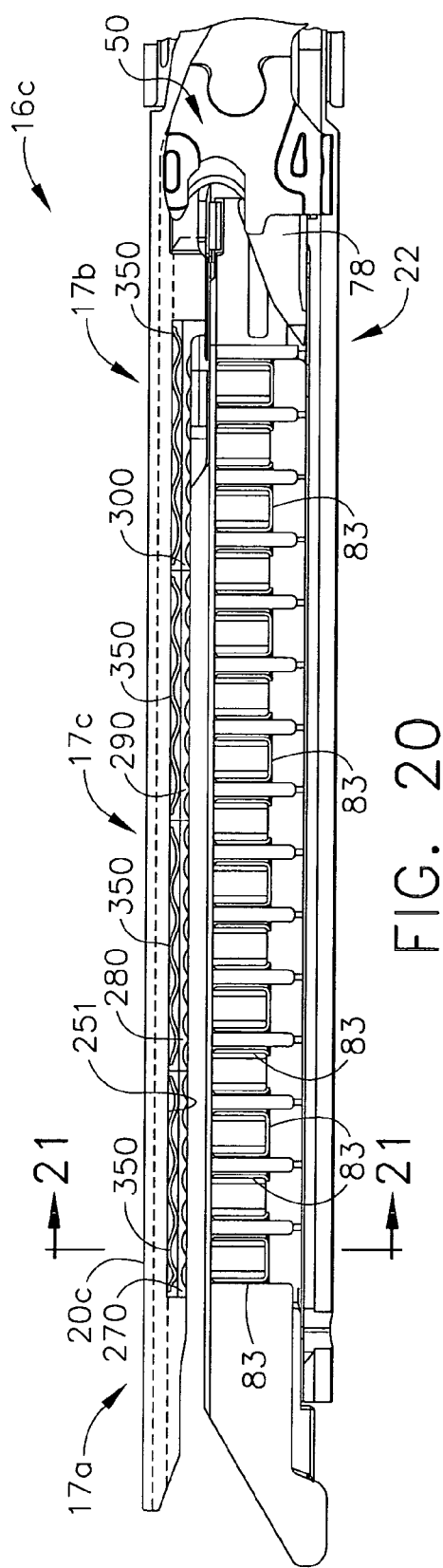
FIG. 20 is a longitudinal cross-sectional view of a staple applying assembly employing the anvil embodiment depicted in FIG. 19.

FIG. 19 is a view of the underside of an anvil 20c that may be employed with a staple applying assembly 16c of various embodiments of the present invention. The anvil 20c includes an anvil body 21c that supports movable staple forming pockets that define different staple zones. In the embodiment depicted in FIG. 19, four left staple zones 252, 254, 256, 258 are provided on a left side 250 of the anvil slot 58c and four right staple zones 262, 264, 266, 268 are provided on a right side 260 of the anvil slot 58c within the anvil body 21c. The first left staple zone 252 is defined by a first left staple forming insert member 270 that has a series of staple forming pockets 272 therein. In this embodiment, three rows 274, 276, 278 of staple forming pockets 272 are provided in the insert 270. As can be seen in FIG. 19, the central row 276 of pockets 272 are slightly longitudinally offset from the outer two rows 274, 278 of pockets 272 and correspond to the arrangement of the corresponding staple apertures 84 in corresponding staple cartridges 42. Those of ordinary skill in the art will appreciate that such arrangement serves to result in the application of the staples 83 in a staggered manner as illustrated in FIG. 18.

Similarly, the second left staple zone 254 may be defined by a second left staple forming insert 280 that may have three rows 282, 284, 286 of staple forming pockets 272 therein. The third left staple zone 256 may be defined by a third left staple forming insert 290 that may have three rows 292, 294, 296 of staple forming pockets 272 therein. The fourth left staple zone 258 may be defined by a fourth left staple forming insert 300 that may have three rows 302, 304, 306 of staple forming pockets 272 therein. The first, second, third and fourth left staple forming inserts 270, 280, 290, 300 are longitudinally aligned in a left side cavity 251 provided in the anvil 20c on the left side 250 of the anvil slot 58.

The first right staple zone 262 may be defined by a first right staple forming insert member 310 that has a series of staple forming pockets 272 therein. In this embodiment, three rows 312, 314, 316 of staple forming pockets 272 are provided in the insert 310. As can he seen in FIG. 19, the central row 314 of staple forming pockets 272 are slightly longitudinally offset from the outer two rows 312, 316 and correspond to the arrangement of the corresponding staple apertures 84 in corresponding staple cartridges 42. Such arrangement serves to result in the application of the staples 83 in a staggered mariner on the right side of the tissue cut line. The second right staple zone 264 may be defined by a second right insert 320 that may have three rows 322, 324, 326 of staple forming pockets 272 therein. The third right staple zone 266 may be defined by a third right staple forming insert 330 that may have three rows 332, 334, 336 of staple forming pockets 272 therein. The fourth right staple zone 268 may be defined by a fourth right staple forming insert 340 that may have three rows 342, 344, 346 of staple forming pockets 272 therein. The first, second, third, and fourth right staple forming inserts 310, 320, 330, 340 are longitudinally aligned in a right side cavity 261 provided in the anvil 20c on the right side 260 of the anvil slot 58. In various embodiments, the staple forming inserts may be fabricated from stainless steel or other suitable materials that are harder than the material from which the staples are fabricated. For example, the inserts may be successfully fabricated from other materials such as cobalt chromium, aluminum, 17-4 stainless steel, 300 series stainless steel, 400 series stainless steel, other precipitant hardened stainless steels, etc.

Figure 22:
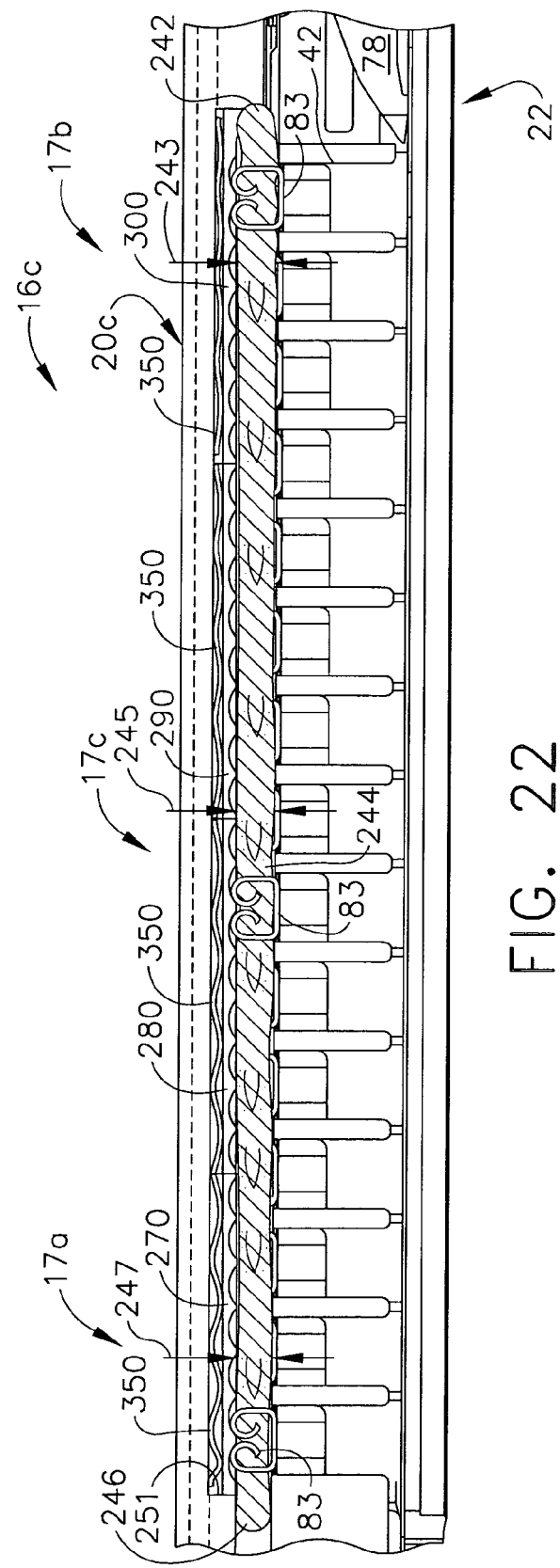
FIG. 22 is another longitudinal cross-sectional view of the staple applying assembly of FIGS. 20 and 21 clamping a piece of tissue therein, wherein the tissue has varying cross-sectional thicknesses.
Figure 21:
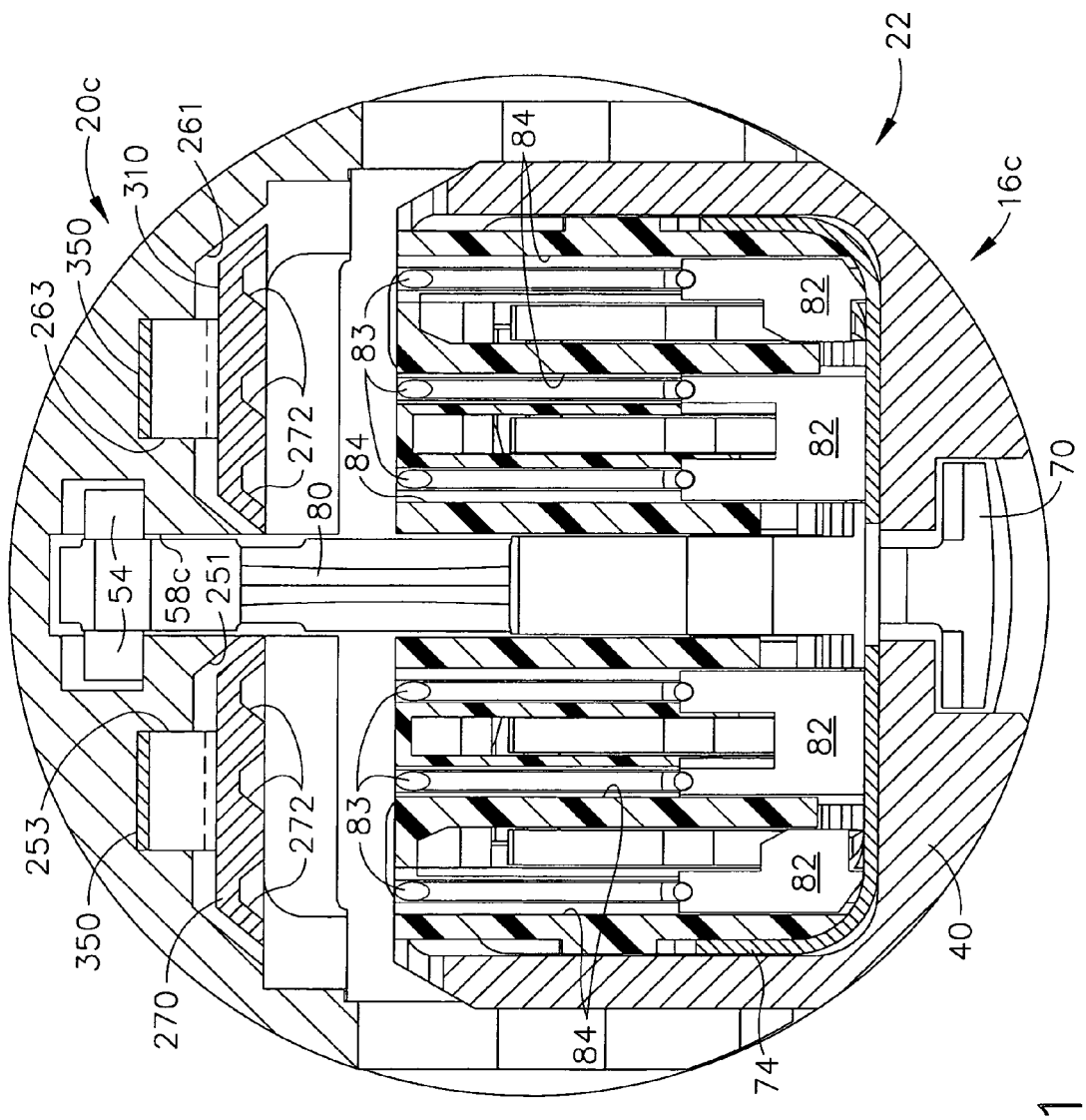
FIG. 21 is a cross-sectional end view of the staple applying assembly of FIG. 20 taken along line 21-21 in FIG. 20, with some elements shown in solid form for clarity.

At least one biasing member or compliant member in the form of a wave spring 350 or other suitable biasing or compliant medium or member corresponding to each of the staple forming inserts 270, 280, 290, 300, 310, 320, 330, 340 is provided between the respective left staple forming inserts 270, 280, 290, 300 and the bottom of the left side cavity 251 as shown in FIGS. 20-23. Wave springs 350 or other suitable biasing or compliant medium or member is also provided between each of the right staple forming inserts 310, 320, 330, 340 and the bottom surface of the right side cavity 261. The wave springs 350 on the left side of the anvil slot 58c may be received in a corresponding spring cavity 253 and the wave springs 350 on the right side of the anvil cavity 58c may be received in a corresponding spring cavity 263. To biasingly retain each insert 270, 280, 290, 300, 310, 320, 330, 340 in the anvil 20c, each insert 270, 280, 290, 300, 310, 320, 330, 340 may be attached to its corresponding spring 350 or biasing member by, for example, adhesive or other fastener arrangements. In addition, each spring 350 may be attached to the anvil 20c by, for example, adhesive or other mechanical fastener arrangements to retain a portion of the wave spring 350 within its respective spring cavity 253 or 263. Such spring/biasing member arrangements serve to bias the inserts 270, 280, 290, 300, 310, 320, 330, 340 toward the tissue 240 and staples and essentially act as resilient "shock absorbers" to accommodate differences in tissue thicknesses. This advantage is illustrated in FIGS. 22-24.

In particular, as can be seen in FIG. 22, the portion 242 of the tissue 240 clamped in the proximal end 17b of the staple applying assembly 16c has a first thickness (arrow 243) that is thicker than the thickness (arrow 245) of the portion 244 of tissue 240 clamped in the central portion 17c of the staple applying assembly 16c. The thickness 245 of tissue portion 244 is greater than the thickness (arrow 247) of the portion 246 of tissue 240 that is clamped in the distal end 17a of the staple applying assembly 16c. Thus, the staples 83 formed in the distal portion 17a of the staple applying assembly 16c are more tightly formed than the staples 83 formed in the central portion 17c of the staple applying assembly 16c which are more tightly formed than those staples 83 formed in the proximal end 17b of the staple applying assembly 16c due to the differences in tissue thicknesses. FIG. 23 further illustrates the variations in staple formation heights based upon the variations in the thicknesses of the tissue clamped within the staple applying assembly 16c. FIG. 24 illustrates a condition wherein the tissue 240 clamped in the central portion 17c of the staple applying assembly 16c is thicker than the portions of tissue clamped in the distal and proximal ends of the staple applying assembly 16c. Thus, the formation heights of the staples in the central portion 17c will be higher than the staple formation heights of the staples associated with the proximal end 17b and distal end 17a of the staple applying assembly 16c.

Figure 25:
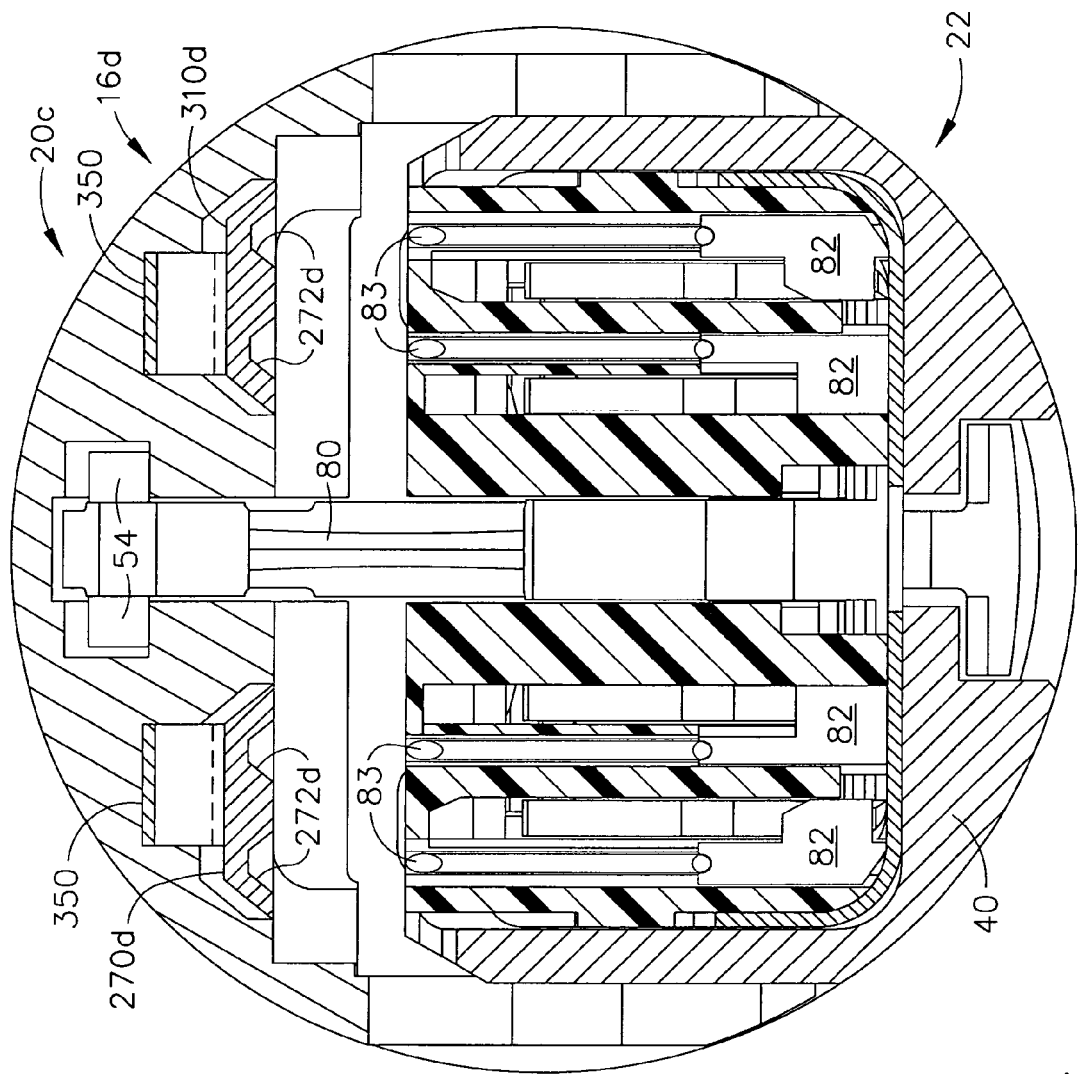
FIG. 25 is an end cross-sectional view of another staple applying assembly of the present invention in a clamped position.

Those of ordinary skill in the art will understand that the unique and novel features of the embodiments depicted in FIGS. 19-24 may also be employed in connection with a staple applying assembly that is essentially identical in construction and operation to staple applying assembly 16c described above, except that the staple forming inserts 270, 280, 290, 300, 310, 320, 330, 340 may have just one row of staple formation pockets 272 therein or two rows of staple formation pockets 272 therein. For example, FIG. 25 illustrates an embodiment that only applies two rows of staples on each side of the tissue cut line. Shown in that Figure are staple forming inserts 270d and 310d that only have two rows of staple forming pockets 272d each.

Figure 26:
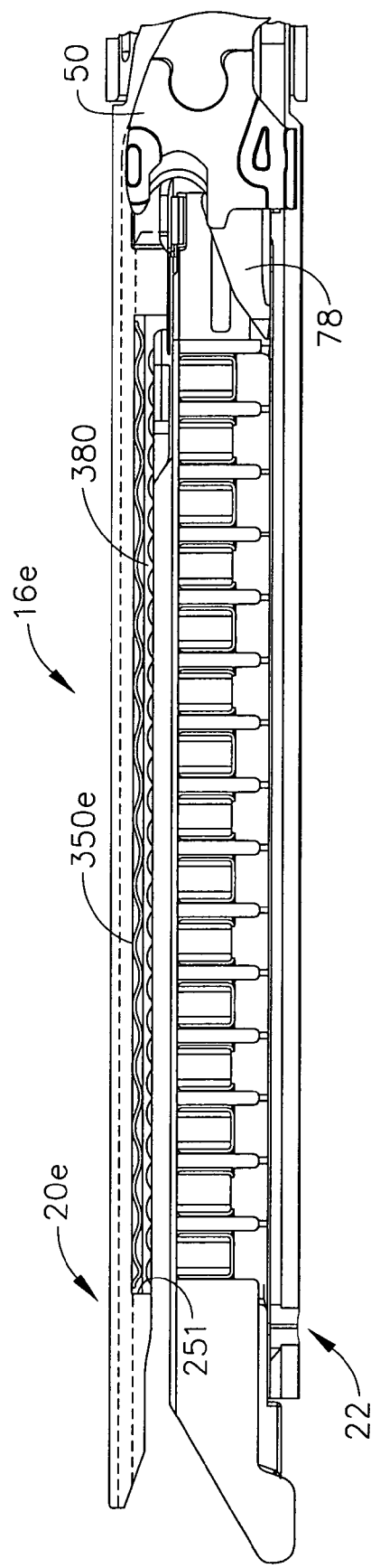
FIG. 26 is longitudinal cross-sectional view of another staple applying assembly of the present invention.

The skilled artisan will further understand that the number of staple forming inserts employed on each side of the anvil slot 58 may vary. For example a single longitudinally extending insert may be used on each side of the anvil slot 58. FIG. 26 illustrates another staple applying assembly 16e of the present invention that only employs one staple forming insert on each side of the anvil slot. FIG. 26 depicts a cross-sectional view of the left side of an anvil 20e that supports a single left staple forming insert 380 that is attached to a single wave spring 350e. Other biasing members or multiple wave springs or biasing members may also be employed. The biasing member or members 350e are supported in the left side cavity 251e and attached to the anvil 20e in one of the various manners described above. A similar right side insert (not shown) would be employed on the right side of the anvil slot 58. Furthermore, although FIGS. 19-24 depict use of four staple forming inserts on each side of the anvil slot greater numbers of staple forming inserts may be employed.

Figure 27:
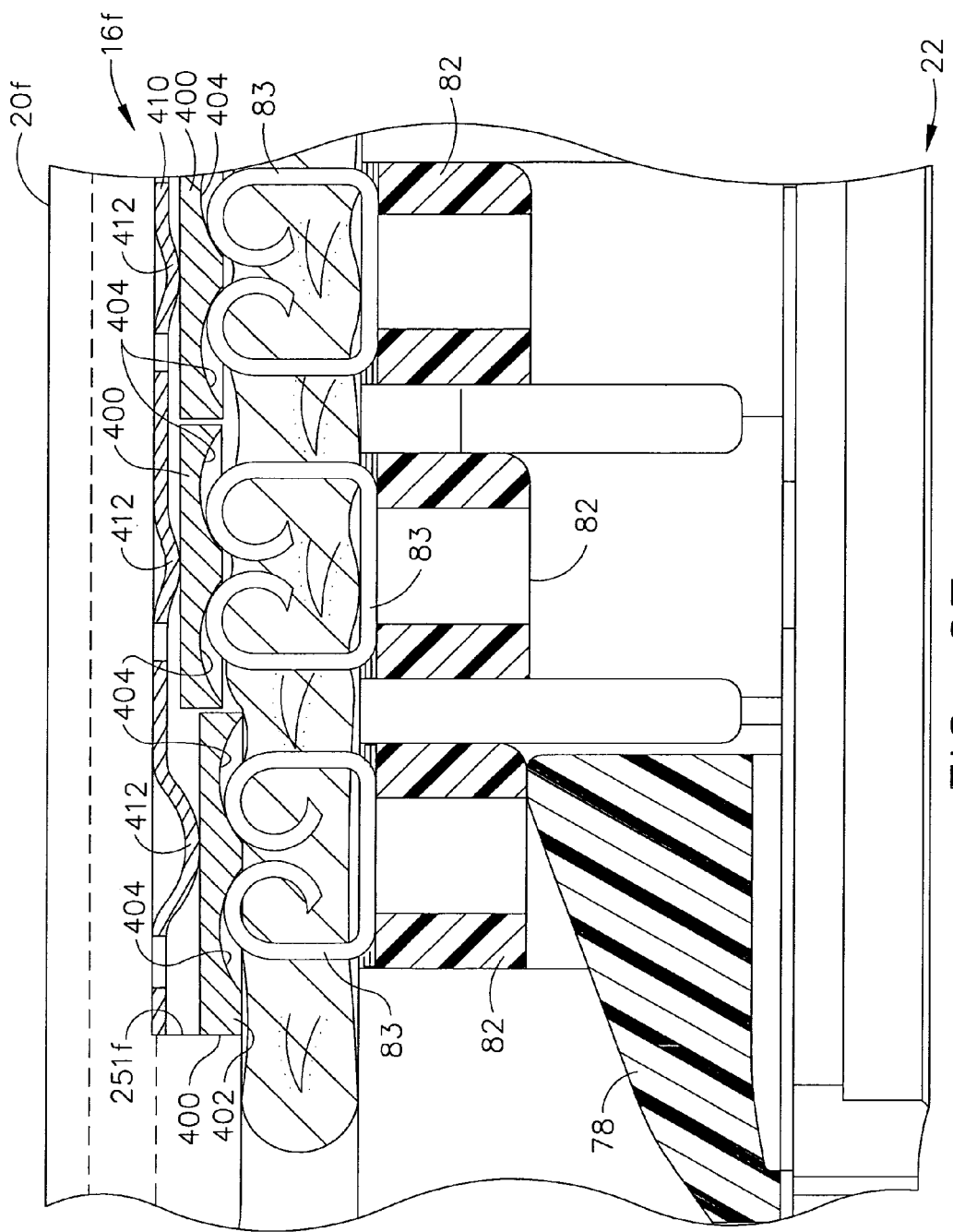
FIG. 27 is a cross-sectional view of a portion of another staple applying assembly of the present invention with a piece of tissue clamped and stapled therein.

FIGS. 27-29 illustrate another staple applying assembly 16f of the present invention wherein a separate movable staple forming insert is provided for each staple 83. In particular, as can be seen in FIG. 27, a single staple forming insert 400 is provided for each staple 83. Each staple forming insert 400 may have staple forming pockets 404 formed on its underside 402 thereof for forming the ends of the corresponding staple 83. As with various embodiments described above, each insert 400 has a biasing member 412 associated therewith. In the example depicted in FIGS. 27-29, the biasing members 412 comprise stamped portions of a biasing plate 410. The biasing plate 410 may comprise a piece of metal or other suitable material wherein each biasing member 412 is stamped or otherwise cut and formed to correspond with a staple forming insert 400. The biasing plate 410 may comprise a single plate that is supported within a cavity 251f in the anvil 20f or multiple plates 410 may be employed on each side of the anvil slot. It will be understood that a similar arrangement may be employed on the right side of the anvil slot. Each staple forming insert 400 may be attached to its corresponding biasing member 412 by adhesive or other suitable fastener arrangement. Thus, it will be appreciated that a variety of different numbers and arrangements of movable staple forming inserts may be employed without departing from the spirit and scope of the present invention. In particular, at least one movable staple forming insert may be employed on each side of the anvil slot.

Figure 30:
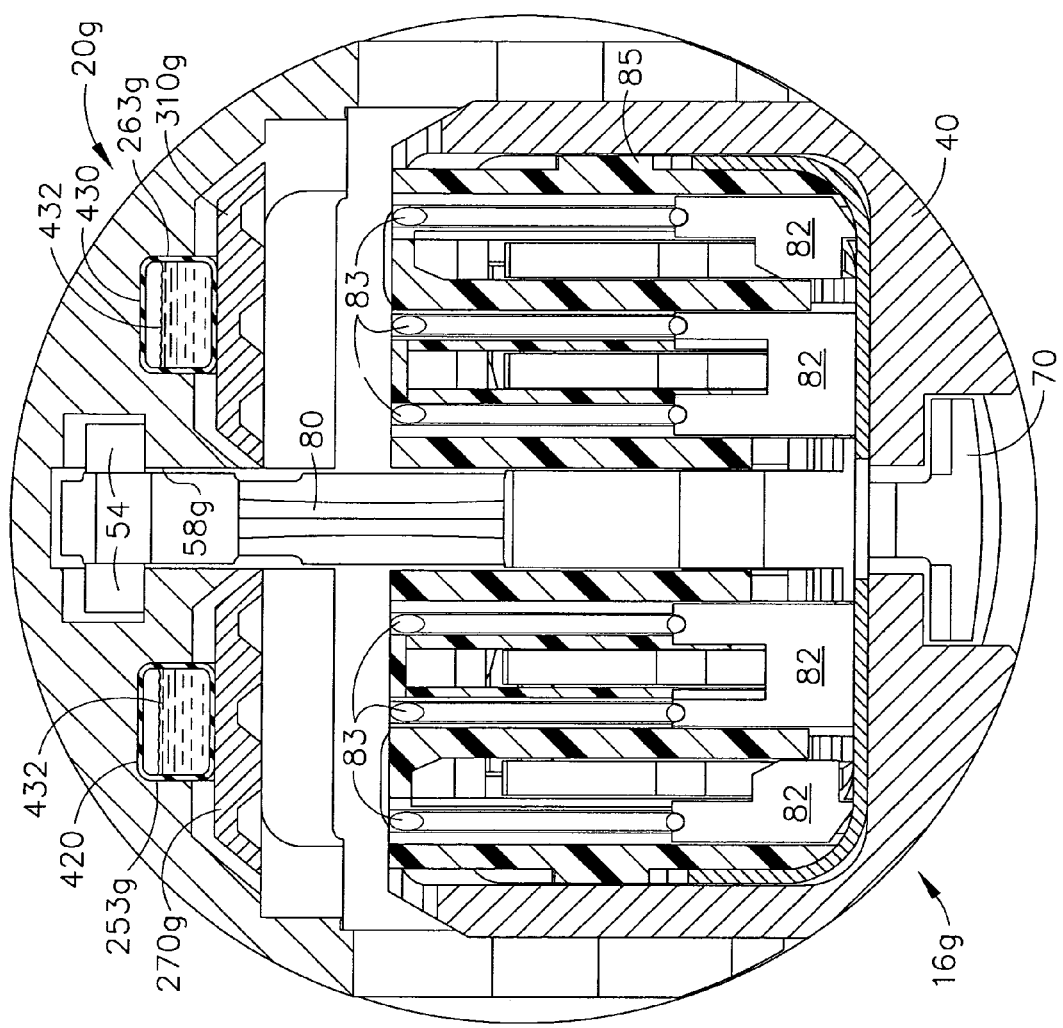
FIG. 30 is an end cross-sectional view of the staple applying assembly of FIG. 27 with some elements shown in solid form for clarity.
Figure 31:
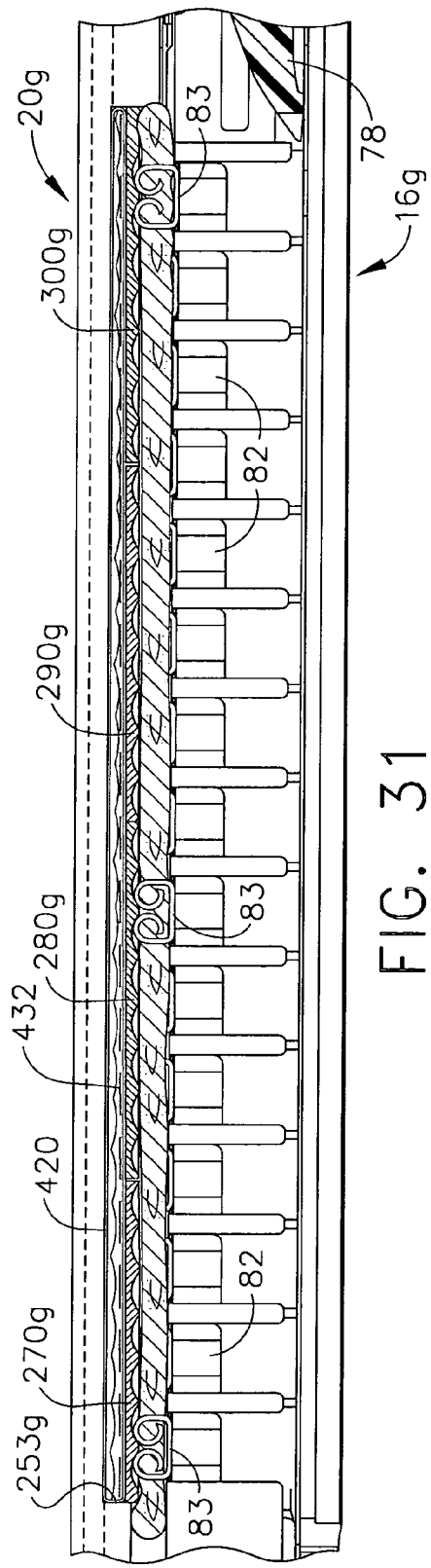
FIG. 31 is a longitudinal cross-sectional view of the staple applying assembly of FIGS. 27 and 30 with tissue clamped and stapled therein.
Figure 32:
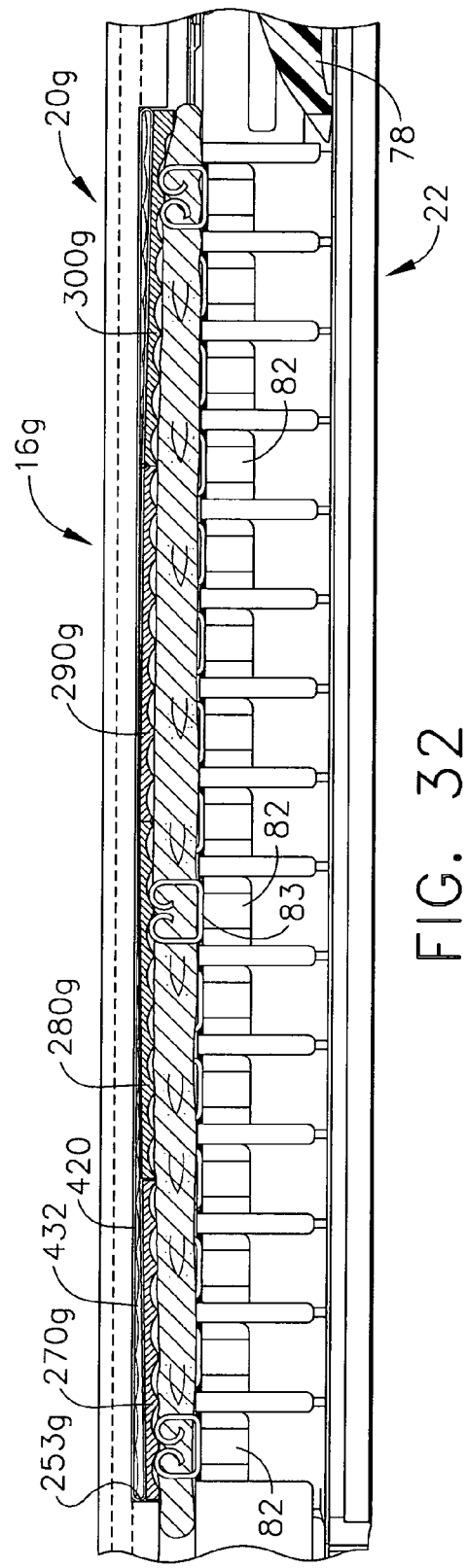
FIG. 32 is another longitudinal cross-sectional view of the staple applying assembly of FIG. 31 with another portion of tissue clamped and stapled therein.

FIGS. 30-32 illustrate another staple applying assembly 16g of other embodiments of the present invention wherein the biasing or compliant medium between the staple forming inserts and the anvil comprises at least one fluid bladder. More specifically, as can be seen in FIG. 30, a left bladder 420 is positioned within a left side cavity 253g on the left side of the anvil slot 58g in the anvil 20g. Likewise, a right side bladder 430 is positioned with a right side cavity 263 in the anvil 20g. The series of left side staple forming inserts 270g, 280g, 290g, 300g may be attached to the left side bladder 430 by a suitable adhesive or other fastener arrangement. Likewise the right side staple forming inserts (not shown) may be attached to the right side bladder 430 by adhesive or other suitable fastener arrangements. In one embodiment, each bladder 420, 430 is sealed and partially filled with a liquid 432 such as, for example, glycerin oil or saline solution. Those of ordinary skill in the art will appreciate that such arrangement will permit the staple forming inserts to move to better accommodate variations in the thickness of the tissue clamped within the staple applying assembly 16g. For example, for tissues that have a relatively constant thickness, the liquid 432 will be relatively evenly distributed within each of the bladders 420, 430 to provide a relatively even support arrangement for the staple forming inserts. See FIG. 31. However, when a thicker portion of tissue is encountered, those staple forming inserts corresponding to the thicker tissue will be compressed into their respective anvil cavity thereby forcing the liquid in that part of the bladder to the portions of the bladder corresponding to the thinner tissue portions. See FIG. 32.

Figure 33:
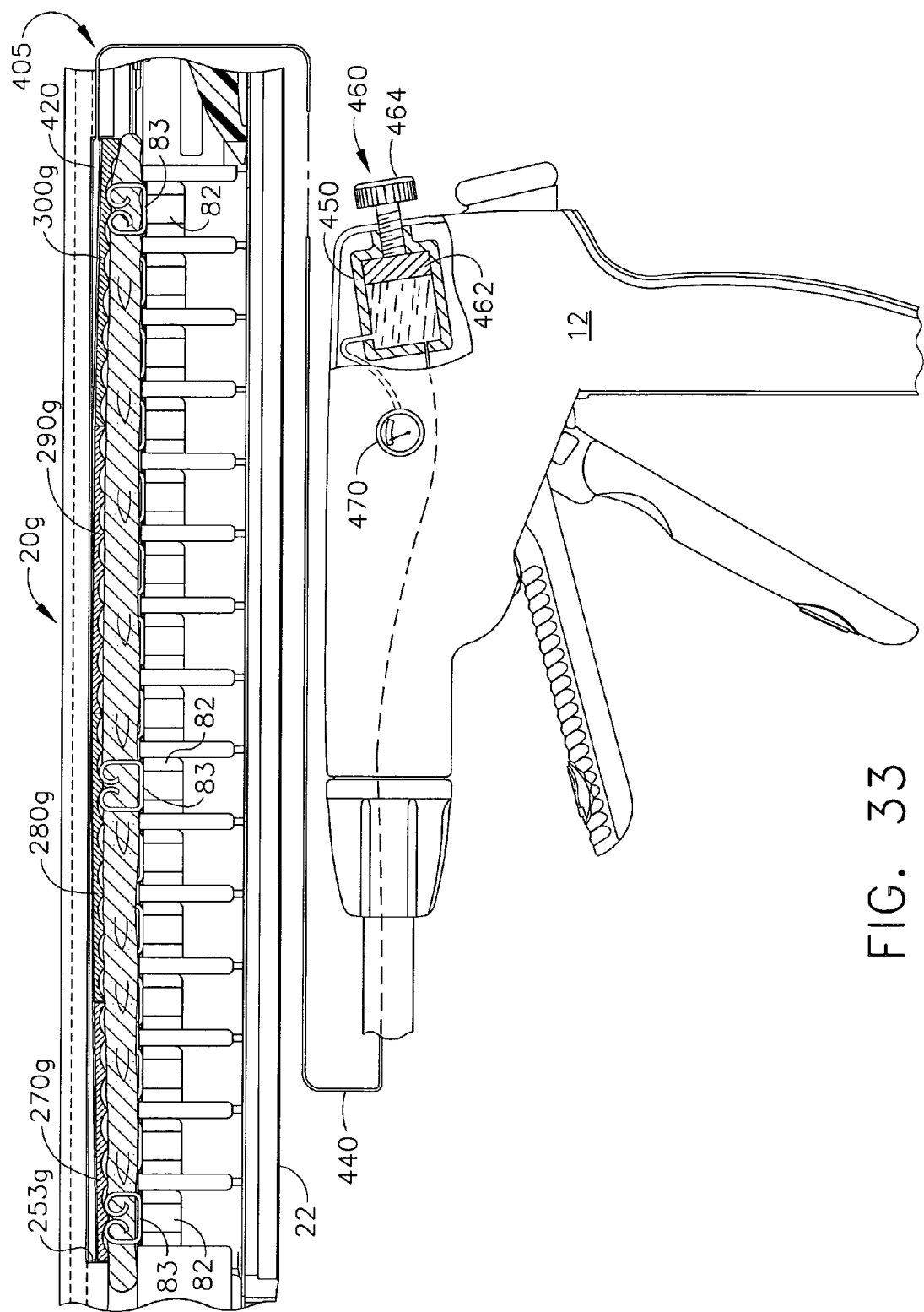
FIG. 33 is another longitudinal cross-sectional view of the staple applying assembly of FIGS. 30-32 fluidically coupled to a fluid reservoir supported by a handle assembly of various embodiments of the present invention.

In some applications, it may be desirable for the clinician to be able to control the amount of pressure within the bladders 420, 430. For example, less pressure may be desirable when cutting and stapling more delicate tissues such as lung tissue and the like. More pressure may be desirable when cutting and stapling thicker tissues such as, for example, stomach tissue, intestine tissue, kidney tissue, etc. To provide the clinician with this additional flexibility, the bladders 420, 430 may each be fluidically coupled by a supply line 440 or conduit to a fluid reservoir 450 supported by the handle portion 12 of the instrument. In the embodiment illustrated in FIG. 33, the clinician can increase or decrease the amount of fluid within the bladders 420, 430 and resulting pressure therein by means of an adjustment mechanism 460 mounted to the fluid reservoir 450. In various embodiments, the adjustment mechanism 460 may comprise a piston 462 that is attached to an adjustment screw 464. By adjusting the adjustment screw 464 inward, the piston 462 forces fluid out of the reservoir 450 to the bladders 420, 430. Conversely, by reversing the adjustment screw 464, the piston 462 permits more fluid 432 to return or remain within the reservoir 450. To assist the clinician in determining the amount of pressure within that hydraulic system, generally designated as 405, a pressure gauge 470 may be employed as shown. Thus, for those tissues requiring a higher amount of pressure, the clinician can preset the pressure in the bladders 420, 430 to a pressure that is conducive to successfully clamp and staple that particular type of tissue. While a piston/screw arrangement has been described for controlling the pressure in the hydraulic system, the skilled artisan will understand that other control mechanisms could successfully be employed without departing from the spirit and scope of the present invention.

Figure 30A:
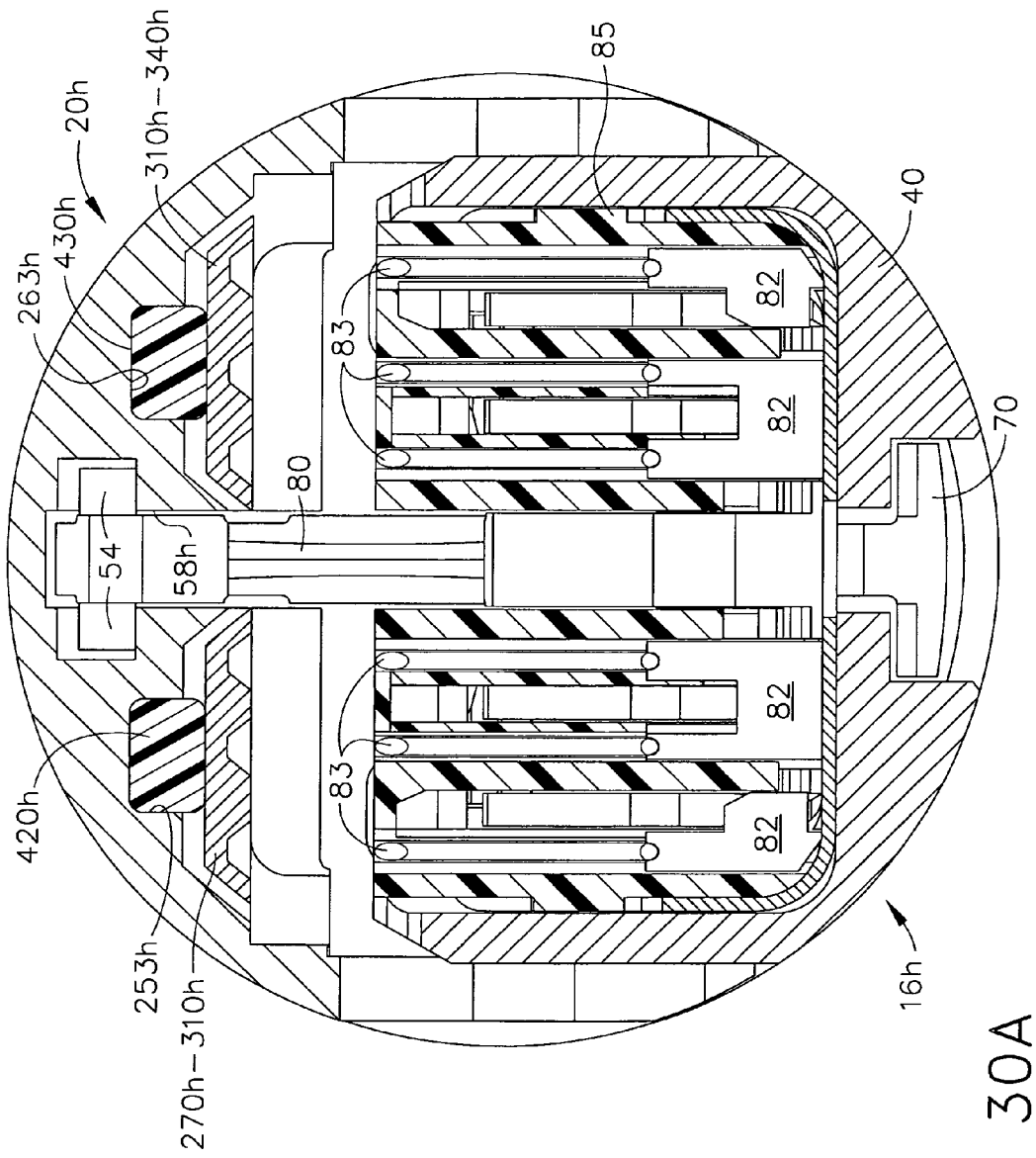
FIG. 30A is an end cross-sectional view of another staple applying assembly of the present invention with some elements shown in solid form for clarity.

FIG. 30A illustrates another staple applying assembly 16h of other embodiments of the present invention wherein the biasing or compliant medium between the staple forming inserts and the anvil comprises at least one compressible polymer member. More specifically, as can be seen in FIG. 30A, a left compressible polymer member 420h is positioned within a left side cavity 253h on the left side of the anvil slot 58h in the anvil 20h. Likewise, a right side compressible polymer member 430h is positioned with a right side cavity 263h in the anvil 20h. The series of left side staple forming inserts 270h-300h may be attached to the left compressible polymer member 420h by a suitable adhesive or other fastener arrangement. Likewise the right side staple forming inserts 310h-340h may be attached to the right side compressible polymer member 430h by adhesive or other suitable fastener arrangements.

FIGS. 34-37 depict a unique and novel collapsible or compressible staple driver arrangement that enables the various staple drivers to accommodate different tissue thicknesses by collapsing or compressing in response to compression forces that the driver encounters during the firing process. As used herein, the term "firing process" refers to the process of driving the staple drivers towards the staple forming undersurface of the anvil. As was mentioned above, prior staple drivers were fabricated from stiff/rigid material designed to resist deflection and deformation when encountering compression forces during the firing process. A variety of such driver configurations are known. For example, some staple drivers are configured to support a single staple and others are designed to support multiple staples. A discussion of single and double staple drivers and how they may be operably supported and fired within a staple cartridge is found in U.S. patent application Ser. No. 11/216,562, filed Sep. 9, 2005, entitled Staple Cartridges For Forming Staples Having Differing Formed Staple Heights to Frederick E. Shelton, IV, the disclosure of which is herein incorporated by reference.

Figure 34:
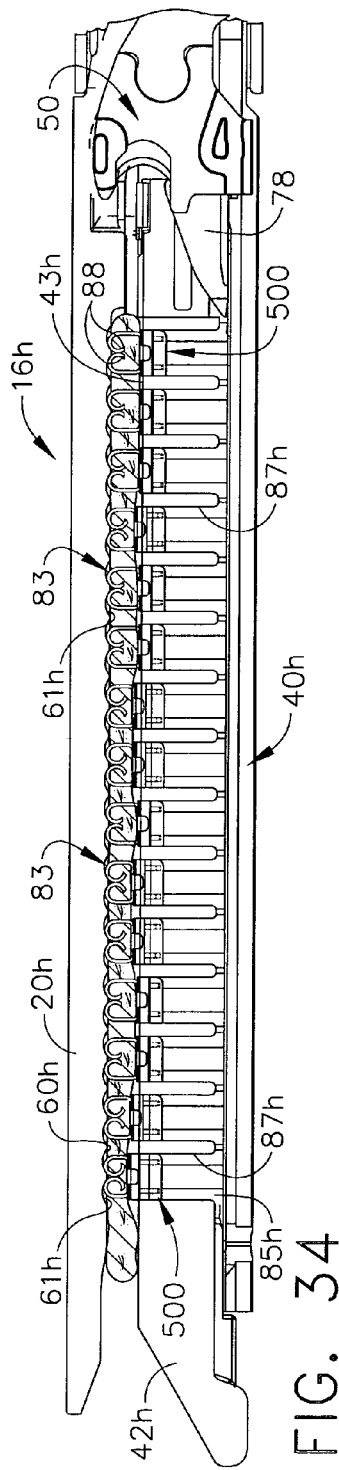
FIG. 34 is a longitudinal cross-sectional view of a staple applying assembly of other embodiments of the present invention wherein tissue of varying thickness is clamped therein.

FIG. 34 depicts a staple applying assembly 16h that includes an elongate channel 40h that has an anvil 20h pivotally coupled thereto in a known manner. The elongate channel 40h is configured to operably support a staple cartridge 42h therein. The anvil 20h has a staple forming undersurface 60h thereon that is adapted to confront the upper surface 43h of the staple cartridge 42h when the anvil 20h is pivoted to the closed position shown in FIG. 34. The staples 83 are each supported on a corresponding staple driver 500, the construction of which will be discussed in further detail below.

Figure 35:
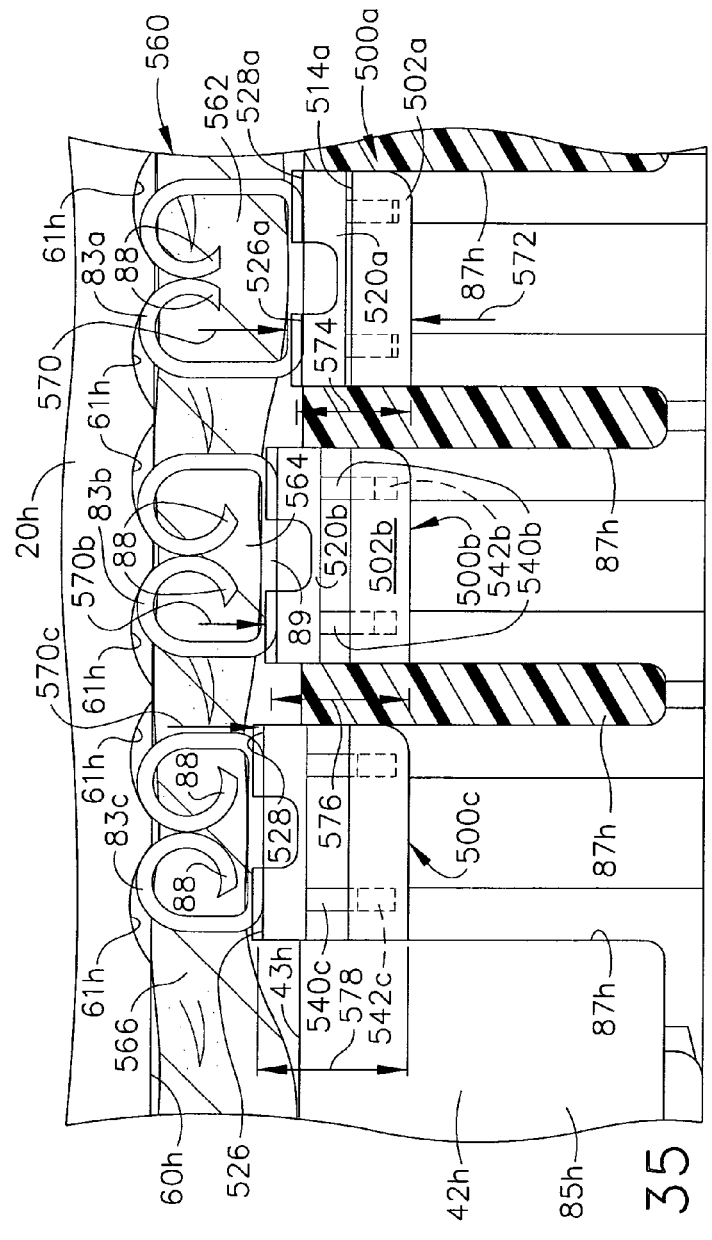
FIG. 35 is an enlarged cross-sectional view of a portion of the staple applying assembly of FIG. 34.

Each staple driver 500 may be movably supported within a corresponding staple channel 87h provided in the cartridge body 85h as shown in FIGS. 34 and 35. Also operably supported within the cartridge body 85h is a driving member or wedge sled 78 that is oriented for engagement by the E-beam firing member 50 during the firing process. See FIG. 34. As the E-beam firing member 50 and wedge sled 78 are driven distally through the elongate channel 40h and staple cartridge 42 in a known manner, the wedge sled 78 drives the staple drivers 500 upwardly within the cartridge body 85h. As the staple drivers 500 are driven upwardly toward the staple forming undersurface 60h of the anvil 20h, they carry with them their respective staple 83 or staples which are driven into forming engagement with the corresponding staple forming pockets 61h in the staple forming undersurface 60h of the anvil 20h. As the ends 88 of the staple 83 contact the forming pockets 61h, they are bent over thus providing the staple 83 with a shape that somewhat resembles a "B". While the various embodiments of the present invention have been described herein in connection with E-beam firing members, it is conceivable that these various embodiments may also be successfully employed with a variety of different firing member and driving member arrangements without departing from the spirit and scope of the present invention.

Figure 36:
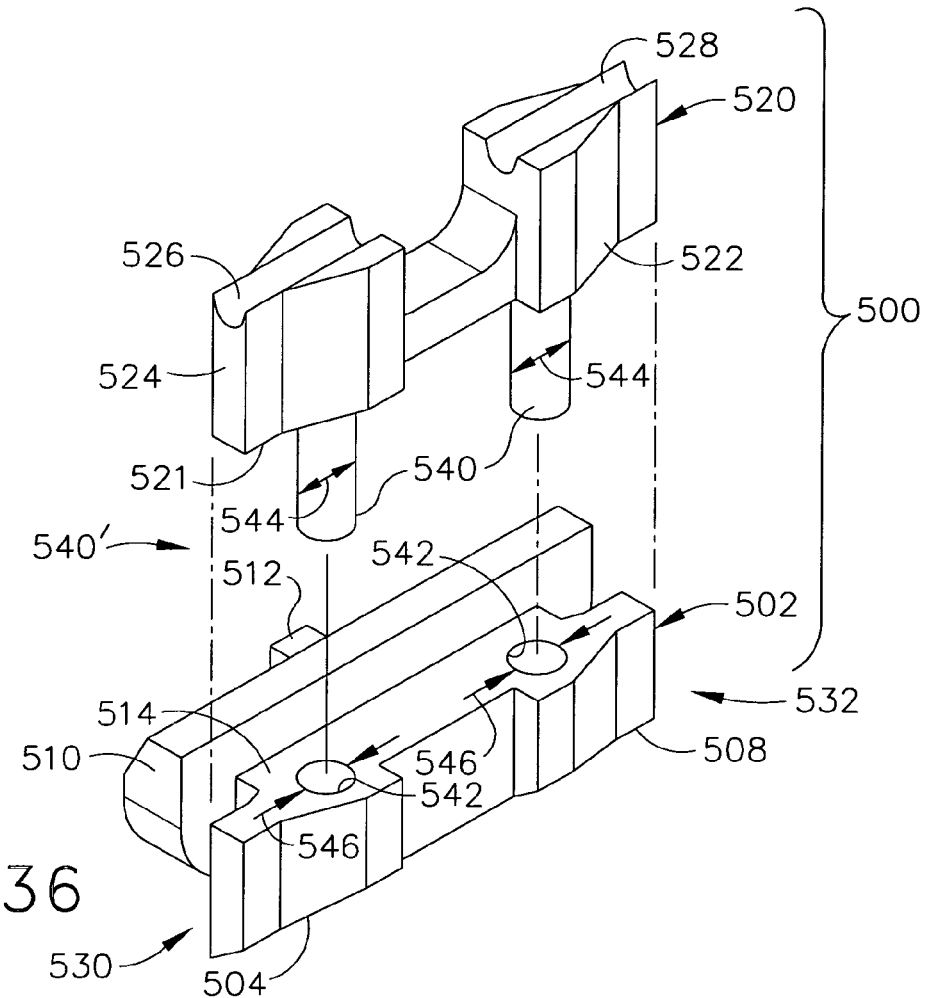
FIG. 36 is an exploded perspective view of a collapsible staple driver embodiment of the present invention in a first (uncollapsed) position.
Figure 37:
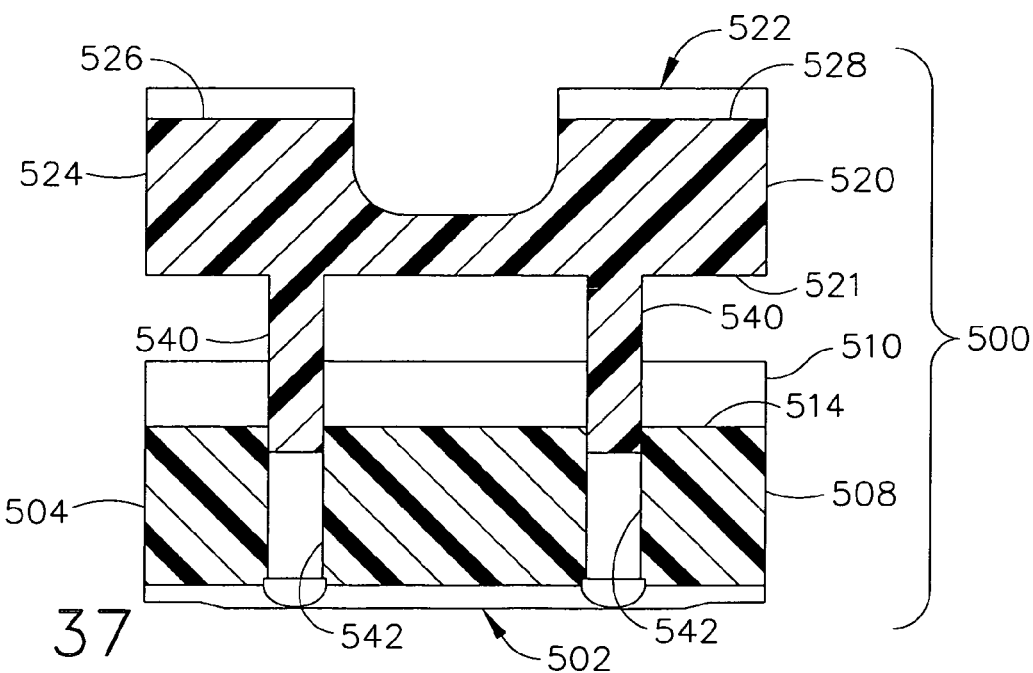
FIG. 37 is a cross-sectional view of the collapsible staple driver embodiment of FIG. 36.

One collapsible staple driver embodiment of the present invention is depicted in FIGS. 36 and 37. As can be seen in those Figures, the collapsible or compressible staple driver 500 includes a base portion 502 and a staple supporting portion 520 that is movable from a first uncollapsed position relative to the base portion 502 in response to compression forces generated during the firing process. In various embodiments, the base portion 502 may have a forward support column segment 504 and a rearward support column segment 508 that is spaced from the forward support column segment 504 and is substantially integrally formed therewith. The base portion 502 may also have an upstanding side portion 510 that has a rib 512 protruding from a backside therefrom. The upstanding side portion 510 serves to define a receiving ledge 514 in the base portion 502 for receiving the staple supporting portion 520 thereon. Those of ordinary skill in the art will understand that when the staple supporting portion 520 is received on the ledge 514, the staple driver 500 is unable to collapse or compress any further.

The staple supporting portion 520 of the staple driver 500 may similarly include a forward support column segment 522 and rearward support column segment 524 that is spaced from the forward support column segment 522. When the staple supporting portion 520 is received on the base portion 502, the forward support column segments 504, 522 serve to form a forward column portion 530 and the reward column segments 508, 524 form a rearward column portion 532. A forward staple receiving groove 526 is formed in the forward support column segment 522 and a rearward staple receiving groove 528 is formed in the rearward support column segment 524. The forward staple receiving groove 526 and the rearward staple receiving groove 528 serve to support a staple 83 therein as illustrated in FIG. 35. The rib 512 and the forward column 530 and rearward column 532 may cooperate with corresponding channels (not shown) in the staple cartridge body 85 to provide lateral support to the staple driver 500 while permitting the driver to be driven upward within the cartridge body 85 during the firing process.

In various embodiments, a resistive attachment structure, generally designated as 540' is provided to support the staple supporting portion 520 in a first uncompressed or uncollapsed orientation relative to the base portion (FIG. 37) prior to encountering any compressive forces during the firing operation and to permit the staple supporting portion 520 and the base portion to move towards each other (collapse or compress) in response to the magnitude of the compression forces applied to the staple supporting portion 520 and base portion 520 during the staple firing operation. As can be seen in FIGS. 36 and 37, the resistive attachment structure 540' in various embodiments may comprise a pair of attachment rods 540 that protrude from the bottom 521 of the staple supporting portion 520 and correspond to holes or apertures 542 in the base portion 502. The rods 540 are sized and shaped relative to the holes 542 to establish an interference fit or "light press fit" (i.e., an interference of approximately 0.001 inches) therebetween such that when the staple supporting portion 520 and base driver portion 502 are compressed together during the staple firing operation as will be discussed in further detail below, the staple supporting portion 520 and the base portion 502 can compress toward each other to reduce the overall height of the staple driver 500 in relation to the amount of compression force encountered during the firing process. In various embodiments, for example, the staple supporting portion 520 and base portion 520 may be fabricated from the same material such as, for example, plastic material such as ULTEM®. In other embodiments, the base portion 502 and the staple supporting portion 520 may be fabricated from different materials. For example, staple supporting portion 520 may be fabricated from ULTEM® and base portion 502 may be fabricated from glass or mineral filled ULTEM®. However, other materials could also be employed. For example, the base portion 502 could be fabricated from Nylon 6/6 or Nylon 6/12.

In various embodiments, a frictional or an interference fit of approximately 0.001 inch may be established between the attachment rods 540 and their corresponding holes 542. However, other degrees of interference fit may be employed to attain the desired amount and rate of driver compression in proportion to the magnitude of compression forces encountered when stapling a particular type/thickness of tissue. For example, in one embodiment, the degree of interference fit between the attachment rods 540 and their respective holes 542 may be approximately 0.002 to 0.005 inches for stapling tissues wherein it is anticipated that compression forces on the order of 2-5 pounds may be generated during the firing operation.

FIG. 35 illustrates various ranges of travel and compression that the staple drivers 500 may experience when encountering tissues of varying thicknesses. More specifically, FIG. 35 illustrates a portion of tissue 560 clamped between the upper surface 43h of the staple cartridge 42h and the staple forming undersurface 60h of the anvil 20h. As illustrated in FIG. 35, the tissue 560 has three thicknesses. The thickest portion of tissue is designated as 562 and comprises the portion of tissue that is on the right side of the Figure. The next thickness portion of tissue is designated as 564 and the thinnest portion of tissue 560 is designated as 566 and is on the left side of the Figure. For the purposes of this explanation, the staple driver associated with tissue portion 562 is designated as staple driver 500a. The staple driver associated with tissue portion 564 is designated as staple driver 500b and the staple driver associated with tissue portion 566 is designated as 500c. It will be understood that staple drivers 500a, 500b, 500c, may be identical in construction to staple driver 500 as described above.

Turning to staple driver 500a first, as the staple driver 500a is driven upwardly towards the staple forming undersurface 60h of the anvil 20h by the wedge sled (not shown in FIG. 35), it encounters the thick tissue portion 562 which resists the upward movement of the staple driver 500a. Such resistive force (represented by arrow 570) opposes the drive force (represented by arrow 572) generated by the wedge sled and serves to overcome the amount of interference established between the attachment rods 540 and their respective holes 542 and forces the rods 540 deeper into their respective holes 542 to thereby permit the staple supporting portion 520a of the staple driver 500a and base portion 502a to move toward each other. This movement of the staple supporting portion 520a and base portion 502a towards each other under a compressive force generated during the staple firing operation is referred to herein as "collapsing" or "compressing". When in the completely compressed position wherein the staple supporting portion 520a is received on the ledge 514a of the base portion 502a, the staple supporting ledges 526a, 528a on the staple supporting portion 520a may preferably support the bottom cross member 89 of the staple 83 above the upper surface 43h of the staple cartridge 42h to avoid catching the staple 83 on the staple cartridge 42h when the staple applying assembly 16h is withdrawn. The compressed height of the staple driver 500a is designated by arrow 574 in FIG. 35.

Turning next to staple driver 500b which corresponds to tissue portion 564, because the tissue portion 564 is not as thick as tissue portion 562, the resistive force 570b encountered by the staple driver 500b during the firing operation is not as great as resistive force 570. Therefore, the attachment pins 540b of staple driver 500b are not advanced into their respective holes 542b as far as the pins 540 of staple driver 500a were advanced into their respective holes 542. Thus, the compressed height 576 of staple driver 500b is greater than the compressed height 574 of staple driver 500a. As can also be seen in FIG. 35, the bottom portion 89 of the staple 83 supported in staple driver 500b is supported above the upper surface 43h of the staple cartridge 42h.

Staple driver 500c is associated with the thinnest tissue portion 566. Thus, the resistive force 570c encountered by the staple driver 500c during the staple firing operation is less than the resistive force 570b that was encountered by staple driver 500b. Thus, the pins 540c of staple driver 500c are not advanced into their respective holes 542c as far as the pins 540b of staple driver 500b were advanced into their respective holes 542b. Thus, the compressed height 578 of staple driver 500c is greater than the compressed height 576 of staple driver 500b.

As can be further seen in FIG. 35, because the compressed height 578 of staple driver 500c is greater than the compressed height 576 of staple driver 500b, the staple 83c supported by staple driver 500c was compressed to a greater extent than the staple 83b that was supported by staple driver 500b. Thus, the formed height of staple 83c is less than the formed height of staple 83b which is less than the formed height of staple 83a as illustrated in FIG. 35.

Those of ordinary skill in the art will appreciate that the number, shape, composition and size of the attachment rods and their respective holes can vary from embodiment to embodiment without departing from the spirit and scope of the present invention. Such interrelationship between the attachment rods and their respective holes serves to establish an amount of frictional interference therebetween which can be overcome in relation to various compression forces encountered when clamping/stapling different thicknesses of tissue. In an alternative version, the attachment to rods 540 may be formed on the base portion 502 and the holes provided in the staple supporting portion 520.

Figure 38:
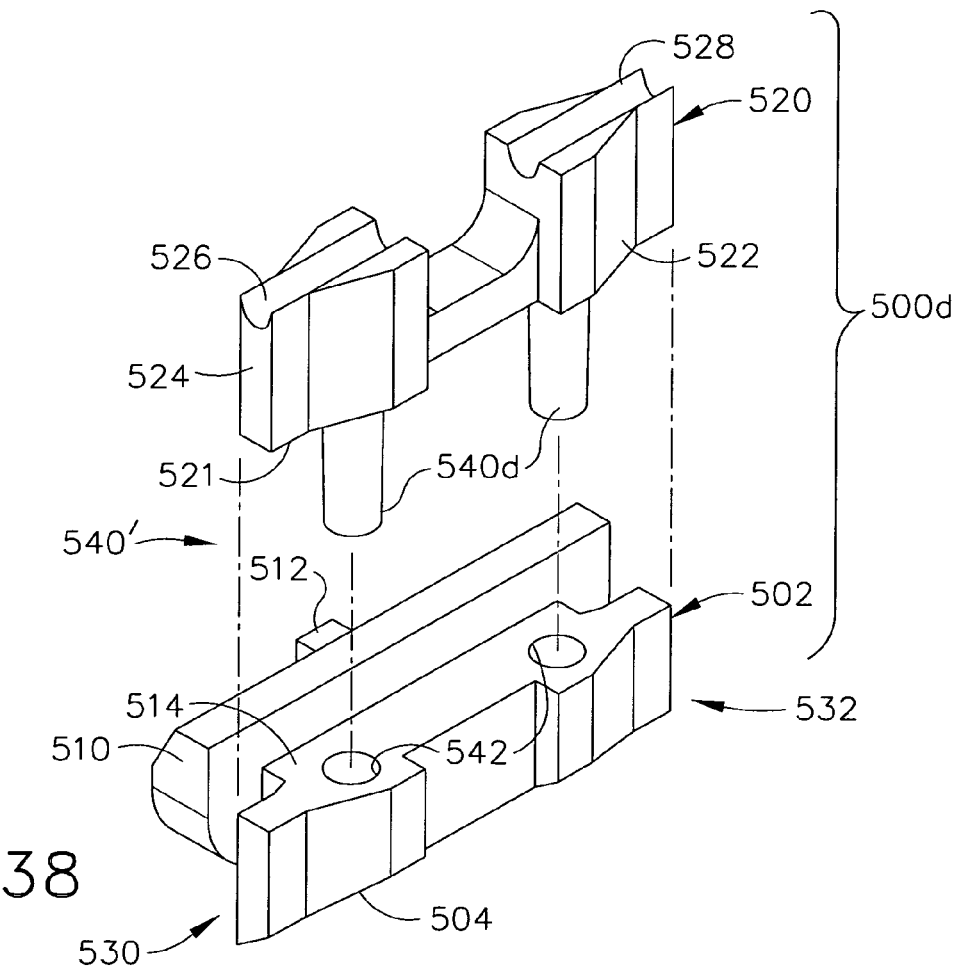
FIG. 38 is an exploded perspective view of another collapsible staple driver embodiment of the present invention in a first (uncollapsed) position.
Figure 39:
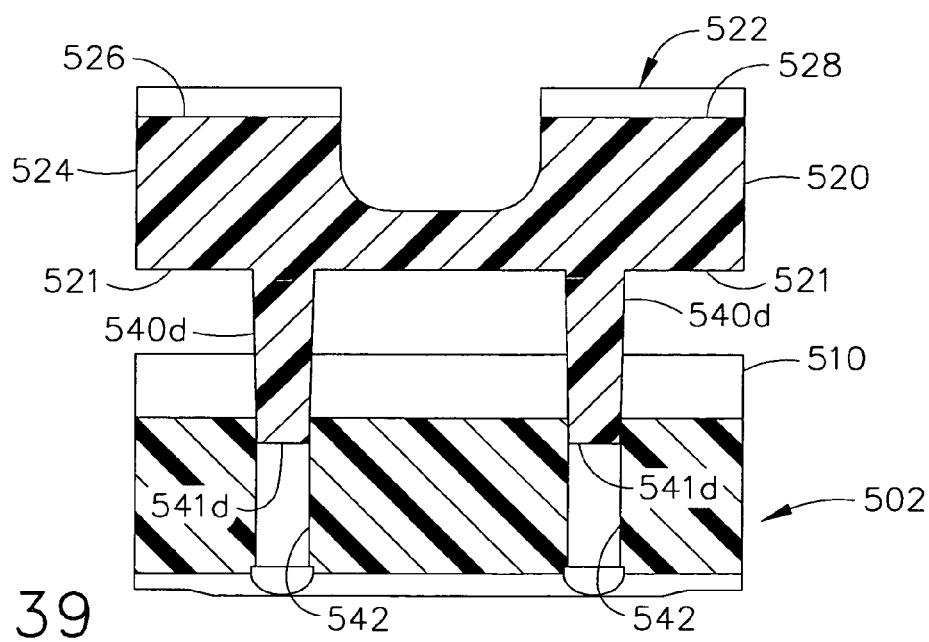
FIG. 39 is a cross-sectional view of the collapsible staple driver embodiment of FIG. 38.
Figure 40:
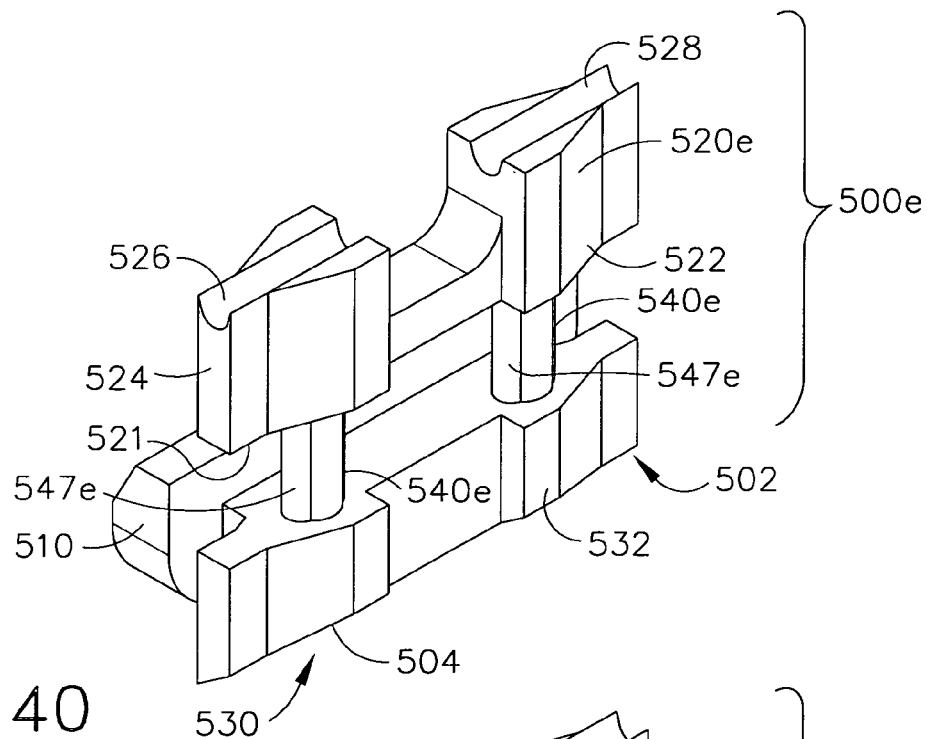
FIG. 40 is a perspective view of another collapsible staple driver embodiment of the present invention.
Figure 41:
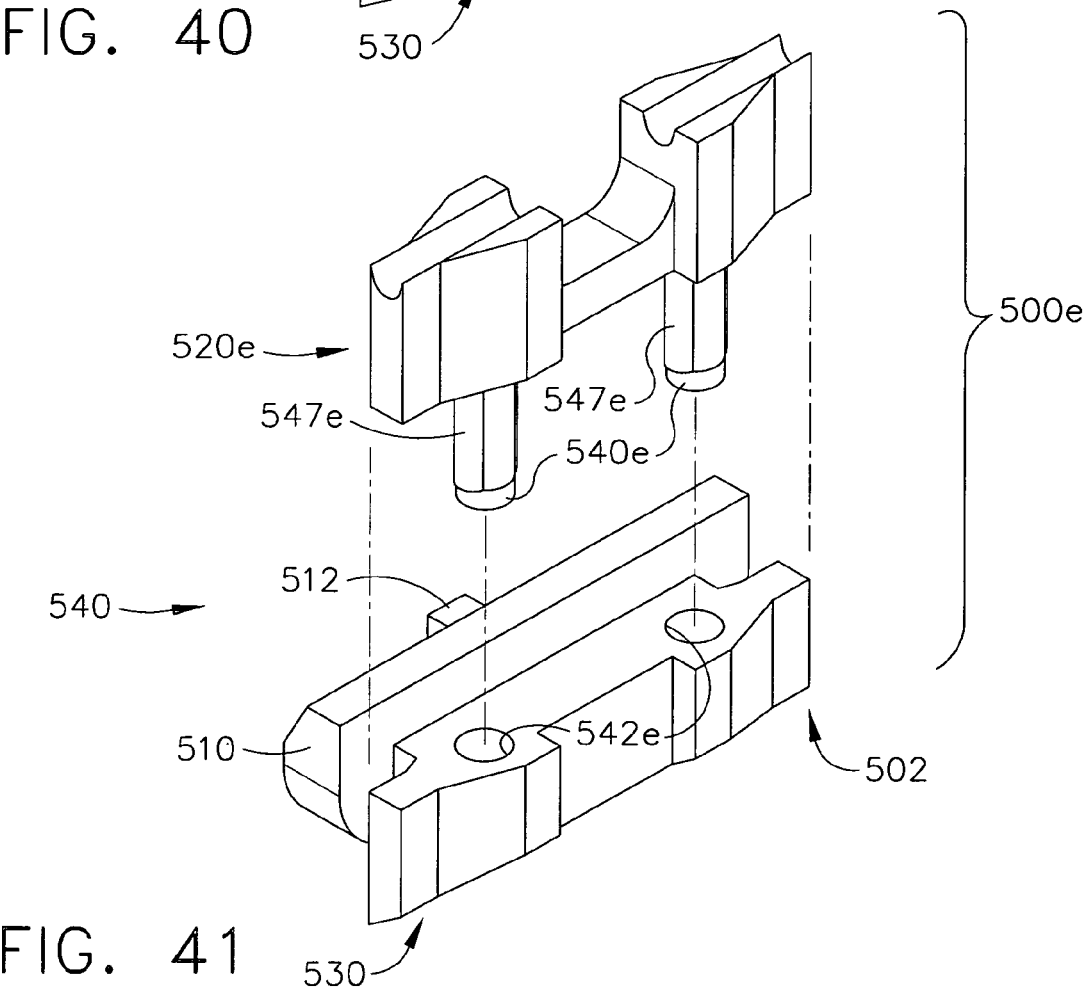
FIG. 41 is an exploded perspective view of the collapsible staple driver embodiment of FIG. 40.
Figure 42:
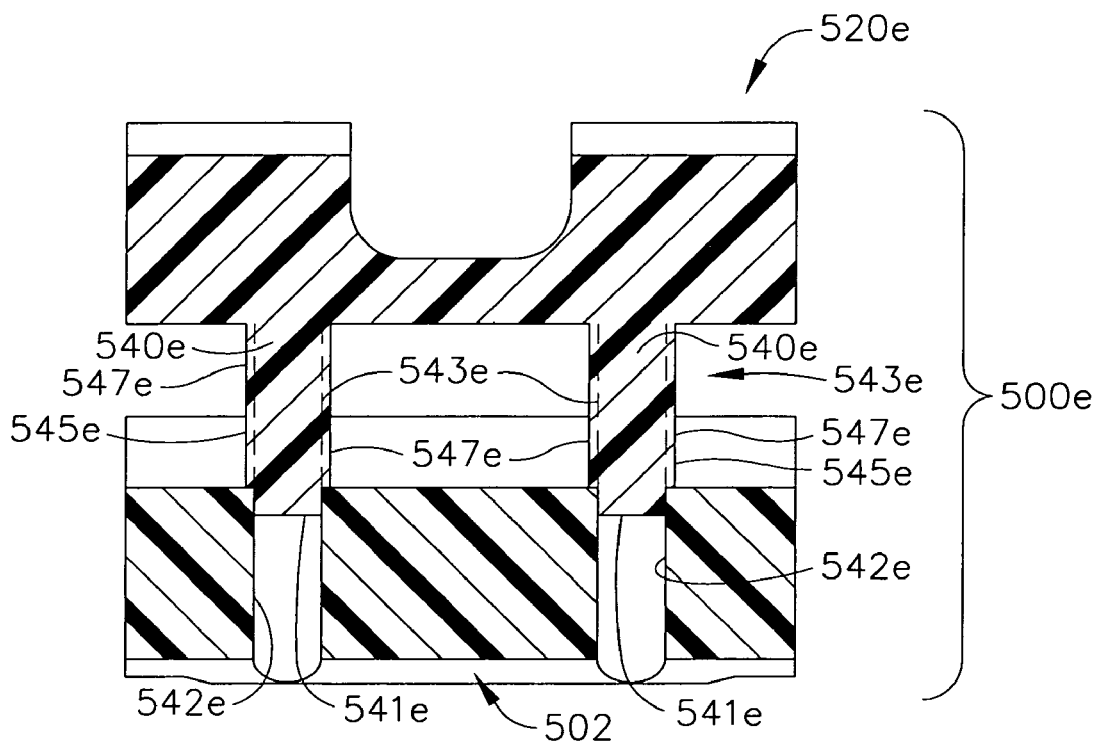
FIG. 42 is a cross-sectional view of the collapsible staple driver embodiment of FIGS. 40 and 41 in a first (uncollapsed) position.
Figure 43:
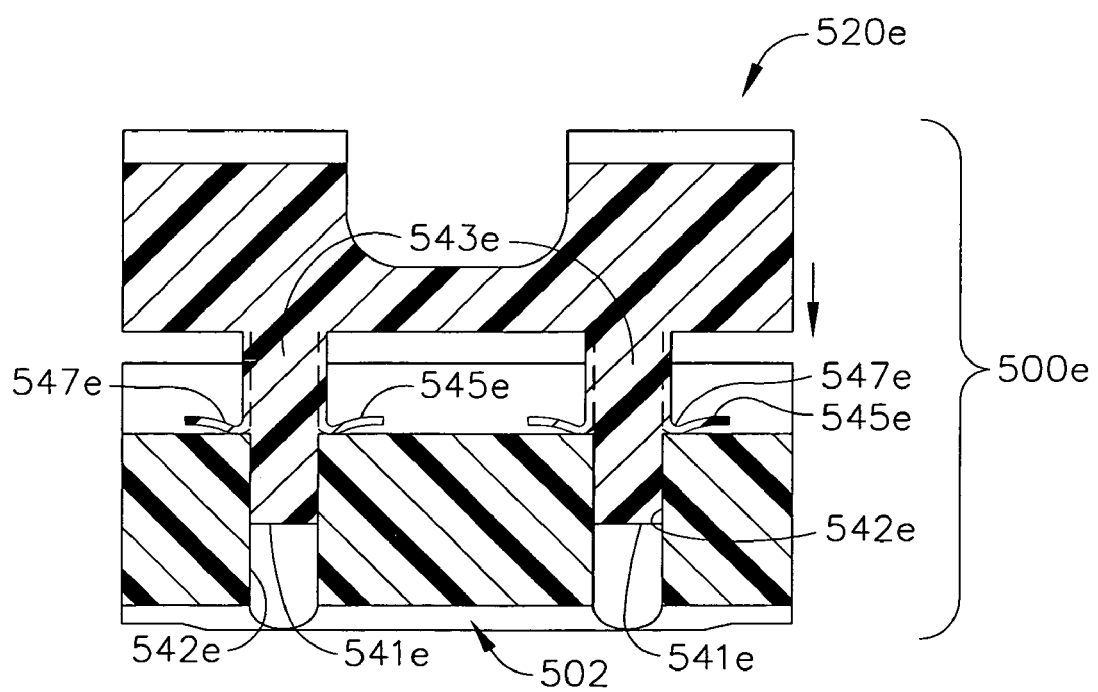
FIG. 43 is another cross-sectional view of the collapsible staple driver embodiment of FIGS. 40-42 after compression forces have been applied thereto.

FIGS. 38 and 39 illustrate another staple driver 500d embodiment of the present invention that may be substantially identical in construction and operation to the staple drivers 500 described above, except that the attachment rods 540d are somewhat tapered or frusto-conically shaped. In various embodiments, for example, the ends 541d of the attachment rods 540d may be sized relative to holes 542 such that a light press fit is established therebetween when in the first uncollapsed state depicted in FIG. 39. The degree of taper of the attachment rods 540d may be tailored to attain the desired amount of staple driver compression in relation to the magnitude of compression forces encountered during the staple firing process. Thus, in these embodiments, the magnitude of the interference fit between the attachment rods 540d and the holes 542 increases as the staple driver 500d encounters greater compression forces which drive the attachment rods 540d deeper into their respective holes 542d. In alternative embodiments, the attachment rods 540 may have a round shape and the holes 542 may be tapered to attain the desired amount and rate of staple driver compression in proportion to the amount of anticipated compression forces applied thereto during the firing operation. In an alternative version, the attachment rods 540d may be formed on the base portion 502 and the holes 542 may be formed in the staple supporting portion 520.

FIGS. 40-43 illustrate another staple driver 500e embodiment of the present invention that may be substantially identical in construction and operation to the staple drivers 500 described above, except that the attachment rods 540e are configured or shaped to include an additional amount of material oriented to be sheared off of the remaining portion of the rods as the staple driver 500e encounters compression forces during the firing operation. More specifically and with reference to FIG. 42, the attachment rods 540e have a tip portion 541e that is received within the corresponding hole 542e. The tip portion 541e may be sized relative to the hole 542e such that a sliding fit is achieved therebetween or, in other embodiments, a small interference fit may be established between those components when in the first uncollapsed position. The remaining portion 543e of each attachment rod 540e may be provided or formed with an additional amount of material 545e that is designed to be sheared therefrom as the staple driver 500e encounters the anticipated compression forces during the firing operation. See FIG. 43. The additional material 545e may extend completely around the circumference of the portion 543e of each attachment rod 540e or the material 543e may comprise one or more segments oriented around the circumference of the attachment rod 540e. For example, in the embodiment depicted in FIGS. 40-43, two segments 547e of material 543e are diametrically opposed on each attachment rod 540e as shown. In various embodiments, the diametric distance between the segments may be somewhat larger than the diameter of the holes 542e to cause the segments 547e to be sheared or removed from at least a portion of the rods 540e as the staple driver 500e encounters the anticipated compression forces during the firing operation.

The portions of additional material 543e may comprise an integral portion of the attachment rod 540e or the additional material 543e may comprise a second material applied to the attachment rod 540e and designed to shear off therefrom when the staple driver 500e encounters the anticipated compression forces. In various embodiments, the base portion 502 may be fabricated from a material that is more rigid that the material from which attachment rods 540e and/or the additional material 543e are fabricated such that the base portion 502 facilitates the shearing off of additional material 543e as the staple support portion 520e and base portion 502e are compressed together during the staple firing operation. In an alternative version, the attachment rods 540e may be formed on the base portion 502 and the holes 542e can be provided in the staple supporting portion 520e.

Figure 44:
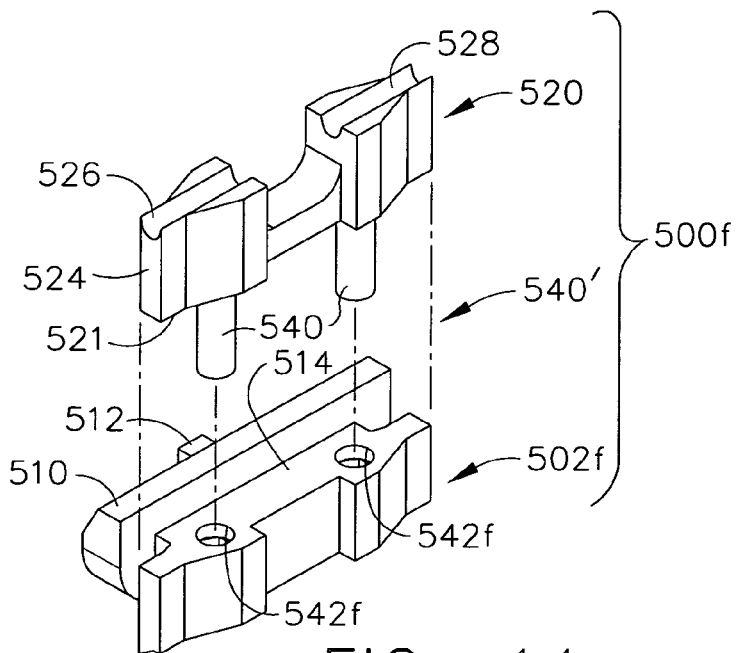
FIG. 44 is an exploded perspective view of another collapsible staple driver embodiment of the present invention.
Figure 45:
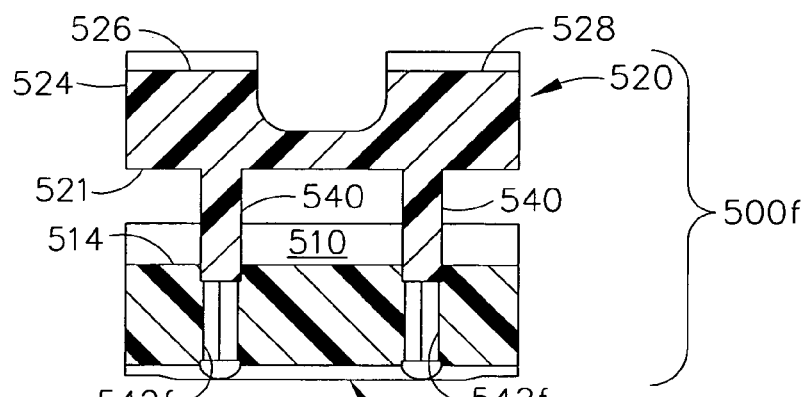
FIG. 45 is a cross-sectional view of the collapsible staple driver embodiment of FIG. 44 in a first (uncollapsed) position.
Figure 46:
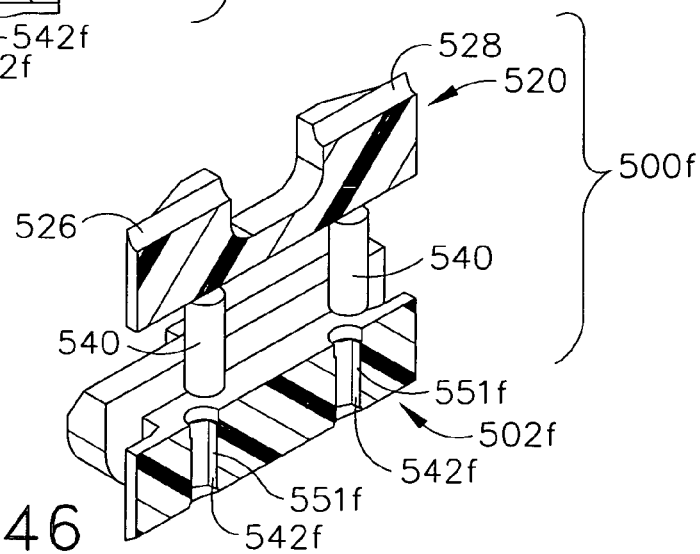
FIG. 46 is an exploded perspective view of the collapsible staple driver embodiment of FIGS. 44 and 45 with some of the elements thereof shown in cross-section.

FIGS. 44-46 illustrate another staple driver 500f of the present invention that may be substantially identical in construction and operation to the staple drivers 500 described above, except that the holes 542f in the base portion 502f may be hexagonally shaped or may have one or more surfaces therein designed to establish an interference fit with the attached rods 540 or to otherwise resist further entry of the attachment rods 540 into the holes 542f. For example, the holes 542f shown have a pair of flat surfaces 551f formed therein that serve to establish an interference fit or a degree of frictional resistance between the attachment rods 540f and the holes 542f which can be overcome by the various compression forces encountered when clamping/stapling different thicknesses of tissue. In the embodiment depicted in FIGS. 44-46, the attachment rods 540 have a substantially circular cross-sectional shape and the holes 542f have flat surfaces 551 formed therein. In alternative embodiments, however, the holes 542 may be round and the flat surfaces may be formed on the attachment rods 540. In an alternative version, the attachment rods 540 may be provided on the base portion 502f and the holes 542f can be provided in the staple supporting portion 520.

Figure 47:
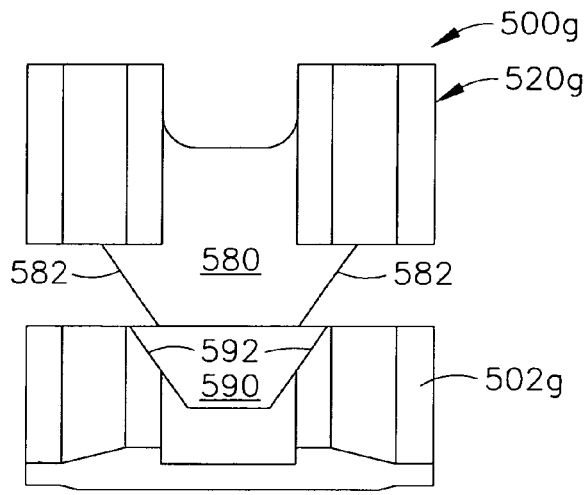
FIG. 47 is an exploded front view of another collapsible staple driver embodiment of the present invention.
Figure 48:
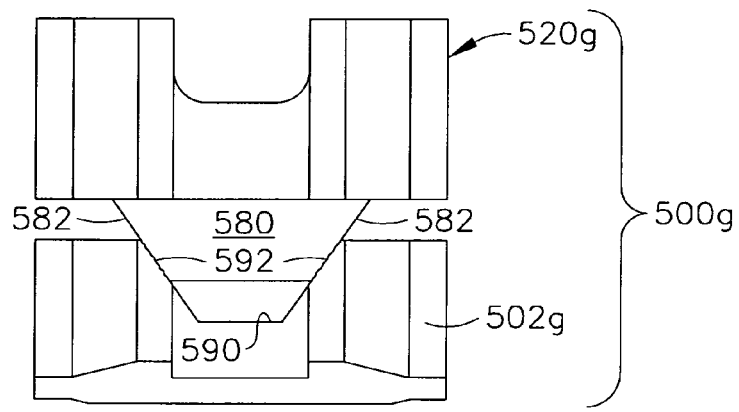
FIG. 48 is another front view of the collapsible staple driver of FIG. 47 in a first (uncollapsed) position.
Figure 49:
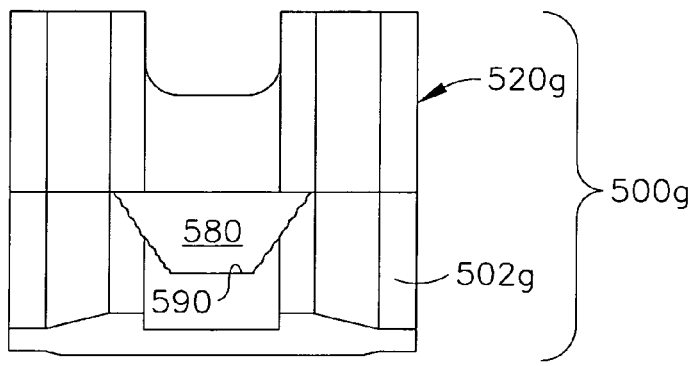
FIG. 49 is another front view of the staple driver of FIGS. 47 and 48 after it has been compressed to a fully collapsed position.

FIGS. 47-49 illustrate another staple driver 500g of the present invention that comprises a base portion 502g and a staple supporting portion 520g. The staple supporting portion 520g has staple supporting grooves (not shown) formed therein and a downwardly protruding tang 580 protruding from its undersurface 521g. The tang 580 has two tapered surfaces 582 and is shaped to be received in a corresponding cavity 590 formed in the base portion 502g. The cavity 590 is formed with tapered sides 592 and is sized to receive the tang 580 therein in the following manner. As the driver staple 500g encounters the compression forces generated during the firing operation, the tang 580 is forced into the cavity 590. FIG. 49 illustrates the staple driver 500g in a fully collapsed or compressed position. The staple supporting portion 520g and/or tang 580 may be fabricated from a material that is somewhat more compliant than the material from which the base portion 502g is formed so that the tang 580 can be forced into the cavity 590 in the base portion 502g without substantially distorting the base portion 502g to the extent that it would hamper the ability of the staple driver 500g to be fully driven to a final firing position. For example, the staple supporting portion and/or the tang 580 may be fabricated from ULTEM® and the base portion 502g may be fabricated from glass filled Nylon to achieve the desired amount of driver compression when encountering the anticipated compression forces during the firing operation. In an alternative version, the tang 580 may be provided on the base portion 502g and the hole 590 can be provided in the staple supporting portion 520g.

Figure 50:
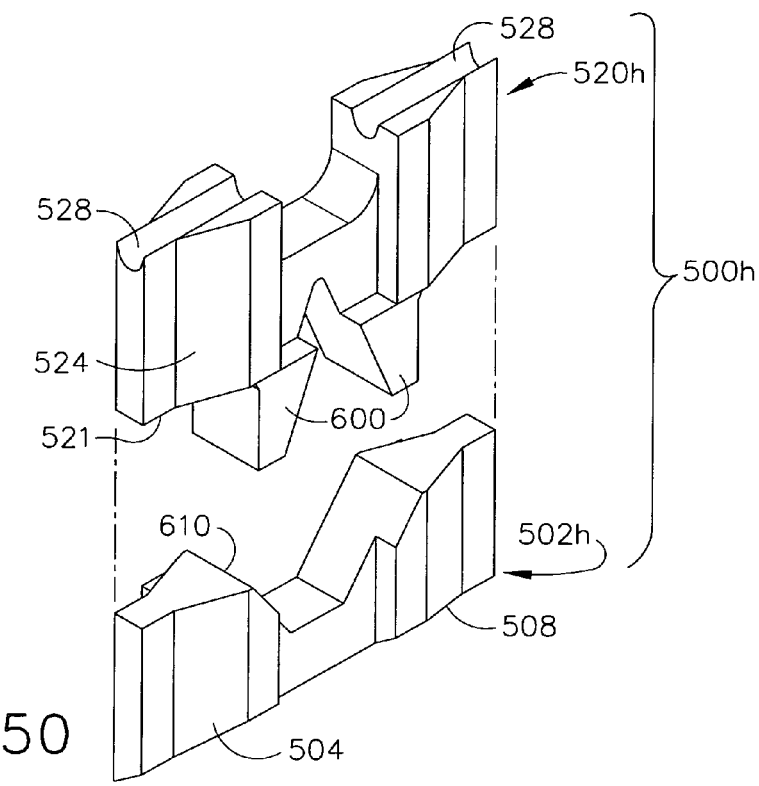
FIG. 50 is an exploded assembly view of another collapsible staple driver embodiment of the present invention.
Figures 51, 52:
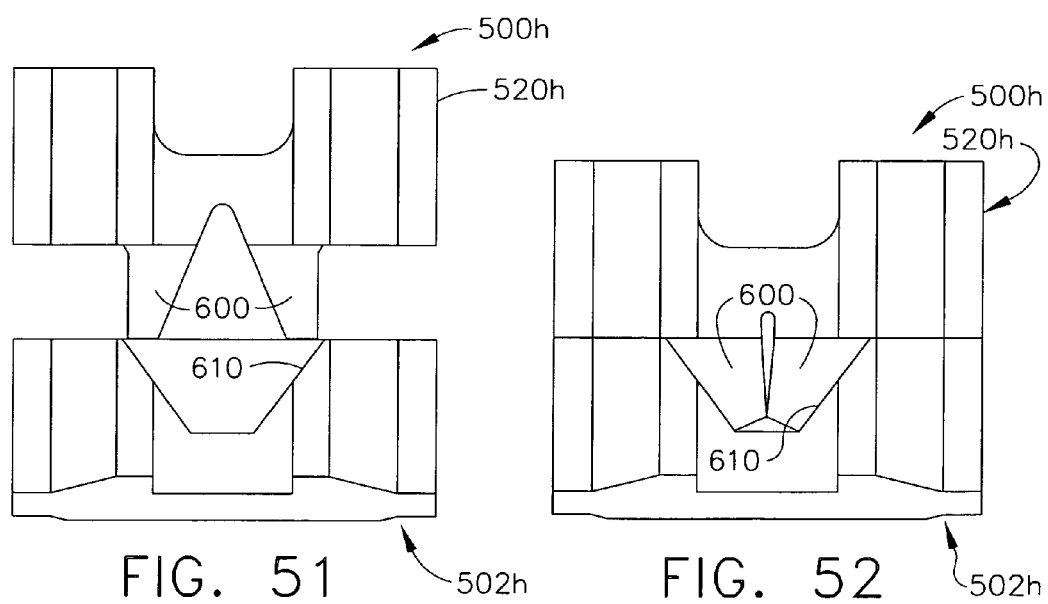
FIG. 51 is an exploded front view of the collapsible staple driver embodiment of FIG. 50.
FIG. 52 is another front view of the collapsible staple driver embodiment of FIGS. 50 and 51 after being compressed into a fully collapsed position.

FIGS. 50-52 illustrate another staple driver 500h embodiment of the present invention that may be substantially identical in construction and operation to the staple drivers 500 described above, except that, instead of attachment rods, the staple supporting portion 520h has two tapered tangs 600 protruding therefrom designed to be compressed into a V-shaped cavity 610 formed in the base portion 502h. Prior to commencement of the firing operation, the staple supporting portion 520h is supported on the base portion 502h within the staple cartridge. As the staple supporting portion 520h and the base portion 502h are compressed together during the firing operation, the tapered tangs 600 are forced inwardly as shown in FIG. 52. The degree to which the tangs 600 are compressed into the V-shaped cavity 610 is dependent upon the magnitude of the compression forces encountered during the firing operation.

The staple supporting portion 500h and/or tangs 600 may be fabricated from a material that is somewhat more compliant than the material from which the base portion 502h is formed so that the tangs 560 can be forced into the V-shaped cavity 610 in the base portion 502h without substantially distorting the base portion 502h to the extent that it would hamper the ability of the staple driver 500h to be fully driven to a final firing position. For example, the staple supporting portion and/or the tangs 600 may be fabricated from Nylon with no fill and the base portion 502h may be fabricated from ULTEM® with a glass or mineral fill to achieve the desired amount of staple driver compression when encountering the anticipated compression forces during the firing operation. In an alternative version, the tangs 600 may be provided on the base portion 502h and the cavity 610 may be provided in the staple supporting portion 520h.

Figure 53:
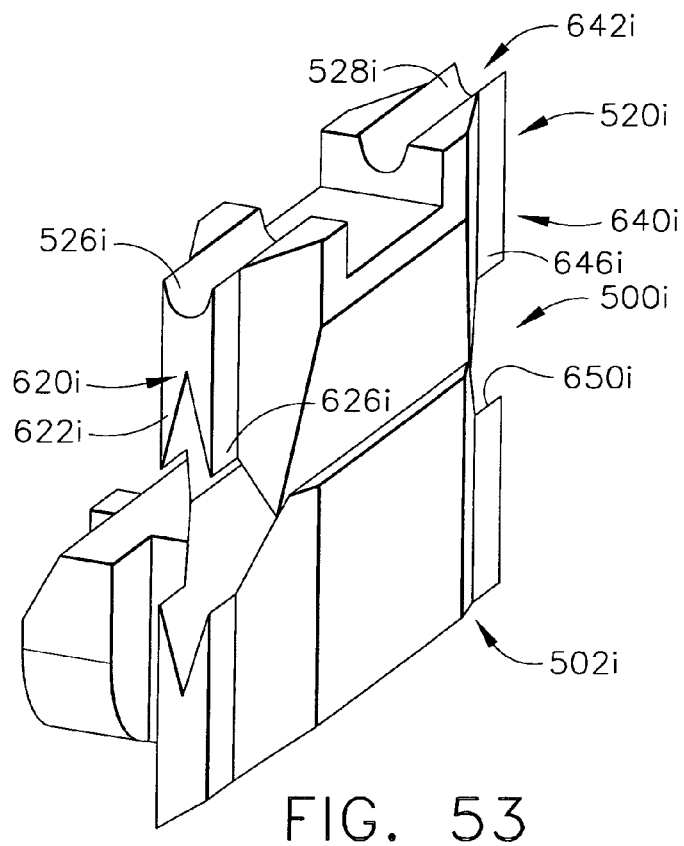
FIG. 53 is a perspective view of another collapsible staple driver embodiment of the present invention.
Figures 54, 55:
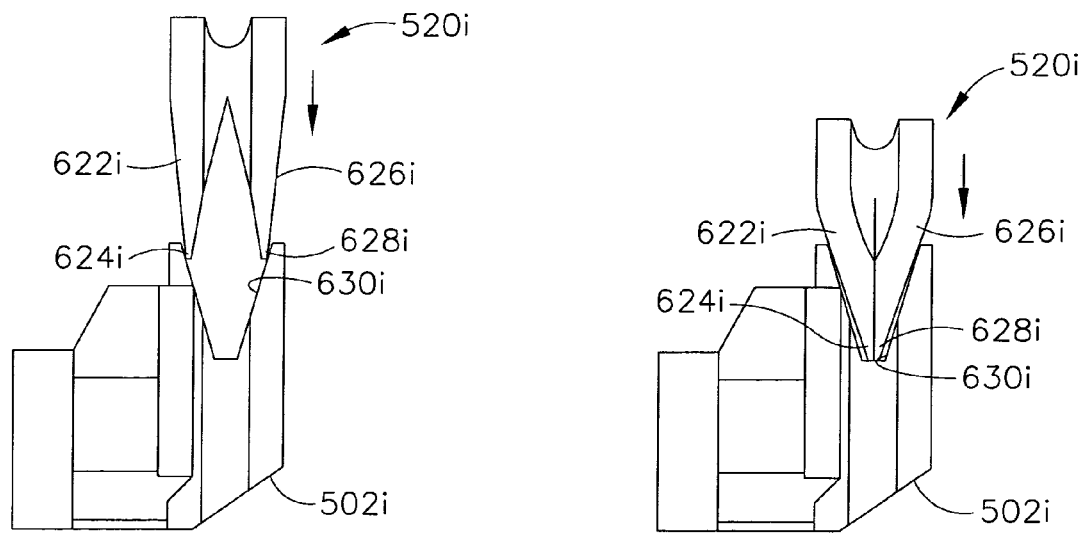
FIG. 54 is a side elevational view of the collapsible staple driver of FIG. 53 in a first (uncollapsed) position.
FIG. 55 is another side elevational view of the collapsible staple driver of FIGS. 53 and 54 after being compressed to a fully collapsed position.

FIGS. 53-55 illustrate yet another staple driver 500i embodiment of the present invention that includes a staple supporting portion 520i that has V-shaped staple supporting grooves 630i, 650i therein. In this embodiment, the staple supporting portion 520i has a first pair 620i of two tapered tangs 622i, 626i protruding therefrom oriented to be compressed into the first V-shaped groove or cavity 630i and a second pair 640i of two tapered tangs 642i, 646i oriented to be compressed into the second V-shaped groove or cavity 650i. More specifically and with reference to FIG. 54, the first tang 622i has an end 624i that is spaced from an end 628i of the second tang 626i prior to commencement of the staple firing operation. When in the position illustrated in FIG. 54, the ends 624i, 628i are biased outwardly into frictional contact with the upper side walls of the first V-shaped groove 630i to retain the staple supporting portion 520i in the uncollapsed position shown in FIG. 54. Although not shown, the second pair 640i of tangs 642i, 646i are also similarly configured as tangs 622i, 626i and serve to engage the second V-shaped groove 650i in the same manner.

As the staple supporting portion 520i and the base portion 502i are compressed together during the firing operation, the ends 624i, 628i of the first tangs 622i, 626i and the ends of the second tangs 642i, 646i are biased toward each other to permit the tangs to be driven deeper into their respective grooves 630i, 650i. FIG. 55 illustrates the first pair 620i of tangs 622i, 626i in their fully compressed state which also corresponds to the fully compressed state of the driver 500i. The degree to which the tangs are compressed into their respective V-shaped grooves is dependent upon the magnitude of the compression forces encountered during the firing operation.

The staple supporting portion 500i and/or tangs 622i, 626i, 642i, 646i may be fabricated from a material that is somewhat more compliant than the material from which the base portion 502i is formed so that the tangs 622i, 626i, 642i, 646i can be forced into their respective V-shaped grooves in the base portion 502i without substantially distorting the base portion 502i to the extent that it would hamper the ability of the driver 500i to be fully driven to a final firing position. For example, the staple supporting portion 520i and/or the tangs 622i, 626i, 642i, 646i may be fabricated from ULTEM® and the base portion 502i may be fabricated from Nylon with a glass or mineral fill to achieve the desired amount of driver compression when encountering the anticipated compression forces during the firing operation. In an alternative version, the tangs 622i, 626i, 642i, 646i may be provided on the base portion 502i and the V-shaped grooves 630i, 650i may be provided in the staple supporting portion 520i.

The various embodiments of the present invention described above and their respective equivalent structures represent vast improvements over prior staple applying assemblies and end effectors. Various embodiments of the present invention provide anvils and/or channels with flexible portions that permit the overall staple height to increase as the compression within the assembly increases due to tissue thickness. Other embodiments employ anvil arrangements that have flexible forming pockets that can be compressed away from the staple cartridge in response to variations in tissue thickness. In doing so, the inherent gap between the forming pocket and the cartridge increases which serves to increase the formed height of the staple. Such advantages can result in improved staple line consistency and provide better clinical outcomes.

Figure 56:
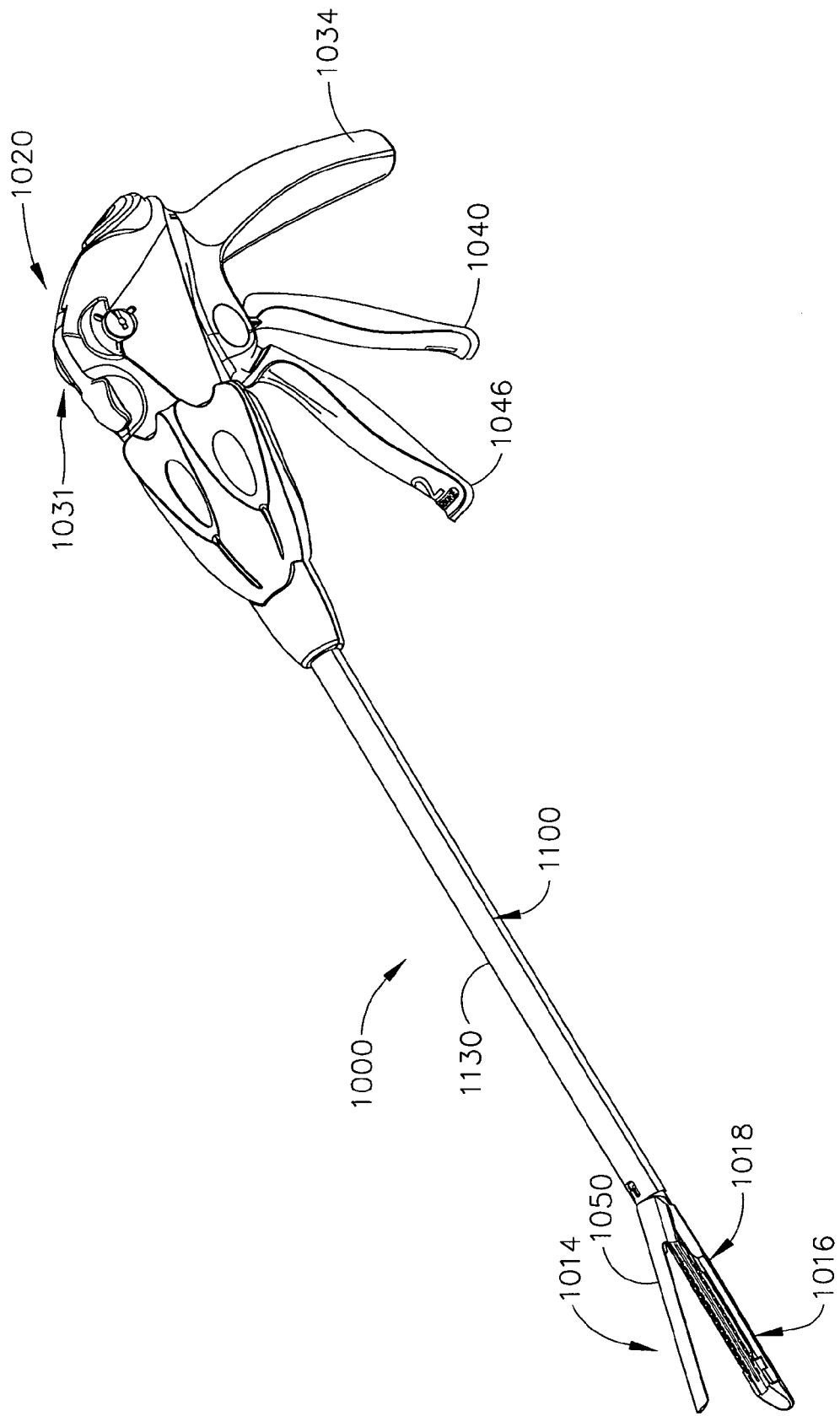
FIG. 56 is a perspective view of a surgical cutting and staple instrument of various embodiments of the present invention.

FIGS. 56-63 illustrate another surgical stapling and severing instrument 1000 of the present invention. As can be seen in FIG. 56, the instrument 1000 includes a handle assembly 1020 that is manipulated to position an implement portion 1014 including a fastening end effector, depicted as a staple applying assembly 1016, distally attached to an elongate shaft assembly 1100. The implement portion 1014 is sized for insertion through a cannula of a trocar (not shown) for an endoscopic or laparoscopic surgical procedure with an upper jaw (anvil) 1050 and a lower jaw 1018 of the staple applying assembly 1016 closed by depression of a closure trigger 1040 toward a pistol grip 1034 of the handle assembly 1020, which advances an outer closure tube assembly 1130 of the elongate shaft assembly 1100 to pivot the anvil 1050 to a closed position as will be discussed in further detail below.

Once inserted into an insufflated body cavity or lumen, the closure trigger 1040 may be released, opening the anvil 1050 so that tissue may be grasped and positioned. Once satisfied with the tissue held in the staple applying assembly 1016, the surgeon depresses the closure trigger 1040 until locked against the pistol grip 1034, clamping tissue inside of the staple applying assembly 1016. Then a firing trigger 1046 is drawn toward the closure trigger 1040 and pistol grip 1034, thereby applying a firing force or motion thereto to distally advance a firing member supported with in the implement 1014 from an unfired position. As the firing member advances through the implement or end effector 1014 in a known manner, it severs the tissue clamped within the end effector 1014 and fires or drives the staples contained with the staple cartridge 42 supported therein.

Figure 57:
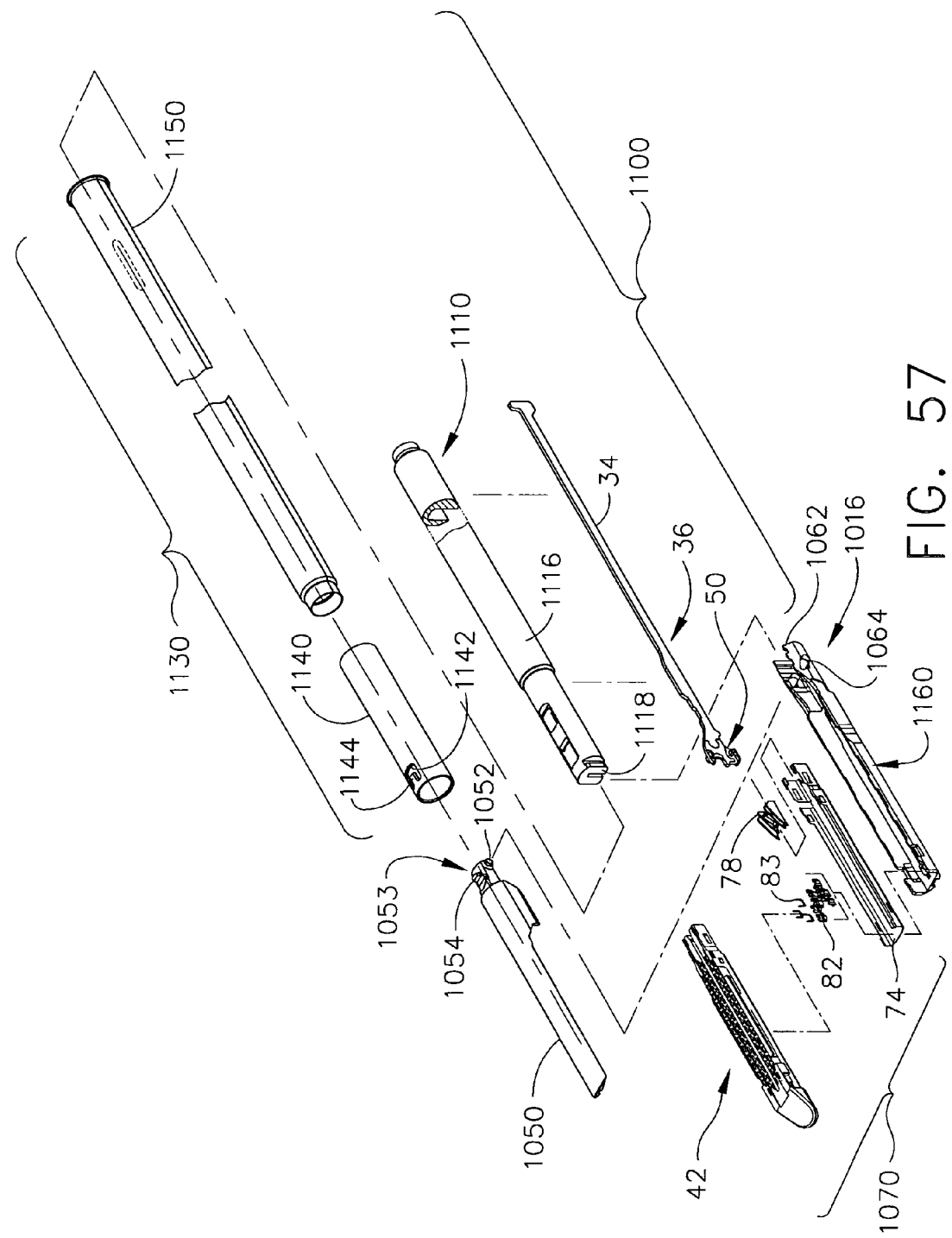
FIG. 57 is an exploded assembly view of an end effector and elongate shaft assembly of various embodiments of the present invention.

As depicted in FIG. 57, this embodiment may employ the firing bar 36 and E-Beam 50 arrangements described above. In other alternative embodiments, the E-Beam arrangements described in U.S. patent application Ser. No. 11/231,456, filed Sep. 21, 2005 and entitled "Surgical Stapling Instrument Having Force Controlled Spacing End Effector", the disclosure of which is herein incorporated by reference may also be employed. In addition, as the present Detailed Description proceeds, those of ordinary skill in the art will appreciate that the advantages provided by these embodiments of the present invention may be effectively attained when used in connection with other known non-E beam firing bar configurations. Thus, these embodiments of the present invention should not be limited solely to use in connection with E-beam type firing and cutting arrangements.

FIG. 57 depicts the firing bar 36 as including a proximal firing rod 34, that is supported within a "frame ground" or spine assembly 1110 that connects the handle assembly 1020 to the staple applying assembly 1016. During the staple firing motion, the firing bar 36 engages an elongate staple channel 1060 and actuates a staple cartridge 42 contained therein, both forming the lower jaw 1018 in the various manners described above.

A variety of different firing arrangements for applying an actuation force to the firing bar 36 to cause the firing bar to linearly advance and retract through the staple applying assembly 1016 are known. Such firing motions may be manually generated such as through use of the various firing system arrangements disclosed in U.S. patent application Ser. No. 11/475,412, filed Jun. 27, 2006, entitled "Manually Driven Surgical Cutting and Fastening Instrument" to Frederick E. Shelton, IV, et al., the disclosure of which is herein incorporated by reference. Still other actuation systems, such as the pneumatically powered actuation systems disclosed in U.S. patent application Ser. No. 11/497,898, filed Aug. 2, 2006, entitled "Pneumatically Powered Surgical Cutting and Fastening Instrument With a Variable Control of the Actuating Rate of Firing With Mechanical Power Assist" to Frederick E. Shelton, IV et al., the disclosure of which is herein incorporated by reference may be successfully employed. Other embodiments may include, for example, the electrical motor driven actuation systems disclosed in U.S. patent application Ser. No. 11/343,562, filed Jan. 31, 2006, entitled "Motor-Driven Surgical Cutting and Fastening Instrument With Articulatable End Effector" to Frederick E. Shelton, IV et al., the disclosure of which is also herein incorporated by reference. Still other embodiments may include other known mechanically, electrically, hydraulically and/or pneumatically powered firing systems without departing from the spirit and scope of the present invention.

In various embodiments, the elongate shaft assembly 1100 consists of a closure tube assembly 1130 that is received on the spine assembly 1110. See FIG. 57. The spine assembly 1110 may comprise a single member or it may comprise multiple segments with an articulation joint (not shown) mounted therein. Such articulation joints are known in the art and may, for example, be mechanically, electrically, hydraulically or pneumatically controlled. In the embodiment depicted in FIGS. 57 and 58, the spine assembly 1110 includes a proximal portion 1112 (FIG. 58) and a distal portion 1116 (FIG. 57). As will be discussed below, the proximal portion 1112 is attached to the handle assembly 1020 such that the closure tube assembly 1130 may be axially moved thereon to cause the anvil 1050 to pivot between open and closed positions. As can be seen in FIG. 57, the elongate channel 1060 has proximally placed attachment cavities 1062 that each receive a corresponding channel anchoring member 1118 formed on the distal end of the distal spine portion 1116.

The elongate channel 1060 also has elongated anvil cam slots 1064 that movably receive a corresponding anvil trunnion 1052 on the anvil 1050 as will be discussed in further detail below.

The closure tube assembly 1130 may comprise a distal closure tube portion 1140 and a proximal closure tube portion 1150. The distal closure tube portion 1140 and the proximal closure tube portion 1150 may be fabricated from a polymer or other suitable material. The distal closure tube portion 1140 and the proximal closure tube portion 1150 are each hollow for receiving a corresponding portion of the spine assembly 1110 therein. The closure tube assembly 1130 is depicted as comprising two separate portions 1140 and 1150 for ease of assembly of the entire elongate shaft assembly 1100. Those portions 1140 and 1150 may be attached together after assembly by adhesive or other suitable fastening means. It is conceivable, however, that the closure tube assembly 1130 may be fabricated as one piece. In addition, as was mentioned above, the spine assembly of various embodiments of the present invention may have an articulation joint mounted therein. For those embodiments, a double pivot closure joint (not shown) may be employed in the closure tube assembly 1130. Examples of such double pivot closure arrangements are disclosed in U.S. patent application Ser. No. 11/497,898, which has been herein incorporated by reference.

In use, the closure tube assembly 1130 is translated distally to close the anvil 1050, for example, in response to the actuation of the closure trigger 1040. The anvil 1050 is closed by distally translating the closure tube assembly 1130 on the spine assembly 1110, causing the back of a horseshoe aperture 1142 in the distal closure tube portion 1140 to strike a closure feature 1053 in the form of an open/closing tab 1052 on the anvil 1050 and cause it to pivot to the closed position. See FIG. 57. To open the anvil 1050, the closure tube assembly 1130 is axially moved in the proximal direction on the spine assembly 1110 causing a tab 1144 on the distal closure tube portion 1140 to contact and push against the open/closing tab 1054 on the anvil 1050 to pivot the anvil 1050 to the opened position.

Figure 58:
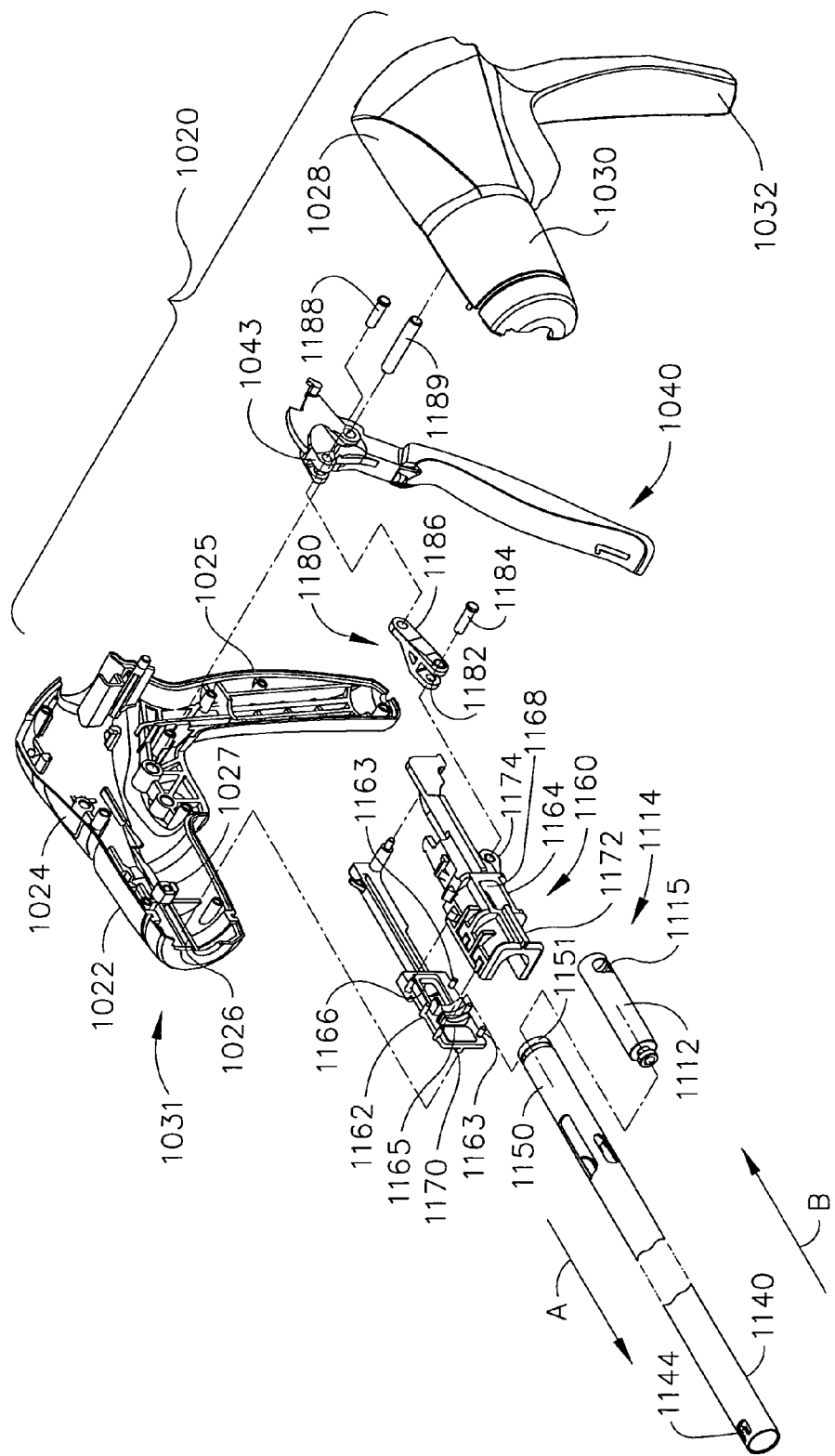
FIG. 58 is an exploded assembly view of a handle assembly and closure shuttle arrangements of various embodiments of the present invention, with the firing system components omitted for clarity.

FIG. 58 illustrates an exploded assembly view of a non-limiting handle assembly 1020 of various embodiments of the present invention wherein the various firing system components have been omitted for clarity. In the embodiment depicted in FIG. 58, the handle assembly 1020 has a "pistol grip" configuration and is formed from a right hand case member 1022 and a left handed case member 1028 that are molded or otherwise fabricated from a polymer or other suitable material and are designed to mate together. Such case members 1022 and 1028 may be attached together by snap features, pegs and sockets molded or otherwise formed therein and/or by adhesive, screws, bolts, clips, etc. The upper portion 1024 of the right hand case member 1022 mates with a corresponding upper portion 1030 of the left hand case member 1028 to form a primary housing portion designated as 1031. Similarly, the lower grip portion 1025 of the right hand case member 1022 mates with the lower grip portion 1032 of the left hand case member 1028 to form a grip portion generally designated as 1034. See FIG. 56. Those of ordinary skill in the art will readily appreciate, however, that the handle assembly 1020 may be provided in a variety of different shapes and sizes.

For the purposes of clarity, FIG. 58 only illustrates the components employed to control the axial movement of the closure tube assembly 1130 which ultimately controls the opening and closing of the anvil 1050. As can be seen in that Figure, a closure shuttle 1160 that is coupled to the closure trigger 1040 by a linkage assembly 1180 is supported within the primary housing portion 1031. Closure shuttle 1160 may also be fabricated in two pieces 1162, 1164 that are molded or otherwise fabricated from a polymer or other suitable material and are designed to mate together. For example, in the embodiment illustrated in FIGS. 58, 60, and 61, the right hand portion 1162 may be provided with fastener posts 1163 that are designed to be received within corresponding sockets 1167 (FIG. 61) in the left hand portion 1164. The right and left hand portions 1162, 1164 may be otherwise retained together by snap members and/or adhesive and/or bolts, screws, clips, etc. As can be seen in those Figures, a retention groove 1152 is provided in the proximal end 1151 of the proximal closure tube portion 1150. The right hand portion 1162 of the closure shuttle 1160 has a right retention flange 1165 (FIG. 60) that is adapted to cooperate with a left hand portion 1164 of the closure shuttle 1160 such that the retention flange 1165 extends into the retention groove 1151 in the proximal closure tube portion 1150. The retention flange 1165 serves to affix the closure tube assembly 1130 to the closure shuttle 1160 while facilitating its limited axial movement relative thereto as will be discussed in further detail below.

As can also be seen in FIG. 58, a right spine assembly retention peg 1027 protrudes inward from the right hand case member 1024. Such peg 1027 protrudes into an elongated slot or window 1166 in the right hand portion 1162 of the closure shuttle 1160. A similar closure shuttle retention peg (not shown) protrudes inward from the left hand case member 1164 to be received in another window or slot 1168 provided in the left hand side portion 1164 of the closure shuttle 1160. The retention pegs are configured to extend into a hole 1115 in the proximal end 1114 of the proximal spine portion 1110 to non-movably affix the spine portion 1110 to the handle assembly 1020 while permitting the closure shuttle 1160 to move axially relative thereto. See FIG. 58. The retention pegs may be mechanically attached to the proximal end 1114 of the proximal spine portion 1112 by, for example, bolts, screws, adhesive, snap features, etc. In addition, the closure shuttle 1160 is provided with laterally extending guide rails 1170, 1172. Rail 1170 is configured to be slidably received within rail guide 1026 in the right hand case member 1024 and rail 1172 is configured to be slidably received within a rail guide (not shown) in left hand case member 1028. See FIG. 58.

Axial movement of the closure shuttle 1160 and closure tube assembly 1130 in the distal direction (arrow "A") is created by moving the closure trigger 1040 toward the grip portion 1034 of the handle assembly 1020 and axial movement of the closure shuttle 1160 in the proximal direction (arrow "B") is created by moving the closure trigger 1040 away from the grip portion 1034. In various embodiments, the closure shuttle 1160 is provided with a connector tab 1174 that facilitates the attachment of the closure linkage assembly 1180 thereto. See FIGS. 58 and 59. The closure linkage assembly 1180 includes a yoke portion 1182 that is pivotally pinned to the connector tab 1174 by a pin 1184. The closure linkage assembly 1180 further has a closure arm 1186 that is pivotally pinned to a yoke assembly 1043 formed on the closure trigger 1042 by a closure pin 1188 as illustrated in FIG. 58. The closure trigger 1140 is pivotally mounted within the handle assembly 1020 by a pivot pin 11890 that extends between the right hand case member 1024 and the left hand case member 1028.

When the clinician desires to close the anvil 1050 to clamp tissue within the end effector 1014, the clinician draws the closure trigger 1040 toward the pistol grip portion 1034. As the clinician draws the closure trigger 1040 toward the pistol grip portion 1034, the closure linkage assembly 1180 moves the closure shuttle 1160 in the distal "A" direction until the closure linkage assembly 1180 moves into the locked position illustrated in FIG. 59. When in that position, the closure linkage assembly 1180 will tend to retain the closure shuttle 1160 in that locked position.

In various embodiments, to further retain the closure shuttle 1160 in the closed position, the closure trigger 1040 may be provided with a releasable locking mechanism 1190 that is adapted to engage the pistol grip portion 1034 and releasably retain the closure trigger 1040 in the locked position. Other locking devices may also be used to releasably retain the closure shuttle 1160 in the locked position.

Figure 59:
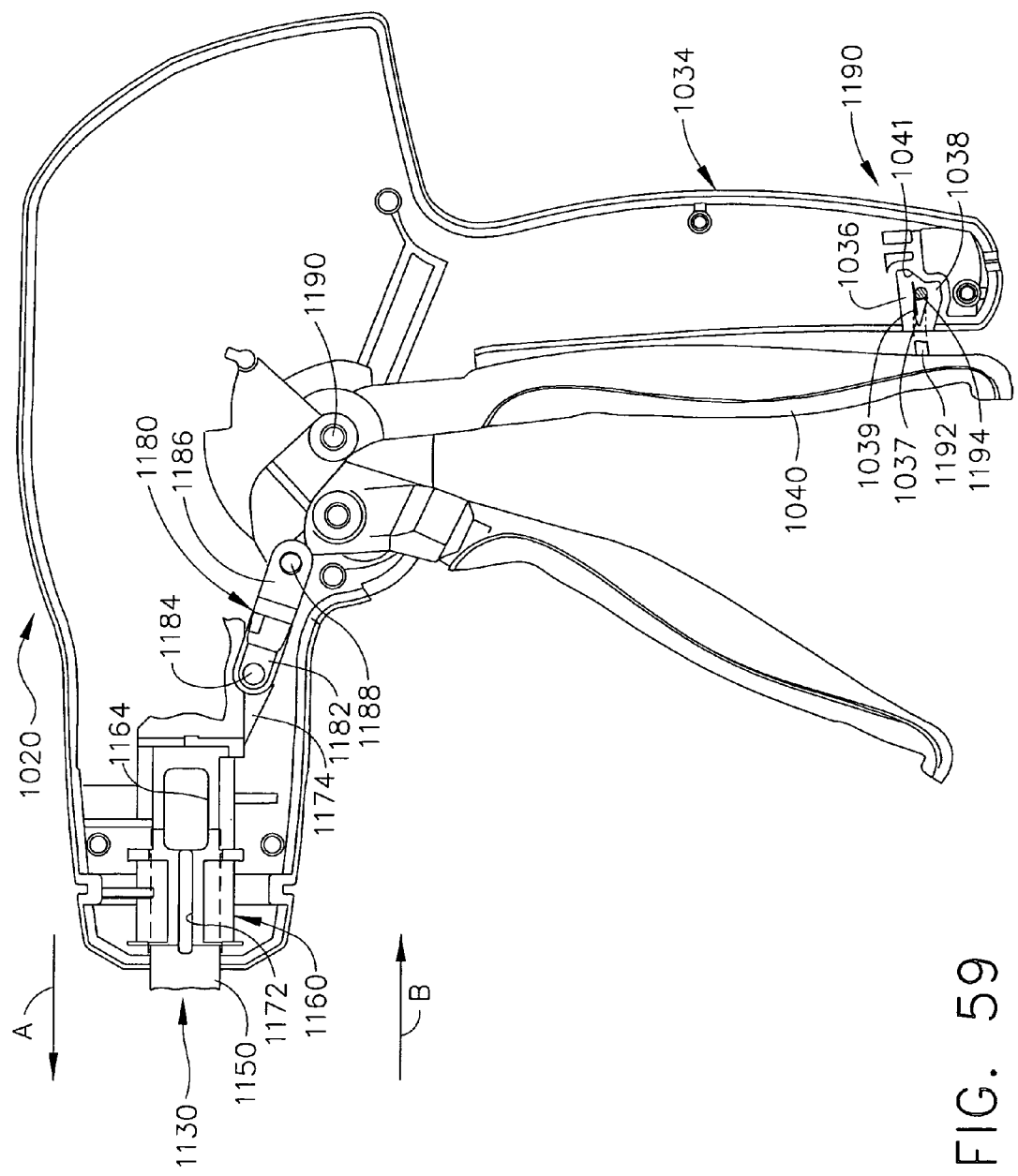
FIG. 59 is a cross-sectional side view of the handle assembly depicted in FIG. 58 with the closure trigger thereof in a locked position.

In the embodiment depicted in FIG. 59, the closure trigger 1040 includes a flexible longitudinal arm 1192 that includes a lateral pin 1194 extending therefrom. The arm 1192 and pin 1194 may be made from molded plastic, for example. The pistol grip portion 1034 of the handle assembly 1020 includes an opening 1036 with a laterally extending wedge 1037 disposed therein. When the closure trigger 1040 is retracted, the pin 1194 engages the wedge 1037, and the pin 1194 is forced downward (i.e., the arm 1192 is rotated clockwise) by the lower surface of the wedge 1037. When the pin 1194 fully passes the lower surface, the clockwise force on the arm 1192 is removed, and the pin 1194 is rotated counterclockwise such that the pin 1194 comes to rest in a notch 1038 behind the wedge 1037 thereby locking the closure trigger 1040. The pin 1194 is further held in place in the locked position by a flexible stop 1039 extending from the wedge 1037.

To unlock the closure trigger 1040, the operator may further squeeze the closure trigger 1040, causing the pin 1194 to engage a sloped back wall 1041 of the opening 1036, forcing the pin 1194 upward past the flexible stop 1039. The pin 1194 is then free to travel out of the opening 1036 such that the closure trigger 1040 is no longer locked to the pistol grip portion 1034. Further details of such arrangement may be found in U.S. patent application Ser. No. 11/344,020, filed Jan. 31, 2006 and entitled "Surgical Instrument Having A Removable Battery" to Shelton, IV et al., the relevant portions of which are herein incorporated by reference. Other releasable locking arrangements could also be employed.

As the closure shuttle 1160 is moved to the locked position, the closure tube assembly 1130 is moved distally on the spine assembly 1110 causing the closure/opening tab 1054 on the anvil 1050 to be contacted by the proximal end of the horseshoe aperture 1142 in the distal closure tube portion 1140 to thereby pivot the anvil 1050 to the closed (clamped) position. Thus, the clamping forces attained by the anvil 1050 during the clamping process are ultimately dependant upon the closure forces generated by the closure tube assembly (represented by arrow 1196 in FIGS. 62 and 63) as it contacts the tab 1054 on the anvil 1050. As was discussed above, prior closure tube arrangements lack means for limiting the amount of actuation force applied to the closure/opening tab 1054 of the anvil 1050.

Various embodiments of the present invention address such shortcomings of prior closure tube arrangements by including a force limiting member generally designated as 1200 for limiting the amount of closure force or load applied by the closure tube assembly to the closure/opening tab 1054 of the anvil. For example, in one embodiment, the force limiting member 1200 may comprise a cushioning member 1210 oriented adjacent to the proximal end 1151 of the proximal closure tube portion 1150. More specifically and with reference to FIGS. 60 and 61, the cushioning member 1210 comprises a wave spring assembly 1212 that may be supported in a cavity 1169 formed in the closure shuttle 1160. The wave spring assembly 1212 may be supported between an attachment post 1163 and the proximal end 1151 of the proximal closure tube portion 1150. In various embodiments, the wave spring assembly 1212 may be fabricated from spring steel in the form depicted in the Figures. However, other cushioning arrangements or compliant member arrangements such as, for example, members fabricated from rubber, elastomer, polymer, foam rubber, etc. could be successfully employed to provided the closure tube assembly 1130 with some freedom to axially move in the proximal direction to reduce the clamping force ultimately applied to the anvil 1050 during the anvil closing process which will be discussed in further detail below.

Figure 60:
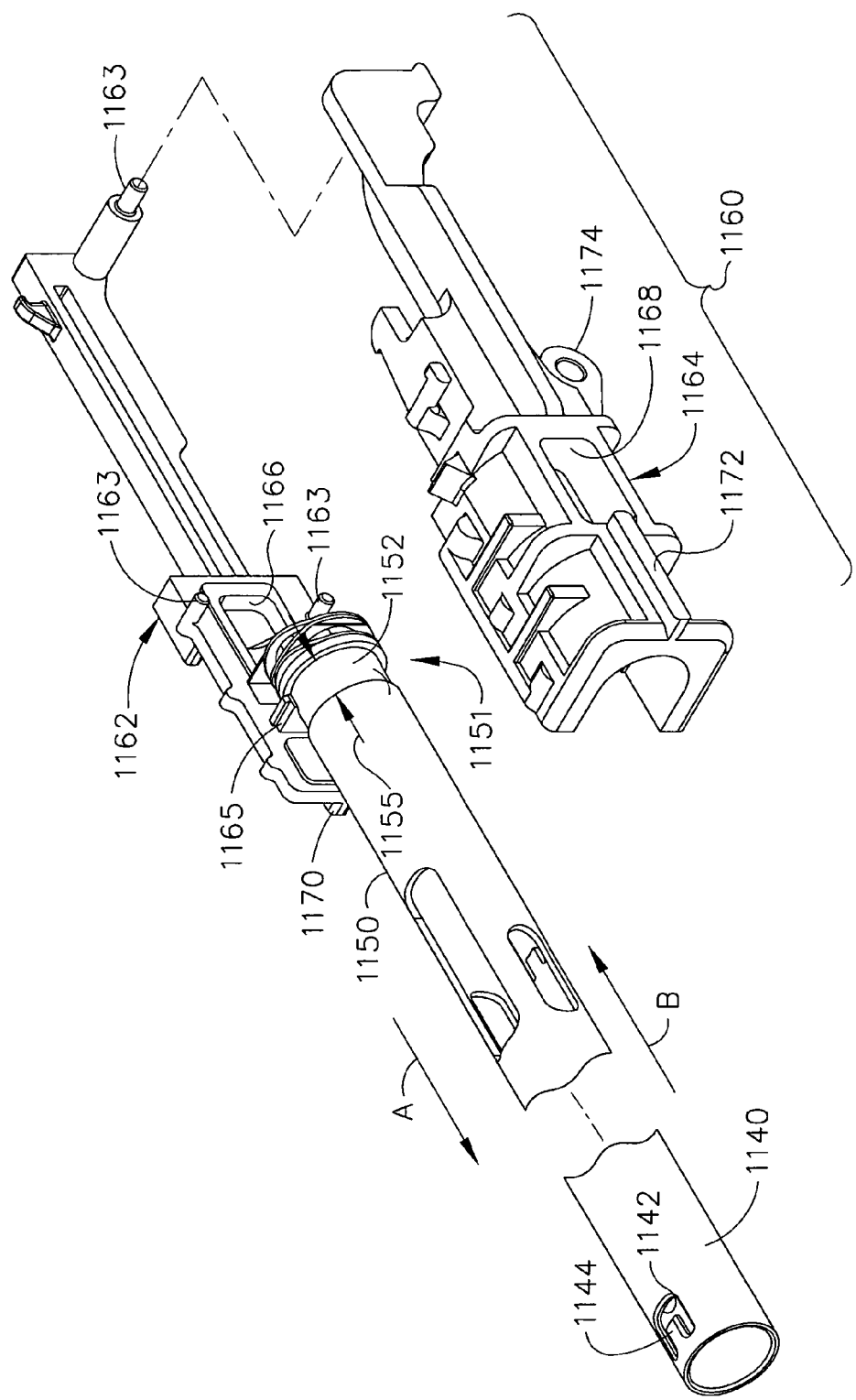
FIG. 60 is a left side exploded assembly view of a closure shuttle and closure tube assembly of various embodiments of the present invention.
Figure 61:
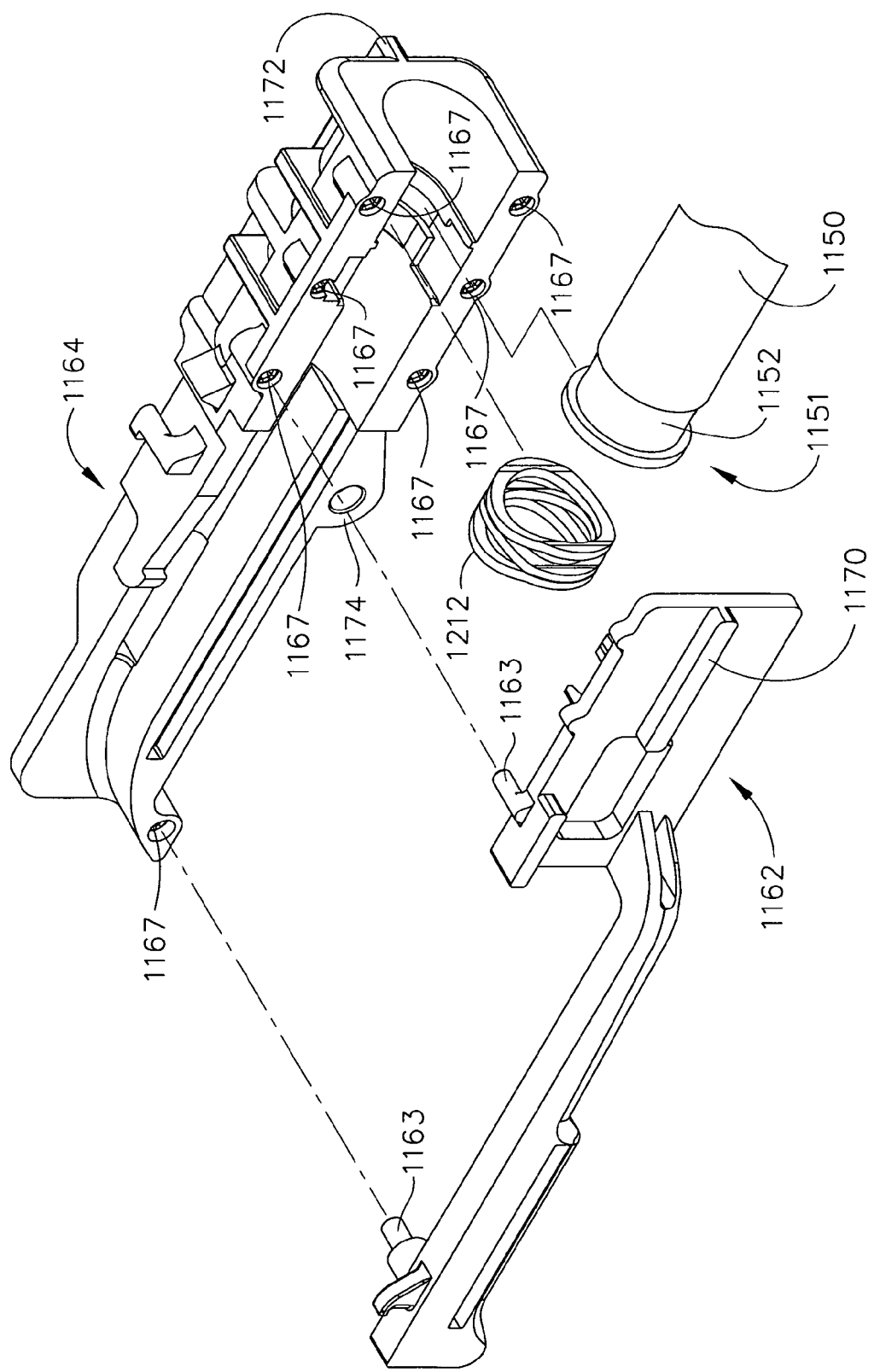
FIG. 61 is a right side exploded assembly view of a closure shuttle and closure tube assembly of various embodiments of the present invention.

As can also be seen in FIGS. 60 and 61, the retention groove 1152 in the proximal closure tube portion 1150 comprises an area 1154 that has a diameter that is less than the outer diameter of the proximal closure tube portion 1150. The area 1154 is axially elongated to provide the closure tube assembly 1130 to move axially and distally relative to the closure shuttle 1160 a distance that is defined by the axial length (arrow 1155 in FIG. 60) of the retention groove 1152.

In this embodiment, as the closure trigger 1040 is moved toward the pistol grip portion 1032, the closure shuttle 1160 is advanced in the distal direction (arrow A). As the closure shuttle 1160 moves distally, the closure tube assembly 1130 is also forced distally. As can be seen in FIGS. 62 and 63, distal end 1141 of the distal closure tube portion 1140 is oriented to move axially up a ramp portion 1070 of the anvil 1050. As the distal end 1141 contacts the anvil ramp 1070 and continues to move distally up the ramp, it imparts a closure force to the anvil 1050. The anvil trunnions 1052 are received in corresponding "kidney-shaped" slots 1064 in the proximal end of the elongate staple channel 1060 and serve to guide the anvil 1050 in a desired closure path which results in the clamping of the tissue between the staple forming undersurface of the anvil 1051 and the upper surface of the staple cartridge 42. As the anvil 1050 contacts the tissue, a resulting resistive force is transferred to the anvil 1050 and ultimately to the distal end 1141 of the distal closure tube portion 1140. The magnitude of such resistive force is effected by the thickness of the tissue being clamped. Thinner tissues will exert less resistive forces than thicker tissues. However, as the resistive forces are encountered, the cushioning member 1210 enables the closure tube assembly 1130 to move proximally to ultimately limit the amount of closure force applied to the anvil 1050 by the closure tube assembly 1130.

The magnitudes of the resistive forces for various thicknesses and types of tissues may be determined and the wave spring 1212 sized accordingly such that the desired amount of clamping force is applied to the tissue between the anvil 1050 and the staple cartridge 42. The wave spring 1212 may be sized and oriented such that when the anvil 1050 is at a fully compressed position, the wave spring 1212 is not fully compressed or "bottomed out".

Figure 64:
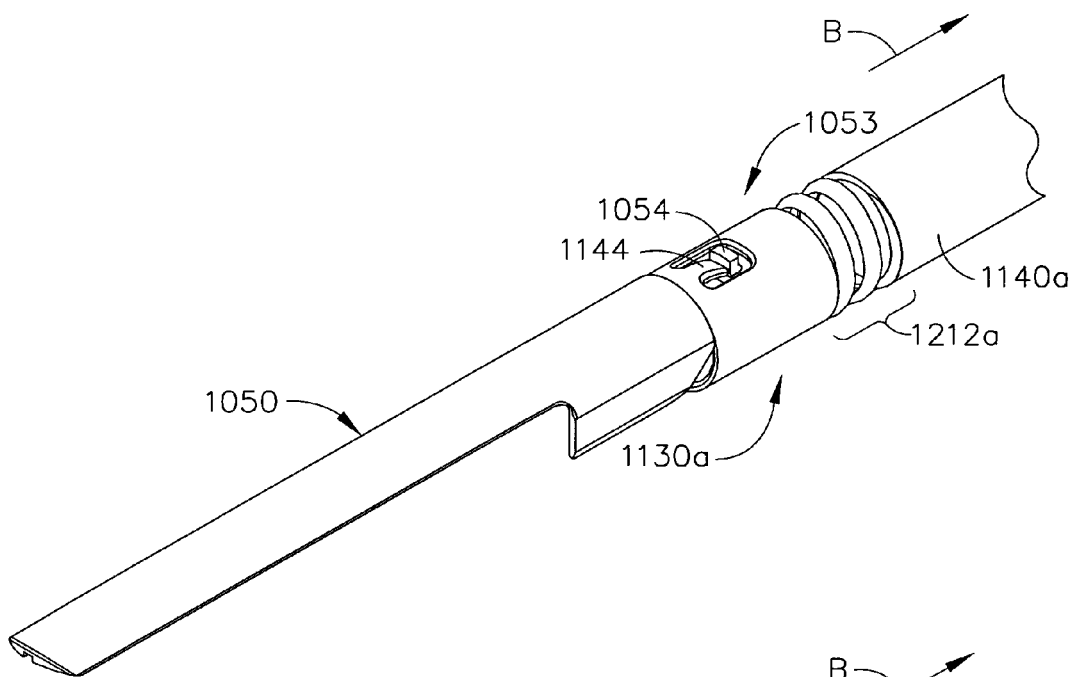
FIG. 64 is a partial perspective view of a closure tube assembly and anvil of various embodiments of the present invention.
Figure 65:
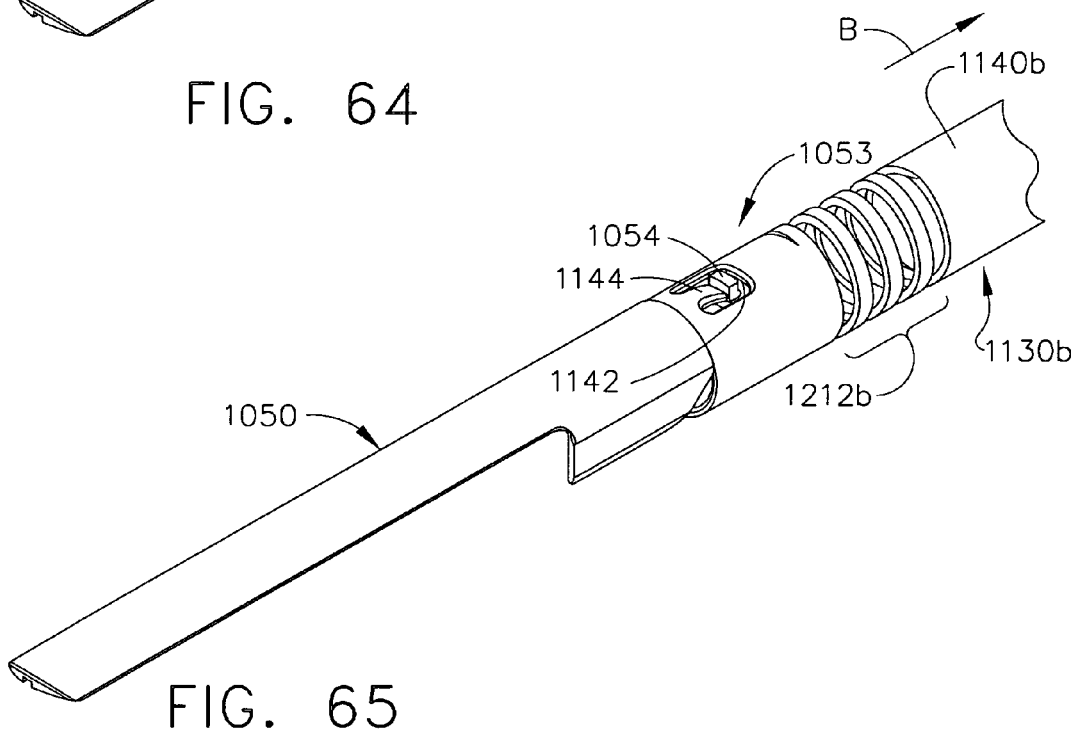
FIG. 65 is a partial perspective view of another closure tube assembly and anvil of various embodiments of the present invention.

FIGS. 64 and 65 illustrate other versions of closure tube assemblies that may be employed to limit closure forces applied to the anvil 1050. As can be seen in those Figures, the force limiting members 1200a, 1200b comprise spring sections 1212a, 1212b actually formed into the distal closure tube portion 1140a, 1140b, respectively. While the spring sections 1140a, 1140b are depicted as being somewhat helical in nature and formed in the distal closure tube portions 1140a, 1140b, those of ordinary skill in the art will understand that the spring sections 1212a, 1212b may be provided in any portion of the closure tube assemblies 1130a, 1130b and could conceivable be provided in different configurations. Those of ordinary skill in the art will understand that in these embodiments, the retention groove 1152 in the proximal closure tube portion may not be elongated such that the closure tube assembly 1130a, 1130b is essentially not axially movable relative to the closure shuttle 1160. In addition, while only one spring section is shown as being provided in the closure tube assembly, it is conceivable that more than one spring section may be formed in a single closure tube assembly. As with the above-described versions, as the resistive forces are encountered during clamping, the spring members 1212a, 1212b enable their respective closure tube assembly 1130a, 1130b to move proximally to ultimately limit the amount of closure force applied to the anvil 1050.

Figure 66:
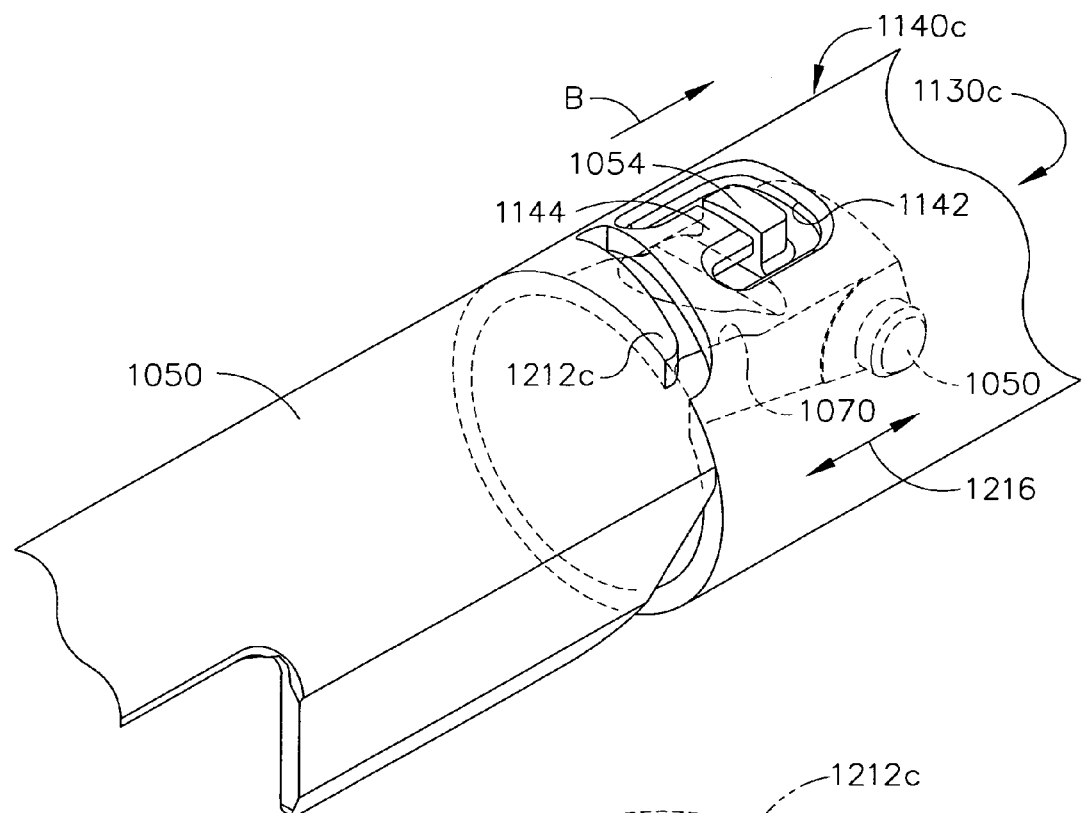
FIG. 66 is a partial perspective view of another closure tube assembly and anvil of various embodiments of the present invention with the anvil in a fully closed position.
Figure 67:
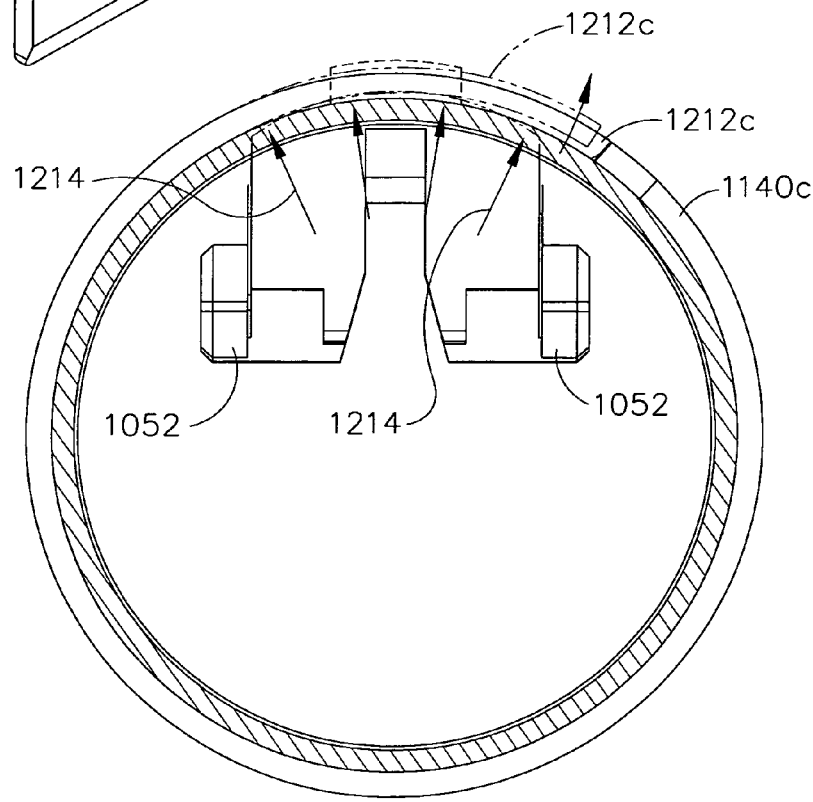
FIG. 67 is cross-sectional end view of the closure tube and anvil arrangement of FIG. 66 with the elongate channel omitted for clarity.

FIGS. 66 and 67 illustrate another closure tube assembly of various embodiments of the present invention that may be employed to limit closure forces applied to the anvil 1050. As can be seen in those Figures, the force limiting member 1200c comprises a leaf spring 1212c formed in the distal end 1141 of the distal closure tube portion 1140c. When the closure tube assembly 1130c is actuated to move distally to close the anvil 1050, the leaf spring 1212c rides up the anvil ramp 1070 and is free to move radially (arrows 1214 in FIG. 66) and axially (arrow 1216 in FIG.). As with the above-described versions, as the resistive forces are encountered during clamping, the leaf spring 1212c enables the closure tube assembly 1130c to move proximally (arrow B) to ultimately limit the amount of closure force applied to the anvil 1050.

Figure 68:
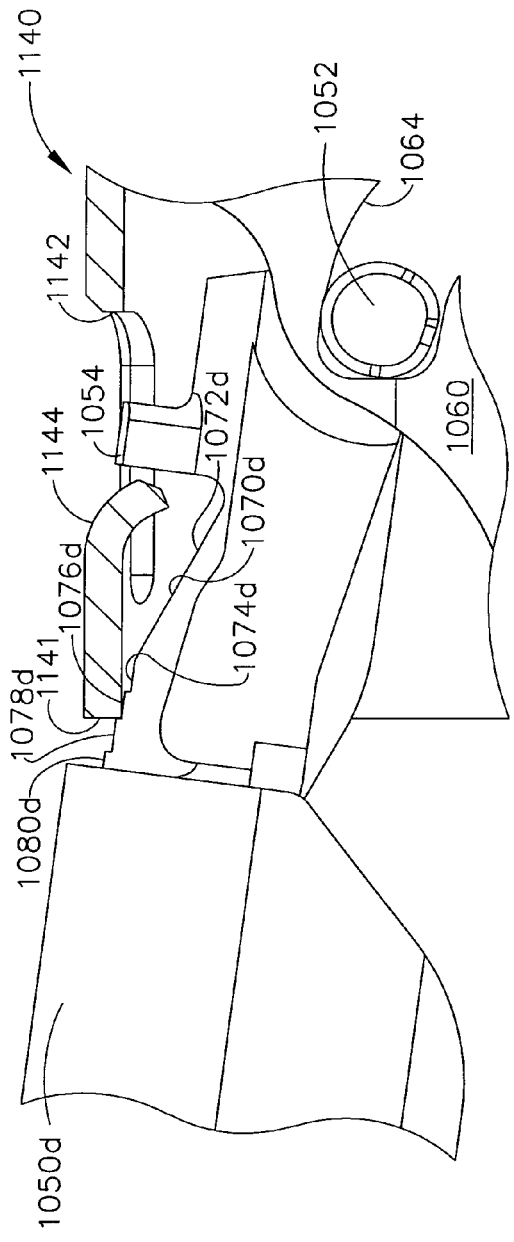
FIG. 68 is a partially enlarged view of a closure tube and anvil arrangement of other various embodiments of the present invention with the anvil in a partially closed position.
Figure 69:
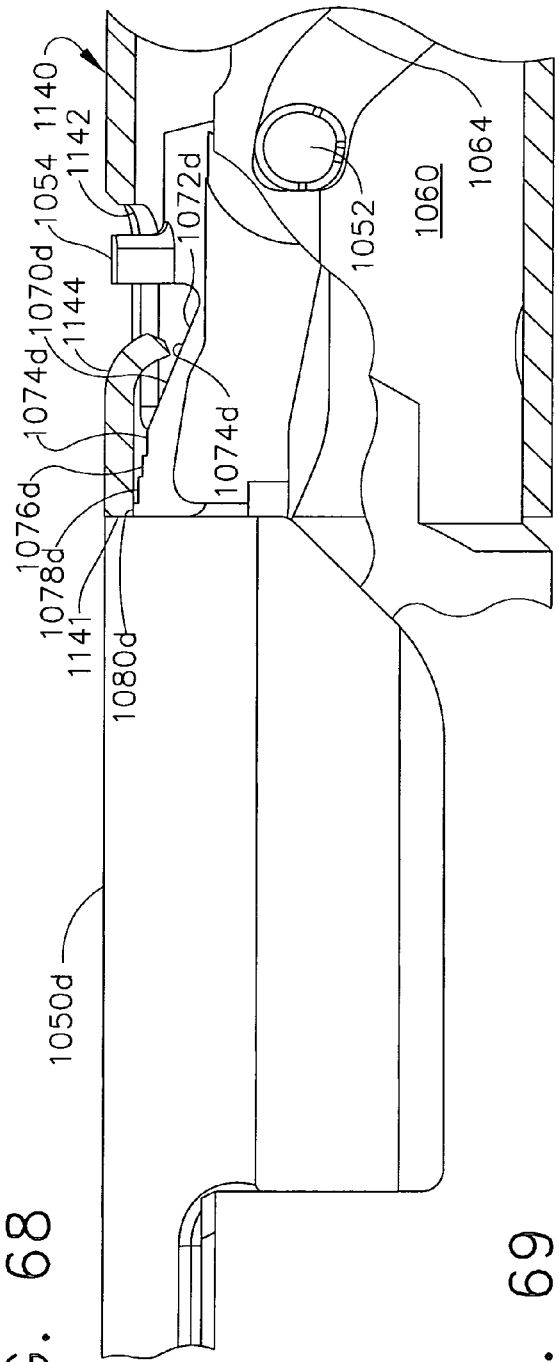
FIG. 69 is another partially enlarged view of the closure tube and anvil arrangement of FIG. 68 with the anvil in a fully closed position.
Figure 72:
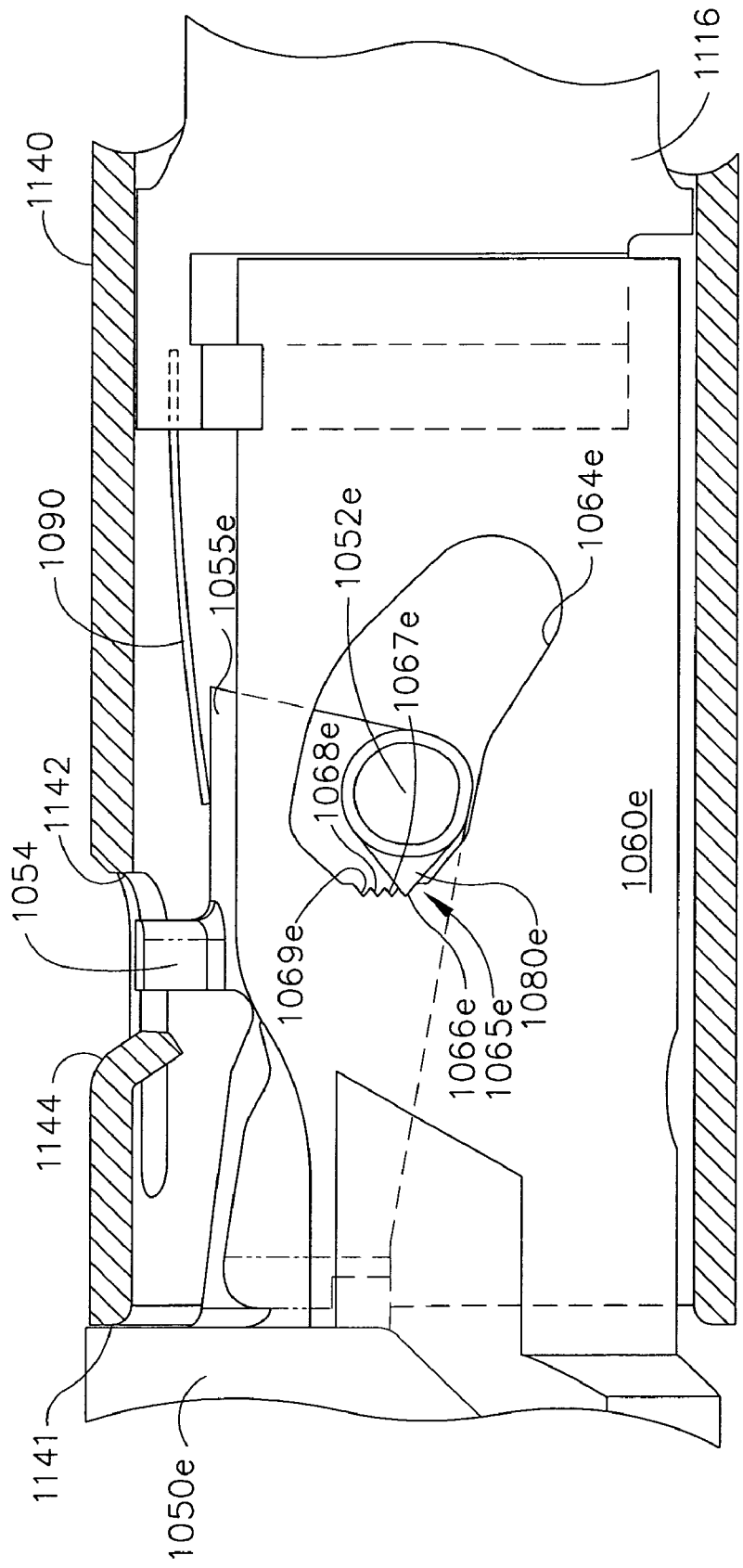
FIG. 72 is an enlarged cross-sectional view of a portion of the anvil and the closure tube assembly of the embodiments depicted in FIGS. 70 and 71 with the anvil in its fully closed position.

FIGS. 68 and 69 illustrate another embodiment of the present invention that may be employed to limit closure forces applied to the anvil 1050 by the closure tube assembly 1130. As can be seen in those Figures, this embodiment employs an anvil 1050d that has a stepped ramp 1070 that is configured to be engaged by the distal end 1141 of the distal closure tube portion 1140. In particular, the anvil 1050d depicted in those Figures has a series of steps 1074d, 1076d, 1078d, 1080d formed therein. As the closure tube assembly 1130 is moved distally, the distal end 1141 starts to ride up the smooth portion 1072d of the ramp 1070 until it contacts the first step 1074d. The closure tube assembly 1130 will not advance further up the ramp 1070d to apply a higher amount of closure force to the anvil until the actuation force applied to the closure tube assembly 1130 attains a sufficient magnitude to cause the distal end 1141 to bump up over the first step 1074d and proceed to engage the next step 1076d. The closure tube assembly 1130 will not advance further up the ramp 1070d until the actuation force attains a sufficient magnitude to cause the distal end 1141 to bump up over the second step 1076d at which time it will engage the next step 1078d and so on. Thus, the stepped anvil 1050d cooperates with the closure tube assembly 1130 to provide a means for relating the amount of clamping forces ultimately applied to the tissue between the anvil 1050d and the staple cartridge 42 based on the amount of resistive forces generated thereby and encountered by the closure tube assembly 1130 during clamping. While four such steps have been disclosed, other numbers of steps may be employed. For example, only one such step may be used or 2, 3, or more than 4 steps could conceivably be employed.

FIGS. 70-76 illustrate another unique and novel endocutter implement portion 1014e of various embodiments of the present invention that includes an elongate channel 1060e and an anvil arrangement 1050e that are "self adjusting" with respect to tissue thickness. In various embodiments, the proximal end of the anvil 1050e is pivotally attached to the proximal end of the elongate channel 1060e by mounting members which may comprise trunnions 1052e movably received in corresponding elongate slots 1064e formed in the proximal end 1061e of the elongate channel 1060e. As can be seen in FIGS. 70-74, at least one of the slots 1064e on each side of the elongate channel 1060e (only one slot 1064e is illustrated in FIGS. 70-74) and preferably both of the slots 1064e each have an end wall 1065e that has a discrete number of predetermined locations in the form of detents or pivot nests 1066e, 1067e, 1068e, 1069e formed therein. As can be seen in these Figures, the detents 1066e, 1067e, 1068e, 1069e may each comprise a V-shaped notch that is adapted to seatingly receive the pointed end of a pawl 1080e formed on the corresponding trunnion 1052e. It is conceivable that other detent and pawl configurations may be successfully employed. As can also be seen in FIGS. 70-74, this embodiment may further include a leaf spring 1090 or other suitable biasing member for applying a downward biasing force to the proximal end 1055e of the anvil 1050e. In various embodiments, the leaf spring 1090 may be attached to the distal portion 1116 of the spine assembly 1110 and oriented to bear upon the proximal end 1055e of the anvil 1050e.

As can be seen in FIG. 74, the slot 1064e is sized relative to the trunnion 1052e to permit the trunnion 1052e to find different clamped heights in response to the thickness of the tissue clamped between the anvil 1050e and the cartridge 42 and the application of the closing motion to the anvil 1050e. The leaf spring 1090 serves to bias the pawl 1080e into a slightly upward position wherein it can be received in any one of the notches 1066e, 1067e, 1068e, 1069e. As the anvil 1050e is closed onto the tissue by means of distally advancing the closure tube assembly 1130 in the above-described manner, the tissue thickness itself may dictate which of the notches 1066e, 1067e, 1068e, 1069e that the pawl 1080 ultimately seatingly engages. Because the leaf spring 1090 biases the pointed pawl upwardly, the pawl 1080 would find the uppermost notch 1069e when no tissue is between the anvil 1050e and the cartridge 42 which would clamp the end effector 1014e to is most closed position. See FIGS. 71 and 74. However, if during the clamping process, the anvil 1050e and channel 1060e encounter resistance, the leaf spring 1090 would be compressed and the anvil trunnions 1052e would find a lower pivot notch which would ultimately result in a larger gap between the anvil 1050e and the cartridge 42.

FIG. 70 illustrates the anvil 1050e in an open position. FIG. 71 illustrates the anvil 1050e in its most closed position. The tissue clamping space or distance between the underside 1051e of the anvil 1050e and the cartridge 42 is designated as "t". FIG. 75 also illustrates the position of the anvil 1050e relative to the staple cartridge 42 and tissue 1092 that has a thickness "t". Similarly, FIG. 73 illustrates the anvil 1050e in its uppermost clamped position wherein the distance between the underside 1051e of the anvil 1050e and the cartridge 42 is designated as "T". FIG. 76 also illustrates the anvil 1050e relative to the staple cartridge 42 and tissue 1094 that has a thickness "T". As can be seen in FIGS. 75 and 76, the staples 83 in the thinner tissue 1092 are more tightly formed than the staples 83 extending through the thicker tissue 1094.

FIGS. 77-88 illustrate another embodiment of the present invention that may be employed in connection with a circular stapler 1600 that includes a unique and novel apparatus for limiting the amount of compression force that can be generated between the anvil and the staple cartridge to avoid over compressing and possibly destroying the tissue to be stapled. A variety of different circular staplers are known in the art. FIGS. 77-88 illustrate an exemplary circular stapler arrangement that may employ the benefits of various aspects of the subject invention. It is conceivable, however, that the various embodiments of the present invention may be successfully employed with other stapler constructions without departing from the spirit and scope of the present invention.

Figure 77:
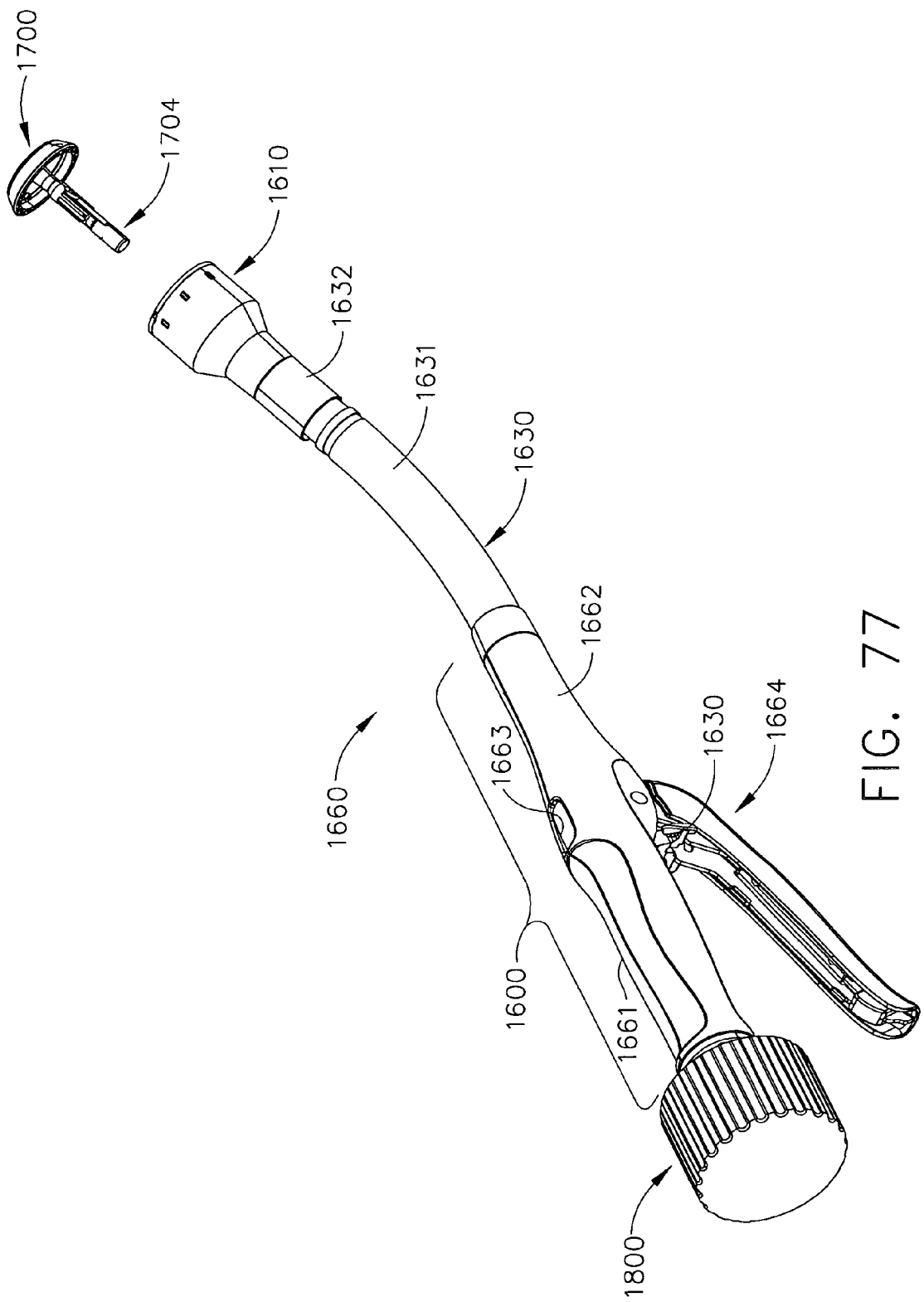
FIG. 77 is a perspective view of another stapling instrument of various embodiments of the present invention.

As seen in FIG. 77, there is disclosed the circular stapler 1600 including a head 1610, an anvil 1700, an adjustment knob assembly 1800, and trigger 1664. The head 1610 is coupled to a handle assembly 1660 by an arcuate shaft assembly 1630. The trigger 1664 is pivotally supported by the handle assembly 1660 and acts to operate the stapler 1600 when a safety mechanism 1670 is released. As will be discussed in further detail below, when the trigger 1664 is activated, a firing mechanism (not shown in FIG. 77) operates within the shaft assembly 1630 so that staples 1618 are expelled from the head 1610 into foiming contact with the anvil 1700. Simultaneously, a knife 1620 operably supported within the head 1610 acts to cut tissue held within the circumference of the stapled tissue. The stapler 1600 is then pulled through the tissue leaving stapled tissue in its place.

Figure 78:
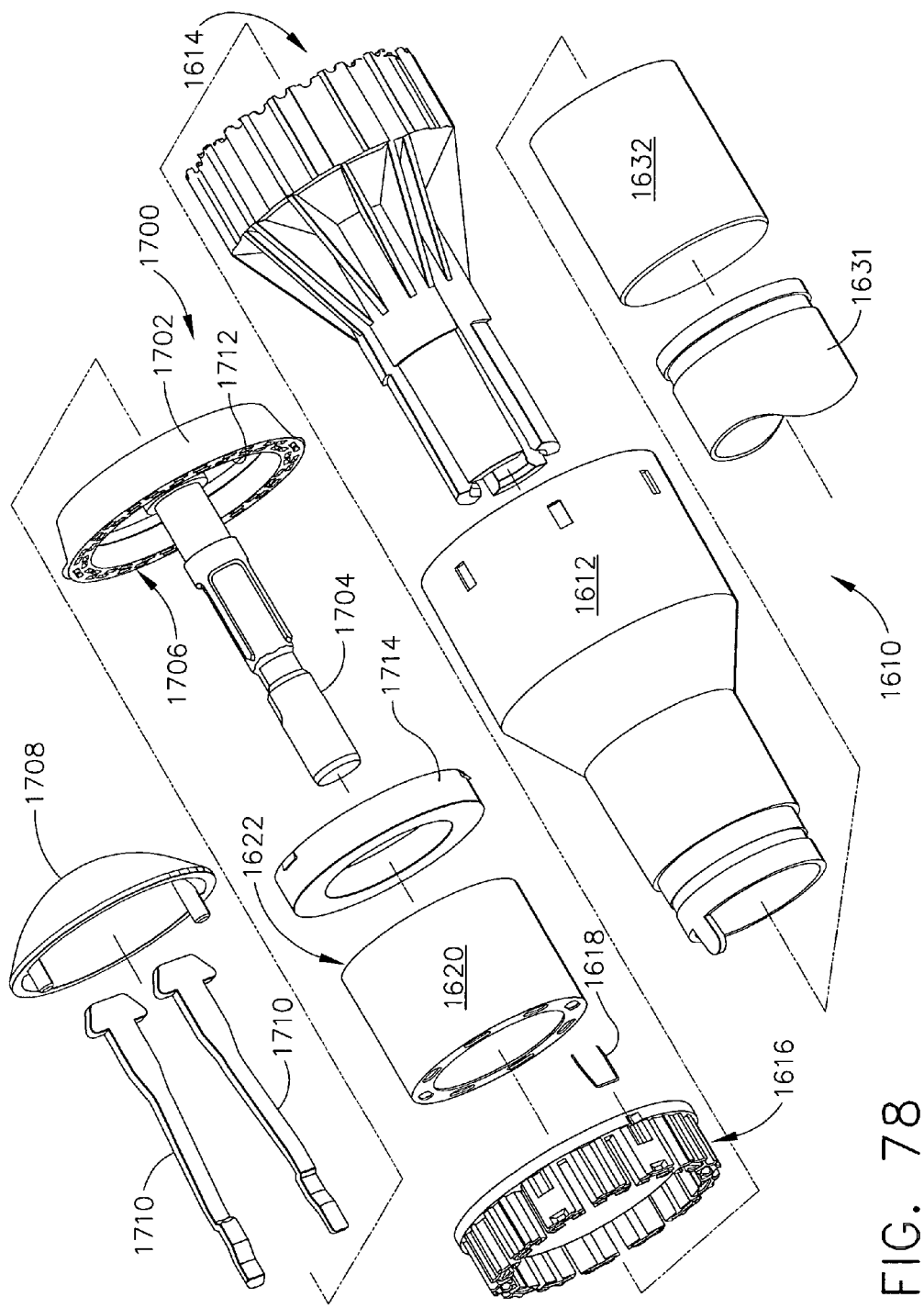
FIG. 78 is an exploded perspective assembly view of an anvil and head arrangement that may be employed with various stapler embodiments of the type depicted in FIG. 77.

FIG. 78 illustrates one form of anvil 1700 and head 1610 that may be employed in connection with various embodiments of the subject invention. As can be seen in that Figure, the anvil 1700 may have a circular body portion 1702 that has an anvil shaft for attaching a trocar thereto. The anvil body 1702 has a staple forming undersurface 1706 thereon and may also have a shroud 1708 attached to the distal end thereof. The anvil 1700 may be further provided with a pair of trocar retaining clips or leaf-type springs 1710 that serve to releasably retain a trocar 1644 in retaining engagement with the anvil shaft 1704 as will be discussed in further detail below. In the embodiment depicted in FIG. 78, a plastic knife board 1714 may be fitted into a cavity 1712 in the anvil body 1702.

As can also be seen in FIG. 78, the head 1610 may comprise a casing member 1612 that supports a cartridge supporting assembly in the form of a circular staple driver assembly 1614 therein that is adapted to interface with a circular staple cartridge 1616 and drive staples 1618 supported therein into forming contact with the staple forming undersurface 1706 of anvil 1700. A circular knife member 1620 is also centrally disposed within the staple driver assembly 1614. The proximal end of the casing member 1612 may be coupled to an outer tubular shroud 1631 of the arcuate shaft assembly 1630 by a distal ferrule member 1632.

Figure 79:
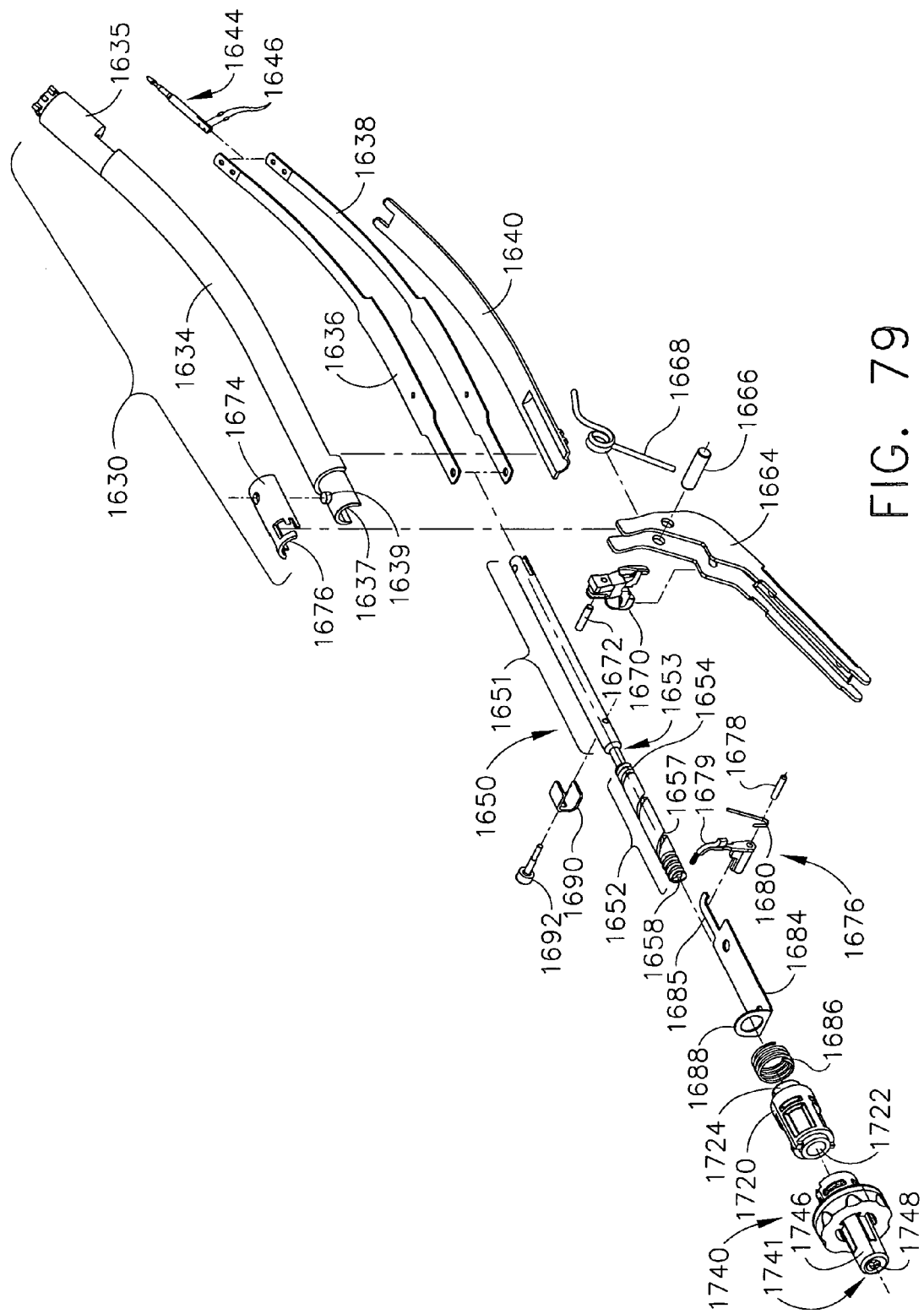
FIG. 79 is an exploded perspective assembly view of a shaft and trigger assembly that may be employed with various embodiments of the stapler depicted in FIG. 77.
Figure 80:
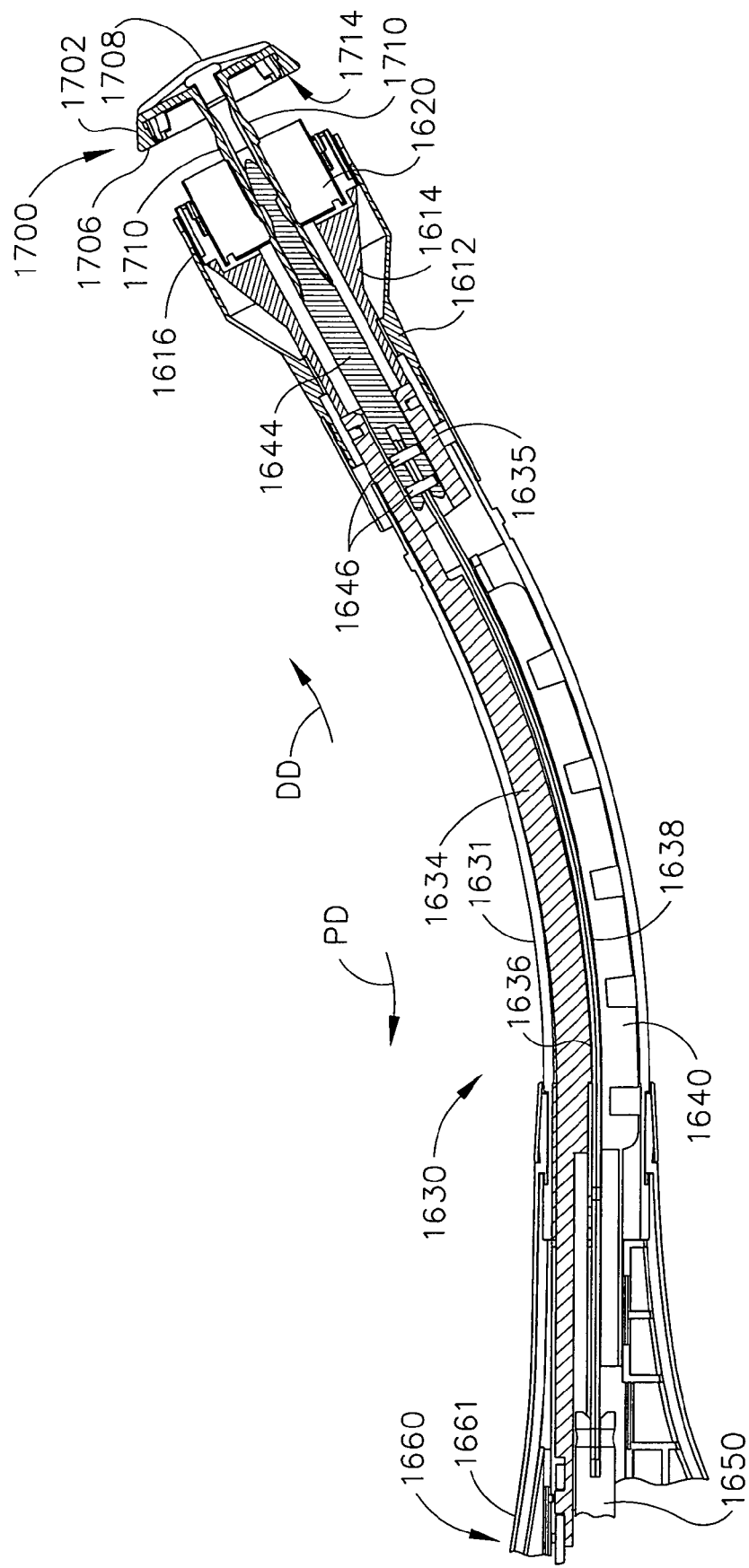
FIG. 80 is a partial cross-sectional view of a shaft assembly and head assembly embodiment of the present invention with the anvil attached to the shaft assembly.

FIGS. 79-82 illustrate one form of arcuate shaft assembly 1630 that may be employed with various embodiments of the present invention. As can be seen in FIGS. 79 and 80, the arcuate shaft assembly 1630 may include a compression shaft 1634, a distal compression shaft portion 1635, a top tension band 1636, a bottom tension band 1638 and a spacer band 1640 that are assembled within the outer tubular shroud 1631 (FIG. 80). A trocar tip 1644 may be attached to the top tension band 1636 and bottom tension band 1638 by fasteners 1646. The proximal ends of the top tension band 1636 and bottom tension band 1638 may be attached to a distal end of an adjustment shaft 1650. As can be seen in FIG. 80, the trocar tip 1644 may be inserted into the anvil shaft 1704 of the anvil 1700 and retained in engagement by trocar retaining clips 1710.

As can be seen in FIG. 80, the distal compression shaft portion 1635 is coupled to the staple driver assembly 1614. Thus, axial movement of the compression shaft 1634 within the outer tubular shroud 1631 causes the staple driver assembly 1614 to move axially within the casing member 1612. As will be discussed below, actuation of the firing trigger 1664 will cause the compression shaft 1634 to move in the distal direction (arrow "DD") thereby driving the staple driver assembly 1614 distally to fire the staples 1618 into forming contact with the staple forming undersurface 1706 of the anvil 1700. As the staple driver assembly 1614 is driven distally, it also drives the distal end 1622 of the knife 1620 through the tissue held within the circumference of the stapled tissue into the knife board 1714 mounted in the anvil 1700. The knife board 1714 may be fabricated from plastic or other suitable material that will permit the sharp distal end 1622 of the knife 1620 to penetrate and achieve a desirable cutting action through the clamped tissue.

In various embodiments, the adjusting shaft 1650 is axially movably supported within a handle assembly 1660 that may comprise two handle casing segments 1661, 1662 that are interconnected together by suitable fastener arrangements for ease of assembly. The trigger 1664 is pivotally attached to the handle assembly 1660 by a pivot pin 1666. A spring 1668 is supported on pivot pin 1666 and serves to bias the trigger 1664 away from the handle assembly 1660 to an unactuated position. A safety yoke 1670 is pivotally coupled to the trigger assembly 1664 by pin 1672 such that it can be pivoted between a safe position wherein the trigger 1664 cannot be depressed towards the handle 1660 and an off position wherein the safety yoke 1670 does not inhibit pivotal travel of the trigger assembly 1664 toward the handle assembly 1660. As can be seen in FIG. 79, the trigger 1664 may have a pair of fins 1665 that are sized to be received in slots 1676 in a firing clip 1674 that is attached to the proximal end 1637 of compression shaft 1634 by a protrusion 1639 or other suitable fastener arrangements. Such arrangement permits the distal axial movement (arrow "DD") and the proximal axial movement (arrow "PD") of the compression shaft 1634 by pivoting the trigger 1664 as will be further discussed below. The trigger 1664, the compression shaft portions 1634, 1635 and the firing cap 1674 and other related components may comprise a firing assembly generally designated as 1675.

Figure 81:
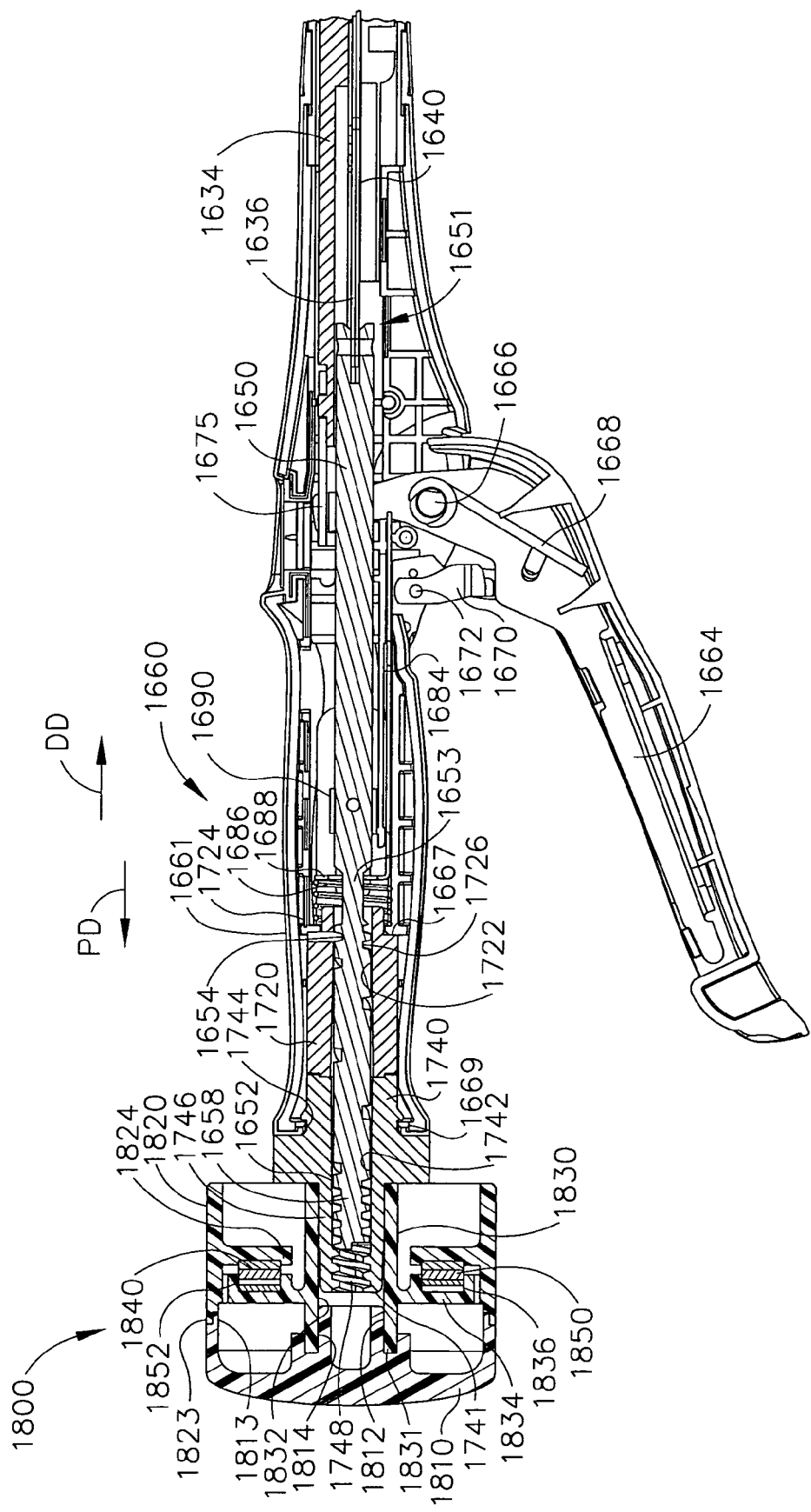
FIG. 81 is a cross-sectional view of the handle assembly and closure knob assembly of various embodiments of the present invention.
Figure 82:
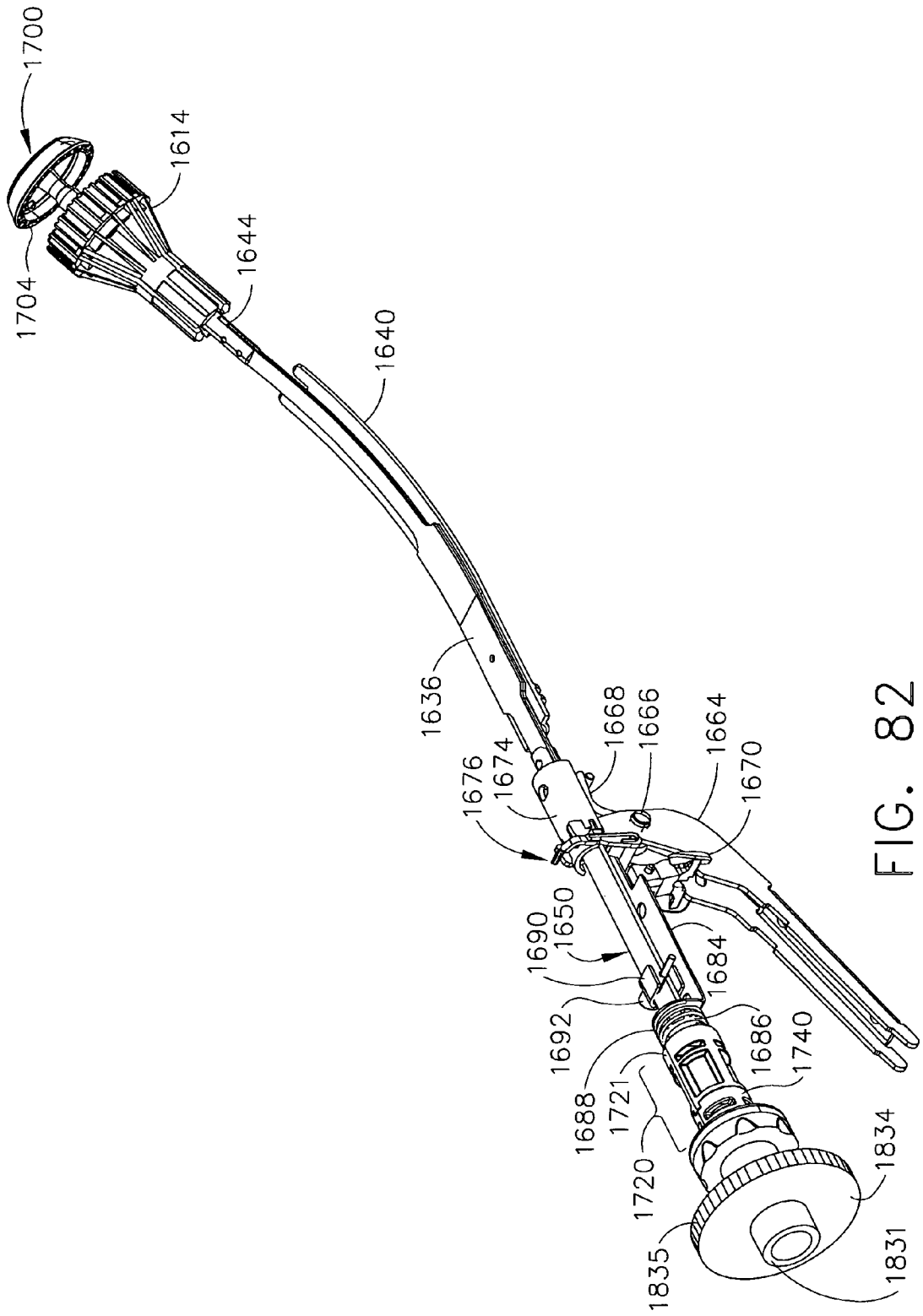
FIG. 82 is a perspective view of the shaft assembly, trigger assembly, staple driver, anvil and closure knob assembly with the handle housing, head casing and outer tubular shroud removed therefrom.
Figure 87:
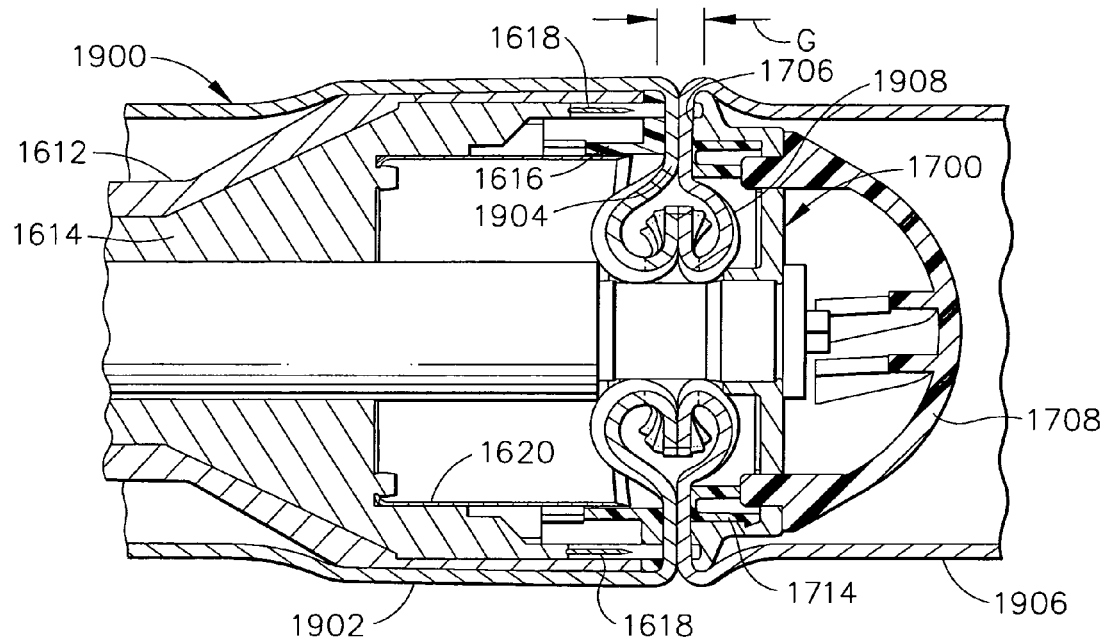
FIG. 87 is another cross-sectional view of the stapler and intestine arrangement of FIGS. 85 and 86 with the anvil retracted to a fully compressed position and prior to firing the stapler.
Figure 88:
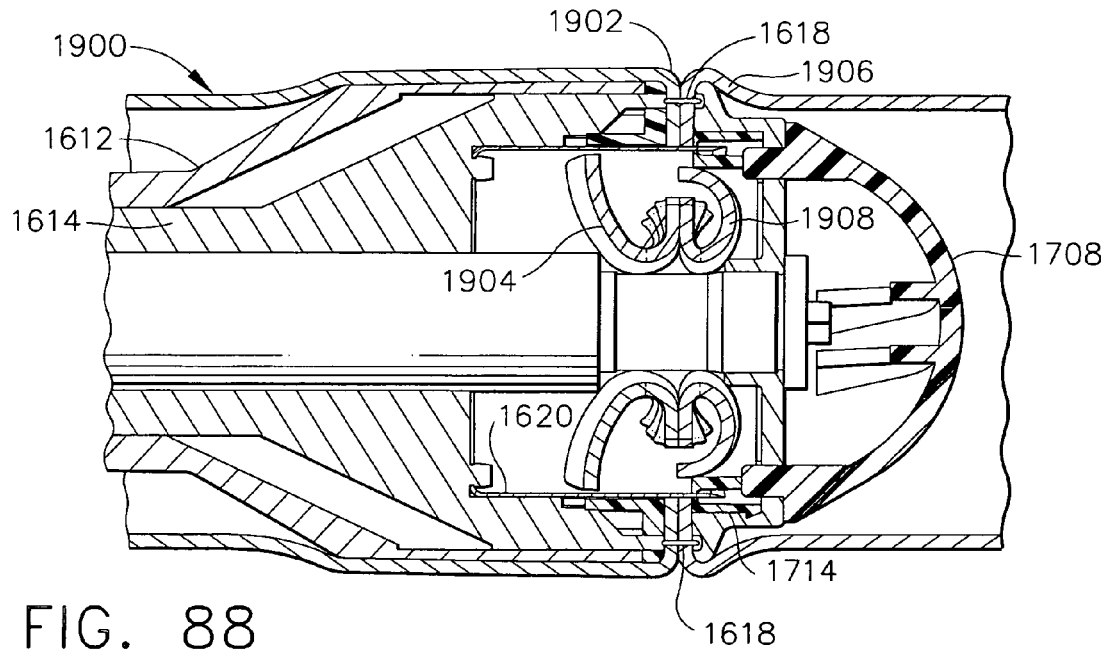
FIG. 88 is another cross-sectional view of the stapler and intestine arrangement of FIGS. 85-87 after the staples have been fired and the knife has severed the portions of sutured intestine.
Figure 89:
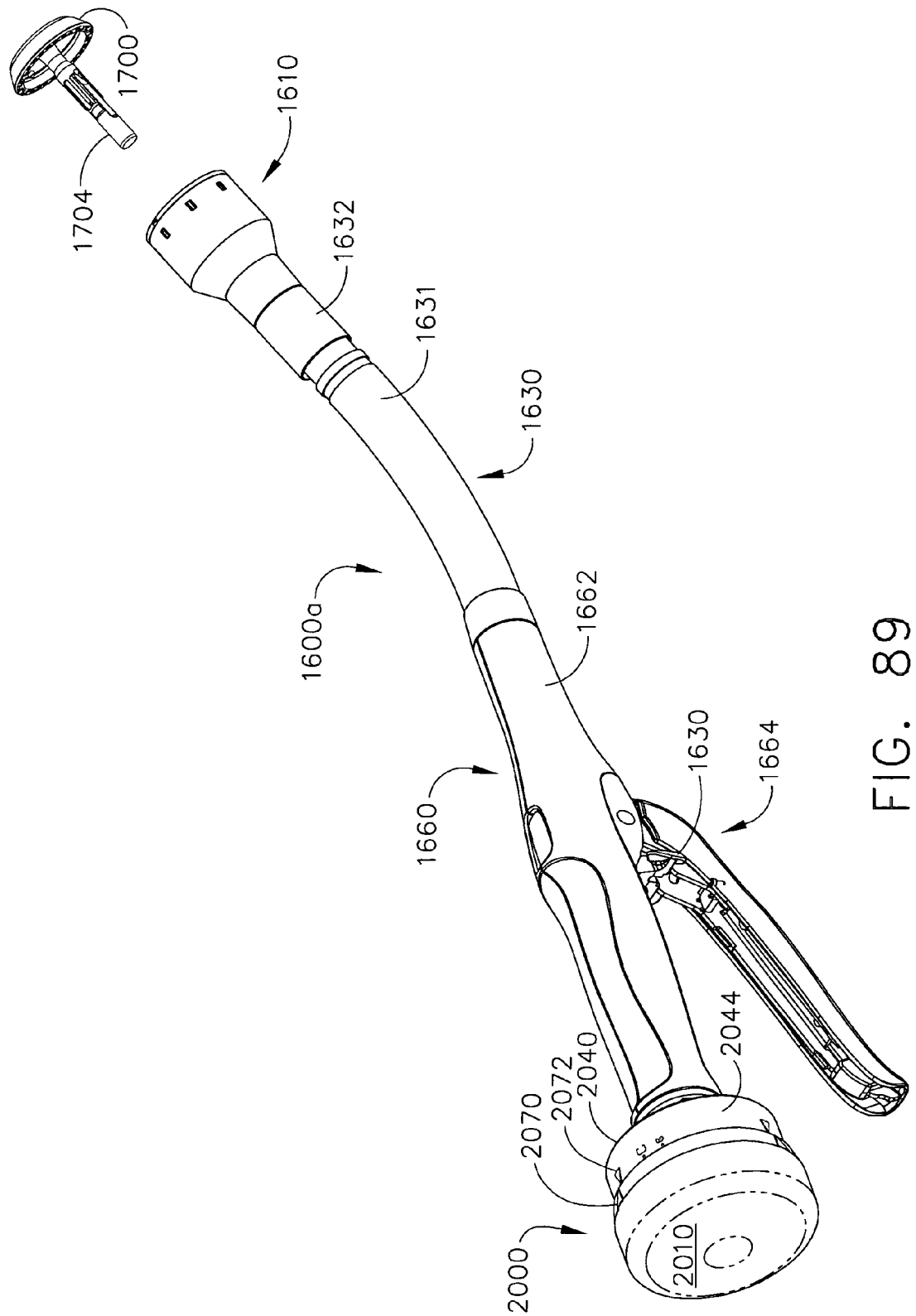
FIG. 89 is a perspective view of another stapler embodiment of the present invention.

As can be seen in FIGS. 79 and 81, the adjustment shaft 1650 has a distal portion 1651 that is attached to the top and bottom tension bands 1636, 1638 and a proximal portion 1652 that is adjoined to the distal portion 1651 by a reduced diameter segment 1653. The proximal portion 1652 is axially received within an axial passage 1722 in the distal closure nut 1720 that is keyed onto or otherwise attached to a proximal closure nut 1740 to form a closure nut assembly generally designated as 1721 such that the distal closure nut 1720 and the proximal closure nut 1740 may rotate together. The distal closure nut 1720 may further have a distally extending hub portion 1724 that abuts an inwardly extending retainer flange 1667 formed inside the handle assembly 1660. See FIG. 81. Such arrangement permits the distal closure nut 1720 to freely rotate within the handle assembly 1660, but is unable to move axially therewithin. Likewise, the proximal end portion 1652 of the adjustment shaft 1650 is axially received within an axial passage 1742 within the proximal closure nut 1740. A circumferentially extending groove 1744 may be provided in the outer surface of the proximal closure nut 1740 for receiving an inwardly protruding proximal retainer flange 1669 formed on the proximal end of the handle assembly 1660. Such arrangement serves to permit the proximal closure nut 1740 to freely rotate relative to the handle assembly 1660.

Also in various embodiments, the closure knob assembly 1800 is attached to the proximal end 1741 of the proximal closure nut 1740. In one embodiment for example, the proximal end 1741 of the proximal closure nut 1740 may be formed with a proximally extending tapered hub portion 1746 that is adapted to be nonrotatably received in an axial passage 1832 in a clutch hub portion 1830. See FIG. 81. The tapered hub portion 1746 can also be formed with a key or spline arrangement to non-rotatably affix the hub portion 1746 with the clutch hub portion 1830. Other fastener arrangements and methods may be employed to non-movably attach the hub portion 1746 of the proximal closure nut 1740 to the clutch hub portion 1830. Thus, rotation of the clutch hub portion 1830 will cause the proximal closure nut 1740 and distal closure nut 1720 to also rotate.

As can also be seen in FIGS. 81, 83, and 84, the knob assembly 1800 may further include a proximal cap portion 1810 and a distal cap portion 1820. The proximal end 1831 of the clutch hub portion may be received in a circular slot 1814 formed in a distal end of the proximal cap portion 1810. The slot 1814 may be sized to permit the proximal cap portion 1810 to rotate about the proximal end 1831 of the clutch hub portion 1830. In addition, the proximal cap portion 1810 may have a protrusion 1812 that rotatably extends into the axial passage 1832 in the clutch hub portion 1830. Also in various embodiments, the closure knob assembly 1800 may comprise a distal cap portion 1820 that is rigidly and non-rotatably coupled to the proximal cap portion 1810. Those of ordinary skill in the art will understand that the closure knob assembly 1800 may be fabricated in multiple parts for ease of assembly of various components of the instrument. In various embodiments, the mating ends of the proximal cap portion 1810 and distal cap portion 1820 may be configured with complementary flanged portions 1813, 1823, respectively as shown in FIGS. 81 and 83, that are interconnected by adhesive, welding, etc. or other fastener arrangements may be employed. Thus, when fastened together, the proximal cap portion 1810 and the distal cap portion 1820 rotate together as a unit.

As can further be seen in FIGS. 81 and 83, various embodiments may comprise a slip clutch assembly generally designated as 1821. The slip clutch assembly 1821 may take various forms that are supported by or are integrally formed in the adjustment knob assembly 1800. In one embodiment, for example, the distal cap portion 1820 may be provided with an inwardly extending cap flange 1824 that is in confronting orientation with an outwardly extending clutch flange 1834 formed on the clutch hub portion 1830. A first friction pad 1840 is non-rotatably affixed to the inwardly extending cap flange 1824. A pad cavity 1836 may be formed within the clutch flange 1834 for movably receiving a second friction pad 1850 and a wave spring 1852 therein. The second friction pad 1850 may be provided with splines or keys (not shown) to prevent rotation thereof in the cavity 1836, but facilitate some axial travel thereof within the cavity 1836. In various embodiments, the first and second friction pads 1840, 1850 may be fabricated from, for example, liquid crystal polymer, Nylon, ULTEM®, polycarbonate, aluminum, etc.

In various embodiments, the proximal portion 1652 of the adjustment shaft 1650 has a low pitch thread segment 1654 formed therein that communicates with a higher pitched threaded segment 1657. See FIG. 79. As can be seen in FIG. 81, a drive pin 1726 protrudes inwardly into the axial passage 1722 for "driving" engagement with the threaded segments 1654, 1657 in the adjustment shaft 1650. In addition, the proximal end 1652 of the adjustment shaft 1650 has a threaded section 1658 adapted for threaded engagement with a threaded cavity 1748 in the tapered hub portion 1746 of the proximal closure nut 1740. In various embodiments, the drive pin 1726 is oriented in the distal closure nut 1720 such that when the drive pin 1726 is still engaged with the low pitched distal thread segment 1654 of the adjustment shaft 1650, the threaded end 1658 of the adjustment shaft 1650 has sufficiently threadedly engaged the threaded cavity 1748 in the tapered hub portion 1746 of the proximal closure nut 1740 for threaded travel therein as the closure knob assembly 1800 is rotated. In particular, as the closure knob assembly 1800 is rotated in the counterclockwise ("CC") direction, the adjustment shaft 1650 is moved in the distal direction "DD" by virtue of the engagement of the drive pin 1726 with the threaded segments 1654 and 1657 formed in the attachment rod 1650. Those of ordinary skill in the art will appreciate that rotation of the distal closure nut 1720 when the drive pin 1726 is engaged with the distal threaded segment 1654 will result in fastener axial movement of the adjustment shaft 1650 than when the drive rod 1726 is engaged with the threaded segment 1567 which has a larger pitch than the threaded segment 1564. Axial movement of the adjustment shaft 1650 moves the top and bottom tension band 1636, 1638, the trocar tip 1644 and the anvil 1700 (when attached to the trocar tip 1644) in the distal "DD" direction away from the head 1610.

To close the anvil 1700 or move it toward the head 1610 and staple cartridge 1616 supported therein in the "PD direction, the surgeon begins to turn the closure knob assembly 1800 in the clockwise ("CW") direction. The frictional forces generated between the first and second friction pads 1840, 1850 serves to retain the closure knob assembly 1800 in frictional engagement with the clutch hub 1830 which is non-rotatably attached to the proximal closure nut 1740. Because the proximal closure nut 1740 is non-rotatably affixed to the distal closure nut 1720, the distal closure nut 1720 is also rotated in the clockwise direction. Rotation of the distal closure nut 1720 results in the driving engagement of the drive pin 1726 with either of the thread segments 1654, 1657 (depending upon the position of the adjustment shaft 1650 relative thereto) and causes the adjustment shaft 1650 to be drawn in the proximal direction ("PD"). As the adjustment shaft 1650 is drawn in the proximal direction, the threaded end 1658 of the adjustment shaft 1650 threadably engages the threaded cavity 1748 of the tapered threaded hub portion 1746 of the proximal closure nut 1740 and reduced diameter segment 1653 moves adjacent to the drive pin such that the drive pin is no longer in driving engagement with the adjustment shaft 1650. Now, the threaded end 1652 is in full threaded engagement with the threaded hole 1748 in the proximal closure nut 1740. Further rotation of the closure knob assembly 1800 in the clockwise direction continues to draw the adjustment shaft 1650 in the proximal direction "PD". As the adjustment shaft 1650 is drawn in the proximal direction, the anvil 1700 is moved towards the cartridge 1616 supported in the staple driver assembly 1614 to clamp an amount of tissue therebetween. As the anvil 1700 continues to move toward the staple cartridge 1616, the tissue is compressed therebetween and resists further travel of the anvil 1700 in the proximal direction.

In various embodiments, to prevent the tissue from being over compressed which could result in damaging or killing the tissue to be stapled, the composition of the first and second friction pads 1840, 1850 and the size of the spring 1852 are selected such that when a predetermined amount of tissue compression is attained, the friction pads 1840, 1850 begin to slip to prevent further rotation of the closure knob assembly 1800 from being transferred to the clutch hub 1830. Thus, even if the surgeon continues to rotate the closure knob assembly 1800 after the tissue has been adequately compressed, such further rotation will not result in continued movement of the adjustment shaft 1650 (and anvil 1700) in the proximal direction to avoid over compressing the tissue. For example, in various embodiments, the instrument may be constructed such that the maximum amount of compression forces that may be applied to the tissue between the anvil 1700 and the cartridge 1616 may be approximately 150 pounds per square inch. For such applications, the first and second friction pads 1840, 1850 and the wave spring 1852 may be so configured to permit slippage between the first and second friction pads 1840, 1850 if the closure knob assembly 1800 continues to be rotated after that maximum amount of compression force has been attained. In such example, the rotation of the closure knob assembly 1800 may generate an approximate amount of torque of, for example, 15 inch pounds which overcomes the frictional forces that are established when the maximum amount of desirable compression has been attained (which serves to retain the first and second friction pads 1840, 1850 in frictional engagement with each other) and permit the desired slippage between the first and second friction pads. In various embodiments, to ensure that the adjustment shaft 1650 is moved distally when the closure knob assembly 1800 is rotated in a counterclockwise direction, a series of circumferentially extending ratchet teeth 1816 may be formed in the interior of the closure knob assembly 1800 for engagement with circumferentially extending engagement teeth 1835 formed on the circumference of the clutch flange 1834. See FIGS. 83 and 84. The teeth 1816, 1835 may be configured such that when the closure knob assembly 1800 is rotated in the clockwise direction to move the anvil 1700 toward the cartridge 1616, the teeth 1816 on the closure knob assembly 1800 slip over the teeth 1835 formed on the clutch flange 1834. However, when the closure knob assembly 1800 is rotated in the counterclockwise direction, the teeth 1816 engage teeth 1845 on the clutch flange 1834 to cause the clutch hub 1830 and the proximal and distal closure nuts 1720, 1740 to rotate therewith to move the anvil 1700 away from the cartridge 1616.

As indicated above, various embodiments may be provided with a safety yoke 1670 that prevents actuation of the trigger assembly 1664 when the safety yoke 1670 is in a "safe" or engaged position. In various embodiments, a safety spring 1686 may be journaled on the adjustment shaft 1650 and be received on the hub portion 1724 of the distal closure nut 1720. The spring 1686 may be oriented between the distal closure nut 1720 and an upstanding end wall portion 1688 of the safety release 1684. See FIG. 81. The safety spring 1686 serves to bias the safety release 1684 in the distal direction and into contact with the safety yoke 1670 to prevent the safety yoke from being pivoted to an off position wherein the trigger 1664 may be actuated. Also in these variations, a rod clip 1690 may be attached to the adjustment shaft 1650 by and adjusting screw 1692 that extends through a slot (not shown) in the rod clip 1690. The rod clip 1690 may be so located on the adjustment shaft 1650 such that when the adjustment shaft 1650 has been axially positioned in its most proximal position which results in the maximum amount of desirable compression being applied to the tissue or in a position wherein the anvil 1700 has begun to clamp the tissue, but has not yet attained the predetermined maximum amount of compression force, the rod clip 1690 has contacted the upstanding end wall 1688 and moved it proximally a sufficient distance to move the distal end 1685 of the safety release 1684 out of retaining engagement with the safety yoke 1670. The surgeon may then pivot the safety yoke 1670 to the off position thereby enabling the trigger 1664 to be depressed.

Various embodiments of the invention may also be fitted with a staple form indicator 1676 that may be pivotally mounted within the handle assembly 1660 by a pivot pin 1678. The staple form indicator 1676 may have a pointer end portion 1679 that is viewable through a viewing window 1663 (FIG. 77) formed in the handle assembly 1660. The end portion 1679 may be biased in the distal direction by an indicator spring 1680. As can be seen in FIG. 79, the staple form indicator 1676 may be formed with a tab 1682 that is oriented for engagement by a hooked end 1685 of a safety release 1684. As the safety release 1684 is moved proximally in connection with the proximal movement of the adjustment shaft 1650, the hooked end 1685 causes the staple form indicator 1676 to pivot in the proximal direction. An indicator plate (not shown) may be positioned within the window 1663 and so calibrated such the indicator 1676 cooperates with the indicator plate to indicate the amount of distance between the anvil 1700 and the cartridge 1616.

One exemplary method of using the circular stapler 1600 will now be described with reference to FIGS. 85-88. When performing an anastomosis using a circular stapler, the intestine 1900 may be stapled using a conventional surgical stapler with multiple rows of staples being emplaced on either side of a target section (i.e., specimen) of intestine 1900. FIG. 85 illustrates the liner staple lines 1910, 1920. The target section is typically simultaneously cut as the section is stapled. The target section has already been removed in FIG. 85. Next, after removing the target specimen, the surgeon inserts the anvil 1700 into the proximal portion 1902 of the intestine 1900, proximal of the staple line 1910. This is done by inserting the anvil head 1700 into an entry port cut into the proximal intestine portion 1902 or the anvil 1700 can be placed transanally, by placing the anvil 1700 on the distal end of the stapler 1600 and inserting the instrument through the rectum. Next, the surgeon attaches the anvil 1700 to the trocar tip 1644 of the stapler 1600 and inserts the anvil 1700 into the distal portion 1906 of the intestine 1900. The surgeon may then tie the distal end 1904 of the proximal section 1902 of the intestine 1900 to the anvil shaft 1704 using a suture 1912 or other conventional tying device and also tie the proximal end 1908 of the distal intestine portion 1906 around the anvil shaft using another suture 1914. See FIG. 86. The surgeon then begins to rotate the closure knob assembly 1800 in the clockwise direction to draw the anvil 1700 toward the cartridge 1616 supported in the staple driver 1614 to close the gap between the anvil 1700 and cartridge 1616 and thereby engage the proximal end 1908 of the distal intestine portion 1906 with the distal end 1904 of the proximal intestine portion 1902 in the gap "G" therebetween. See FIG. 87. The surgeon continues to rotate the closure knob assembly 1800 until the first and second friction pads 1840, 1850 slip and the desired amount of compression (the desired gap G) is attained. When in that position, the surgeon may then pivot the safety yoke 1670 to the off position and fire the stapler 1600 by depressing the firing trigger 1664. Depressing the trigger 16614 causes the compression shaft 1634 to drive the staple driver 1614 distally to drive the staples 1618 to be driven through both ends 1904, 1908 of the intestine 1900, thereby joining the portions 1902 and 1906 and forming a tubular pathway. Simultaneously, as the staples 1618 are driven and formed, the knife 1620 is driven through the intestinal tissue ends 1904 and 1908, cutting the ends adjacent to the inner row of staples 1618. The surgeon then withdraws the stapler 1600 from the intestine and the anastomosis is complete.

FIGS. 89-95 illustrate another stapler embodiment 1600a of the present invention. Stapler 1600a may essentially employ the same components described above with respect to stapler 1600 except for the changes that will be discussed in detail below. For example, in this embodiment, a slip clutch assembly may not be employed. However, this embodiment may employ a closure actuator assembly 2000 that includes a proximal cap portion 2010 and a distal cap portion 2040 that are rotatably retained together.

Figure 90:
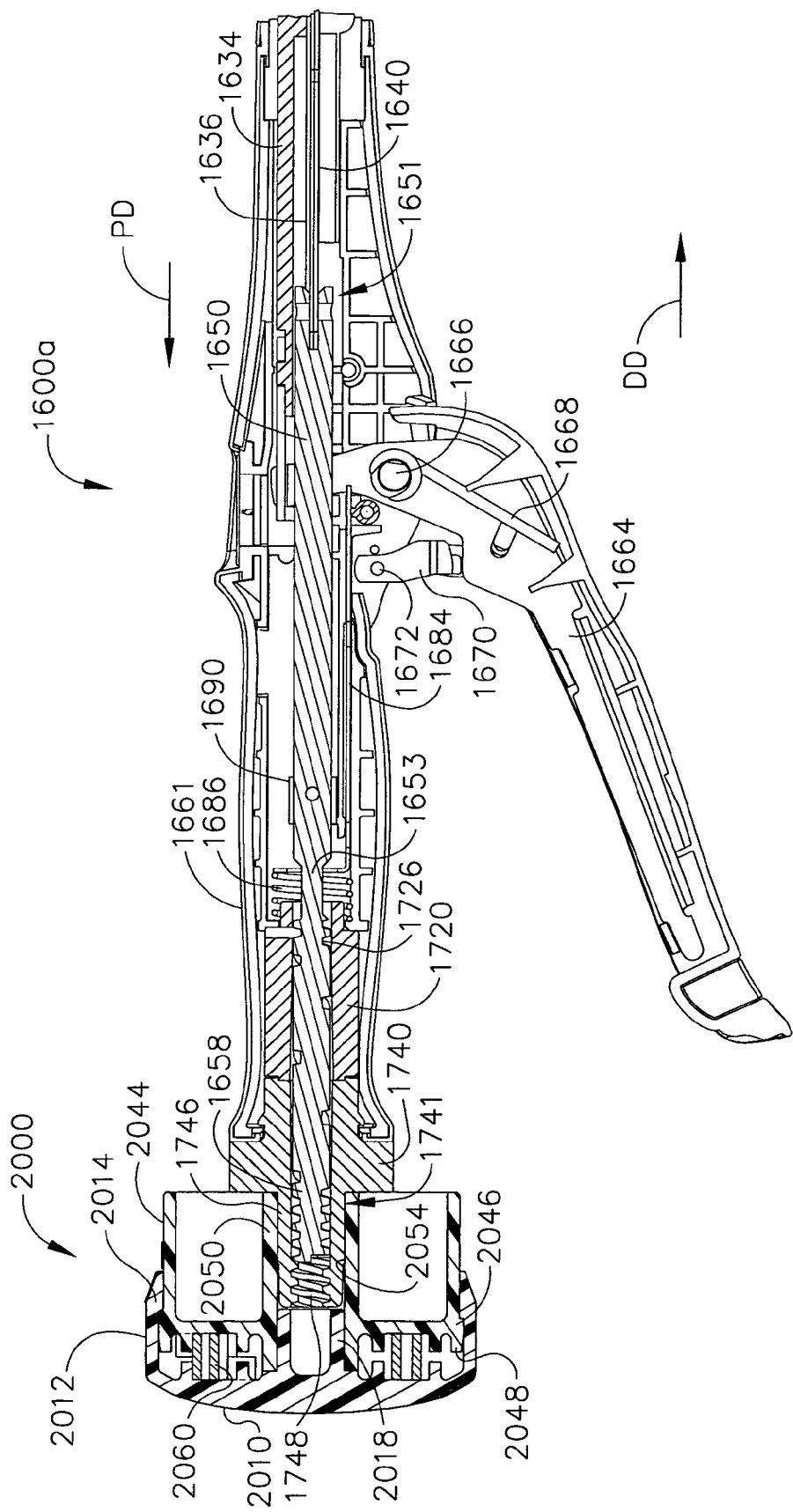
FIG. 90 is partial cross-sectional view of a portion of the stapler of FIG. 89.
Figure 93:
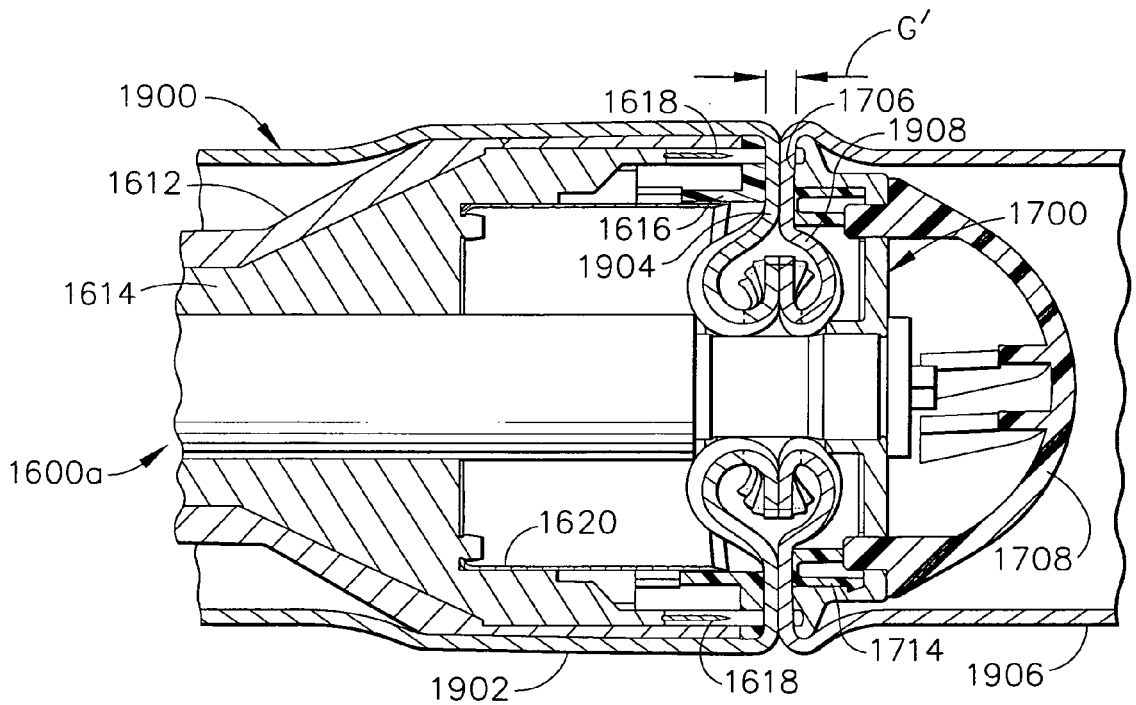
FIG. 93 is a cross-sectional view of a portion of the stapler of FIGS. 89-92 inserted in a portion of an intestine with the stapler anvil retracted to a fully compressed position and prior to firing the stapler.

More specifically, as shown in FIGS. 90 and 91, in various embodiments, the proximal cap portion 2010 may have a sleeve portion 2012 that is sized to extend over the outer wall portion 2044 of the distal cap portion 2040 and be retained thereon by virtue of an inwardly extending flange 2014 formed on the sleeve portion 2012. Flange 2014 may be snapped over an outwardly protruding rim 2046 formed on the circumference of the wall portion 2044 of the distal cap portion 2020. Such arrangement serves to attach the proximal cap portion 2010 to the distal cap portion 2040 while facilitating its rotation relative thereto. To facilitate ease of attachment, a beveled edge 2048 may be provided on the end 2041 of the wall portion 2044.

As can also be seen in FIGS. 90 and 91, the distal cap portion 2040 may further have a cap hub portion 2050 that has a proximal end 2052 that may be rotatably received in a circular slot 2016 formed in the proximal cap portion 2010. The slot 2016 may be sized relative to the cap hub portion 2050 such that the proximal cap portion 2010 can freely rotate around the cap hub portion 2050. In addition, the proximal cap portion 2010 may have a protrusion 2018 that rotatably extends into an axial passage 2054 in the cap hub portion 2050 to provide additional rotational support to the closure knob assembly 2000. As can be seen in FIG. 90, the proximal end 1741 of the proximal closure nut 1740 may be formed with a proximally extending tapered hub portion 1746 that is adapted to be nonrotatably received in the axial passage 2054 in the cap hub portion 2050. The tapered hub portion 1746 may also be formed with a key or spline arrangement to non-rotatably affix the hub portion 1746 with the cap hub portion 2050. Other fastener arrangements and methods may be employed to non-movably attach the hub portion 1746 of the proximal closure nut 1740 to the cap hub portion 2050. Thus, rotation of the cap hub portion 2050 will cause the proximal closure nut 1740 and distal closure nut 1720 to also rotate in the manners described above and axially advance the adjustment shaft 1650 distally or proximally depending upon the direction in which the proximal and distal closure nuts are rotated.

Rotation of the proximal and distal closure nuts 1740, 1720 is attained by rotating the proximal cap portion 2010 relative to the distal cap portion 2040. The interaction between the proximal cap portion 2010 and the distal cap portion 2040 may be controlled by a variable force generating member 2060 that interconnects those components and serves to apply a resistive force to the proximal cap portion 2010 in relation to the amount of compression experienced by the tissue compressed between the anvil 1700 and the staple cartridge 1616. In various embodiments, for example, the variable force generating member may comprise a spiral spring 2060. In some embodiments, the innermost end 2062 of the spiral spring 2060 may be configured as shown in FIG. 92 and inserted into a retaining slot 2020 in the proximal cap portion 2010. End 2062 of spring 2060 may also be attached to the proximal cap portion 2010 by other fastener arrangements. Likewise, the outer end 2064 of the spring 2060 may be configured as shown in FIG. 92 and received in a retention slot 2045 formed in the distal cap portion 2040. However, the outer end 2064 of spring 2060 may be attached to the distal cap portion 2040 by other suitable fastener arrangements.

In various embodiments, a reference indicator mark 2070 may be provided on the proximal cap portion 2010 such that it aligns with a corresponding initial mark 2072 on the outer wall 2044 of the distal cap portion 2040 when the stapler 1600a is in the unadvanced or neutral position. See FIGS. 89 and 95. When in that aligned position, the spiral spring 2060 may essentially be unloaded or it may be under a relatively small amount of load necessary to retain the proximal cap portion 2010 in that starting position. Rotation of the proximal cap portion 2010 in the clockwise "CW" direction will be transferred to the distal cap portion 2040 through the spring 2060 and to the proximal closure nut 1740 attached to the distal cap portion 2040. Rotation of the proximal closure nut

1740 also causes the distal closure nut 1720 to rotate and axially draw the adjustment shaft in the proximal "PD" direction. When the adjustment shaft 1650 is drawn proximally, is also causes the anvil 1700 to move towards the cartridge because it is attached to the trocar tip 1644 which is attached to the adjustment shaft 1650 by means of the top and bottom tension bands 1636, 1638 as was discussed above. As the anvil 1700 moves closer to the staple cartridge 1616 supported in the head 1610, the tissue 1904, 1908 clamped therebetween begins to compress and resist further travel of the anvil 1700 to the cartridge. See FIG. 93. Such resistive compressive force also must be overcome by the spring load to enable the anvil 1700 to further compress the tissue 1904, 1908 between the anvil 1700 and the cartridge 1616.

Figure 94:
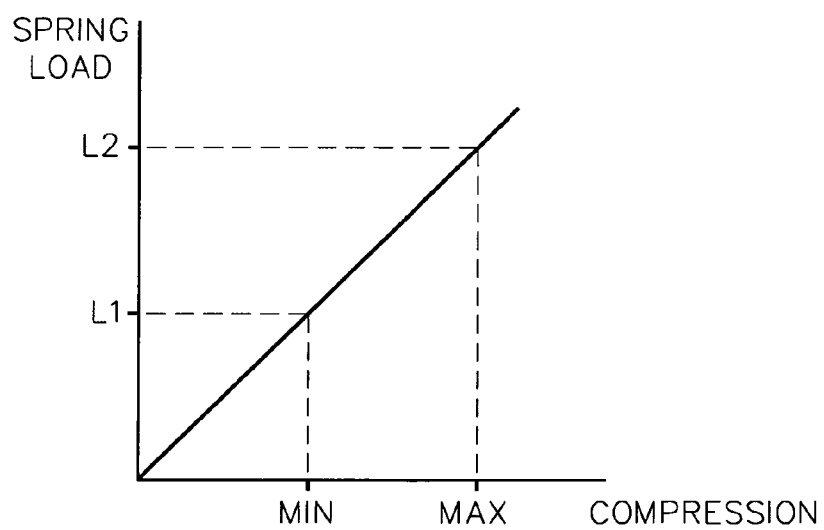
FIG. 94 is a graph illustrating the relationship between a compression force and resistive load generated by a variable force generator that may be used in connection with various embodiments of the present invention.

In various embodiments, the amount of spring load ("L1") necessary to attain a minimum amount of tissue compression ("Min") may be determined as well as the amount of spring load "(L2")" required to attain a maximum amount of tissue compression ("Max") may also be determined. In addition, the distance "D1" that the proximal cap portion 2010 must be rotated from the neutral position to generate spring load "L1" and the distance "D2" that the proximal cap portion 2010 must be rotated to generate spring load "L2" may be determined. The graph depicted in FIG. 94 illustrates an example of a relationship between these parameters. Those of ordinary skill in the art will appreciate that such relationships may change depending upon the spring used and various other factors such as, for example, frictional forces encountered by the moving components of the device.

Figure 95:
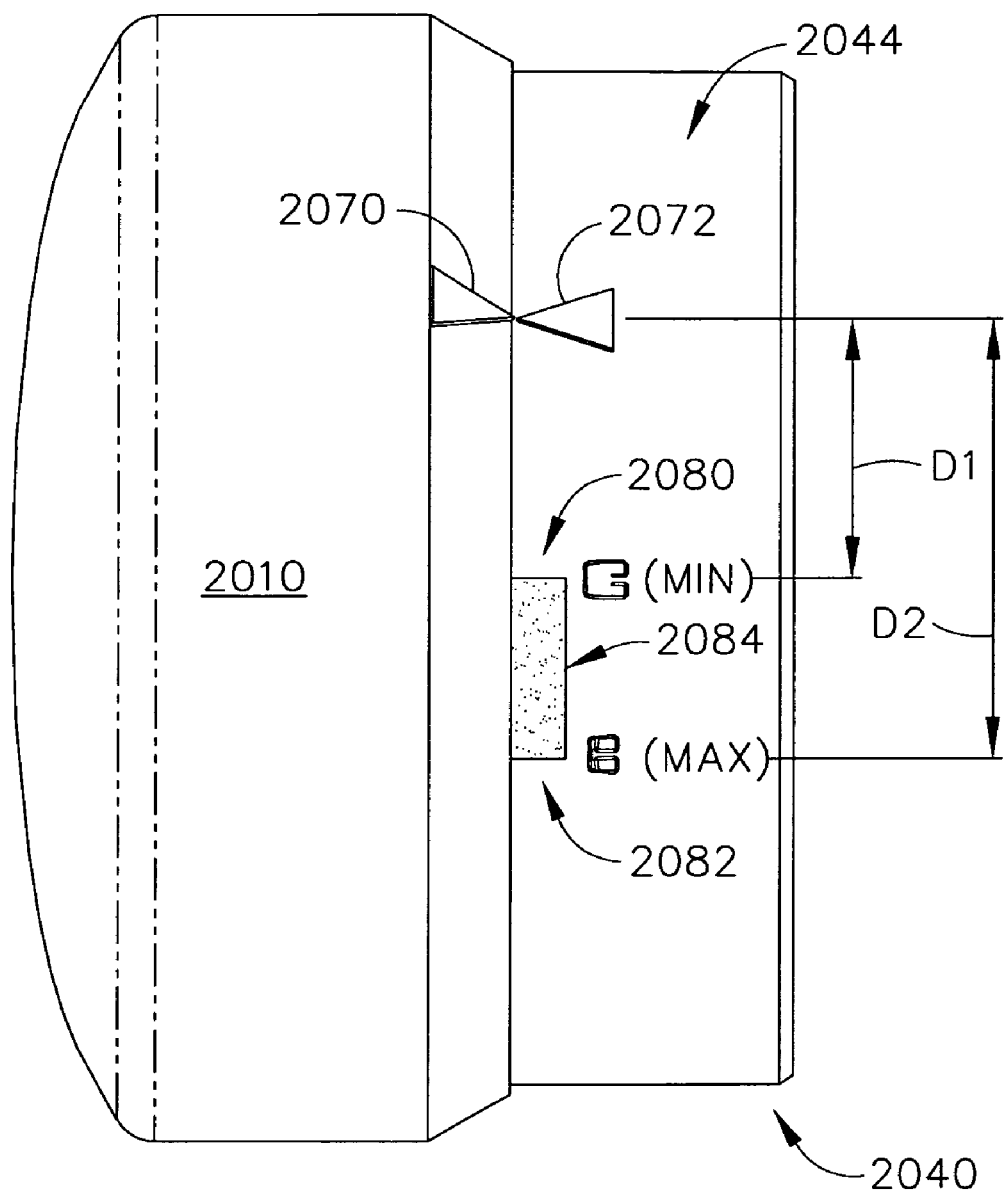
FIG. 95 is another view of the closure actuator of FIGS. 91 and 92.

As can be seen in FIG. 95, a second indicator mark or indicia 2080 corresponding to the position of the proximal cap portion 2010 when it has been rotated to generate the minimum amount of compression force "Min" is provided on the outer wall 2044 of the distal cap portion 2040 such that the second indicia 2080 coincides with the reference indicator 2070 on the proximal cap portion 2010. Likewise a third indicator mark or indicia 2082 may be provided on the outer wall 2044 of the distal cap portion 2040 such that the third indicia 2082 coincides with the reference indicator 2070 on the proximal cap portion 2010 when the proximal cap portion 2010 has been rotated to that position which generates the maximum amount of compression force "Max". See FIG. 95. Those of ordinary skill in the art will recognize that a variety of different indicia arrangements may he employed without departing from the spirit and scope of the present invention. For example, the area 2084 on the outer wall 2044 of the distal cap portion 2040 between the second indicia member 2080 and the third indicia member 2082 may be painted or otherwise colored green to indicate to the surgeon that if the reference indicator 2070 is located in that region and acceptable amount of compression force may be attained.

Thus, in these embodiments, the spring 2060 provides a means for interrelating the amount of compression experienced by the tissue located between the anvil 1700 and the staple cartridge 1616 and the distance that the proximal cap portion 2010 must be rotated to attain that amount of compression. Such arrangement permits the use of reference indicators and indicia on the proximal and distal cap portions 2010, 2040 to enable the surgeon to accurately determine when the anvil has been located in a position that will result in acceptable staple formation. These reference indicators and indicia can be so oriented to inform the surgeon when the anvil has been moved to a position that will result in a minimum amount of compression being applied to the tissue while still facilitating the formation of sealing staples. Likewise, such reference indicators and indicia may be so oriented to inform the surgeon that the anvil has been moved to a position that will result in a maximum amount of compression being applied to the tissue while still facilitating the formation of sealing staples.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, while various manually operated surgical instruments have been depicted for clarity, it should be appreciated that such devices may also be robotically manipulated. In addition, those skilled in the art will appreciate that the embodiments, features and improvements disclosed herein may be readily employed in connection with a variety of other known surgical cutter/staplers, staplers, etc. that may have application in open, laparoscopic, endoscopic and/or intralumenal surgical procedures. In particular, such unique and novel features may be practiced in connection with linear staplers, cutters, contour cutters, etc. Thus, the scope and protection afforded to the various embodiments disclosed herein should not be limited solely to endocutter-type surgical staplers.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

As used herein, the term "fluidically coupled" means that the elements are coupled together with an appropriate line or other means to permit the passage of pressurized gas therebetween. As used herein, the term "line" as used in "supply line" or "return line" refers to an appropriate passage formed from rigid or flexible conduit, pipe, tubing, etc. for transporting fluid from one component to another.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

As known in the art, surgical staples can be used to hold several layers of tissue together after the tissue has been resected, for example. Often, as described above, a surgical stapler is used to deform the staples from an undeployed shape into a deployed, i.e., deformed, shape. Referring to FIG. 27, the staples, such as staples 83, for example, include a base, or crown, and deformable legs extending therefrom. In use, the deformable legs are typically deformed toward the crown by an anvil in the surgical stapler. Referring to FIG. 27, the amount of this deformation is usually dependent upon the thickness of the tissue being stapled. More particularly, if the tissue is thinner, the anvil is brought closer to the staple cartridge before the anvil contacts the tissue and, as a result, the staples will have less distance to be deployed before they are deformed against the anvil. For example, the legs of the staple on the left in FIG. 27 are inserted through thinner tissue while the legs of the staple on the right are inserted through thicker tissue and, as a result, the legs of the staple on the left are deformed more than the legs of the staple on the right. As a result of the foregoing, a common staple design can be readily adapted to various tissues having different thicknesses.

As described above, referring to FIG. 27, the legs of staples 83 are bent toward the base, or crown, of the staple. More particularly, the ends of the legs are curled by the anvil of the stapler until the desired deformation is achieved. Stated another way, when the ends of the legs contact the anvil of the stapler, the ends are guided by the anvil such that the legs are continuously bent into an arcuate configuration until the staple is deformed into a "B" shape, for example. In embodiments where the staple has long legs, and/or embodiments where the staples are used in very thin tissue, the legs may be curled significantly such that their ends project outwardly from the staple. In these embodiments, the ends may be sharp and may impinge on surrounding tissue causing discomfort to the patient. To ameliorate this problem, the present invention includes staple 1300 which can be bent in segments, as opposed to a continuous arcuate shape as described above.

Figure 105:
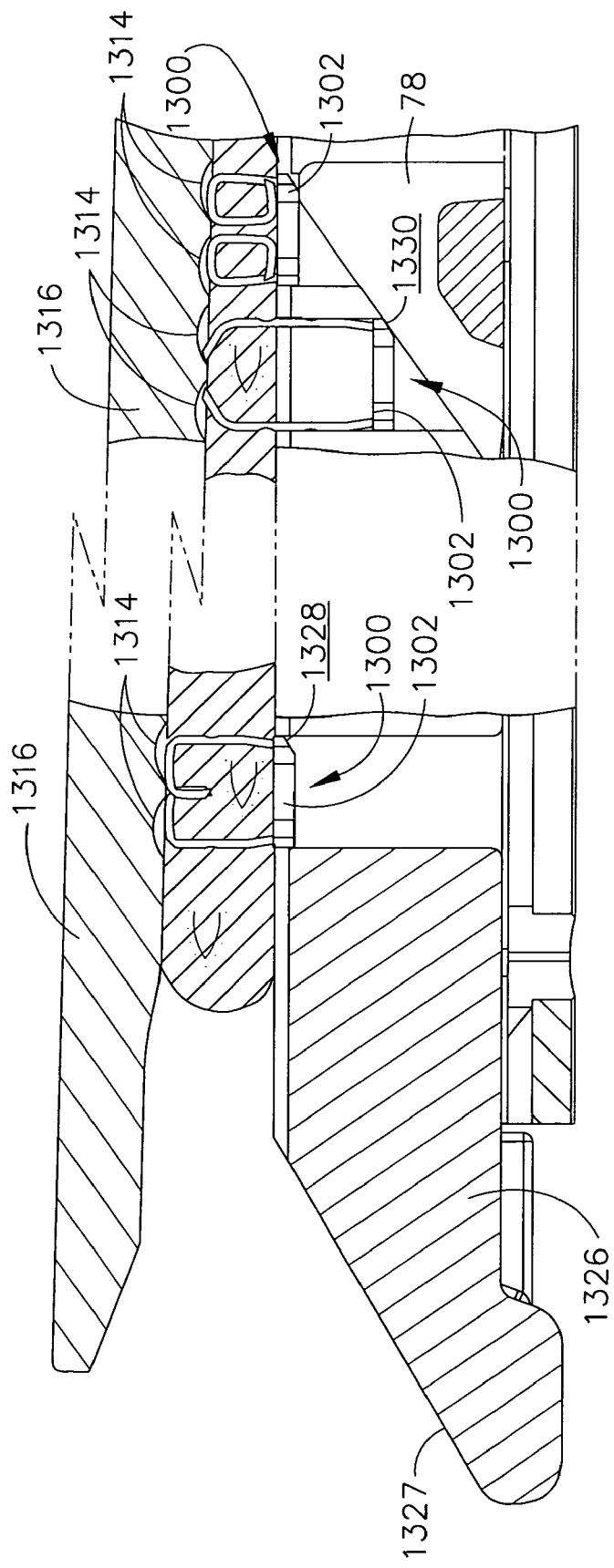
FIG. 105 is a partial cross-sectional view of a surgical stapler, and surgical staples illustrated in various deformed shapes in accordance with an embodiment of the present invention.

Similar to the above, referring to FIG. 96, staple 1300 includes crown 1302 and deformable legs 1304 and 1306 extending therefrom. Legs 1304 and 1306 include first notches 1310, second notches 1312, and third notches 1313 therein. In use, referring to FIG. 105, when ends 1308 of legs 1304 and 1306 contact pockets 1314 of anvil 1316, ends 1308 can be guided toward each other, for example. As the staple is further driven toward anvil 1316 by sled driver 78, referring to staple 1300b, legs 1304 and 1306 may bend significantly at first notches 1310. Referring to FIG. 97, owing to the reduced cross-section of legs 1304 and 1306 at first notches 1310, legs 1304 and 1306 are more susceptible to deformation at this location. For example, when legs 1304 and 1306 are bent at notches 1310, first segments 1318 may bend at an approximately 90 degree angle, for example, with respect to second segments 1320 of legs 1304 and 1306. In other embodiments, first segments 1318 may be bent at any suitable angle with respect to second segments 1320.

Figure 98:
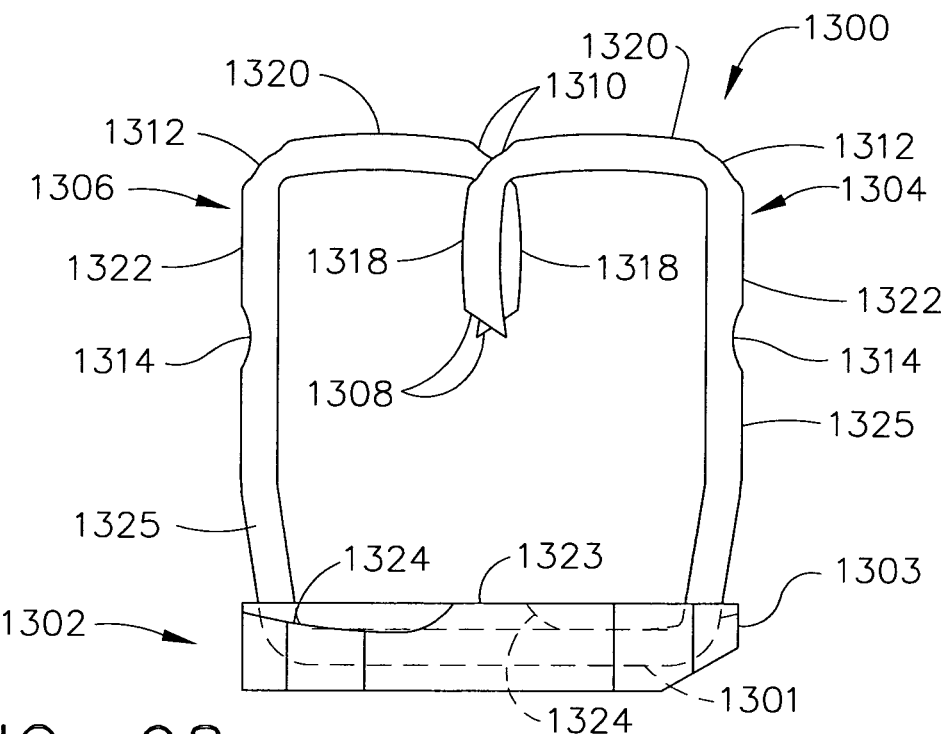
FIG. 98 is a side view of the staple of FIG. 96 in a second deformed shape.
Figure 99:
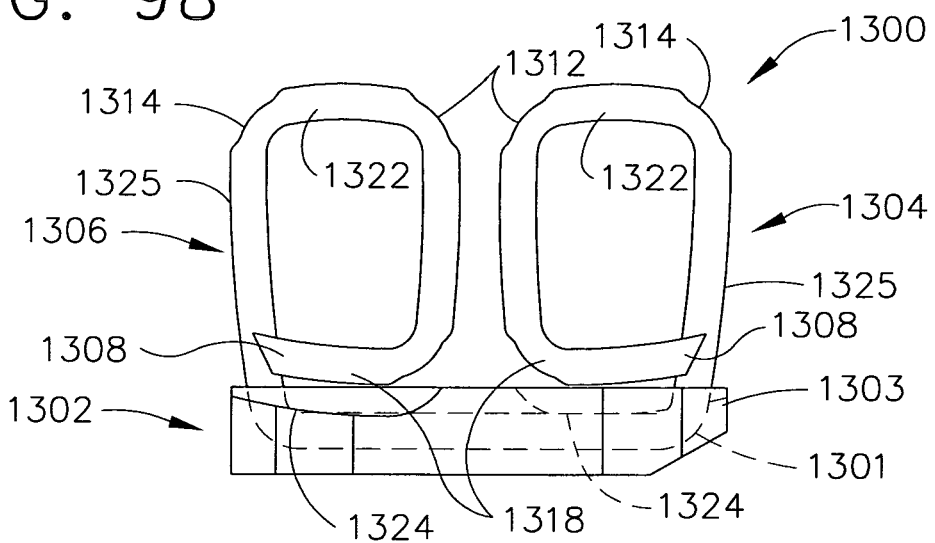
FIG. 99 is a side view of the staple of FIG. 96 in a third deformed shape.
Figure 100:
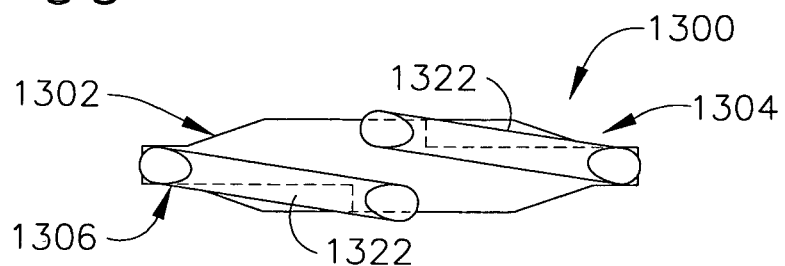
FIG. 100 is a top view of the staple of FIG. 99.

Further to the above, referring to FIG. 98, second notches 1312 in legs 1304 and 1306 permit second segments 1320 to bend with respect to third segments 1322 at an approximately 90 degree angle, for example. In other embodiments, second segments 1320 may be bent at any other suitable angle with respect to third segments 1322. Similar to the above, notches 1313 permit third segments 1322 to bend with respect to fourth segments 1325. As a result of notches 1310, 1312, and 1313, legs 1304 and 1306 may not be bent into a continuous curl as described above; rather, they can be bent into a segmented, rectangular configuration. As a result of the above, staples having long legs 1304 and 1306 may be deformed in a manner such that the ends of the deformable members do not extend outwardly from the staple, rather, they can be positioned intermediate legs 1304 and 1306 as illustrated in FIG. 99. While the legs of the illustrated staples in FIGS. 96-105 have three notches and four segments, various embodiments are envisioned which have additional, or less, notches and segments. Furthermore, while the segments of the staple legs described above are substantially straight, various embodiments are envisioned in which the segments are curved, curvilinear, or other otherwise suitably configured to achieve a desired shape.

To facilitate the bending of third segments 1322 with respect to fourth segments 1325, for example, crown 1302 may include a forming surface, or anvil, for guiding and/or deforming legs 1304 and 1306 when they contact crown 1302. More particularly, referring to FIGS. 99 and 101-104, as legs 1304 and 1306 are being deformed from the shape illustrated in FIG. 98 to the shape illustrated in FIG. 99, ends 1308 of deformable members 1304 and 1306 may contact crown 1302. To guide ends 1308, anvil 1323 of crown 1302 includes recesses 1324 which can direct ends 1308 to move outwardly as illustrated in FIG. 99. or in any other suitable direction. In various embodiments, recesses 1324 may not deform legs 1304 and 1306 significantly, however, in the illustrated embodiment, recesses 1324 are configured to deform legs 1304 and 1306 at an approximately 90 degree angle. In various embodiments, anvil 1316 of the stapler and anvil 1323 in crown 1302 can co-operate to deform staple 1300 into the shape illustrated in FIG. 99, for example, or any other suitable shape.

In various embodiments, although not illustrated, a forming surface, or anvil, can be included in staple cartridge 1326 in addition to, or in lieu of, anvil 1323 in crown 1302. In these embodiments, anvil 1316 deforms legs 1304 and 1306 such that ends. 1308 contact the recesses in stapler cartridge 1326. Similar to the above, the staple cartridge recesses can be configured to guide and/or deform legs 1304 and 1306 when they contact stapler cartridge 1326. In various embodiments, anvils on both crown 1302 and stapler cartridge 1326 can be utilized to deform and/or guide the staple. In the illustrated embodiment, crown 1302 includes material 1303 overmolded onto base 1301. As discussed in greater detail below, material 1303 can be comprised of a plastic material, for example, a bioabsorbable material, and/or a non-bioabsorbable material. In at least one of these embodiments, the material 1303 is formed around a single continuous wire comprising base 1301 and deformable members 1304 and 1306. In other embodiments, deformable members 1304 and 1306 can include separate deformable members embedded in plastic material 1303. Further, in various embodiments, the wire comprising base 1301 can be deformed to provide the recesses and anvils described above.

Referring to FIGS. 106 and 107, similar to the above, the staple, in various embodiments, can include several necked down sections in the staple legs which can be configured to cause the staple legs to deform and/or buckle at the necked down sections. More specifically, staple 1340 can include several necked-down or tapered sections 1342 which allow staple legs 1344 to deform in segments as described above. Tapered sections 1342, similar to notches 1310, 1312, and 1313, provide a stress concentration area. Stress concentration areas are typically locations in which a loaded member, for example, will fail. Stated another way, stress concentration areas may magnify the stress in a particular area of a loaded member causing the loaded member to yield, or plastically strain, at the stress concentration area before the remainder of the loaded member plastically strains. As used herein, the term "yield" generally refers to the point of maximum stress and/or strain above which a material will no longer behave in a completely elastic manner. However, various embodiments are envisioned in which the materials used herein do not have a traditional yield point, for example. These materials can include materials which strain plastically as soon as they are stressed and /or super-elastic materials which do not have a discernable yield point. These materials can include shape memory alloys, such as Nitinol, for example, that allow for large strain deformations during the above-described forming processes. Typically, engineers are charged with eliminating stress concentration areas to achieve a desired goal; however, according to the teachings of the present invention, stress concentration areas can be utilized to achieve the above-described goals.

Figure 108:
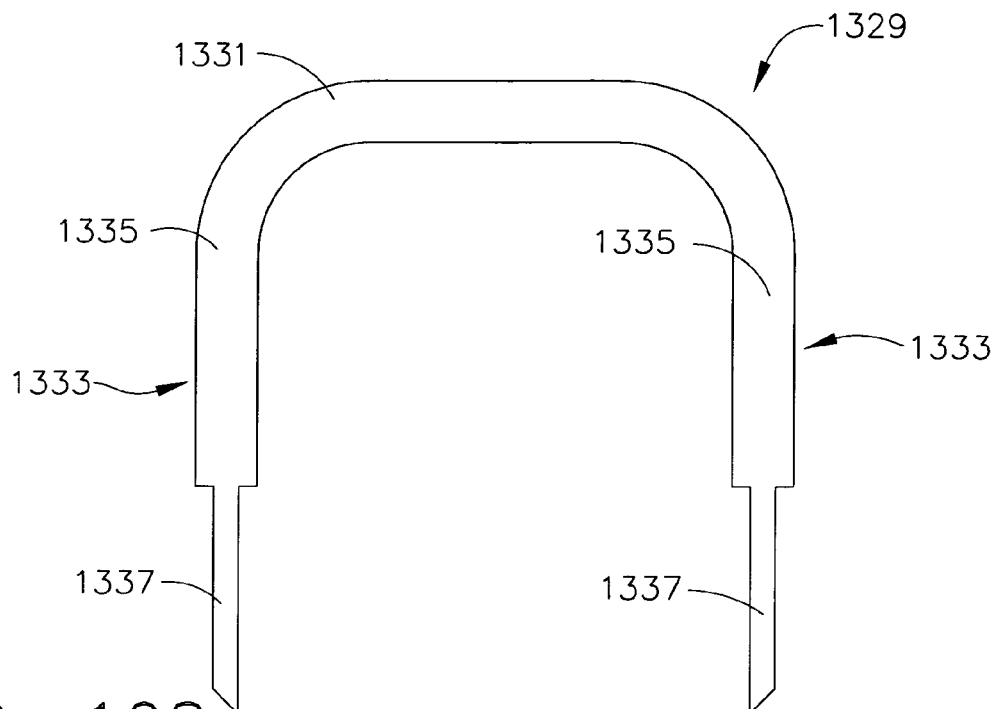
FIG. 108 is a side view of a staple in accordance with an alternative embodiment of the present invention.
Figure 109:
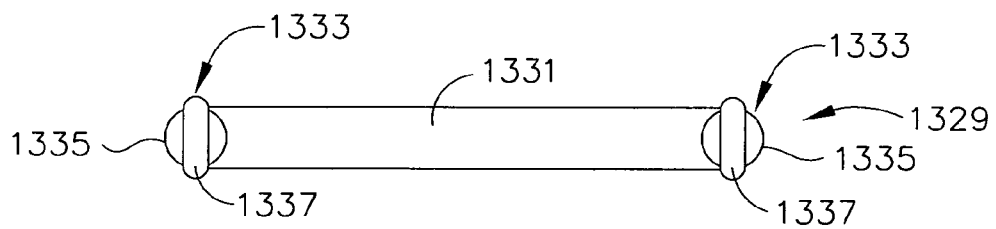
FIG. 109 is a top view of the staple of FIG. 108.
Figure 110:
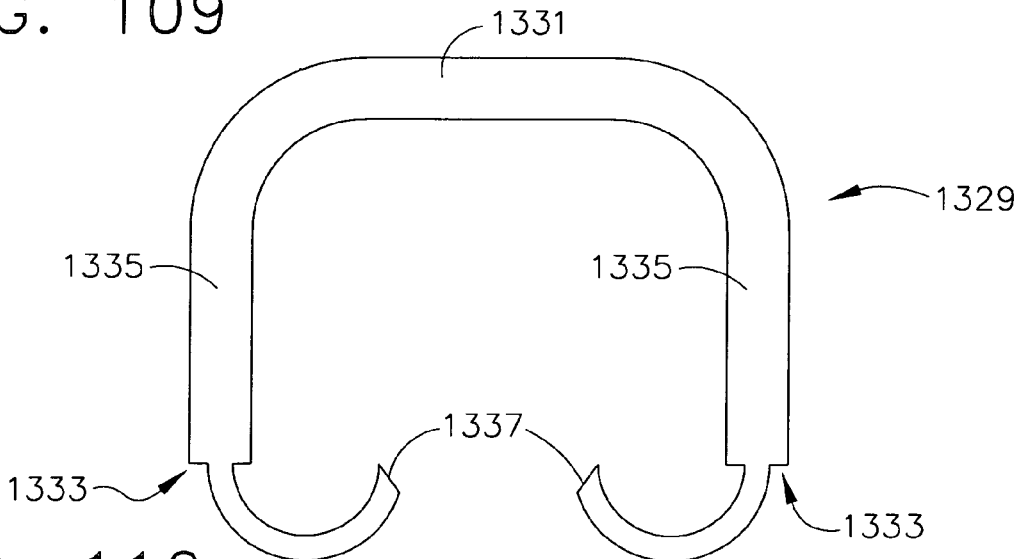
FIG. 110 is a side view of the staple of FIG. 108 in a deformed shape.

In various embodiments, referring to FIGS. 108-110, staple 1329 includes base portion 1331 and two deformable legs 1333 extending therefrom. Legs 1333 can each include a first portion 1335 having a substantially round cross-section and a second portion 1337 having a substantially flat cross-section. In at least one embodiment, legs 1333 and base 1331 are comprised of a metal wire that is coined, or formed, on its ends to create substantially flat portions 1337. As known in the art, coining, or forming, a metal wire may be performed with a stamping press before and/or after, the wire is bent into the "U" shape illustrated in FIG. 108. Referring to FIG. 110, legs 1333 are configured such that flat portions 1337 can be bent to secure tissue within the staple while round portions 1335 can remain substantially unbent. In use, as a result, staple 1329 can be used to secure thicker tissues. More specifically, owing to substantially unbent portions 1335, thicker tissues can be accommodated between portions 1335 while flat portions 1337 can be bent to retain the tissue therebetween. The amount in which flat portions 1337 are deformed is typically dependent upon the thickness of the tissue captured in the staple.

Figure 111:
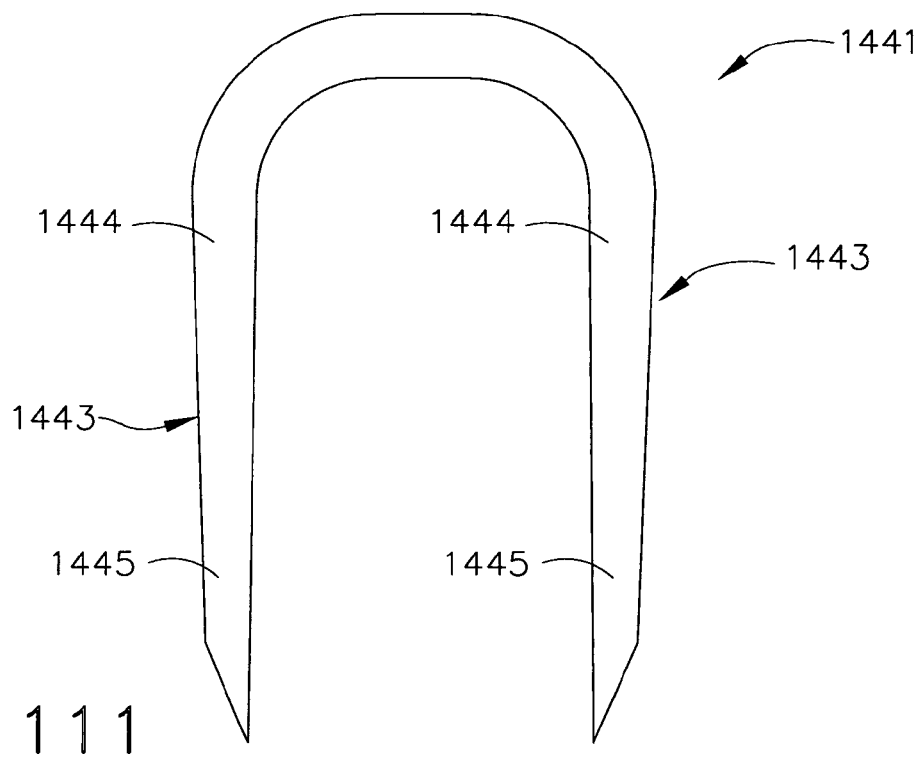
FIG. 111 is a side view of a staple in accordance with an alternative embodiment of the present invention.
Figure 112:
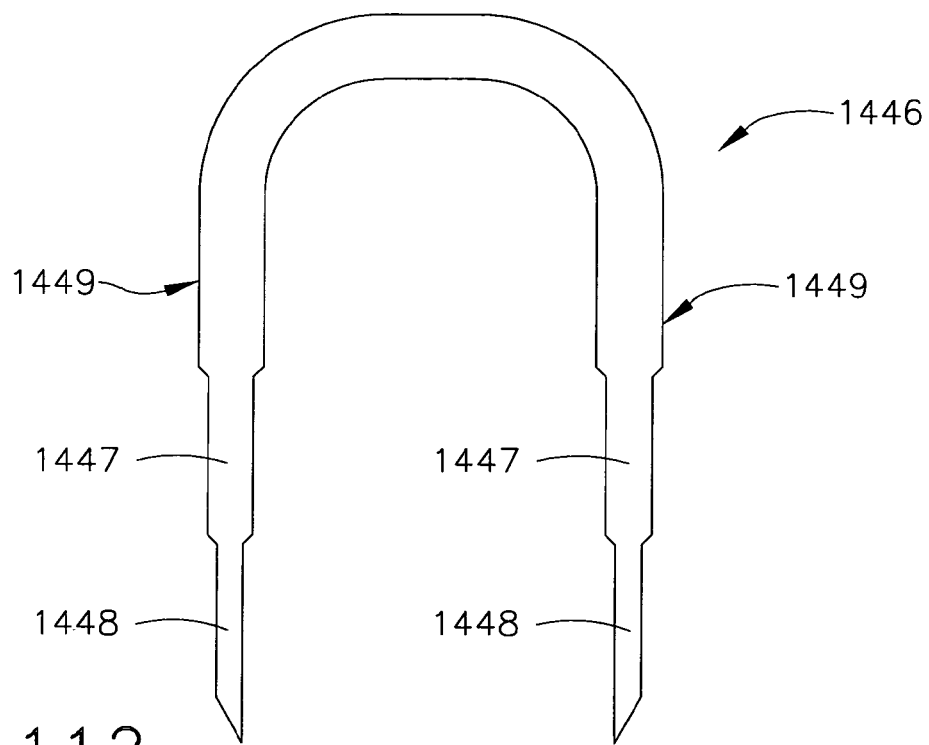
FIG. 112 is a side view of a staple in accordance with an alternative embodiment of the present invention.

In various embodiments, referring to FIG. 111, staple 1441 can include deformable legs 1443 which have a tapered configuration. More particularly, staple legs 1443 can include a base portion 1444 that has a larger cross-section than the cross-section of tip portion 1445. In use, similar to the above, staple 1441 can accommodate thicker tissues as, owing to the thicker cross-section of base portions 1444, base portions 1444 may remain substantially unbent while tip portions 1445 are bent to retain the tissue in the staple. In other various embodiments, referring to FIG. 112, staple 1446 can include several stepped portions 1447 and 1448 which allow some portions of legs 1449 to be bent, some portions to be only partially bent, and other portions to remain substantially unbent. The suitable amount and configurations of the stepped portions may be selected to accommodate the type and/or thickness of the tissue being secured.

Referring to FIGS. 113 and 114, staple 1350, similar to staple 1340, includes crown 1302 and deformable legs 1344. Staple 1340, as described above, in at least one embodiment, is configured to compress tissue between deformable legs 1344 and crown 1302. However, in applications in which the tissue is very thin, for example, sufficient compression of the tissue between deformable legs 1344 and crown 1302 may be difficult to achieve and a gap between the tissue and legs 1344, for example, may exist. For these applications, it may be desirable to include an additional member intermediate the tissue and the deformable members and/or crown which not only fills the gap, but compresses the tissue against at least one of the crown and/or deformable members.

Staple 1350, referring to FIGS. 113 and 114, can include, in various embodiments, deformable, or compressible, member 1352. As described above, referring to FIG. 114, compressible member 1352 can bias tissue 1353 against deformable legs 1344. As a result of this compression, the lumens, or vessels, in tissue 1353 can be compressed and thereby slow the flow of blood therethrough. In at least one embodiment, compressible member 1352 is entirely elastic after it has been compressed, i.e., the addition of, or the removal of, any stress onto compressible member 1352 will result in a linearly corresponding increase, or decrease, in strain thereof. Stated in another way, in these elastic embodiments, compressible member 1352 can substantially act like a spring. However, in at least one embodiment, compressible member 1352 can be crushable, i.e., after it has been compressed, at least a portion, if not all, of compressible member 1352 is permanently deformed and the addition of, or removal of, any stress onto compressible member 1352 does not necessarily result in a linearly corresponding strain. In various embodiments, compressible member 1352 can be comprised of foam. The foam can be absorbable or non-absorbable. The foam can be comprised of synthetic materials and/or mammalian-derived materials including, but not limited to, polyglycolide trimethylene carbonate copolymer, polyglycolic acid, caprolactone/glycolide, EPTFE, and bovine pericardium. Further, in at least one embodiment, compressible member 1352 may include a first portion which is elastically deformable and a second portion which is plastically deformable.

Figure 115:
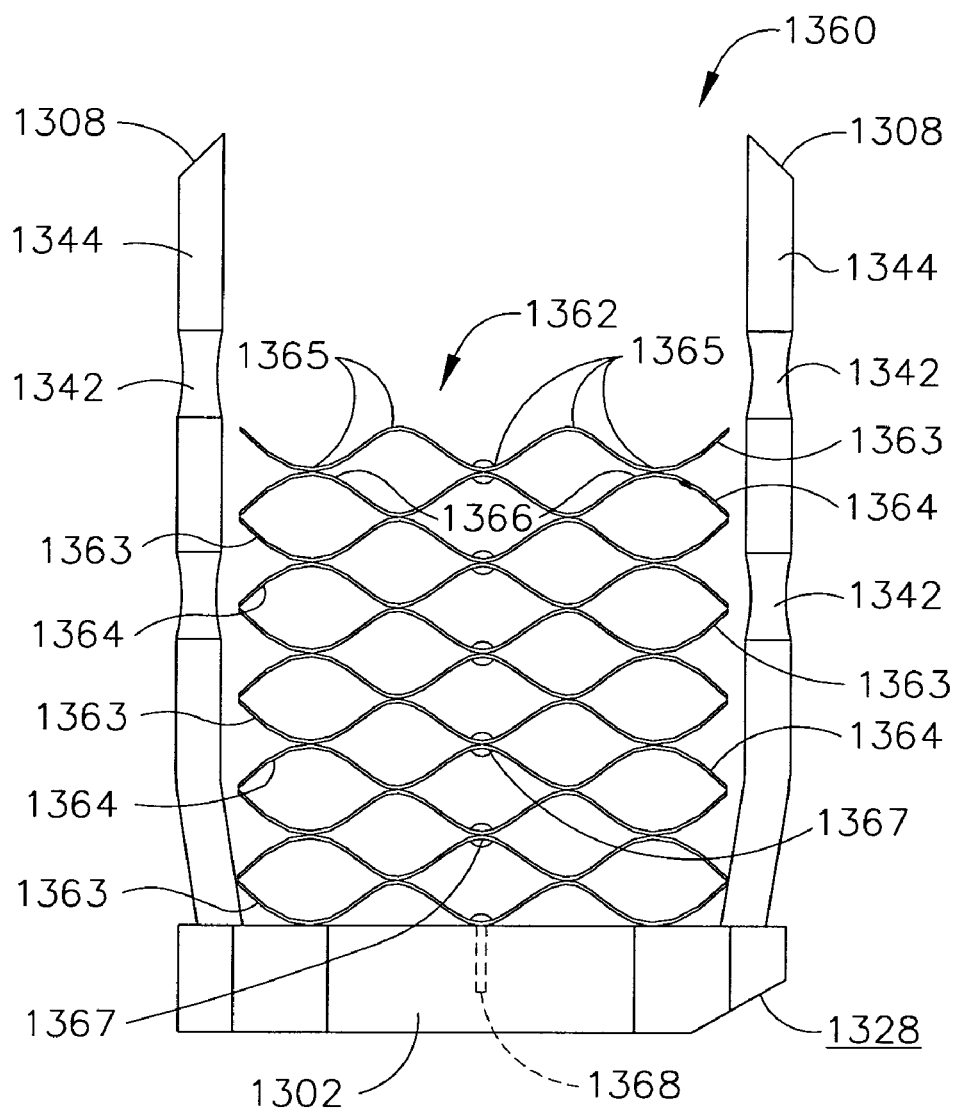
FIG. 115 is a side view of a surgical staple in accordance with an embodiment of the present invention including a spring having a first elastic member and a second elastic member.
Figure 116:
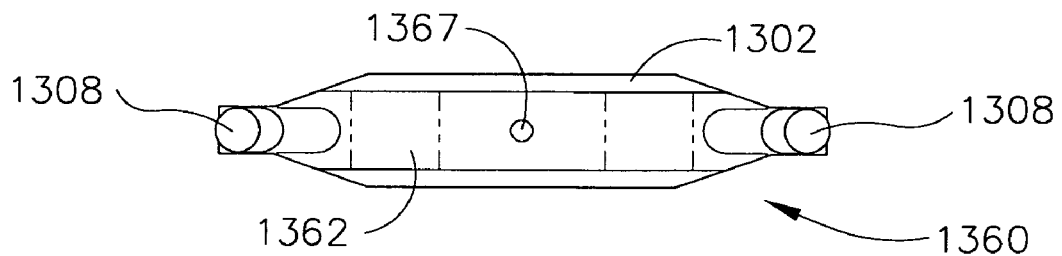
FIG. 116 is a top view of the staple of FIG. 115.

Referring to FIGS. 115 and 116, staple 1360 can include collapsible spring member 1362. Collapsible spring member 1362 can include a plurality of first elastic members 1363 and second elastic members 1364. Each first elastic member 1363 can include an arcuate profile which includes projections 1365 extending therefrom which are sized and configured to contact corresponding projections 1366 extending from each second elastic member 1364. More specifically, first elastic members 1363 and second elastic members 1364 are configured such that they can be stacked upon each other and, when a compressive load is applied to such a stack, the first and elastic members can flatten and thereby "collapse" the stack of elastic members. In the illustrated embodiment, collapsible spring member 1362 further includes fasteners 1367 and 1368. Referring to FIG. 115, fasteners 1367 can connect the central portions of adjacent first elastic members 1363 and second elastic members 1364 to prevent the elastic members from becoming dislodged or misaligned with respect to each other. Similarly, fastener 1368 can prevent collapsible spring member 1362 from becoming dislodged with respect to crown 1302. In use, collapsible spring member 1362 can provide a compressive load to tissue in between said deformable members and said crown.

Figure 117:
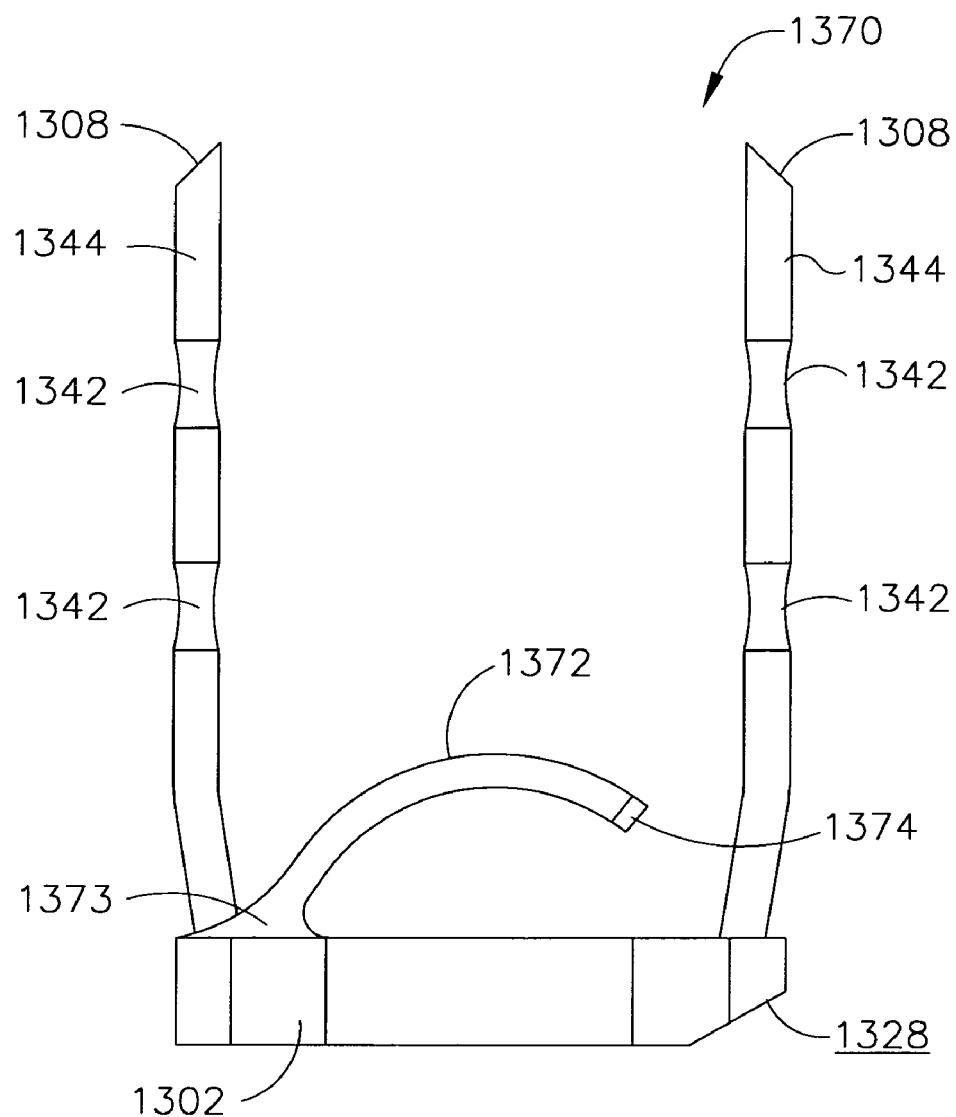
FIG. 117 is a side view of a surgical staple in accordance with an embodiment of the present invention including a cantilever spring.
Figure 118:
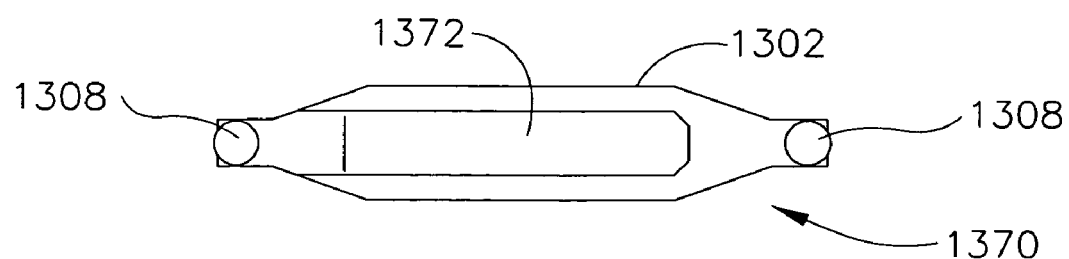
Figure 119:
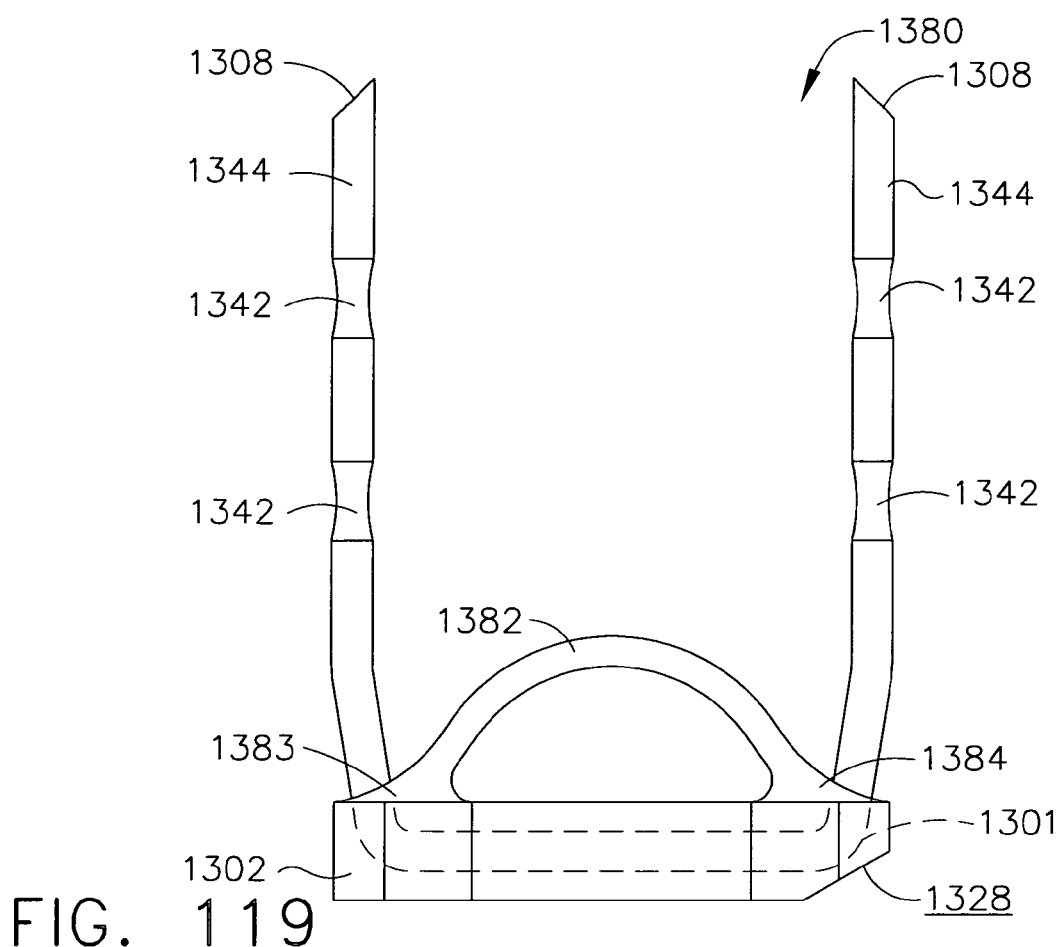
Figure 120:
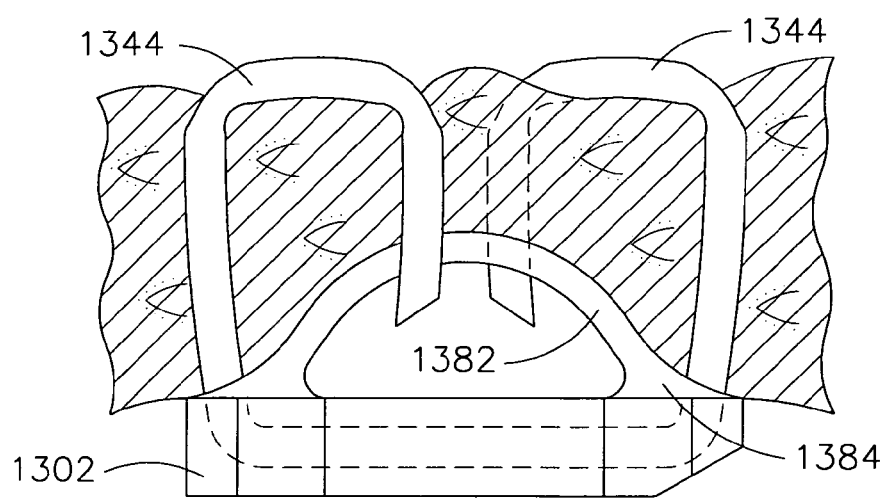
Figure 121:
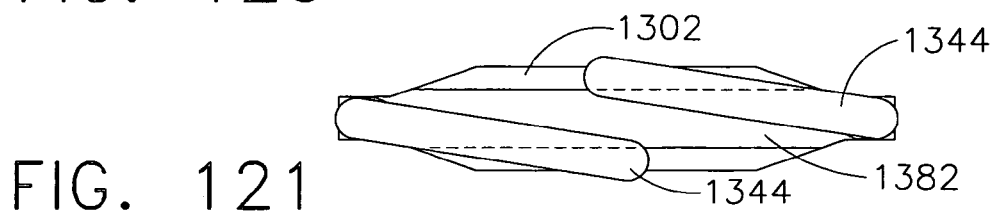

Referring to FIGS. 117 and 118, staple 1370 can include cantilever spring 1372. Cantilever spring 1372 includes first end 1373 attached to crown 1302 and second end 1374 which is free to move with respect to first end 1373. In use, when tissue is compressed between spring 1372 and deformable legs 1344, spring 1372 can apply an upwardly-directed biasing, or compressive, force against the tissue. More particularly, as deformable legs 1344 are deformed and pushed against the tissue, second end 1374 of spring 1372 can move downwardly with respect to first end 1373. As a result of this deflection, spring member 1372 stores potential energy and acts to release this potential energy by applying an upward force against the tissue, thereby compressing the tissue between spring member 1372 and deformable legs 1344. In an alternative embodiment, referring to FIGS. 119-121, spring member 1382 of staple 1380 can have first and second ends, 1382 and 1384, respectively, attached to crown 1302. In at least one embodiment, springs 1372 and 1382, for example, can be integrally molded with crown 1302. In these embodiments, springs 1372 and 1382 can be comprised of a dissolvable, bioabsorbable, or biofragmentable material such that, as the material dissolves, the biasing force of springs 1372 and 1382 can decrease throughout the healing process. As a result, a larger compressive force can be applied during the initial healing stages when the restriction of blood loss is important and a smaller compressive force can be applied during the later healing stages when tissue regeneration is important wherein the smaller force permits expansion and growth of the tissue within the staple.

In other various embodiments, although not illustrated, the tissue can be positioned, and compressed between, the compressible member and the crown of the staple. In these embodiments, the deformable members are deformed against the compressible member which, as a result, is compressed between the deformable legs and the tissue.

Figure 122:
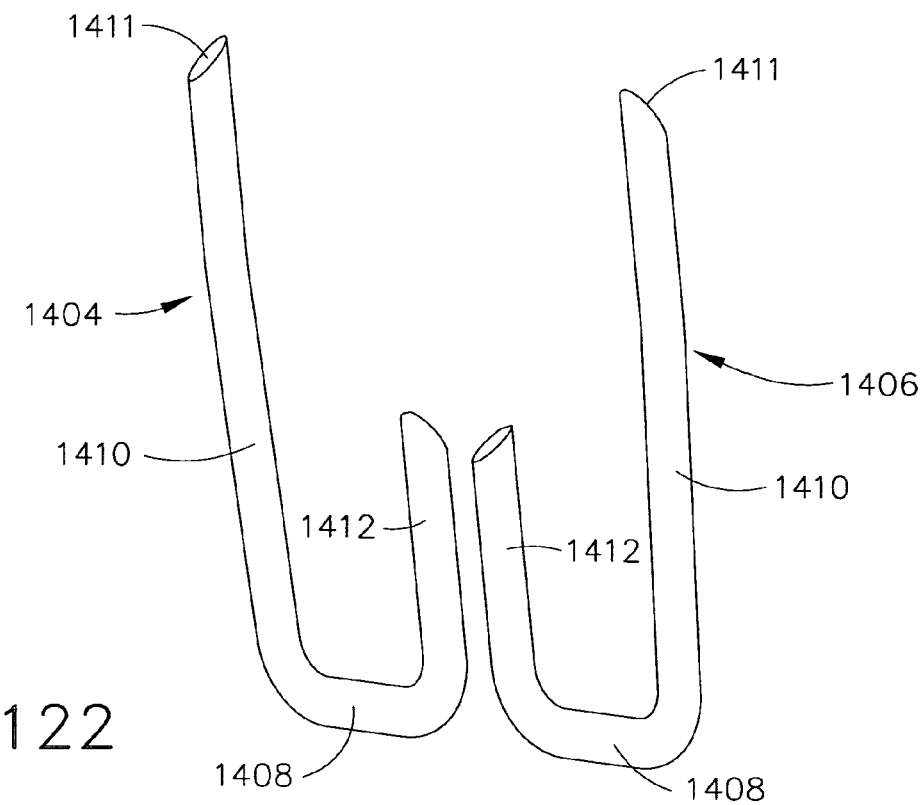
Figure 123:
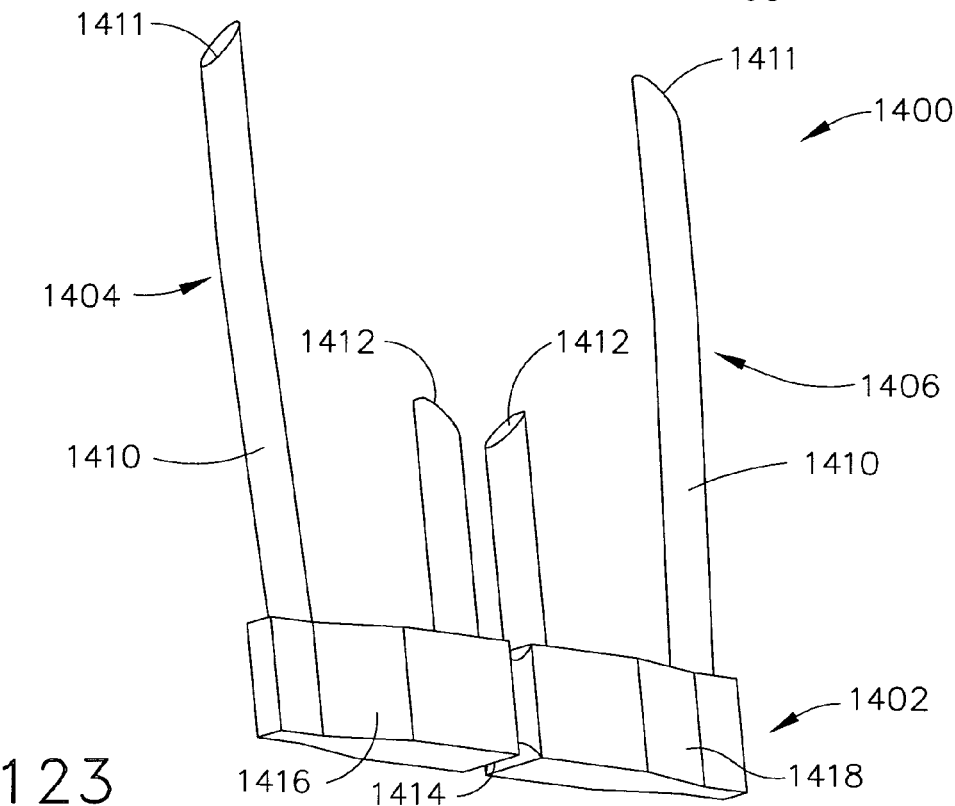

Referring to FIGS. 122 and 123, staple 1400 includes crown 1402, first deformable member 1404, and second deformable member 1406. Deformable members 1404 and 1406 each include a base 1408, a deformable leg 1410, and a second leg 1412 which, in the illustrated embodiment, are comprised of a single continuous wire. In other various embodiments, staples 1400 may be configured in any other suitable manner to achieve the goals of the invention described herein. In the illustrated embodiment, members 1404 and 1406 are connected together by a material that is overmolded onto the bases 1408 of members 1404 and 1406. In various embodiments, the material can include a dissolvable, bioabsorbable, or biofragmentable material such as Vicryl and PDS from Ethicon, Inc., for example. As used herein, the terms dissolvable, bioabsorbable, and biofragmentable all generally refer to materials that can be at least partially assimilated by the body after being implanted into a patient, for example.

Figure 124:
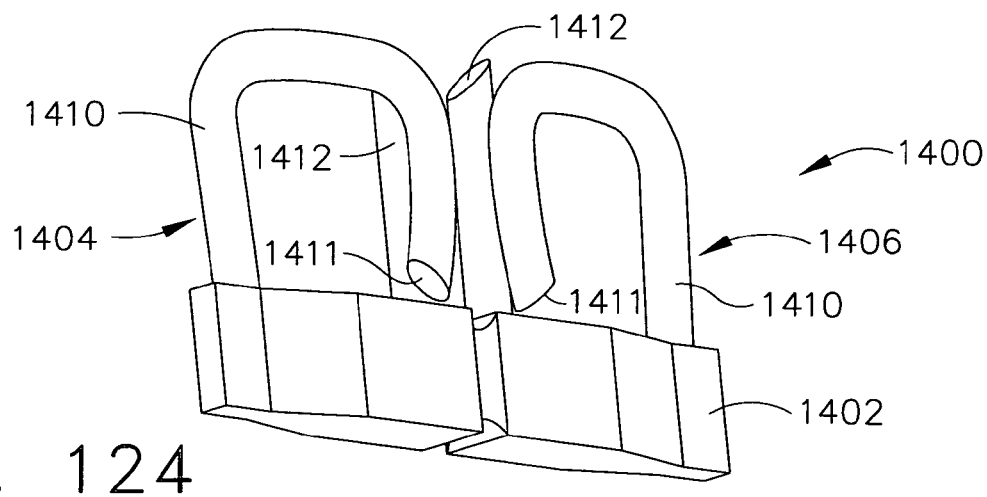
Figure 125:
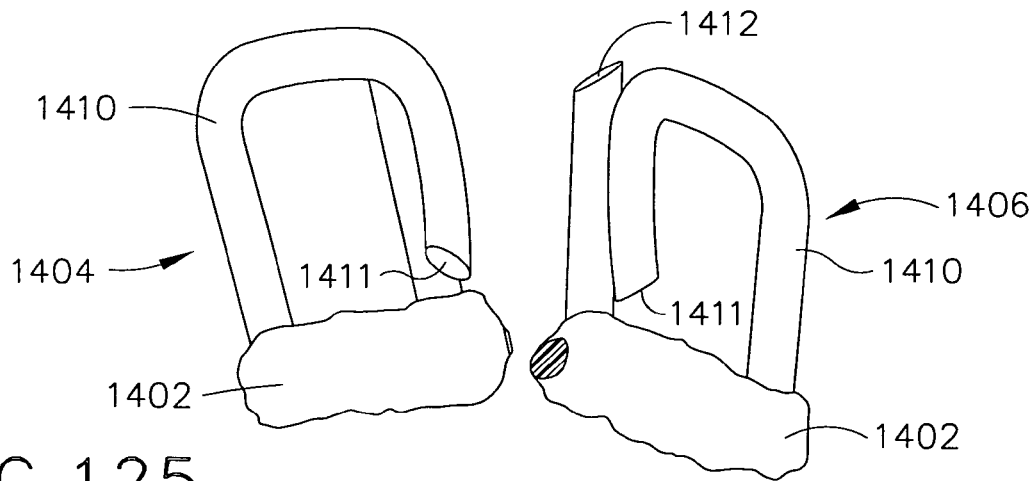
Figure 126:
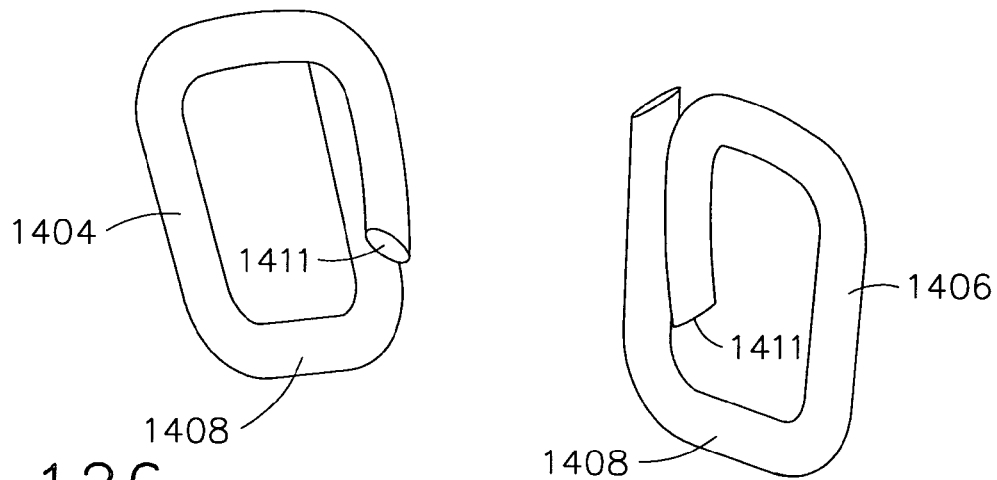

In use, staple 1400 can be inserted into the soft tissue of a person, for example, via a stapler and can be deformed into the configuration illustrated in FIG. 124. More particularly, in the illustrated embodiment, deformable members 1404 and 1406 can be deformed by the anvil of the stapler such that ends 1411 of legs 1410 are brought into close proximity to crown 1402. Once staple 1400 is implanted into the tissue, crown 1402 may begin to break down, dissolve and weaken. More particularly, referring to FIG. 125, the bioabsorbable material of crown 1402 may deteriorate to the point where first member 1404 and second deformable member 1406 become disconnected from each other as illustrated in FIG. 126. Once first member 1404 and second member 1406 have become disconnected, they can move relative to one another. The time required for crown 1402 to sufficiently dissolve may depend on the material used and/or the size of crown 1402. Polyglatin 910 material, sold under the tradename Vicryl, for example, may dissolve in 7-14 days.

In various embodiments, dissolvable crown 1402 may provide several therapeutic advantages. For example, when staple 1400 is initially deployed, deformable members 1404 and 1406 may significantly compress the tissue within the staple against crown 1402. In some applications, this compression may be desirable to limit bleeding from the tissue. As crown 1402 deteriorates, the gap between the deformed members 1404 and 1406 and crown 1402 may increase thereby relaxing the compressive forces acting on the tissue. In some applications, relaxing the compression forces during the healing process may allow the tissue to slowly expand and return to its normal thickness over a period of time. In some embodiments, crown 1402 can be coated with a hydrophilic material that initially expands to compress the tissue captured within the staple before dissolving away thereafter. In these embodiments, the hydrophilic material expands by absorbing water from the surrounding tissue and fluids. In addition to the above, staple 1400, when it is inserted into the tissue, may be very stiff and, if several staples are inserted into the tissue, the tissue may not be permitted to move and expand during the healing process. However, after crowns 1402 of staples 1400 have dissolved, the deformable members 1404 and 1406 of the staples may be able to move relative to each other while still holding the underlying tissue together.

In various embodiments, deformable members 1404 and 1406 may be comprised of a substantially non-dissolvable or non-bioabsorbable material. In other embodiments, at least one of deformable members 1404 and 1406 may be comprised of a dissolvable, bioabsorbable, or biofragmentable material such as magnesium or iron, for example. In at least one embodiment, the iron is pure iron. In either event, the dissolvable material of members 1404 and 1406 can be selected such that they dissolve at the same rate as, slower than, or faster than the dissolvable material of crown 1402. For example, the material of crown 1402 can be selected such that it completely dissolves away while deformable members 1404 and 1406 are still holding tissue together. Further, in various embodiments, the material of first deformable member 1404 can be selected such that it dissolves faster than the material of second deformable member 1406. Accordingly, the deformable members of these embodiments may allow for a staggered release of the tissue. Further, in various embodiments, at least two adjacent staples 1400, as described in greater detail below, can be connected by a bridge before and/or after the staples have been deployed into the tissue. In these embodiments, a first staple can be comprised of bioabsorbable materials that dissolve away at a faster rate than the materials of a second staple attached thereto. Similarly, the bridge connecting the staples can be comprised of materials that dissolve away at the same rate, and/or a different rate, than the first and second staples. In these embodiments, the first staples can dissolve away before the second staples allowing for a staggered release of the tissue.

The staples described above can be used to approximate tissue, i.e., the staples can secure resected or damaged tissue such that the strength of the resected or damaged tissue approximates that of healthy tissue. To this end, a method of approximating tissue can include suturing tissue with a surgical staple comprised of a dissolvable material and a non-dissolvable material to approximate tissue in a first state, and dissolving the dissolvable material to cause the remaining non-dissolvable material to approximate the tissue in a second state. In at least one embodiment, the tissue approximation in the second state is more flexible than in the first state.

In addition to the above, referring to FIG. 132, crown 1402 may be comprised of at least two overmolded or co-molded materials. More particularly, crown 1402 may be comprised of a first material 1435 overmolded onto deformable members 1404 and 1406 and a second material 1436 overmolded onto second material 1436, for example. In this embodiment, second material 1436 can be configured to dissolve away quickly thereby allowing deformable members 1404 and 1406 to separate from each other early on in the healing process. However, first material 1435 can be selected to dissolve at a slower rate than second material 1436 in order for crown 1302 to continue to provide a compressive force on the tissue even after second material 1436 has completely dissolved away. In at least one embodiment, first material 1435 can be injection molded onto deformable members 1404 and 1406 and then permitted to cure, and/or substantially solidify, before second material 1436 is injection molded onto first material 1435. In other various embodiments, first material 1435 and second material 1436 can be injection molded onto deformable members 1404 and 1406 at substantially the same time or in rapid succession. In these embodiments, the first and second materials can chemically bond together to provide sufficient strength therebetween so that the staple may be handled without the first and second materials separating from one another. In other embodiments, the first and second materials can form mechanically interlocking features to accomplish the same result.

In the embodiment illustrated in FIG. 123, crown 1402 may include reduced cross-section 1414 intermediate portions 1416 and 1418. In use, intermediate section 1414, as it has a smaller cross-section than portions 1416 and 1418, may completely dissolve away before sections 1416 and 1418 thereby allowing first member 1404 to become unconnected from second member 1406 before the entirety of crown 1402 has dissolved (FIG. 125). In at least one embodiment, the cross-sections of sections 1414, 1416, and 1418 can be selected such that deformable members 1404 and 1406 become unconnected at a desired stage in the healing process. In at least one embodiment, referring to FIG. 133, crown 1402 can include score marks 1437 which reduce the thickness of crown 1402 in the scored areas. In these embodiments, the score marks may be formed when crowns 1402 are overmolded onto deformable members 1404 and 1406 or formed by a cutting tool thereafter. As a result of score marks 1437, crown 1402, as it dissolves, can break up into several small pieces which are, in some circumstances, more easily absorbable by the body. In at least one embodiment, referring to FIG. 134, crown 1402 may include a plurality of pockets 1438 intermediate raised portions 1439. In use, the material intermediate raised portions 1439 may dissolve away leaving behind a lattice, or grid, of raised portions 1439 intermediate deformable members 1404 and 1406.

In at least one embodiment, crown 1402 is also comprised of at least one therapeutic drug. In these embodiments, as the dissolvable material deteriorates, the therapeutic drug can be absorbed by the surrounding tissue. In some embodiments, the drug is dispersed throughout the dissolvable material such that the drug is steadily released during the healing process, however, in other embodiments, the therapeutic drug may be unevenly dispersed throughout the dissolvable material, or layered within and/or on the material to provide an increased dosage of the drug at a particular stage in the healing process.

In at least one embodiment, having an absorbable staple with an absorbable insulator reduces the possibility of arcing along a row of staples when an electrocautery device is used in situ, for example. The absorbable insulators, or crowns, on the staples substantially prevent an electrical current from jumping betweens staples as the top of each staple is not electrically conductive under normal operating conditions. As a result, the possibility of damaging tissue is reduced.

Figure 127:
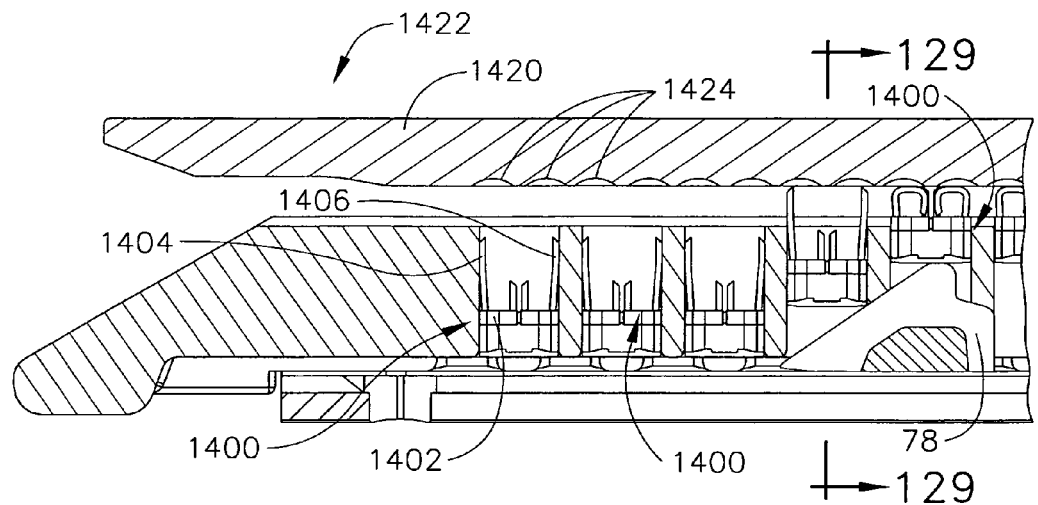
Figure 128:
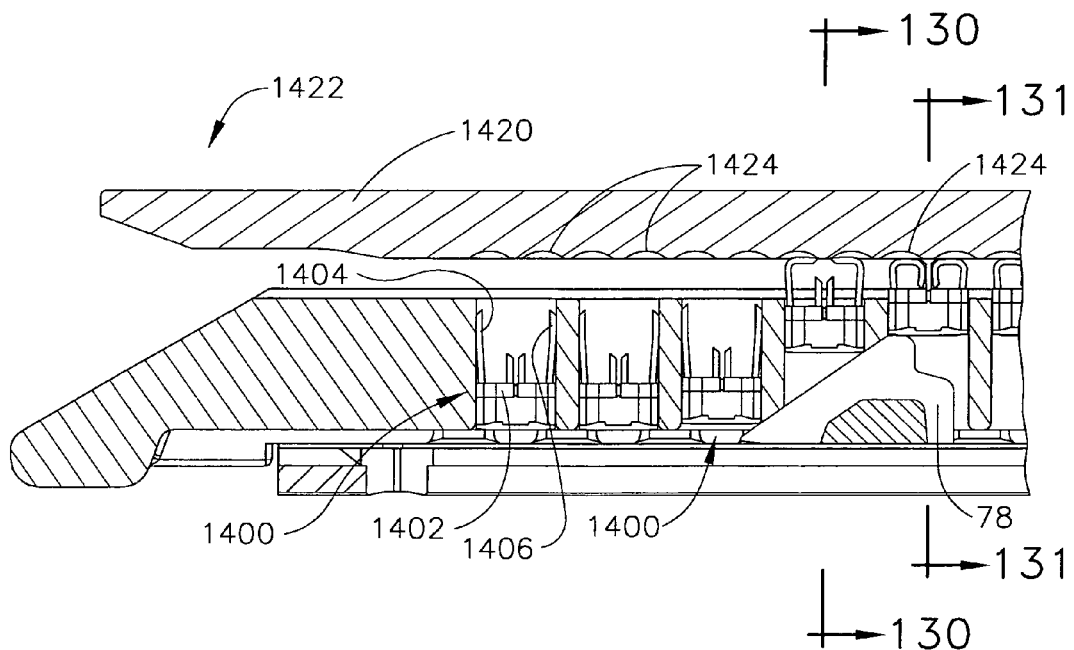

In use, as described above, and referring to FIGS. 127 and 128, deformable members 1404 and 1406 of staple 1400 are deformed by anvil 1420 of stapler 1422. More particularly, ends 1411 of members 1404 and 1406 are received within recesses 1424 in anvil 1420 and are guided toward crown 1402 as members 1404 and 1406 are deformed by anvil 1420. Referring to FIG. 129 and 129A, recesses 1424 can include a configuration which causes the ends of members 1404 and 1406 to bend out of plane with members 1412 and bases 1408. More particularly, referring to FIGS. 130 and 131, each recess 1424 includes several planar surfaces oriented to initially deflect end 1411 laterally, and then downwardly, to curl the top portion of deformable leg 1410 alongside the bottom portion of deformable leg 1410 as illustrated in FIG. 131. Referring to FIGS. 130 and 131, recess 1424 includes surfaces 1426 and 1428 which form vertex 1430 therebetween. Surfaces 1426 and 1428, and vertex 1430, are configured to receive end 1411 of deformable member 1406, for example. After sufficient pressure is applied by anvil 1420, leg 1410 of deformable member 1406 is curled within vertex 1430. Thereafter, as leg 1410 is further deformed, leg 1410 also contacts vertex 1432 which is intermediate surfaces 1428 and 1434 of recess 1424. As illustrated in FIG. 131, vertex 1432 assists in deforming member 1406 into a desired shape. While the above anvils are described in connection with staples 1400, these anvils can be used to deform other differently-configured staples including the suitable staples disclosed in this application.

Referring to FIGS. 96 and 97, staple 1300 includes an integral staple crown and driver. More particularly, referring to FIG. 105, crown 1302 is configured to be directly driven by cam sled 78. In use, as described in detail above, cam sled 78 is progressed through staple cartridge 1326 from the position illustrated in FIG. 105 toward distal end 1327 of staple cartridge 1326. As cam sled 78 is moved in this direction, staples 1300 are successively lifted by cam sled 78 toward anvil 1316. In previous surgical staplers, a separate driver was positioned intermediate the cam sled and the staple. However, the present invention simplifies these previous systems by including features in crown 1302 which allow staples 1300 to be directly lifted by cam sled 78. More particularly, referring to FIGS. 96 and 97, crown 1302 includes beveled surfaces 1328 which are configured to co-operate with angled surface 1330 of cam sled 78 such that crowns 1302 slide up cam surface 1330. In the illustrated embodiment, both beveled surfaces 1328 and cam surface 1330 are oriented at an approximately 30 degree angle with respect to the horizontal. As a result, in the present embodiment, beveled surface 1328 may sit flushly on cam surface 1330, however, embodiments are envisioned in which beveled surfaces 1328 and cam surface 1330 are not oriented at the same angle. Furthermore, the present invention is not limited to embodiments having 30 degree angles. On the contrary, any suitable angle, or angles, can be used.

Referring to FIGS. 96 and 97, base 1301 of staple 1300, in the illustrated embodiment, is embedded in crown 1302. More particularly, crown 1302 can be overmolded onto base 1301 such that crown 1302 tightly surrounds base 1301 and wherein, in the present embodiment, base 1301 is enveloped or enclosed by crown 1302. In other various embodiments, crown 1302 may be separately manufactured and then assembled to base 1301. In either event, base 1301 and/or deformable members 1304 and 1306 can be at least partially embedded into crown-driver 1302. As a result, staple 1300 can include larger deformable members 1304 and 1306 than in previous designs. In these embodiments, as a result of the above, staple 1300 may accommodate larger tissues intermediate the deformable members and tissue-contacting surface 1336 of crown 1302. In one embodiment, crown-driver 1302 may be comprised of a dissolvable or bioabsorbable material, as described above, that, as it dissolves, allows the tissue compressed within staple 1300 to expand and grow. In various embodiments, as described above, crown-driver 1302 may be comprised of, or coated by, a hydrophilic material that expands when exposed to water in the body to further compress the tissue in the staple. Further, similar to the above, crown-driver 1302 may be configured to increase the contact area between crown 1302 and the tissue. In some embodiments, increasing this contact area reduces the localized stress on the tissue surface which may reduce the possibility of tissue necrosis, for example.

As indicated above, an integral staple crown and driver may reduce the quantity of components needed to deploy the staples. As a result, embodiments in accordance with the present invention may reduce the cost and/or manufacturing time to produce the stapling systems. Further, eliminating the separate driver components may reduce the possibility of misalignment between the staples and the cam sled.

In an alternative embodiment of the present invention, referring to FIG. 135, staples 1450 can each include a crown 1451 and two deformable legs 1452 extending therefrom. Referring to FIG. 135, the crowns of staples 1450 can be connected together by bridge 1455. Similar to the above, crowns 1451 and bridge 1455 can be integrally molded onto staple legs 1452. Also similar to the above, crowns 1451 can include beveled surfaces 1453 which, referring to FIG. 139, can be configured to cooperate with angled surface 1454 of cam driver 1462. As above, cam driver 1462 is configured to successively raise staples 1450 toward an anvil positioned opposite deck 1456 of staple cartridge 1457. As discussed in greater detail below, bridges 1455 can be configured to connect staples 1450 even after they have been deployed or, alternatively, staple cartridge 1457 can include shears which break bridges 1455 and separate staples 1450 when they are deployed.

Staple cartridge 1457, referring to FIGS. 136-138, further includes cavities 1458 configured to receive staples 1450. In at least one embodiment, cavities 1458 include keys 1459 which are sized and configured to fit within slots 1460 in crowns 1451. More particularly, slots 1460 and keys 1459, in the present embodiment, are configured to substantially limit the motion of staples 1450 with respect to staple cartridge 1457 to a substantially linear motion, i.e., in the present embodiment, an upwardly and/or downwardly motion. As a result of these features, the possibility of staples 1450 becoming bound within or misaligned with respect to cavities 1458 can be reduced. In alternative embodiments, cavities 1458 can include slots and staples 1450 can have keys.

Although surfaces 1453 have been described herein as being beveled, surfaces 1453 are not limited to flat surfaces. On the contrary, various embodiments are envisioned in which surfaces 1453 are curved, radiused, curvilinear, and/or include several sections having various configurations. In either event, surfaces 1453 are configured to co-operate with cam sled 1462 such that staples 1450 are deployed as described above. Similarly, surface 1454 of cam sled 1462 is not limited to a flat surface. On the contrary, surface 1454 can be curved, radiused, curvilinear, and/or have any other suitable configuration.

Staple cartridge 1500, referring to FIG. 140, includes recesses 1502 for receiving staple strips 1504. Referring to FIGS. 140 and 141, staple strips 1504 include several staples 1506 connected together by bridges 1508. Recesses 1502 include several pockets 1510 which are sized and configured for receiving staples 1506 therein. In at least one embodiment, staples 1506 include deformable members 1512 which are sized and configured to be biased against the sidewalls of notches 1514 in recesses 1502. More particularly, deformable members 1512 can be configured to create a press-fit between staples 1506 and pockets 1510 such that staple strips 1504 remain seated within recesses 1502 under normal usage conditions. However, in the present embodiment, staple strips 1504 can be removed from recesses 1502 with a moderate application of force.

As illustrated in FIG. 140, recesses 1502 open to top surface 1516 of staple cartridge 1500 such that staple strips 1504 can be inserted into staple cartridge 1500 by aligning strips 1504 with recesses 1502 in top surface 1516 and pressing them into the position illustrated in FIG. 141. Referring to FIG. 141, recesses 1502 further include recess portions 1518 intermediate adjacent pockets 1510 which are sized and configured for receiving bridges 1508. In the embodiment illustrated in FIGS. 140-143, bridges 1508 are configured such that adjacent staples 1506 can move with respect to each other when being inserted into pockets 1510. Accordingly, bridges 1508 can accommodate dimensional differences, and/or manufacturing tolerances, in the alignment of strips 1504 with recesses 1502. More particularly, each bridge 1508 can include a curved portion 1520 configured to allow portions 1522 of bridge 1508 to move with respect to each other.

In the illustrated embodiments, the deformable members of each staple 1506 comprise a single continuous wire that can be bent into a "U" and/or "V" shape. Crowns 1513, in the present embodiment, can be overmolded onto a portion of these wires such that the wires are embedded into and supported by crown 1513. In addition, as illustrated in FIG. 143, bridges 1508 can be integrally molded with crowns 1513 when crowns 1513 are overmolded onto the wire. As a result, bridges 1508 and crowns 1513, in the present embodiment, can comprise an integral, continuous body of plastic, for example. Although not illustrated, bridges 1508 and crowns 1513, in various embodiments, may be molded as a separate component, or components, that are attached to the staples. In these embodiments, the wires of the staples can be press-fit and/or glued into recesses in the separately molded components, for example.

In use, referring to FIG. 144, as sled 78 is moved forward, sled 78 lifts staples 1506 upwardly toward an anvil positioned opposite top surface 1516. Owing to the angled orientation of surface 1523 of sled 78, staples 1506a-1506e, for example, are incrementally lifted in successive order. More particularly, staples 1506a and 1506b, while they are being lifted by sled 78, may be lifted to different relative heights with respect to surface 1516 at any given moment. To accommodate this difference in relative position, bridge 1508a can be flexible such that it does not break as staple 1506a is being deployed. Bridge 1508a, in the embodiment illustrated in FIG. 144, can be configured such that it remains attached to staples 1506a and 1506b during the deployment thereof and, in addition, during the initial healing process of the patient.

In other various embodiments, referring to FIGS. 145-147, staples 1506 can be connected together by bridges 1526 to form staple strips 1528. Similar to bridges 1508, bridges 1526 can be integrally formed with crowns 1513 when crowns 1513 are overmolded onto deformable members 1512 as described above. However, bridges 1526, unlike bridges 1508, can be configured such that they break away from at least one of the two adjacent staples 1506 that they connect. More particularly, referring to FIGS. 146 and 147, bridges 1526 can include notches 1530 therein which are configured to reduce the cross-sectional thickness, and strength, of bridges 1526. In use, referring to FIG. 147, as staple 1506a is lifted upwardly with respect to staple 1506b, bridge 1526a can break away from staple 1506a. Stated another way, when staple is 1506a is lifted upwardly, the stress created within bridge 1526a by pulling staple 1506a away from staple 1506b may cause bridge 1526a to break, especially in the portion of bridge 1526a having notch 1530 therein.

In the illustrated embodiment, bridge 1526a may remain attached to staple 1506b after it has been deployed. In other embodiments, bridge 1526a may remain attached to staple 1506a. In either event, notches 1530 can be designed such that bridges 1526 remain attached to a desired staple. In other embodiments, bridges 1526 may separate from both adjacent staples 1506 and fall into a cavity (not illustrated) within staple cartridge 1500, and/or sled 78. In these embodiments, the separated bridges 1526 may be removed from the stapler by removing the staple cartridge and/or removing them through an access panel in either the staple cartridge and/or the sled. In various embodiments, notches 1530 are not included in every bridge 1526. In these embodiments, several staples may remain attached to each other after being deployed while other staples may be detached. In these embodiments, the stiffness of the row of staples, when inserted into the tissue, can be controlled by selectively alternating whether the staples are attached or detached.

Referring to FIG. 146, bridges 1526 may include a substantially flat top surface 1532 which is substantially flush with top surfaces of crowns 1513. Bridges 1526 may further include a substantially arcuate surface, or lobe, 1534 in the bottom of bridges 1526 such that the thickest portions of bridges 1526 are adjacent to staples 1506. As a result of this configuration, the overall deflection of staple strip 1528 may be reduced making staple strip 1528 easier to insert into the staple cartridge. In other embodiments, referring to FIGS. 148-150, bridges 1536 may have lobes 1534 which face upward, i.e., in the opposite direction that they face on bridges 1526. In lieu of the configurations of bridges 1526 and 1536 which have a flat surface 1532, the bridges may comprise an arcuate configuration on both sides of the bridge. In these embodiments, similar to the embodiment in FIGS. 142 and 143, the bridges may deflect to permit some relative movement between adjacent staples 1506.

In various other embodiments, referring to FIGS. 151-157, the staple strips may be loaded into the staple cartridge from the bottom of the staple cartridge. For example, referring to FIGS. 155-157, staple cartridge 1550 includes cavities 1552 and 1554 which are sized and configured for receiving staple strips 1540 and 1542, respectively. In use, staple strips 1540 and 1542 are aligned with openings 1555 and 1557 in bottom surface 1551 and are inserted into cavities 1552 and 1554, respectively. In various embodiments, staple strips 1540 and 1542 may be configured such that they are press fit into cavities 1552 and 1554. In these embodiments, similar to the above, deformable members 1512 could engage the sidewalls of the cavities to retain staple strips 1540 and 1542 in staple cartridge 1550. In various embodiments, crowns 1513 and/or bridges 1538 of staple strips 1540 and 1542 can be dimensioned such that they engage the sidewalls of cavities 1552 and 1554 in a friction-fit manner. In other embodiments, staple cartridge 1550 and staple strips 1540 and 1542 may include co-operating detent features which retain the staple strips in the staple cartridge. Once inserted into the cavities, staples 1541 of staple strips 1540 and 1542 can be positioned such that a portion of their deformable members 1512 extend through openings 1559 and 1561 in top surface 1553. Deformable members 1512 of staples 1541, as illustrated in FIG. 151, can extend substantially perpendicularly from crowns 1513.

Similar to the above, referring to FIGS. 155 and 156, staple strips 1540 and 1542 can be advanced upward through cavities 1552 and 1554 toward an anvil positioned opposite top surface 1553 from a first position illustrated in FIG. 155 to a second position illustrated in FIG. 156. When staple strips 1540 and 1542 are advanced into the position illustrated in FIG. 153, bridges 1538 may be pressed against shears 1560 of staple cartridge 1550. Thereafter, the staple strips may be pushed further upward causing shears 1560 to break bridges 1538 away from one or more of staples 1541, as described above. Referring to FIG. 154, shears 1560 in cavity 1552 include projections 1562 which extend therefrom and are configured to break bridges 1538 away from crowns 1531 at locations 1564 (FIG. 151).

In any of the embodiments described herein, the material overmolded onto the staples to form crowns 1513 and bridges 1526, and/or bridges 1508, may be comprised of a dissolvable, bioabsorbable or biofragmentable material. Further, similar to the above, in various embodiments, the bioabsorbable material may include at least one therapeutic drug mixed therein or coated thereon, for example. Similar to the above, in various embodiments, drivers may be connected to, and/or integrally molded with, the crowns of the staples.

In alternative embodiments, the staples may be connected in "puck" configurations in lieu of strips, for example. In various embodiments, referring to FIG. 158, staple pucks 1571 and 1572 include staples 1506 which are interconnected by bridges 1574 and 1575. Staple pucks 1571 have five staples 1506 which are interconnected by two bridges 1574 and two bridges 1575. As illustrated in FIG. 158, bridges 1575 connect adjacent staples 1506 such that the tops of their crowns 1513 are substantially flush with each other, however, bridges 1574 connect adjacent staples 1506 such that the top of their crowns 1513 are vertically offset from each other. Similarly, staple pucks 1572 include four staples 1506 which are interconnected by two bridges 1574 and two bridges 1575.

Referring to FIGS. 159 and 159A, staple cartridge 1576 includes cavities 1577 which are sized and configured for receiving staple pucks 1571, and cavities 1578 which are sized and configured for receiving staple pucks 1572. Referring to FIG. 160, staple cartridge 1576 further includes drivers 1579 and 1580 which are sized and configured for supporting staple pucks 1571 and 1572, respectively, thereon. More specifically, referring to FIGS. 161-163, drivers 1579 and 1580 can include shears 1581 upon which staples pucks 1571 and 1572 are supported. After being inserted into cavities 1577 and 1578, referring to FIG. 163, bridges 1574 and 1575 are positioned over shears 1581. In use, as described above, drivers 1579 and 1580 are lifted toward deck 1582 of staple cartridge 1576 by a cam sled. However, referring to FIG. 163, once drivers 1579 and 1580 contact bridges 1574 and 1575, and the upward movement of staple pucks 1571 and 1572 is prohibited by staple cartridge 1576, further upward movement of drivers 1579 and 1580 causes shears 1581 to break bridges 1574 and 1575, thereby separating staples 1306. Once bridges 1574 and 1575 have been broken, support surfaces 1582 of drivers 1579 and 1580 are configured to push staples 1306 upwardly toward an anvil, as described above. Referring to FIGS. 164 and 164A, an alternative staple cartridge 1583 is illustrated having recesses sized and configured for receiving alternate configurations of the staple pucks.

In at least one alternative embodiment of the present invention, referring to FIGS. 165 and 166, staple pucks 1584 and 1585 can be configured such that bridges 1586 interconnecting staples 1587, for example, include shears 1588 extending therefrom. In the present embodiment, referring to FIG. 167, shears 1588 can be configured to dissect deck 1589 of staple cartridge 1590. More particularly, as staple pucks 1585 are raised by cam sled 1591, for example, shears 1588 can break through deck 1589 such that pucks 1585 can be raised above deck 1589 when deployed. As a result, staples 1587 can be completely deployed from staple cartridge 1590 before staple cartridge 1590 is removed from the surgical site. In alternative embodiments, although not illustrated, the staple cartridge can also include shears which detach staples 1587 from bridges 1586, and/or shears 1588, after shears 1588 have dissected staple cartridge deck 1589. Similar to the above, bridges 1589 can include beveled surfaces 1592 which are configured to co-operate with cam sled 1591.

Referring to FIG. 168, staples 1465 can each include a first deformable leg 1466, a second deformable leg 1467, and a base 1468 connecting deformable legs 1466 and 1467. Unlike previous staples which have a base that is substantially co-planar with its legs, base 1468 can extend in at least one direction that is transverse to a plane defined by legs 1466 and 1467. More particularly, base 1468 can include first portion 1469 and second portion 1470 which extend laterally from legs 1466 and 1467 and form an angle therebetween. In the present embodiment, referring to FIG. 169, first portion 1469 forms an approximately 90 degree angle with respect to second portion 1470. However, the present invention is not limited to 90 degree angles; rather, any suitable angle may be used. More particularly, the angle between first portion 1469 and second portion 1470 may, in some embodiments, be greater than 90 degrees and may, in other embodiments, be less than 90 degrees. Furthermore, in other embodiments, base 1468 may include several substantially linear segments and/or curved sections.

Staple 1465 can further include crown 1471 overmolded onto base 1468. More particularly, owing to the configuration of base 1468 as described above, crown 1471 can also extend transversely with respect to the plane defined between legs 1466 and 1467. Referring to FIGS. 168 and 169, crown 1471 can include tissue-contacting surface 1472 which is sized and configured for supporting tissue thereon. Tissue-contacting surface 1472, owing to the configuration of crown 1471, can be larger than the tissue contacting surfaces of previous staples. Accordingly, the larger contact surface can reduce the localized pressure acting on the tissue captured within the staple. As known in the art, reducing this localized pressure can reduce the possibility of tissue necrosis without reducing the compressive force acting on the tissue. Stated another way, the pressure acting on the tissue is a function of the force acting on the tissue divided by the area in which it acts. Increasing the area can reduce the localized pressure while not reducing the clamping force applied by the staple.

Further, owing to the configurations of base 1468 and crown 1471, the larger surface area of crown 1471 can improve the stability of crown 1471, and the surrounding tissue, after the staple has been deployed into the tissue. More particularly, after previous staples are deployed, the relatively-narrow crowns of these previous staples may not prevent the staples from rocking with respect to the tissue or straining the tissue surrounding the staple. Staples 1465, owing to the configuration of crown 1471, can reduce, and possibly eliminate, these previous problems. More specifically, owing to larger contact surface 1472, crown 1471 is more stable, i.e., it is less likely to rotate with respect to the tissue. Furthermore, the crowns of previous staples, owing to their narrower configurations, may cut through the underlying tissue. Staple 1465, owing to the larger configuration of crown 1471, may reduce, or even eliminate, this possibility. In an alternative embodiment, referring to FIG. 173, staple assembly 1479 can include several of the "J" deformable members of staple 1400 (FIGS. 122 and 123).

To further improve the stability of staples 1465, two adjacent staples 1465, for example, may be connected together by bridge 1473. More specifically, referring to FIGS. 168 and 169, the base 1468, and crown 1471, of the first staple may be laterally disposed in one direction and the base 1468, and crown 1471, of the second staple may be laterally disposed in the opposite direction. These oppositely disposed features may improve the stability of the staples by providing stabilizing surfaces on opposite sides of the assembly. The two staples, referring to FIG. 172, may be deployed from staple cartridge 1475 by cam sled 1474 at the same time. To facilitate the deployment of the staples, staple cartridge 1475 may include, similar to the above, slots 1476 sized and configured for receiving keys 1477 extending from crowns 1471 of staples 1465. More particularly, keys 1477 and slots 1476 can be configured to limit the movement of staples 1465 with respect to staple cartridge 1475 to a substantially linear upward motion. In addition, similar to the above, each bridge 1473 can include an integral driver 1478 which is configured to co-operate with cam sled 1474. In at least one embodiment, crowns 1471, bridge 1473 and driver 1478 can be comprised of a dissolvable or bioabsorbable material.

As known in the art, staples can be deployed into tissue such that staples are aligned in a row. However, in the past, staples configured in diagonal patterns have been disincentivized owing to potential leak paths between the staples. The staples of the present invention can overcome these previous problems. Referring to FIGS. 174 and 175, staples 1480 each include two deformable members 1481 extending from a crown 1482 and bridge 1483 connecting crowns 1482. When staples 1480 are inserted into tissue, as described above, the tissue is compressed between crowns 1482 and deformable members 1481. However, in the embodiments in which bridges 1483 are inserted into the body along with staples 1480, bridges 1483 can also compress the tissue and close off any leak paths therebetween. Referring to FIG. 175, staple cartridge 1484 includes recesses 1485 therein which are configured to receive staples 1480 in a diagonal pattern such that staples 1480 can be deployed into the tissue as described above.

In an alternative embodiment, a portion of the staple cartridge can be broken away therefrom during the deployment of the staple. This portion can be configured to be positioned intermediate the base of the staple and the tissue captured within the staple. More particularly, referring to FIGS. 176-178, a surgical stapling system can include staple cartridge 1486 having staple pads 1487 integrally molded into deck 1488 of staple cartridge 1486. Staple cartridge 1486 can include score marks 1489 and slots 1490 surrounding staple pads 1487 such that staple pads 1487 can be easily separated from deck 1488. More particularly, referring to FIG. 178, the stapling system can include drivers 1491 having shears 1492 which are configured to press against staple pads 1487 when base 1493 is brought in close proximity to staple saddle 1494 and "punch-out" staple pads 1487. In at least one embodiment, after they have been punched out, the staple pads can be positioned intermediate base 1493 and the tissue captured within the staple. As a result, staple pads 1487 can be configured to act as the crown of the staple or, in alternative embodiments, act as a buttressing member intermediate the staple and the tissue. In at least one embodiment, similar to the above, staple pads 1487 can be comprised of a bioabsorbable material.

The staples described above can be used in various surgical techniques. For example, one surgical technique can include a method of transecting tissue or a hollow organ by positioning a surgical stapling system adjacent tissues to be transected, the surgical stapling system including at least one of the staples described above, actuating the surgical stapling system to compress the tissues together, actuating the surgical stapling system to fasten and divide the tissue with said staple, and removing the surgical stapling system from the operative site. In at least one embodiment, the surgical technique can include the anastomosis of two hollow organs and/or the fixation of at least two tissues.

What is claimed is:

1. A surgical staple for stapling tissue, comprising:
   a crown, said crown comprised of a dissolvable material;
   a first deformable member comprising a tissue-piercing end, wherein said first deformable member is configured to hold tissue after it has been deformed; and
   a second member configured to hold tissue, said crown connecting said first deformable member and said second member when said crown is undissolved, said first deformable member being unconnected to said second member after said crown has been dissolved, wherein said first deformable member and said second member are configured to hold tissue independently of one another after said crown has been dissolved.

2. The surgical staple of claim 1, wherein said crown further includes at least one second material, wherein said second material comprises a therapeutic drug, and wherein the dissolution of said crown releases said therapeutic drug.

3. The surgical staple of claim 1, wherein said crown comprises a first side and a second side, wherein said second side is opposite said first side, wherein said first deformable member and said second member extend from said first side, and wherein said first deformable member and said second member do not extend from said second side.

4. The surgical staple of claim 1, wherein said crown comprises:
   a first end adjacent said first deformable member; and
   a second end adjacent said second member.

5. The surgical staple of claim 4, wherein said first deformable member is configured to be deformed toward said second end.

6. The surgical staple of claim 1, wherein said first deformable member includes a first leg and a second leg, and wherein said first leg is deformable such that, after said first leg has been deformed, said first leg and said second leg define an at least substantially enclosed area for holding tissue.

7. A surgical staple for stapling tissue, comprising:
   a crown, said crown comprised of a first dissolvable material;
   a first deformable member comprising a tissue-piercing end, wherein said first deformable member is configured to hold tissue after it has been deformed; and
   a second member configured to hold tissue, said crown connecting said first deformable member and said second member when said crown is undissolved, said first deformable member being unconnected to said second member after said crown has been dissolved, wherein at least one of said first deformable member and said second member are comprised of a second dissolvable material which dissolves at a slower rate than said first dissolvable material such that at least one of said first deformable member and said second member is configured to hold tissue after said crown has been dissolved.

8. The surgical staple of claim 7, wherein said second dissolvable material includes at least one of iron and magnesium.

9. The surgical staple of claim 7, wherein said crown comprises a first side and a second side, wherein said second side is opposite said first side, wherein said first deformable member and said second member extend from said first side, and wherein said first deformable member and said second member do not extend from said second side.

10. The surgical staple of claim 7, wherein said crown comprises:
    a first end adjacent said first deformable member; and
    a second end adjacent said second member.

11. The surgical staple of claim 10, wherein said first deformable member is configured to be deformed toward said second end.

12. The surgical staple of claim 7, wherein said first deformable member includes a first leg and a second leg, and wherein said first leg is deformable such that, after said first leg has been deformed, said first leg and said second leg define an at least substantially enclosed area for holding tissue.

* * * * *